US012161477B1

(12) United States Patent
Berme et al.

(10) Patent No.: US 12,161,477 B1
(45) Date of Patent: *Dec. 10, 2024

(54) FORCE MEASUREMENT SYSTEM

(71) Applicant: Bertec Corporation, Columbus, OH (US)

(72) Inventors: Necip Berme, Worthington, OH (US); Aysun Dolan, Columbus, OH (US); Megan Elaine Cotterman, Columbus, OH (US); Mohan Chandra Baro, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/401,696

(22) Filed: Jan. 1, 2024

Related U.S. Application Data

(63) Continuation-in-part of application No. 18/092,414, filed on Jan. 2, 2023, now Pat. No. 11,857,331, which
(Continued)

(51) Int. Cl.
*A61B 5/00* (2006.01)
*A61B 5/103* (2006.01)
(Continued)

(52) U.S. Cl.
CPC .......... *A61B 5/4023* (2013.01); *A61B 5/1036* (2013.01); *A61B 5/16* (2013.01);
(Continued)

(58) Field of Classification Search
CPC ....... A61B 5/4023; A61B 5/1036; A61B 5/16; A61B 5/6895; A61B 5/702; A61B 5/7445;
(Continued)

(56) References Cited

U.S. PATENT DOCUMENTS 4,009,607 A 3/1977 Ficken
4,489,932 A 12/1984 Young
(Continued)

OTHER PUBLICATIONS

BalanceCheck Screener—Protocol Guide, Bertec Corporation, Version 1.1.0, last updated Mar. 2012.
(Continued)

*Primary Examiner* — May A Abouelela
(74) *Attorney, Agent, or Firm* — The Law Office of Patrick F. O'Reilly III, LLC

(57) ABSTRACT

A force measurement system is disclosed herein. The force measurement system includes at least one user input device, a force measurement assembly configured to receive a subject, at least one visual display device, and one or more data processing devices operatively coupled to the user input device, the force measurement assembly, and the visual display device. The one or more data processing devices are programmed to receive the one or more input signals from the at least one user input device based upon one or more selections by the user, the one or more selections by the user including a scene parameter for one or more scenes on the output screen of the at least one visual display device; and display the one or more scenes on the output screen of the at least one visual display device based upon the scene parameter selected by the user.

14 Claims, 65 Drawing Sheets

Related U.S. Application Data is a continuation-in-part of application No. 17/728,241, filed on Apr. 25, 2022, now Pat. No. 11,540,744, which is a continuation-in-part of application No. 17/367,575, filed on Jul. 5, 2021, now Pat. No. 11,311,209, which is a continuation-in-part of application No. 17/114,139, filed on Dec. 7, 2020, now Pat. No. 11,052,288, which is a continuation-in-part of application No. 16/870,987, filed on May 10, 2020, now Pat. No. 10,856,796, which is a continuation-in-part of application No. 16/571,103, filed on Sep. 14, 2019, now Pat. No. 10,646,153, which is a continuation-in-part of application No. 16/297,615, filed on Mar. 9, 2019, now Pat. No. 10,413,230, which is a continuation-in-part of application No. 16/025,321, filed on Jul. 2, 2018, now Pat. No. 10,231,662, which is a continuation-in-part of application No. 15/713,166, filed on Sep. 22, 2017, now Pat. No. 10,010,286, which is a continuation-in-part of application No. 15/365,325, filed on Nov. 30, 2016, now Pat. No. 9,770,203, which is a continuation-in-part of application No. 14/797,149, filed on Jul. 12, 2015, now Pat. No. 9,526,443, which is a continuation-in-part of application No. 14/474,110, filed on Aug. 30, 2014, now Pat. No. 9,081,436, which is a continuation-in-part of application No. 13/958,348, filed on Aug. 2, 2013, now Pat. No. 8,847,989, which is a continuation-in-part of application No. 13/904,751, filed on May 29, 2013, now Pat. No. 8,704,855.

(60) Provisional application No. 61/754,556, filed on Jan. 19, 2013.

(51) Int. Cl.
*A61B 5/16* (2006.01)
*G06F 3/04847* (2022.01)
*H04N 9/31* (2006.01)

(52) U.S. Cl.
CPC .......... *A61B 5/6895* (2013.01); *A61B 5/702* (2013.01); *A61B 5/7445* (2013.01); *A61B 5/749* (2013.01); *G06F 3/04847* (2013.01); *H04N 9/3194* (2013.01); *A61B 2560/0223* (2013.01)

(58) Field of Classification Search
CPC .......... A61B 5/749; A61B 2560/0223; G06F 3/04847; H04N 9/3194
See application file for complete search history.

(56) References Cited

U.S. PATENT DOCUMENTS

| | | |
|---|---|---|
| 4,738,269 A | 4/1988 | Nashner |
| 4,830,024 A | 5/1989 | Nashner et al. |
| 5,052,406 A | 10/1991 | Nashner |
| 5,130,794 A | 7/1992 | Ritchey |
| 5,269,318 A | 12/1993 | Nashner |
| 5,303,715 A * | 4/1994 | Nashner ............... A61B 5/1036 600/595 |
| 5,366,375 A | 11/1994 | Sarnicola |
| 5,429,140 A | 7/1995 | Burdea et al. |
| 5,474,087 A | 12/1995 | Nashner |
| 5,476,103 A | 12/1995 | Nashner |
| 5,490,784 A | 2/1996 | Carmein |
| 5,523,890 A | 6/1996 | Reaney |
| 5,551,445 A | 9/1996 | Nashner |
| 5,562,572 A | 10/1996 | Carmein |
| 5,623,944 A | 4/1997 | Nashner |
| 5,695,406 A | 12/1997 | Park |
| 5,697,791 A | 12/1997 | Nashner et al. |
| 5,745,126 A | 4/1998 | Jain et al. |
| 5,769,640 A | 6/1998 | Jacobus et al. |
| 5,846,134 A | 12/1998 | Latypov |
| 5,980,256 A | 11/1999 | Carmein |
| 5,980,429 A | 11/1999 | Nashner |
| 6,010,465 A | 1/2000 | Nashner |
| 6,038,488 A | 3/2000 | Barnes et al. |
| 6,063,046 A * | 5/2000 | Allum ............... A61B 5/389 600/595 |
| 6,113,237 A | 9/2000 | Ober et al. |
| 6,152,564 A | 11/2000 | Ober et al. |
| 6,173,218 B1 | 1/2001 | Vian |
| 6,176,837 B1 | 1/2001 | Foxlin |
| 6,190,287 B1 | 2/2001 | Nashner |
| 6,289,299 B1 | 9/2001 | Daniel et al. |
| 6,295,878 B1 | 10/2001 | Berme |
| 6,307,567 B1 | 10/2001 | Cohen-Or |
| 6,317,658 B1 | 11/2001 | Vian |
| 6,354,155 B1 | 3/2002 | Berme |
| 6,389,883 B1 * | 5/2002 | Berme ............... A61B 5/706 73/65.01 |
| 6,397,136 B1 | 5/2002 | Breed et al. |
| 6,449,103 B1 | 9/2002 | Charles |
| 6,632,158 B1 | 10/2003 | Nashner |
| 6,704,694 B1 | 3/2004 | Basdogan et al. |
| 6,738,065 B1 | 5/2004 | Even-Zohar |
| 6,774,885 B1 | 8/2004 | Even-Zohar |
| 6,936,016 B2 | 8/2005 | Berme et al. |
| 7,127,376 B2 | 10/2006 | Nashner |
| 7,179,234 B2 | 2/2007 | Nashner |
| 7,195,355 B2 | 3/2007 | Nashner |
| RE40,427 E | 7/2008 | Nashner |
| 7,500,752 B2 | 3/2009 | Nashner |
| 7,697,750 B2 | 4/2010 | Simmons |
| 7,719,563 B2 | 5/2010 | Richards |
| 7,761,269 B1 | 7/2010 | Kraal et al. |
| 7,780,573 B1 | 8/2010 | Carmein |
| 7,931,604 B2 | 4/2011 | Even-Zohar et al. |
| 8,085,318 B2 | 12/2011 | Ciudad et al. |
| 8,152,699 B1 * | 4/2012 | Ma ............... A61H 1/0229 482/54 |
| 8,181,541 B2 | 5/2012 | Berme |
| 8,262,590 B2 * | 9/2012 | Padula ............... A61B 5/6831 600/595 |
| 8,296,858 B2 | 10/2012 | Striegler et al. |
| 8,315,822 B2 | 11/2012 | Berme et al. |
| 8,315,823 B2 | 11/2012 | Berme et al. |
| RE44,396 E | 7/2013 | Roston et al. |
| 8,509,965 B2 | 8/2013 | Lin |
| D689,388 S | 9/2013 | Berme |
| D689,389 S | 9/2013 | Berme |
| 8,543,540 B1 | 9/2013 | Wilson et al. |
| 8,544,347 B1 * | 10/2013 | Berme ............... G01G 19/44 73/862.041 |
| 8,626,472 B2 | 1/2014 | Solinsky |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,790,279 B2 | 7/2014 | Brunner |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,149,222 B1 * | 10/2015 | Zets ............... A61B 5/4023 |
| 9,162,106 B1 | 10/2015 | Scheiman |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |

(56) References Cited

U.S. PATENT DOCUMENTS

| | | | |
|---|---|---|---|
| 9,517,008 B1 | 12/2016 | Berme et al. | |
| 9,526,443 B1 | 12/2016 | Berme et al. | |
| 9,526,451 B1 | 12/2016 | Berme | |
| 9,526,946 B1* | 12/2016 | Zets | G09B 19/0038 |
| 9,558,399 B1 | 1/2017 | Jeka et al. | |
| 9,568,382 B1 | 2/2017 | Berme et al. | |
| 9,591,993 B2* | 3/2017 | Morris Bamberg | A61B 5/6807 |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,548,512 B2* | 2/2020 | Hausdorff | A61B 5/1117 |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 8/2021 | Berme et al. | |
| 11,158,422 B1 | 10/2021 | Wilson et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |
| 11,348,279 B1 | 5/2022 | Akbas et al. | |
| 11,458,362 B1 | 10/2022 | Berme et al. | |
| 11,521,373 B1 | 12/2022 | Akbas et al. | |
| 11,540,744 B1 | 1/2023 | Berme | |
| 11,604,106 B2 | 3/2023 | Berme et al. | |
| 11,631,193 B1 | 4/2023 | Akbas et al. | |
| 11,688,139 B1 | 6/2023 | Karagoz et al. | |
| 11,705,244 B1 | 7/2023 | Berme | |
| 11,712,162 B1 | 8/2023 | Berme et al. | |
| 11,790,536 B1 | 10/2023 | Berme et al. | |
| 11,798,182 B1 | 10/2023 | Karagoz et al. | |
| 11,816,258 B1 | 11/2023 | Berme et al. | |
| 11,826,601 B1 | 11/2023 | Berme | |
| 11,850,078 B1 | 12/2023 | Berme | |
| 11,857,331 B1 | 1/2024 | Berme et al. | |
| 11,865,407 B1 | 1/2024 | Berme et al. | |
| 11,911,147 B1 | 2/2024 | Berme et al. | |
| 2001/0024512 A1 | 9/2001 | Yoronka et al. | |
| 2002/0010571 A1 | 1/2002 | Daniel et al. | |
| 2002/0059022 A1 | 5/2002 | Breed et al. | |
| 2002/0196554 A1 | 12/2002 | Cobb | |
| 2003/0011561 A1 | 1/2003 | Stewart et al. | |
| 2003/0036835 A1 | 2/2003 | Breed et al. | |
| 2003/0122872 A1 | 7/2003 | Chiang et al. | |
| 2003/0216656 A1 | 11/2003 | Berme et al. | |
| 2003/0216895 A1 | 11/2003 | Ghaboussi et al. | |
| 2004/0027394 A1 | 2/2004 | Schonberg | |
| 2004/0127337 A1 | 7/2004 | Nashner | |
| 2004/0216517 A1 | 11/2004 | Xi et al. | |
| 2004/0227727 A1 | 11/2004 | Schena et al. | |
| 2005/0030620 A1 | 2/2005 | Goto et al. | |
| 2005/0043661 A1 | 2/2005 | Nashner | |
| 2005/0075833 A1 | 4/2005 | Nashner | |
| 2005/0148432 A1 | 7/2005 | Carmein | |
| 2005/0243277 A1 | 11/2005 | Nashner | |
| 2006/0115348 A1 | 6/2006 | Kramer | |
| 2006/0183083 A1 | 8/2006 | Moran | |
| 2006/0195858 A1 | 8/2006 | Takahashi et al. | |
| 2006/0264786 A1 | 11/2006 | Nashner | |
| 2007/0064311 A1 | 3/2007 | Park | |
| 2007/0093989 A1 | 4/2007 | Nashner | |
| 2007/0121066 A1 | 5/2007 | Nashner | |
| 2007/0135265 A1 | 6/2007 | Nashner | |
| 2007/0184953 A1 | 8/2007 | Luberski et al. | |
| 2007/0271056 A1 | 11/2007 | Nussbaumer | |
| 2008/0009686 A1* | 1/2008 | Hendrich | G16H 50/30 600/301 |
| 2008/0034383 A1 | 2/2008 | Harwin et al. | |
| 2008/0088529 A1 | 4/2008 | Tang | |
| 2008/0088921 A1 | 4/2008 | Yonekubo et al. | |
| 2008/0204666 A1 | 8/2008 | Spearman | |
| 2008/0221487 A1 | 9/2008 | Even-Zohar et al. | |
| 2008/0228110 A1 | 9/2008 | Berme | |
| 2009/0059096 A1 | 3/2009 | Yamamoto et al. | |
| 2009/0062092 A1* | 3/2009 | Mortimer | A63B 24/00 482/142 |
| 2009/0119030 A1 | 5/2009 | Fang et al. | |
| 2009/0126096 A1 | 5/2009 | Bocos | |
| 2009/0137933 A1 | 5/2009 | Lieberman et al. | |
| 2009/0185759 A1 | 7/2009 | Liu et al. | |
| 2009/0240170 A1* | 9/2009 | Rowley | A61B 5/6831 600/595 |
| 2009/0325699 A1 | 12/2009 | Delgiannidis | |
| 2010/0075808 A1 | 3/2010 | Luberski et al. | |
| 2010/0092267 A1 | 4/2010 | Najdovski et al. | |
| 2010/0097526 A1 | 4/2010 | Jacob | |
| 2010/0118044 A1 | 5/2010 | Ishihara | |
| 2010/0131113 A1 | 5/2010 | Even-Zohar | |
| 2010/0137064 A1 | 6/2010 | Shum et al. | |
| 2010/0176952 A1 | 7/2010 | Bajcsy et al. | |
| 2010/0182136 A1 | 7/2010 | Pryor | |
| 2010/0197462 A1 | 8/2010 | Piane, Jr. | |
| 2010/0216104 A1 | 8/2010 | Reichow et al. | |
| 2010/0240454 A1 | 9/2010 | Xiao | |
| 2010/0302142 A1 | 12/2010 | French et al. | |
| 2011/0009241 A1* | 1/2011 | Lane | G06F 3/011 482/8 |
| 2011/0009777 A1* | 1/2011 | Reichow | A63B 71/0622 600/595 |
| 2011/0072367 A1 | 3/2011 | Bauer | |
| 2011/0092882 A1 | 4/2011 | Firlik et al. | |
| 2011/0098157 A1* | 4/2011 | Whalen | A61H 9/00 482/52 |
| 2011/0115787 A1 | 5/2011 | Kadlec | |
| 2011/0120567 A1* | 5/2011 | Kuehne | A63B 21/00181 601/1 |
| 2011/0152727 A1* | 6/2011 | Ten Kate | A61B 5/6829 600/595 |
| 2011/0196264 A1* | 8/2011 | Asada | A61B 5/4023 600/595 |
| 2011/0200251 A1 | 8/2011 | Chin et al. | |
| 2011/0208444 A1 | 8/2011 | Solinsky | |
| 2011/0229862 A1 | 9/2011 | Parikh | |
| 2011/0237396 A1 | 9/2011 | Lu | |
| 2011/0256983 A1 | 10/2011 | Malack | |
| 2011/0275959 A1* | 11/2011 | Casali | A61B 3/0083 600/595 |
| 2011/0277562 A1 | 11/2011 | Berme | |

(56) References Cited

U.S. PATENT DOCUMENTS

| | | | |
|---|---|---|---|
| 2011/0294390 A1 | 12/2011 | Michalk et al. | |
| 2011/0300994 A1 | 12/2011 | Verkaaik et al. | |
| 2011/0312473 A1* | 12/2011 | Chu | A63B 69/0053 482/54 |
| 2012/0013530 A1 | 1/2012 | Tsuboi et al. | |
| 2012/0065784 A1 | 3/2012 | Feldman | |
| 2012/0071300 A1 | 3/2012 | Shapiro et al. | |
| 2012/0108909 A1* | 5/2012 | Slobounov | A61B 5/16 600/300 |
| 2012/0113209 A1 | 5/2012 | Ritchey et al. | |
| 2012/0122062 A1 | 5/2012 | Yang et al. | |
| 2012/0123701 A1 | 5/2012 | Drueding et al. | |
| 2012/0130280 A1* | 5/2012 | Lee | A61B 5/1121 600/587 |
| 2012/0176411 A1 | 7/2012 | Huston | |
| 2012/0253233 A1* | 10/2012 | Greene | G16H 50/30 600/592 |
| 2012/0253234 A1* | 10/2012 | Yang | A61B 5/1038 600/595 |
| 2012/0266648 A1 | 10/2012 | Berme et al. | |
| 2012/0271565 A1 | 10/2012 | Berme et al. | |
| 2012/0281152 A1 | 11/2012 | Nemeth et al. | |
| 2012/0303332 A1 | 11/2012 | Magione-Smith | |
| 2013/0005415 A1 | 1/2013 | Thomas et al. | |
| 2013/0012357 A1 | 1/2013 | Wang | |
| 2013/0022947 A1 | 1/2013 | Muniz Simas et al. | |
| 2013/0033967 A1 | 2/2013 | Chuang et al. | |
| 2013/0035613 A1* | 2/2013 | Curtiss | A61B 5/4023 600/595 |
| 2013/0050260 A1 | 2/2013 | Reitan | |
| 2013/0083003 A1 | 4/2013 | Perez et al. | |
| 2013/0117377 A1 | 5/2013 | Miller | |
| 2013/0127980 A1 | 5/2013 | Haddick et al. | |
| 2013/0158364 A1* | 6/2013 | Hayn | A61B 5/0059 600/301 |
| 2013/0162673 A1 | 6/2013 | Bohn | |
| 2013/0253367 A1* | 9/2013 | Newman | A61B 3/113 600/558 |
| 2013/0258486 A1 | 10/2013 | Ionescu | |
| 2013/0278631 A1 | 10/2013 | Border et al. | |
| 2013/0286004 A1 | 10/2013 | McCulloch et al. | |
| 2013/0335302 A1 | 12/2013 | Crane et al. | |
| 2014/0024972 A1* | 1/2014 | Greene | A61B 5/1038 600/595 |
| 2014/0081177 A1* | 3/2014 | Eguibar | A61B 5/1036 600/595 |
| 2014/0137050 A1 | 5/2014 | Alhashash | |
| 2014/0148929 A1* | 5/2014 | Stechschulte | A63B 69/3623 700/91 |
| 2014/0195023 A1* | 7/2014 | Statham | A63B 69/0028 700/91 |
| 2014/0213951 A1* | 7/2014 | Pietrusisnki | A61H 3/008 602/23 |
| 2014/0315689 A1 | 10/2014 | Vauquelin et al. | |
| 2014/0354514 A1 | 12/2014 | Aronsson | |
| 2014/0361988 A1 | 12/2014 | Katz et al. | |
| 2015/0049004 A1 | 2/2015 | Deering et al. | |
| 2015/0096387 A1 | 4/2015 | Berme et al. | |
| 2015/0320339 A1* | 11/2015 | Larson | A61B 5/1117 600/595 |
| 2015/0379351 A1 | 12/2015 | Dibenedetto et al. | |
| 2016/0245711 A1 | 8/2016 | Berme et al. | |
| 2016/0334288 A1 | 11/2016 | Berme et al. | |
| 2018/0024015 A1 | 1/2018 | Berme et al. | |
| 2019/0078951 A1 | 3/2019 | Berme et al. | |
| 2020/0077892 A1 | 3/2020 | Tran | |
| 2020/0139229 A1 | 5/2020 | Berme et al. | |
| 2020/0408625 A1 | 12/2020 | Berme et al. | |
| 2021/0333163 A1 | 10/2021 | Berme et al. | |
| 2022/0178775 A1 | 6/2022 | Berme et al. | |

OTHER PUBLICATIONS

BalanceCheck Trainer—Protocol Guide, Bertec Corporation, Version 1.1.0, last updated Mar. 2012.

"Standing, walking, running, and jumping on a force plate", Rod Cross, Am. J. Phys. 67 (4), Apr. 1999.

First office action on the merits (Non-Final Rejection) in U.S. Appl. No. 13/904,751, mailed on Jul. 19, 2013.

Second office action on the merits (Final Rejection) in U.S. Appl. No. 13/904,751, mailed on Oct. 31, 2013.

First office action on the merits (Non-Final Rejection) in U.S. Appl. No. 13/958,348, mailed on Dec. 5, 2013.

First office action on the merits (Non-Final Rejection) in U.S. Appl. No. 14/474, 110, mailed on Dec. 17, 2014.

Wrap Augmented Reality Glasses, Vuzix Website, Web page <http://www.vuzix.com/augmented-reality/products_wrap1200ar.html>, 2 pages, dated Jul. 2, 2013, retrieved from Internet Archive Wayback Machine <https://web.archive.org/web/20130702182224/http://www.vuzix.com/augmented-reality/products_wrap1200ar.html#description> on Oct. 15, 2014.

Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.

Wireless Data Glove, Meta Motion Website, Web page <http://www.metamotion.com/hardware/motion-capture-hardware-gloves-Cybergloves.htm>, 3 pages, dated May 14, 2012, retrieved from Internet Archive Wayback Machine <https://web.archive.org/web/20120514105507/http://www.metamotion.com/hardware/motion-capture-hardware-gloves-Cybergloves.htm> on Oct. 15, 2014.

Gates et al., Journal of NeuroEngineering and Rehabilitation 2012, 9:81, "Comparison of walking overground and in a Computer Assisted Rehabilitation Environment (CAREN) in individuals with and without transtibial amputation".

Mark Fondren, Monica Foster, Mitch Johnson, Drew Parks, Adam Vaclavik, "Virtual Rehabilitation", http://engineeringworks.tamu.edu/2011/virtual-reality-for-high-tech-rehabilitation-2/; 2011.

Dynamic Control of a Moving Platform using the CAREN System to Optimize Walking in Virtual Reality Environments; 31st Annual International Conference of the IEEE EMBS Minneapolis, Minnesota, USA, Sep. 2-6, 2009, by Hassan El Makssoud, Carol L. Richards, and Francois Comeau.

Geijtenbeek T, Steenbrink F, Otten B, Even-Zohar, O (2011) D-Flow: Immersive Virtual Reality and Real-Time Feedback for Rehabilitation. In: Proceedings of the 10th International Conference on Virtual Reality Continuum and its Applications in Industry (VRCAI '11). ACM, New York, pp. 201-208.

Erik J. Wolf, Overview of CAREN Research. State of the Science Symposium: Virtual Reality and Its Role in Wounded Warrior and Veteran Care, Sep. 15, 2012, pp. 1-34.

Eye Gaze Tracking Under Natural Head Movements, Zhiwei Zhu and Qiang Ji, 2005 IEEE.

Efficient real-time algorithms for eye state and head pose tracking in Advanced Driver Support Systems, Riad L. Hammoud, Andrew Wilhelm, Phillip Malawey, and Gerald J. Witt, 2005, IEEE.

Combined Head and Eye Tracking System for Dynamic Testing of the Vestibular System, Robert S. Allison, Moshe Eizenman, and Bob S. K. Cheung, IEEE Transactions on Biomedical Engineering, vol. 41, No. 11, Nov. 1996.

Active Eye-Tracking System by Using Quad PTZ Cameras, Chao-Ning Chan, Shunichiro OE, Chem-Sheng Lint, IEEE 2007.

A Cascaded Scheme for Eye Tracking and Head Movement Compensation, X. Xie, R. Sudhakar, H. Zhuang, Systems and Humans, vol. 28, No. 4, Jul. 1998.

First office action on the merits (Non-Final Rejection) in U.S. Appl. No. 14/797,149, mailed on Apr. 28, 2016.

First office action on the merits (Non-Final Rejection) in U.S. Appl. No. 15/365,325, mailed on Feb. 14, 2017.

First office action on the merits (Non-Final Rejection) in U.S. Appl. No. 15/713,166, mailed on Nov. 24, 2017.

First office action on the merits (Non-Final Rejection) in U.S. Appl. No. 16/025,321, mailed on Jul. 30, 2018.

(56) References Cited

OTHER PUBLICATIONS

First office action on the merits (Non-Final Rejection) in U.S. Appl. No. 16/297,615, mailed on Apr. 10, 2019.
First office action on the merits (Non-Final Rejection) in U.S. Appl. No. 16/571,103, mailed on Oct. 15, 2019.
"Speeding up or slowing down?: Gait adaptations to preserve gait stability in response to balance perturbations", Laura Hak et al., year 2012.
"Walking variability during continuous pseudorandom oscillations of the support surface and visual field", Patricia M. McAndrew et al., J Biomech. May 28, 2010; 43(8): pp. 1470-1475.
"Does walking in a virtual environment induce unstable gait? An examination of vertical ground reaction forces", John H. Hollman et al., Gait & Posture 26 (2007): pp. 289-294.
First office action on the merits (Non-Final Rejection) in U.S. Appl. No. 16/870,987, mailed on Jun. 12, 2020.
First office action on the merits (Non-Final Rejection) in U.S. Appl. No. 17/114,139 mailed on Feb. 4, 2021.
Emily H. Sinitski et al., "Characteristics of a dual force plate system embedded in a six degree of freedom motion platform", 2013 IEEE International Symposium on Medical Measurements and Applications, May 4-5, 2013, pp. 1-5.
First office action on the merits (Non-Final Rejection) in U.S. Appl. No. 17/367,575, mailed on Aug. 27, 2021.
First office action on the merits (Non-Final Rejection) in U.S. Appl. No. 17/728,241, mailed on Jun. 3, 2022.
First office action on the merits (Non-Final Rejection) in U.S. Appl. No. 18/092,414, mailed on Apr. 17, 2023.

\* cited by examiner

FORCE MEASUREMENT SYSTEM

CROSS-REFERENCE TO RELATED APPLICATIONS

This is a continuation-in-part of U.S. Nonprovisional patent application Ser. No. 18/092,414, entitled "Force Measurement System", filed on Jan. 2, 2023; which is a continuation-in-part of U.S. Nonprovisional patent application Ser. No. 17/728,241, entitled "Force Measurement System", filed on Apr. 25, 2022, now U.S. Pat. No. 11,540,744; which is a continuation-in-part of U.S. Nonprovisional patent application Ser. No. 17/367,575, entitled "Force Measurement System And A Motion Base Used Therein", filed on Jul. 5, 2021, now U.S. Pat. No. 11,311,209; which is a continuation-in-part of U.S. Nonprovisional patent application Ser. No. 17/114,139, entitled "Force Measurement System", filed on Dec. 7, 2020, now U.S. Pat. No. 11,052,288; which is a continuation-in-part of U.S. Nonprovisional patent application Ser. No. 16/870,987, entitled "Force Measurement System", filed on May 10, 2020, now U.S. Pat. No. 10,856,796; which is a continuation-in-part of U.S. Nonprovisional patent application Ser. No. 16/571,103, entitled "Force Measurement System", filed on Sep. 14, 2019, now U.S. Pat. No. 10,646,153; which is a continuation-in-part of U.S. Nonprovisional patent application Ser. No. 16/297,615, entitled "Force Measurement System", filed on Mar. 9, 2019, now U.S. Pat. No. 10,413,230; which is a continuation-in-part of U.S. Nonprovisional patent application Ser. No. 16/025,321, entitled "Force Measurement System", filed on Jul. 2, 2018, now U.S. Pat. No. 10,231,662; which is a continuation-in-part of U.S. Nonprovisional patent application Ser. No. 15/713,166, entitled "Force Measurement System", filed on Sep. 22, 2017, now U.S. Pat. No. 10,010,286; which is a continuation-in-part of U.S. Nonprovisional patent application Ser. No. 15/365,325, entitled "Force Measurement System and a Method of Testing a Subject", filed on Nov. 30, 2016, now U.S. Pat. No. 9,770,203; which is a continuation-in-part of U.S. Nonprovisional patent application Ser. No. 14/797,149, entitled "Force and/or Motion Measurement System and a Method of Testing a Subject", filed on Jul. 12, 2015, now U.S. Pat. No. 9,526,443; which is a continuation-in-part of U.S. Nonprovisional patent application Ser. No. 14/474,110, entitled "Force and/or Motion Measurement System and a Method of Testing a Subject Using the Same", filed on Aug. 30, 2014, now U.S. Pat. No. 9,081,436; which is a continuation-in-part of U.S. Nonprovisional patent application Ser. No. 13/958,348, entitled "Force and/or Motion Measurement System and a Method for Training a Subject Using the Same", filed on Aug. 2, 2013, now U.S. Pat. No. 8,847,989; which is a continuation-in-part of U.S. Nonprovisional patent application Ser. No. 13/904,751, entitled "Force Measurement System Having A Displaceable Force Measurement Assembly", filed on May 29, 2013, now U.S. Pat. No. 8,704,855; which claims the benefit of U.S. Provisional Patent Application No. 61/754,556, entitled "Force Measurement System Having A Displaceable Force Measurement Assembly", filed on Jan. 19, 2013, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a force measurement system. More particularly, the invention relates to a force measurement system for testing and/or training a subject.

2. Background

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

A balance assessment of a human subject is frequently performed using a specialized type of a force plate, which is generally known as a balance plate. In general, individuals maintain their balance using inputs from proprioceptive, vestibular and visual systems. Conventional balance systems are known that assess one or more of these inputs. However, these conventional balance systems often employ antiquated technology that significantly affects their ability to accurately assess a person's balance and/or renders them cumbersome and difficult to use by patients and the operators thereof (e.g., clinicians and other medical personnel). For example, some of these conventional balance systems employ displaceable background enclosures with fixed images imprinted thereon that are not readily adaptable to different testing schemes.

Therefore, what is needed is a force measurement system having a force measurement assembly that employs virtual reality scenarios and/or simulated environments for effectively assessing the balance characteristics of a subject and offering much greater flexibility in the balance assessment testing that can be employed. Moreover, what is needed is a method of testing a subject that utilizes a force measurement system employing flexible and interactive virtual reality scenarios and/or simulated environments. Furthermore, a force and motion measurement system is needed that includes an immersive visual display device that enables a subject being tested to become effectively immersed in a virtual reality scenario or an interactive game. In addition, a force measurement system is needed that is capable of determining whether a measurement error is present. Also, a force measurement system is needed that is capable of determining a balance strategy of a subject disposed thereon.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one or more embodiments of the present invention, there is provided a force measurement system that comprises at least one user input device, the at least one user input device configured to output one or more input signals based upon one or more selections by a user performing a testing or training routine on a subject; a force measurement assembly configured to receive the subject, the force measurement assembly including a top surface configured to receive at least one portion of the body of the subject; and at least one force transducer, the at least one force transducer configured to output one or more output signals that are representative of forces and/or moments being applied to the top surface of the force measurement assembly by the subject; at least one visual display device having an output screen, the at least one visual display device configured to display one or more scenes on the output screen so that the one or more scenes are visible to the subject; and one or more data processing devices operatively coupled to the at least one user input device, the force measurement assembly, and the at least one visual display device, the one or more data processing devices being programmed to: (i) receive the one or more input signals from the at least one user input device based upon the one or more selections by the user, the one or more selections by the user including a scene parameter for one or more scenes on the output screen of the at least one visual display device; (ii) display the one or more scenes on the output screen of the at least one visual display device based upon the scene parameter selected by the user; (iii) receive, from the force measurement assembly, the one or more output signals that are representative of the forces and/or moments being applied to the top surface of the force measurement assembly by the subject; and (iv) convert the one or more output signals into output force and/or moment data.

In a further embodiment of the present invention, the scene parameter selected by the user is selected from the group consisting of: (i) a direction of movement of one or more objects being displaced in the one or more scenes, (ii) a speed of movement of the one or more objects being displaced in the one or more scenes, and (iii) a density of the one or more objects being displaced in the one or more scenes.

In yet a further embodiment, the one or more scenes displayed on the output screen of the at least one visual display device comprise at least one of: (i) a starfield, (ii) a fountain, (iii) an airport, and (iv) a checkered room.

In still a further embodiment, the one or more data processing devices are further programmed to: (v) generate and display a cognitive task on the output screen of the at least one visual display device with the one or more scenes; and (vi) determine whether the subject is able to correctly perform the cognitive task when the one or more scenes are being displayed on the output screen.

In yet a further embodiment, the one or more data processing devices are further programmed to: (v) generate and display at least one displaceable visual object and a plurality of visual targets on the output screen of the at least one visual display device, the plurality of visual targets being superimposed on the one or more scenes being displayed on the output screen; (vi) receive one or more additional input signals from the at least one user input device based upon an input response by the user; and (vii) control the movement of the at least one displaceable visual object towards the plurality of visual targets based upon the one or more additional input signals received from the input device.

In still a further embodiment, the at least one visual display device further comprises a projector having a lens and a projection screen, the projector being configured to project an image through the lens, and onto the projection screen.

In yet a further embodiment, the one or more data processing devices are further programmed to: (v) generate and display a projector calibration image on the projection screen of the at least one visual display device, the projector calibration image comprising one or more alignment lines that correspond to one or more edges of the projection screen. In this further embodiment, the one or more alignment lines are configured to be displaced towards the one or more corresponding edges of the projection screen when the user adjusts one or more lens settings on the lens of the projector.

In still a further embodiment, the force measurement system further comprises at least one lens actuator, the at least one lens actuator configured to adjust one or more lens settings on the lens of the projector; and at least one calibration reference camera, the at least one calibration reference camera configured to capture one or more images displayed on the projection screen. In this further embodiment, the one or more data processing devices are further programmed to: (v) generate and display a projector calibration image on the projection screen of the at least one visual display device, the projector calibration image comprising one or more alignment lines that correspond to one or more edges of the projection screen; (vi) capture the projector calibration image using the at least one calibration reference camera; (vii) compute one or more image parameters based upon the projector calibration image captured by the at least one calibration reference camera; and (viii) adjust, based upon the one or more computed image parameters, the one or more lens settings on the lens of the projector using the at least one lens actuator.

In yet a further embodiment, the one or more image parameters affect at least one of: (i) image position, (ii) image distortion, (iii) image focus, and (iv) image brightness.

In still a further embodiment, the force measurement assembly is in the form of a force plate or a balance plate.

In yet a further embodiment, the force measurement system further comprises a base assembly having a stationary portion and a displaceable portion, the force measurement assembly forming a part of the displaceable portion of the base assembly, and the force measurement system additionally comprising at least one actuator operatively coupled to the one or more data processing devices, the at least one actuator configured to displace the force measurement assembly relative to the stationary portion of the base assembly.

In still a further embodiment, the at least one actuator comprises a first actuator configured to rotate the force measurement assembly about a transverse rotational axis and a second actuator configured to translate the displaceable portion of the base assembly that includes the force measurement assembly.

In yet a further embodiment, the force measurement assembly is in a form of an instrumented treadmill.

In still a further embodiment, the at least one user input device comprises at least one of: (i) a mouse, (ii) a keyboard, (iii) a touchscreen user interface, and (iv) a voice recognition device.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
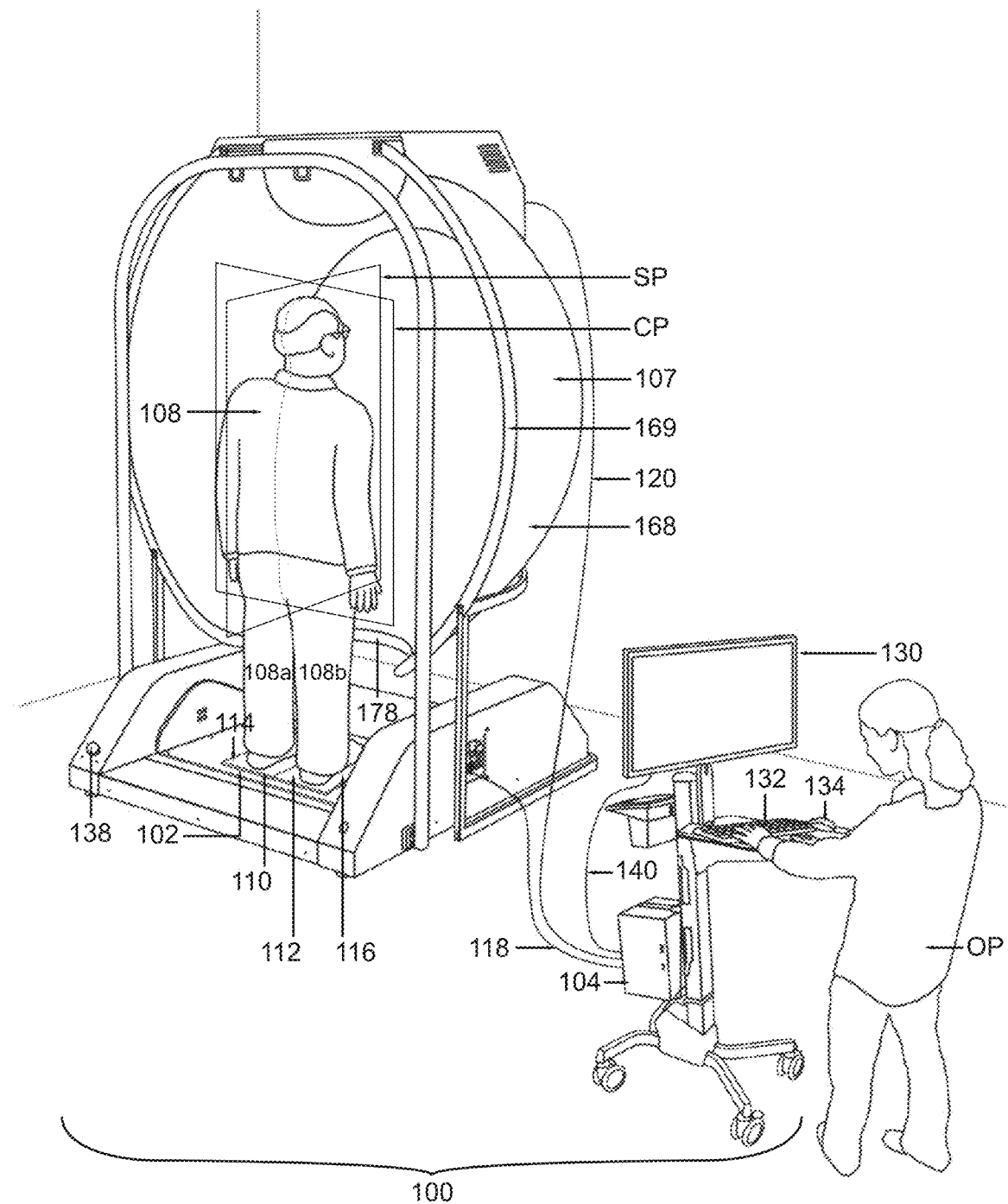
FIG. 1 is a diagrammatic perspective view of a force measurement system having a displaceable force measurement assembly according to an embodiment of the invention.

An exemplary embodiment of the measurement and testing system is seen generally at 100 in FIG. 1. In the illustrative embodiment, the force measurement system 100 generally comprises a force measurement assembly 102 that is operatively coupled to a data acquisition/data processing device 104 (i.e., a data acquisition and processing device or computing device that is capable of collecting, storing, and processing data), which in turn, is operatively coupled to a subject visual display device 107 and an operator visual display device 130. As illustrated in FIG. 1, the force measurement assembly 102 is configured to receive a subject 108 thereon, and is capable of measuring the forces and/or moments applied to its substantially planar measurement surfaces 114, 116 by the subject 108.

As shown in FIG. 1, the data acquisition/data processing device 104 includes a plurality of user input devices 132, 134 connected thereto. Preferably, the user input devices 132, 134 comprise a keyboard 132 and a mouse 134. In addition, the operator visual display device 130 may also serve as a user input device if it is provided with touch screen capabilities. While a desktop-type computing system is depicted in FIG. 1, one of ordinary of skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the invention.

Referring again to FIG. 1, it can be seen that the force measurement assembly 102 of the illustrated embodiment is in the form of a displaceable, dual force plate assembly. The displaceable, dual force plate assembly includes a first plate component 110, a second plate component 112, at least one force measurement device (e.g., a force transducer) associated with the first plate component 110, and at least one force measurement device (e.g., a force transducer) associated with the second plate component 112. In the illustrated embodiment, a subject 108 stands in an upright position on the force measurement assembly 102 and each foot of the subject 108 is placed on the top surfaces 114, 116 of a respective plate component 110, 112 (i.e., one foot on the top surface 114 of the first plate component 110 and the other foot on the top surface 116 of the second plate component 112). The at least one force transducer associated with the first plate component 110 is configured to sense one or more measured quantities and output one or more first signals that are representative of forces and/or moments being applied to its measurement surface 114 by the left foot/leg 108a of the subject 108, whereas the at least one force transducer associated with the second plate component 112 is configured to sense one or more measured quantities and output one or more second signals that are representative of forces and/or moments being applied to its measurement surface 116 by the right foot/leg 108b of subject 108. In one or more embodiments, when the subject is displaced on the force measurement assembly 102, the subject 108 generally does not move relative to the displaceable force measurement assembly 102 (i.e., the subject 108 and the force measurement assembly 102 generally move together in synchrony). Also, in one or more embodiments, the top surfaces 114, 116 of the respective plate components 110, 112 are not rotated underneath the feet of the subject 108, but rather remain stationary relative to the feet of the subject 108 (i.e., the top surfaces 114, 116 are displaced in generally the same manner as the feet of the subject).

In one non-limiting, exemplary embodiment, the force plate assembly 102 has a load capacity of up to approximately 500 lbs. (up to approximately 2,224 N) or up to 500 lbs. (up to 2,224 N). Advantageously, this high load capacity enables the force plate assembly 102 to be used with almost any subject requiring testing on the force plate assembly 102. Also, in one non-limiting, exemplary embodiment, the force plate assembly 102 has a footprint of approximately eighteen (18) inches by twenty (20) inches. However, one of ordinary skill in the art will realize that other suitable dimensions for the force plate assembly 102 may also be used.

Figure 2:
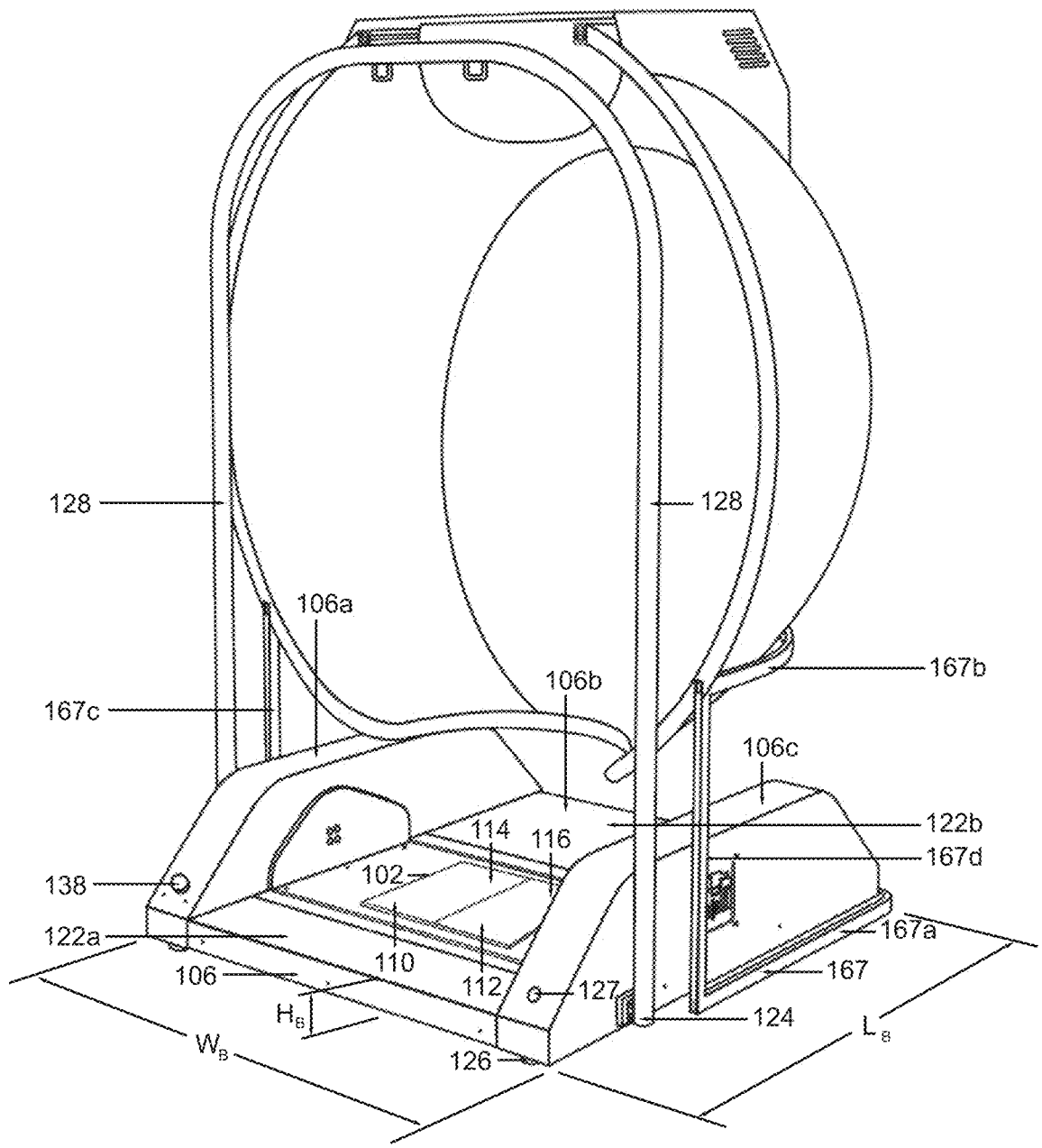
FIG. 2 is a perspective view of an immersive subject visual display device, a base assembly, and displaceable force measurement assembly of the force measurement system according to an embodiment of the invention.

Now, with reference to FIG. 2, it can be seen that the displaceable force measurement assembly 102 is movably coupled to a base assembly 106. The base assembly 106 generally comprises a substantially planar center portion 106b with two spaced-apart side enclosures 106a, 106c that are disposed on opposed sides of the center portion 106b. As shown in FIG. 2, the displaceable force measurement assembly 102 is recessed-mounted into the top surface of the center portion 106b of the base assembly 106 (i.e., it is recess-mounted into the top surface of the translatable sled assembly 156 which is part of the center portion 106b of the base assembly 106) so that its upper surface lies substantially flush with the adjacent stationary top surfaces 122a, 122b of the center portion 106b of the base assembly 106. The upper surface of the displaceable force measurement assembly 102 also lies substantially flush with the top surface of the translatable sled assembly 156. Moreover, in the illustrated embodiment, it can be seen that the base assembly 106 further includes a pair of mounting brackets 124 disposed on the outward-facing side surfaces of each side enclosure 106a, 106c. Each mounting bracket 124 accommodates a respective support rail 128. The support rails 128 can be used for various purposes related to the force measurement system 100. For example, the support rails 128 can be used for supporting a safety harness system, which is worn by the subject during testing so as to prevent injury.

Referring again to FIG. 2, each side enclosure 106a, 106c houses a plurality of electronic components that generate a significant amount of waste heat that requires venting. Because the bottom of each side enclosure 106a, 106c is substantially open, the waste heat is vented through the bottom thereof. In FIG. 2, it can be seen that the side enclosure 106a comprises an emergency stop switch 138 (E-stop) provided in the rear, diagonal panel thereof. In one embodiment, the emergency stop switch 138 is in the form of a red pushbutton that can be easily pressed by a user of the force measurement system 100 in order to quasi-instantaneously stop the displacement of the force measurement assembly 102. As such, the emergency stop switch 138 is a safety mechanism that protects a subject disposed on the displaceable force measurement assembly 102 from potential injury.

Figure 3:
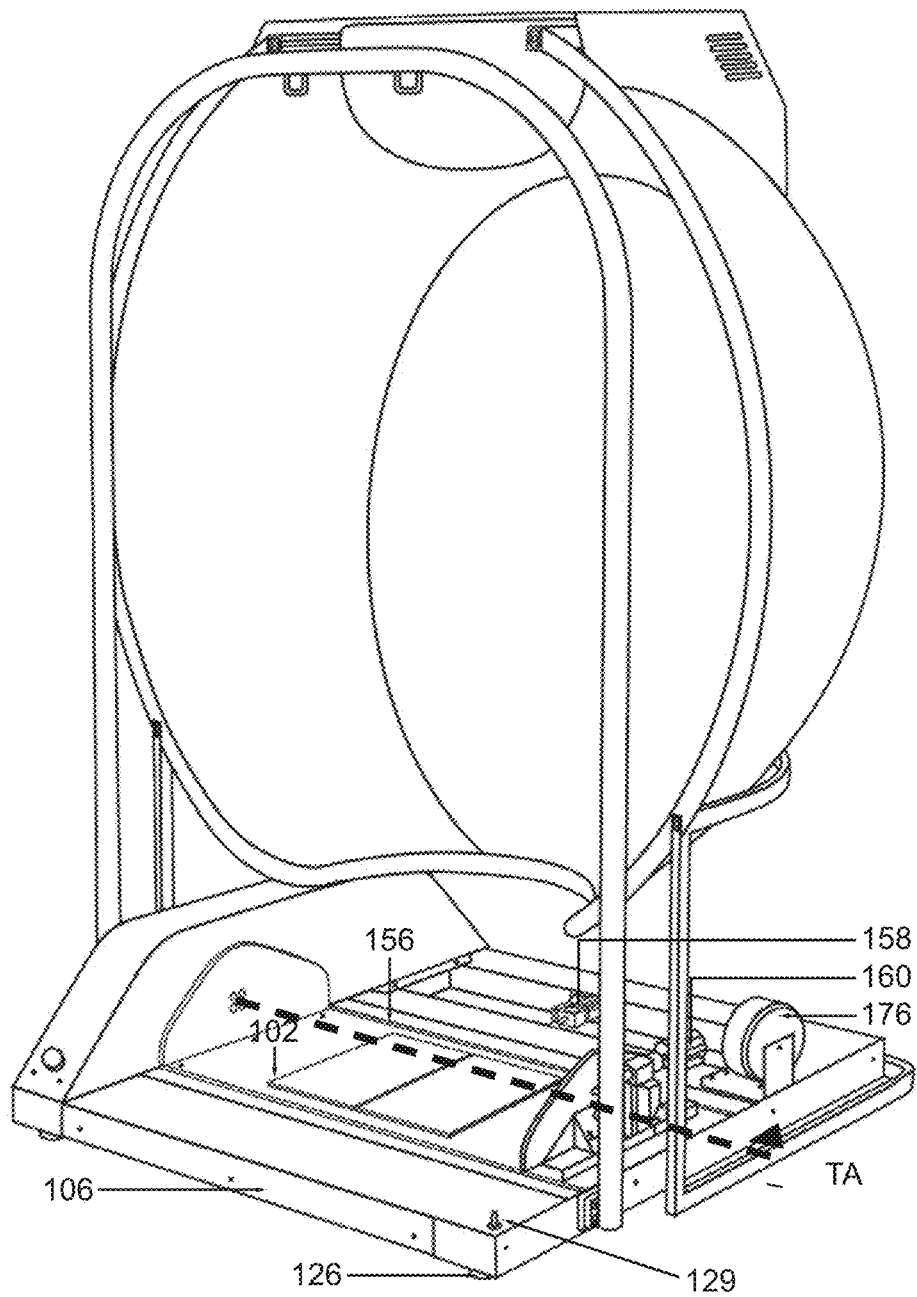
FIG. 3 is a perspective view of an immersive subject visual display device and a cutaway perspective view of a base assembly and displaceable force measurement assembly of the force measurement system according to an embodiment of the invention, wherein several covers of the base assembly are removed.

Next, turning to FIG. 3, the drive components of the base assembly 106 will be described in detail. Initially, the actuator system for producing the translation of the force measurement assembly 102 will be explained. In FIG. 3, the front top cover of the center portion 106b of the base assembly 106 has been removed to reveal the translation drive components. As shown in this figure, the force measurement assembly 102 is rotatably mounted to a translatable sled assembly 156. The translatable sled assembly 156 is displaced forward and backward (i.e., in directions generally parallel to the sagittal plane SP of the subject (see e.g., FIG. 1) disposed on the force measurement assembly 102) by means of a first actuator assembly 158. That is, the first actuator assembly 158 moves the translatable sled assembly 156 backwards and forwards, without any substantial rotation or angular displacement (i.e., the first actuator assembly 158 produces generally pure translational movement). In the illustrated embodiment, the first actuator assembly 158 is in the form of ball screw actuator, and includes an electric motor that drives a rotatable screw shaft which, in turn, is threadingly coupled to a nut fixedly secured to the translatable sled assembly 156. As such, when the screw shaft of the first actuator assembly 158 is rotated by the electric motor, the translatable sled assembly is displaced forward and backward along a substantially linear path. The electric motor of the first actuator assembly 158 is operatively coupled to a gear box (e.g., a 4:1 gear box) which, in turn, drives the rotatable screw shaft. Advantageously, because the nut of the ball screw actuator runs on ball bearings, friction is minimized and the actuator assembly 158 is highly efficient. However, an undesirable consequence of the highly efficient ball screw actuator design is its back-driveability. This poses a potential safety hazard to a subject disposed on the displaceable force measurement assembly 102 because the force plate could inadvertently move when a subject's weight is applied thereto. In order to prevent the force measurement assembly 102 from inadvertently being translated, the first actuator assembly 158 is additionally provided with a brake assembly disposed adjacent to the electric motor thereof. The brake assembly of the first actuator assembly 158 prevents any unintentional translation of the force measurement assembly 102.

Figure 42:
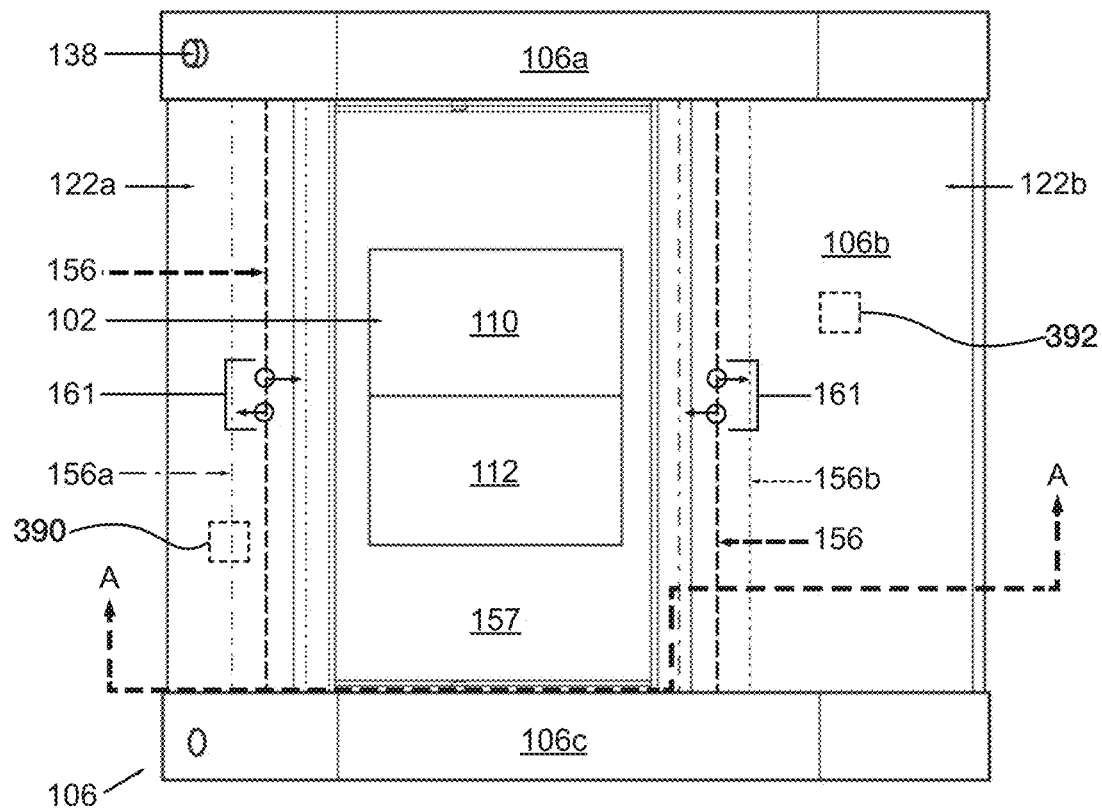
FIG. 42 is a top view of the base assembly illustrated in FIGS. 2 and 3, according to an embodiment of the invention.
Figure 43:
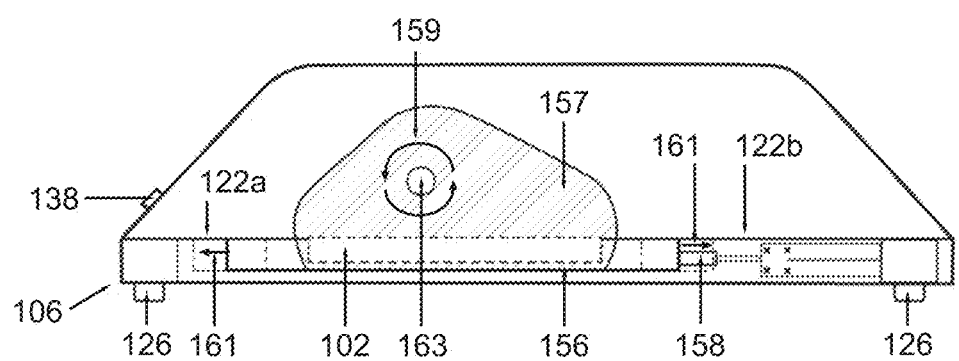
FIG. 43 is a longitudinal section cut through the base assembly illustrated in FIG. 42, wherein the section is cut along the cutting plane line A-A in FIG. 42, according to an embodiment of the invention.

In FIG. 42, a top view of the base assembly 106 is illustrated, while in FIG. 43, a longitudinal cross-sectional view of the base assembly 106 is illustrated. As shown in FIGS. 42 and 43, the force measurement assembly 102 is mounted on a rotatable carriage assembly 157 (i.e., a swivel frame 157). The rotatable carriage assembly 157 is mounted to, and rotates relative to, the translatable sled assembly 156 (i.e., the translatable frame 156). The rotatable carriage assembly 157 is rotated by a second actuator assembly 160 (see FIG. 3) about a rotational shaft 163 (see FIG. 43—the rotatable carriage assembly 157 is provided with diagonal hatching thereon). As indicated by the curved arrows 159 in FIG. 43, the rotatable carriage assembly 157 is capable of either clockwise or counter-clockwise rotation about the transverse rotational axis TA in FIG. 3 (i.e., generally single degree-of-freedom rotation about the transverse axis TA). In contrast, as indicated by the straight arrows 161 in FIGS. 42 and 43, the translatable sled assembly 156 is capable of forward and backward translational movement by virtue of being linearly displaced by first actuator assembly 158. In FIGS. 42 and 43, a rearwardly displaced position 156a of the translatable sled assembly 156 is indicated using center lines, while a forwardly displaced position 156b of the translatable sled assembly 156 is indicated using dashed lines with small dashes.

Again, referring to FIG. 3, the actuator system for producing the rotation of the force measurement assembly 102 will now be described. In FIG. 3, the top cover of the side enclosure 106c of the base assembly 106 has been removed to reveal the rotational drive components. The force measurement assembly 102 is rotated within the translatable sled assembly 156 by the second actuator assembly 160. Like the first actuator assembly 158, the second actuator assembly 160 is also in the form of ball screw actuator, and includes an electric motor with a gear box (e.g., a 4:1 gear box) that drives a rotatable screw shaft which, in turn, is threadingly coupled to a nut that runs on ball bearings. Although, unlike the first actuator assembly 158, the second actuator assembly 160 further includes a swing arm which is operatively coupled to the nut of the ball screw actuator. When the nut undergoes displacement along the screw shaft, the swing arm, which is attached to the rotatable carriage assembly 157 with the force measurement assembly 102, is rotated. As such, when the swing arm is rotated, the rotatable carriage assembly 157 with the force measurement assembly 102 is also rotated about a transverse rotational axis TA (see FIG. 3). That is, the force measurement assembly 102 undergoes generally single degree-of-freedom rotation about the transverse rotational axis TA. In one embodiment, the imaginary transverse rotational axis TA approximately passes through the center of the ankle joints of the subject 108 when he or she is disposed on the force measurement assembly 102. Because the second actuator assembly 160 is also in the form of a highly efficient ball screw actuator, it includes a brake assembly disposed adjacent to the electric motor to prevent it from being back-driven, similar to that of the first actuator assembly 158. The brake assembly of the second actuator assembly 160 prevents the force measurement assembly 102 from being inadvertently rotated so as to protect a subject disposed thereon from its inadvertent movement. When the translatable sled assembly 156 is translated by the first actuator assembly 158, the second actuator assembly 160 is translated with the sled assembly 156 and the force plate. In particular, when the translatable sled assembly 156 is translated backwards and forwards by the first actuator assembly 158, the second actuator assembly 160 is displaced along a rail or rod of the base assembly 106.

In a preferred embodiment of the invention, both the first actuator assembly 158 and the second actuator assembly 160 are provided with two (2) electrical cables operatively coupled thereto. The first cable connected to each actuator assembly 158, 160 is a power cable for the electric motor and brake of each actuator, while the second cable transmits positional information from the respective actuator encoder that is utilized in the feedback control of each actuator assembly 158, 160.

Referring back to FIG. 1, it can be seen that the base assembly 106 is operatively coupled to the data acquisition/data processing device 104 by virtue of an electrical cable 118. The electrical cable 118 is used for transmitting data between the programmable logic controller (PLC) of the base assembly 106 and the data acquisition/data processing device 104 (i.e., the operator computing device 104). Various types of data transmission cables can be used for cable 118. For example, the cable 118 can be a Universal Serial Bus (USB) cable or an Ethernet cable. Preferably, the electrical cable 118 contains a plurality of electrical wires bundled together that are utilized for transmitting data. However, it is to be understood that the base assembly 106 can be operatively coupled to the data acquisition/data processing device 104 using other signal transmission means, such as a wireless data transmission system.

Figure 4:
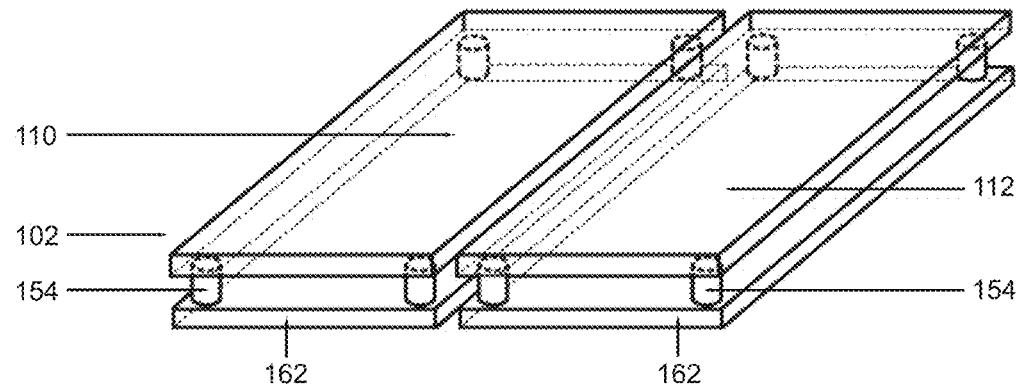
FIG. 4 is a diagrammatic perspective view of one force measurement assembly used in the force measurement system, according to an embodiment of the invention, wherein the force measurement assembly is in the form of a dual force plate.

In the illustrated embodiment, the at least one force transducer associated with the first and second plate components 110, 112 comprises four (4) pylon-type force transducers 154 (or pylon-type load cells) that are disposed underneath, and near each of the four corners (4) of the first plate component 110 and the second plate component 112 (see FIG. 4). Each of the eight (8) illustrated pylon-type force transducers has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 102. As shown in FIG. 4, a respective base plate 162 can be provided underneath the transducers 154 of each plate component 110, 112 for facilitating the mounting of the force plate assembly to the rotatable carriage assembly 157 of the translatable sled assembly 156 of the base assembly 106. Alternatively, a plurality of structural frame members (e.g., formed from steel) could be used in lieu of the base plates 162 for attaching the dual force plate assembly to the rotatable carriage assembly 157 of the translatable sled assembly 156 of the base assembly 106.

In an alternative embodiment, rather than using four (4) pylon-type force transducers 154 on each plate component 110, 112, force transducers in the form of transducer beams could be provided under each plate component 110, 112. In this alternative embodiment, the first plate component 110 could comprise two transducer beams that are disposed underneath, and on generally opposite sides of the first plate component 110. Similarly, in this embodiment, the second plate component 112 could comprise two transducer beams that are disposed underneath, and on generally opposite sides of the second plate component 112. Similar to the pylon-type force transducers 154, the force transducer beams could have a plurality of strain gages attached to one or more surfaces thereof for sensing the mechanical strain imparted on the beam by the force(s) applied to the surfaces of the force measurement assembly 102.

Rather, than using four (4) force transducer pylons under each plate, or two spaced apart force transducer beams under each plate, it is to be understood that the force measurement assembly 102 can also utilize the force transducer technology described in U.S. Pat. No. 8,544,347, the entire disclosure of which is incorporated herein by reference.

Figure 6:
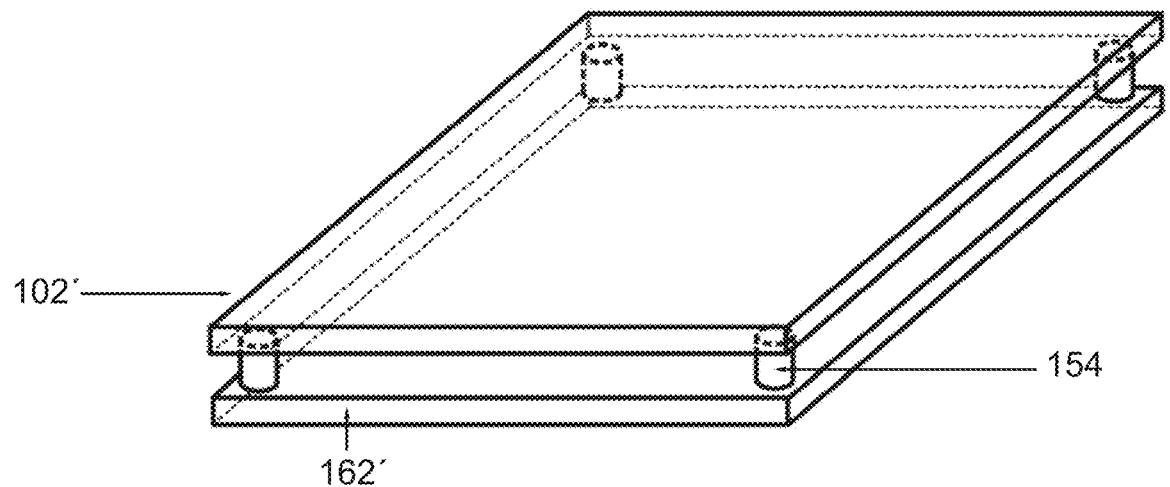
FIG. 6 is a diagrammatic perspective view of another force measurement assembly used in the force measurement system, according to an embodiment of the invention, wherein the force measurement assembly is in the form of a single force plate.

In other embodiments of the invention, rather than using a force measurement assembly 102 having first and second plate components 110, 112, it is to be understood that a force measurement assembly 102' in the form of a single force plate may be employed (see FIG. 6). Unlike the dual force plate assembly illustrated in FIGS. 1 and 4, the single force plate comprises a single measurement surface on which both of a subject's feet are placed during testing. Although, similar to the measurement assembly 102, the illustrated single force plate 102' comprises four (4) pylon-type force transducers 154 (or pylon-type load cells) that are disposed underneath, and near each of the four corners (4) thereof for sensing the load applied to the surface of the force measurement assembly 102'. Also, referring to FIG. 6, it can be seen that the single force plate 102' may comprise a single base plate 162' disposed beneath the four (4) pylon-type force transducers 154.

Referring to FIGS. 2 and 3, the base assembly 106 is preferably provided with a plurality of support feet 126 disposed thereunder. Preferably, each of the four (4) corners of the base assembly 106 is provided with a support foot 126. In one embodiment, each support foot 126 is attached to a bottom surface of base assembly 106. In one preferred embodiment, at least one of the support feet 126 is adjustable so as to facilitate the leveling of the base assembly 106 on an uneven floor surface (e.g., see FIG. 3, the support foot can be provided with a threaded shaft 129 that permits the height thereof to be adjusted). For example, referring to FIG. 2, the right corner of the base assembly 106 may be provided with a removable cover plate 127 for gaining access to an adjustable support foot 126 with threaded shaft 129.

In one exemplary embodiment, with reference to FIG. 2, the base assembly 106 has a length $L_B$ of approximately five feet (5'-0"), a width $W_B$ of approximately five feet (5'-0"), and a step height $H_B$ of approximately four (4) inches. In other words, the base assembly has an approximately 5'-0" by 5'-0" footprint with step height of approximately four (4) inches. In other exemplary embodiments, the base assembly 106 has a width $W_B$ of slightly less than five feet (5'-0"), for example, a width $W_B$ lying in the range between approximately fifty-two (52) inches and approximately fifty-nine (59) inches (or between fifty-two (52) inches and fifty-nine (59) inches). Also, in other exemplary embodiments, the base assembly 106 has a step height lying in the range between approximately four (4) inches and approximately four and one-half (4½) inches (or between four (4) inches and four and one-half (4½) inches). Advantageously, the design of the base assembly 106 is such that its step height is minimized. For example, the placement of the second actuator assembly 160 above the top surface of the base assembly 106 facilitates a reduction in the step height of the base assembly 106. It is highly desirable for the base assembly 106 to have as low a profile as possible. A reduced step height especially makes it easier for subjects having balance disorders to step on and off the base assembly 106. This reduced step height is particularly advantageous for elderly subjects or patients being tested on the force measurement system 100 because it is typically more difficult for elderly subjects to step up and down from elevated surfaces.

Figure 8:
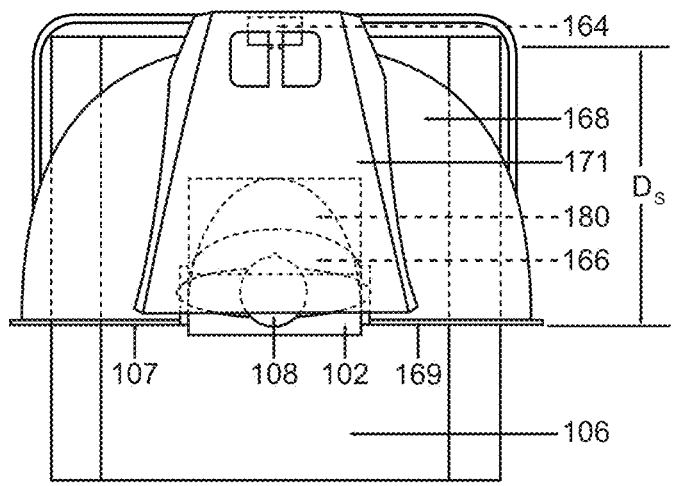
FIG. 8 is a diagrammatic top view of the base assembly and the immersive subject visual display device of the force measurement system according to an embodiment of the invention.
Figure 9:
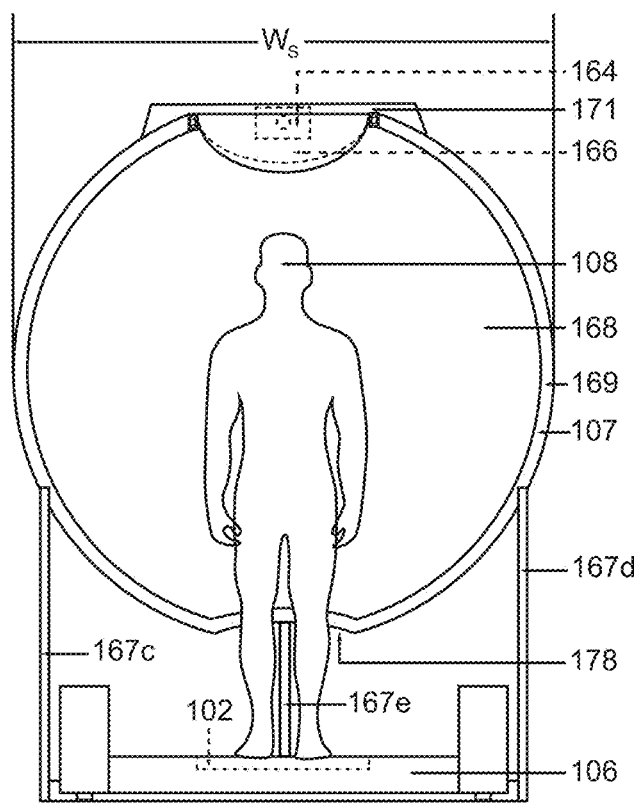
FIG. 9 is a diagrammatic rear view of the base assembly and the immersive subject visual display device of the force measurement system according to an embodiment of the invention.
Figure 10:
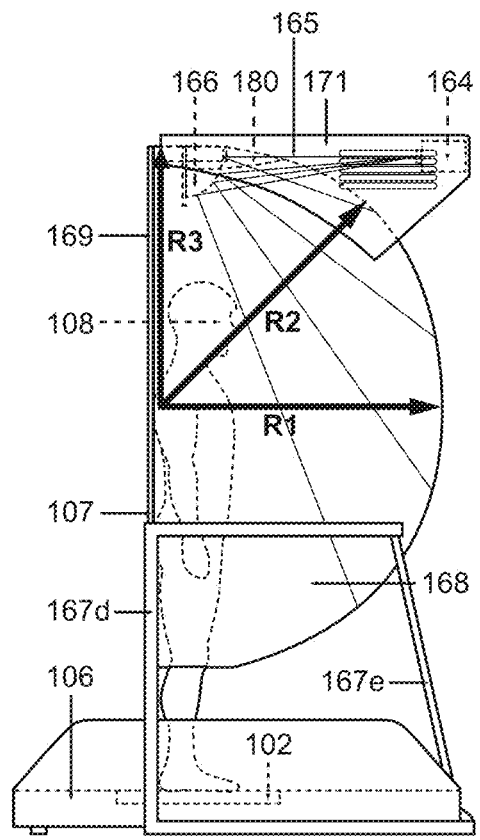
FIG. 10 is a diagrammatic side view of the base assembly and the immersive subject visual display device of the force measurement system according to an embodiment of the invention.

Now, with reference to FIGS. 8-10, the subject visual display device 107 of the force measurement system 100 will be described in more detail. In the illustrated embodiment, the subject visual display device 107 generally comprises a projector 164, a generally spherical mirror 166 (i.e., a convexly curved mirror that has the shape of a piece cut out of a spherical surface), and a generally hemispherical concave projection screen 168 with a variable radius (i.e., the radius of the hemispherical projection screen 168 becomes increasingly larger from its center to its periphery—see radii R1, R2, and R3 in FIG. 10). As shown in FIGS. 8-10, the hemispherical projection screen 168 may be provided with a peripheral flange 169 therearound. The lens of the projector 164 projects an image onto the generally spherical mirror 166 which, in turn, projects the image onto the generally hemispherical projection screen 168 (see FIG. 10). As shown in FIGS. 8 and 10, the top of the generally hemispherical projection screen 168 is provided with a semi-circular cutout 180 for accommodating the projector light beam 165 in the illustrative embodiment. Advantageously, the generally hemispherical projection screen 168 is a continuous curved surface that does not contain any lines or points resulting from the intersection of adjoining planar or curved surfaces. Thus, the projection screen 168 is capable of creating a completely immersive visual environment for a subject being tested on the force measurement assembly 102 because the subject is unable to focus on any particular reference point or line on the screen 168. As such, the subject becomes completely immersed in the virtual reality scene(s) being projected on the generally hemispherical projection screen 168, and thus, his or her visual perception can be effectively altered during a test being performed using the force measurement system 100 (e.g., a balance test). In order to permit a subject to be substantially circumscribed by the generally hemispherical projection screen 168 on three sides, the bottom of the screen 168 is provided with a semi-circular cutout 178 in the illustrative embodiment. While the generally hemispherical projection screen 168 thoroughly immerses the subject 108 in the virtual reality scene(s), it advantageously does not totally enclose the subject 108. Totally enclosing the subject 108 could cause him or her to become extremely claustrophobic. Also, the clinician would be unable to observe the subject or patient in a totally enclosed environment. As such, the illustrated embodiment of the force measurement system 100 does not utilize a totally enclosed environment, such as a closed, rotating shell, etc. Also, as shown in FIGS. 1-3 and 8-10, the subject visual display device 107 is not attached to the subject 108, and it is spaced apart from the force measurement assembly 102 disposed in the base assembly 106.

In one embodiment of the invention, the generally hemispherical projection screen 168 is formed from a suitable material (e.g., an acrylic, fiberglass, fabric, aluminum, etc.) having a matte gray color. A matte gray color is preferable to a white color because it minimizes the unwanted reflections that can result from the use of a projection screen having a concave shape. Also, in an exemplary embodiment, the projection screen 168 has a diameter (i.e., width $W_S$) of approximately 69 inches and a depth $D_S$ of approximately 40 inches (see FIGS. 8 and 9). In other exemplary embodiments, the projection screen 168 has a width $W_S$ lying in the range between approximately sixty-eight (68) inches and approximately ninety-two (92) inches (or between sixty-eight (68) inches and ninety-two (92) inches). For example, including the flange 169, the projection screen 168 could have a width $W_S$ of approximately seventy-three (73) inches. In some embodiments, the target distance between the subject and the front surface of the projection screen 168 can lie within the range between approximately 25 inches and approximately 40 inches (or between 25 inches and 40 inches). Although, those of ordinary skill in the art will readily appreciate that other suitable dimensions and circumscribing geometries may be utilized for the projection screen 168, provided that the selected dimensions and circumscribing geometries for the screen 168 are capable of creating an immersive environment for a subject disposed on the force measurement assembly 102 (i.e., the screen 168 of the subject visual display device engages enough of the subject's peripheral vision such that the subject becomes, and remains immersed in the virtual reality scenario). In one or more embodiments, the projection screen 168 fully encompasses the peripheral vision of the subject 108 (e.g., by the coronal plane CP of the subject being approximately aligned with the flange 169 of the projection screen 168 or by the coronal plane CP being disposed inwardly from the flange 169 within the hemispherical confines of the screen 168). In other words, the output screen 168 of the at least one visual display 107 at least partially circumscribes three sides of a subject 108 (e.g., see FIG. 1). As shown in FIGS. 8-10, a top cover 171 is preferably provided over the projector 164, the mirror 166, and the cutout 180 in the output screen 168 so as to protect these components, and to give the visual display device 107 a more finished appearance.

In a preferred embodiment, the data acquisition/data processing device 104 is configured to convert a two-dimensional (2-D) image, which is configured for display on a conventional two-dimensional screen, into a three-dimensional (3-D) image that is capable of being displayed on the hemispherical output screen 168 without excessive distortion. That is, the data acquisition/data processing device 104 executes a software program that utilizes a projection mapping algorithm to "warp" a flat 2-D rendered projection screen image into a distorted 3-D projection image that approximately matches the curvature of the final projection surface (i.e., the curvature of the hemispherical output screen 168), which takes into account both the distortion of the lens of the projector 164 and any optical surfaces that are used to facilitate the projection (e.g., generally spherical mirror 166). In particular, the projection mapping algorithm utilizes a plurality of virtual cameras and projection surfaces (which are modeled based upon the actual projection surfaces) in order to transform the two-dimensional (2-D) images into the requisite three-dimensional (3-D) images. Thus, the projector 164 lens information, the spherical mirror 166 dimensional data, and the hemispherical projection screen 168 dimensional data are entered as inputs into the projection mapping algorithm software. When a human subject is properly positioned in the confines of the hemispherical output screen 168, he or she will see a representation of the virtual reality scene wrapping around them instead of only seeing a small viewing window in front of him or her. Advantageously, using a software package comprising a projection mapping algorithm enables the system 100 to use previously created 3-D modeled virtual worlds and objects without directly modifying them. Rather, the projection mapping algorithm employed by the software package merely changes the manner in which these 3-D modeled virtual worlds and objects are projected into the subject's viewing area.

Figure 28:
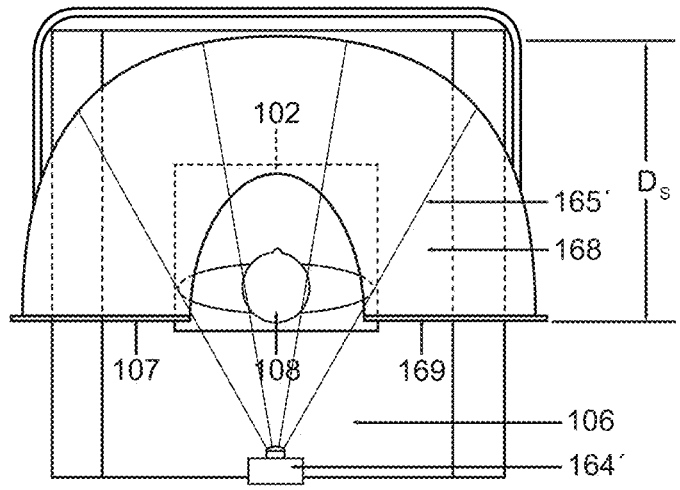
FIG. 28 is a diagrammatic top view of the base assembly and the immersive subject visual display device of the force measurement system according to an alternative embodiment of the invention, wherein a projector with a fisheye lens is disposed in the front of the visual display device and behind the subject.
Figure 29:
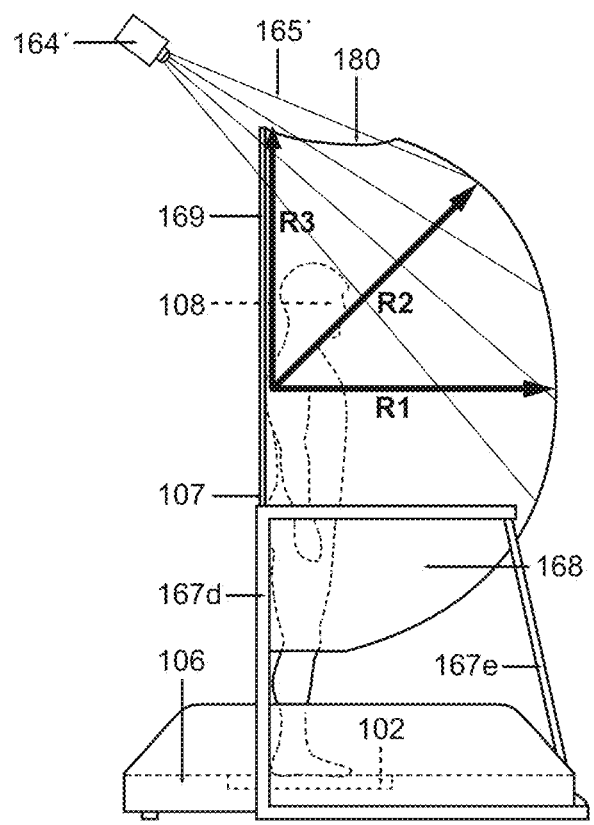
FIG. 29 is a diagrammatic side view of the base assembly and the immersive subject visual display device of the force measurement system according to an alternative embodiment of the invention, wherein the projector with the fisheye lens is disposed in the front of the visual display device and behind the subject.
Figure 30:
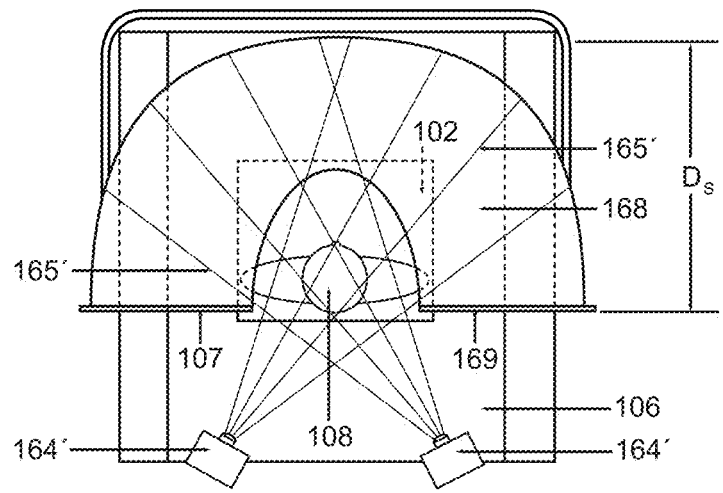
FIG. 30 is a diagrammatic top view of the base assembly and the immersive subject visual display device of the force measurement system according to yet another alternative embodiment of the invention, wherein two projectors with respective fisheye lens are disposed in the front of the visual display device and behind the subject.
Figure 31:
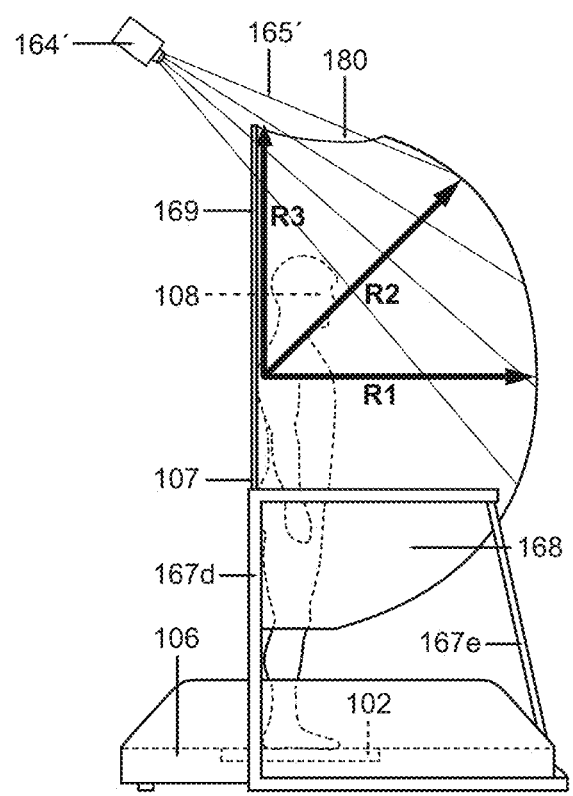
FIG. 31 is a diagrammatic side view of the base assembly and the immersive subject visual display device of the force measurement system according to yet another alternative embodiment of the invention, wherein the two projectors with respective fisheye lens are disposed in the front of the visual display device and behind the subject.

Those of ordinary skill in the art will also appreciate that the subject visual display device 107 may utilize other suitable projection means. For example, rather using an overhead-type projector 164 as illustrated in FIGS. 8-10, a direct or rear projection system can be utilized for projecting the image onto the screen 168, provided that the direct projection system does not interfere with the subject's visibility of the target image. In such a rear or direct projection arrangement, the generally spherical mirror 166 would not be required. With reference to FIGS. 28 and 29, in one exemplary embodiment, a single projector 164' with a fisheye-type lens and no mirror is utilized in the subject visual display system to project an image onto the screen 168 (e.g., the projector 164' is disposed behind the subject 108). As illustrated in these figures, the projector 164' with the fisheye-type lens projects a light beam 165' through the cutout 180 in the top of the generally hemispherical projection screen 168. In another exemplary embodiment, two projectors 164', each having a respective fisheye-type lens, are used to project an image onto the screen 168 (see FIGS. 30 and 31—the projectors 164' are disposed behind the subject 108). As depicted FIGS. 30 and 31, the projectors 164' with the fisheye-type lens project intersecting light beams 165' through the cutout 180 in the top of the generally hemispherical projection screen 168. Advantageously, the use of two projectors 164' with fisheye-type lens, rather than just a single projector 164' with a fisheye lens, has the added benefit of removing shadows that are cast on the output screen 168 by the subject 108 disposed on the force measurement assembly 102.

Figure 44:
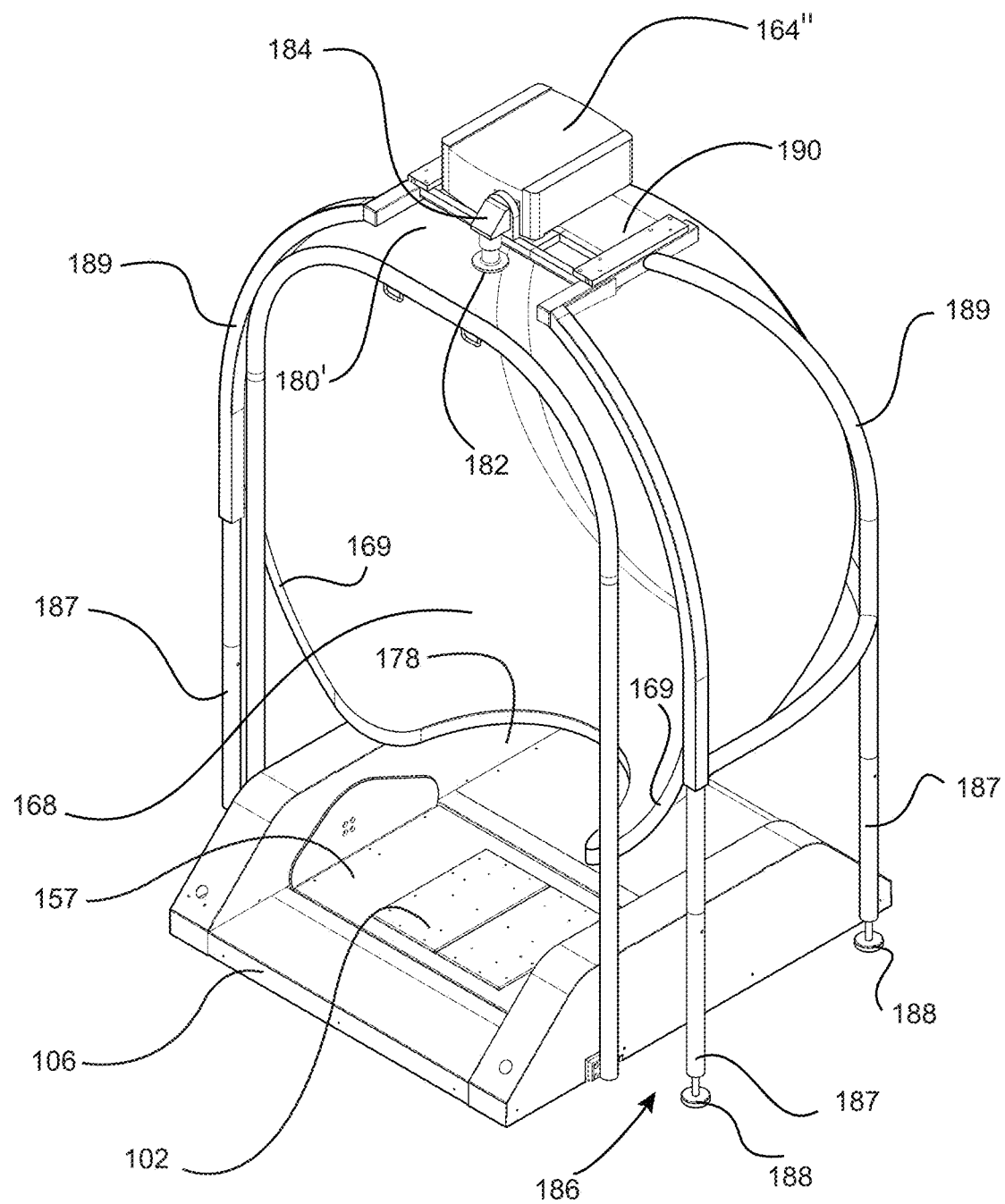
FIG. 44 is a perspective view of the base assembly and the immersive subject visual display device of the force measurement system according to another alternative embodiment of the invention, wherein a projector with an angled fisheye lens is disposed on the top of the visual display device.

Another alternative embodiment of the projector arrangement is illustrated in FIG. 44. As shown in this figure, a projector 164" having a fisheye lens 182 is mounted on the top of the hemispherical projection screen 168. In FIG. 44, it can be seen that the fisheye lens 182 is connected to the body of the projector 164" by an elbow fitting 184. In other words, the fisheye lens 182 is disposed at a non-zero, angled orientation relative to a body of the projector 164". In the illustrated embodiment, the non-zero, angled orientation at which the fisheye lens 182 is disposed relative to the body of the projector 164" is approximately 90 degrees. The elbow fitting 184 comprises a one-way mirror disposed therein for changing the direction of the light beam emanating from the projector 164". As illustrated in FIG. 44, the fisheye lens 182 is disposed at approximately the apex of the hemispherical projection screen 168, and it extends down through the cutout 180' at the top of the screen 168. Because a fisheye lens 182 is utilized in the arrangement of FIG. 44, the generally spherical mirror 166 is not required, similar to that which was described above for the embodiment of FIGS. 28 and 29.

Referring again to FIG. 44, it can be seen that the generally hemispherical projection screen 168 can be supported from a floor surface using a screen support structure 186, which is an alternative design to that which is illustrated in FIGS. 2 and 8-10. As described above for the screen support structure 167, the screen support structure 186 is used to elevate the projection screen 168 a predetermined distance above the floor of a room. With continued reference to FIG. 44, it can be seen that the illustrated screen support structure 186 comprises a plurality of lower leg members 187 (i.e., four (4) leg members 187) that support an upper support cage portion 189, which is disposed around the upper portion of the generally hemispherical projection screen 168. In particular, the upper support cage portion 189 is securely attached to the peripheral flange 169 of the hemispherical projection screen 168 (e.g., by using a plurality of fasteners on each side of the flange 169). Because the upper support cage portion 189 is mostly attached to the upper portion (e.g., upper half) of the screen 168, the screen 168 is generally supported above its center-of-gravity, which advantageously results in a screen mounting arrangement with high structural stability. As shown in FIG. 44, one pair of the plurality of lower leg members 187 are disposed on each of the opposed lateral sides of the screen 168. Also, it can be seen that each of the lower leg members 187 is provided with a height-adjustable foot 188 for adjusting the height of the screen 168 relative to the floor. Also, as shown in FIG. 44, the projector 164" is supported on the top of the screen 168 by a projector support frame 190, which is secured directly to the upper support cage portion 189 of the screen support structure 186 so as to minimize the transmission of vibrations from the projector 164" to the hemispherical projection screen 168. Advantageously, the mounting arrangement of the projector 164" on the projector support frame 190 affords adjustability of the projector 164" in a front-to-back direction. It is highly desirable for the hemispherical projection screen 168 to be maintained in a stationary position essentially free from external vibrations so that the subject is completely immersed in the virtual environment being created within the hemispherical projection screen 168. Advantageously, the structural rigidity afforded by the screen support structure 186 of FIG. 44 virtually eliminates the transmission of vibrations to the projection screen 168, including those vibrations emanating from the building itself in which the force measurement system 100 is located. In particular, the screen support structure 186 is designed to minimize any low frequency vibrations that are transmitted to the screen 168. In addition, the elimination of the generally spherical mirror 166 from the projector arrangement in FIG. 44, minimizes the transmission of visible vibrations to the screen image that is projected onto the hemispherical projection screen 168 by the projector 164".

In one or more embodiments, the base assembly 106 has a width $W_B$ (see e.g., FIG. 2) measured in a direction generally parallel to the coronal plane CP of the subject (see e.g., FIG. 1) and a length $L_B$ (FIG. 2) measured in a direction generally parallel to the sagittal plane SP of the subject (FIG. 1). In these one or more embodiments, a width $W_S$ of the output screen 168 of the at least one visual display device 107 (see FIG. 9) is less than approximately 1.5 times the width $W_B$ of the base assembly 106 (or less than 1.5 times the width $W_B$ of the base assembly 106), and a depth $D_S$ of the output screen 168 of the at least one visual display device 107 (see FIG. 8) is less than the length $L_B$ of the base assembly 106 (FIG. 2). As shown in FIG. 9, in the illustrated embodiment, the width $W_S$ of the output screen 168 of the at least one visual display device 107 is greater than the width $W_B$ of the base assembly 106. In some embodiments, a width $W_S$ of the output screen 168 of the at least one visual display device 107 (see FIG. 9) is greater than approximately 1.3 times the width $W_B$ of the base assembly 106 (or greater than 1.3 times the width $W_B$ of the base assembly 106).

As illustrated in FIGS. 2 and 8-10, the generally hemispherical projection screen 168 can be supported from a floor surface using a screen support structure 167. In other words, the screen support structure 167 is used to elevate the projection screen 168 a predetermined distance above the floor of a room. With continued reference to FIGS. 2 and 8-10, it can be seen that the illustrated screen support structure 167 comprises a lower generally U-shaped member 167a, an upper generally U-shaped member 167b, and a plurality of vertical members 167c, 167d, 167e. As best shown in FIGS. 2, 9, and 10, the two vertical members 167c, 167d are disposed on opposite sides of the screen 168, while the third vertical member 167e is disposed generally in the middle of, and generally behind, the screen 168. The screen support structure 167 maintains the projection screen 168 in a stationary position. As such, the position of the projection screen 168 is generally fixed relative to the base assembly 106. In the side view of FIG. 10, it can be seen that the rearmost curved edge of the projection screen 168 is generally aligned with the back edge of the base assembly 106.

Next, referring again to FIG. 1, the operator visual display device 130 of the force measurement system 100 will be described in more particularity. In the illustrated embodiment, the operator visual display device 130 is in the form of a flat panel monitor. Those of ordinary skill in the art will readily appreciate that various types of flat panel monitors having various types of data transmission cables 140 may be used to operatively couple the operator visual display device 130 to the data acquisition/data processing device 104. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the visual display device 130 can be operatively coupled to the data acquisition/data processing device 104 using wireless data transmission means. Electrical power is supplied to the visual display device 130 using a separate power cord that connects to a building wall receptacle.

Also, as shown in FIG. 1, the subject visual display device 107 is operatively coupled to the data acquisition/data processing device 104 by means of a data transmission cable 120. More particularly, the projector 164 of the subject visual display device 107 is operatively connected to the data acquisition/data processing device 104 via the data transmission cable 120. Like the data transmission cable 140 described above for the operator visual display device 130, various types of data transmission cables 120 can be used to operatively connect the subject visual display device 107 to the data acquisition/data processing device 104 (e.g., the various types described above).

Those of ordinary skill in the art will appreciate that the visual display device 130 can be embodied in various forms. For example, if the visual display device 130 is in the form of flat screen monitor as illustrated in FIG. 1, it may comprise a liquid crystal display (i.e., an LCD display), a light-emitting diode display (i.e., an LED display), a plasma display, a projection-type display, or a rear projection-type display. The operator visual display device 130 may also be in the form of a touch pad display. For example, the operator visual display device 130 may comprise multi-touch technology which recognizes two or more contact points simultaneously on the surface of the screen so as to enable users of the device to use two fingers for zooming in/out, rotation, and a two finger tap.

Figure 11:
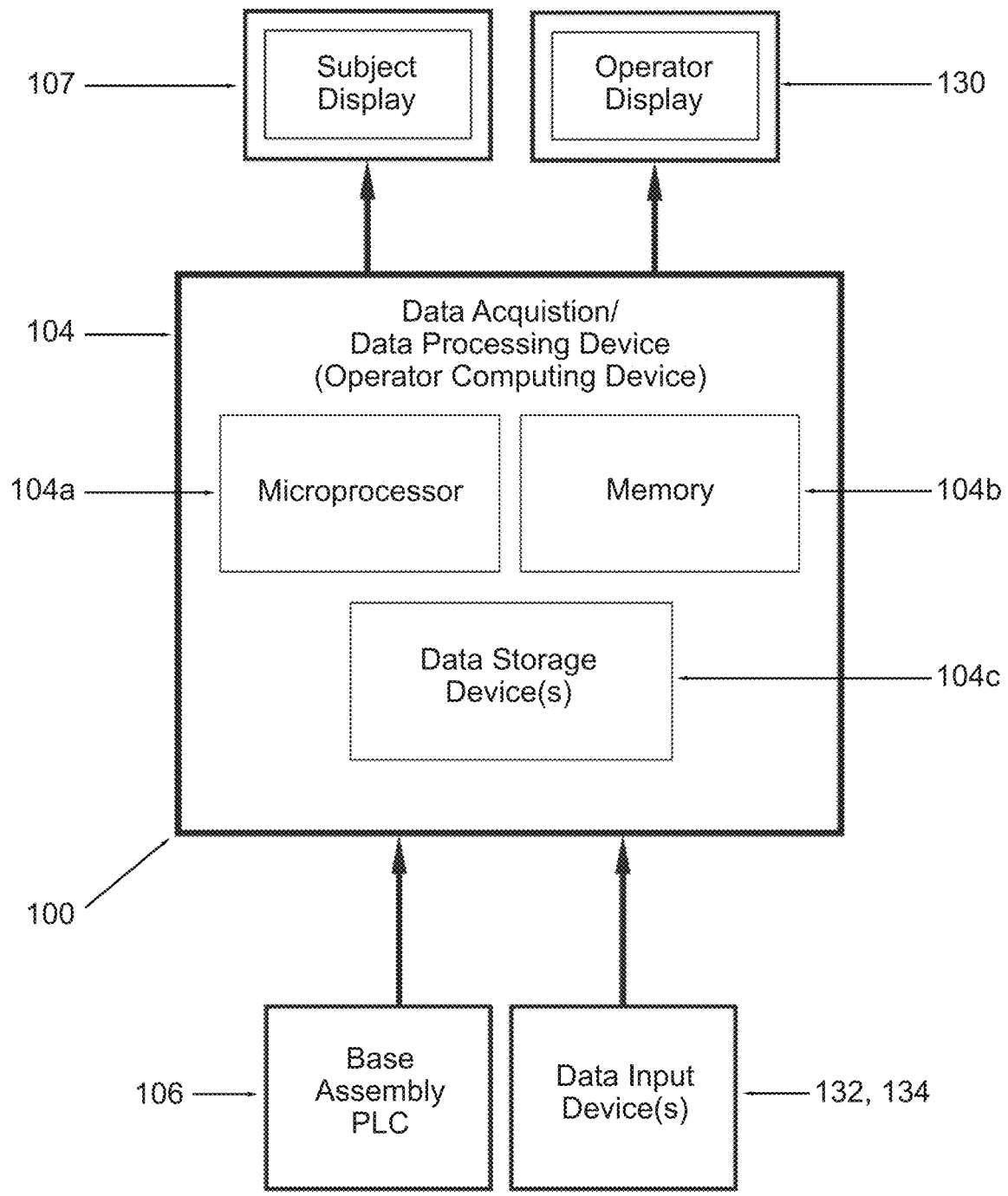
FIG. 11 is a block diagram of constituent components of the force measurement system having a displaceable force measurement assembly, according to an embodiment of the invention.

Now, turning to FIG. 11, it can be seen that the illustrated data acquisition/data processing device 104 (i.e., the operator computing device) of the force measurement system 100 includes a microprocessor 104a for processing data, memory 104b (e.g., random access memory or RAM) for storing data during the processing thereof, and data storage device(s) 104c, such as one or more hard drives, compact disk drives, floppy disk drives, flash drives, or any combination thereof. As shown in FIG. 11, the programmable logic controller (PLC) of the base assembly 106, the subject visual display device 107, and the operator visual display device 130 are operatively coupled to the data acquisition/data processing device 104 such that data is capable of being transferred between these devices 104, 106, 107, and 130. Also, as illustrated in FIG. 11, a plurality of data input devices 132, 134 such as the keyboard 132 and mouse 134 shown in FIG. 1, are operatively coupled to the data acquisition/data processing device 104 so that a user is able to enter data into the data acquisition/data processing device 104. In some embodiments, the data acquisition/data processing device 104 can be in the form of a desktop computer, while in other embodiments, the data acquisition/data processing device 104 can be embodied as a laptop computer.

Advantageously, the programmable logic controller 172 of the base assembly 106 (see e.g., FIGS. 12 and 13, which is a type of data processing device) provides real-time control of the actuator assemblies 158, 160 that displace the force measurement assembly 102 (i.e, force plate assembly 102). The real-time control provided by the programmable logic controller 172 ensures that the motion control software regulating the displacement of the force plate assembly 102 operates at the design clock rate, thereby providing fail-safe operation for subject safety. In one embodiment, the programmable logic controller 172 comprises both the motion control software and the input/output management software, which controls the functionality of the input/output (I/O) module of the programmable logic controller 172. In one embodiment, the programmable logic controller 172 utilizes EtherCAT protocol for enhanced speed capabilities and real-time control.

In one or more embodiments, the input/output (I/O) module of the programmable logic controller 172 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 172. As another example, a head movement tracking system, which is instrumented with one or more accelerometers, could be operatively connected to the input/output (I/O) module.

Figure 12:
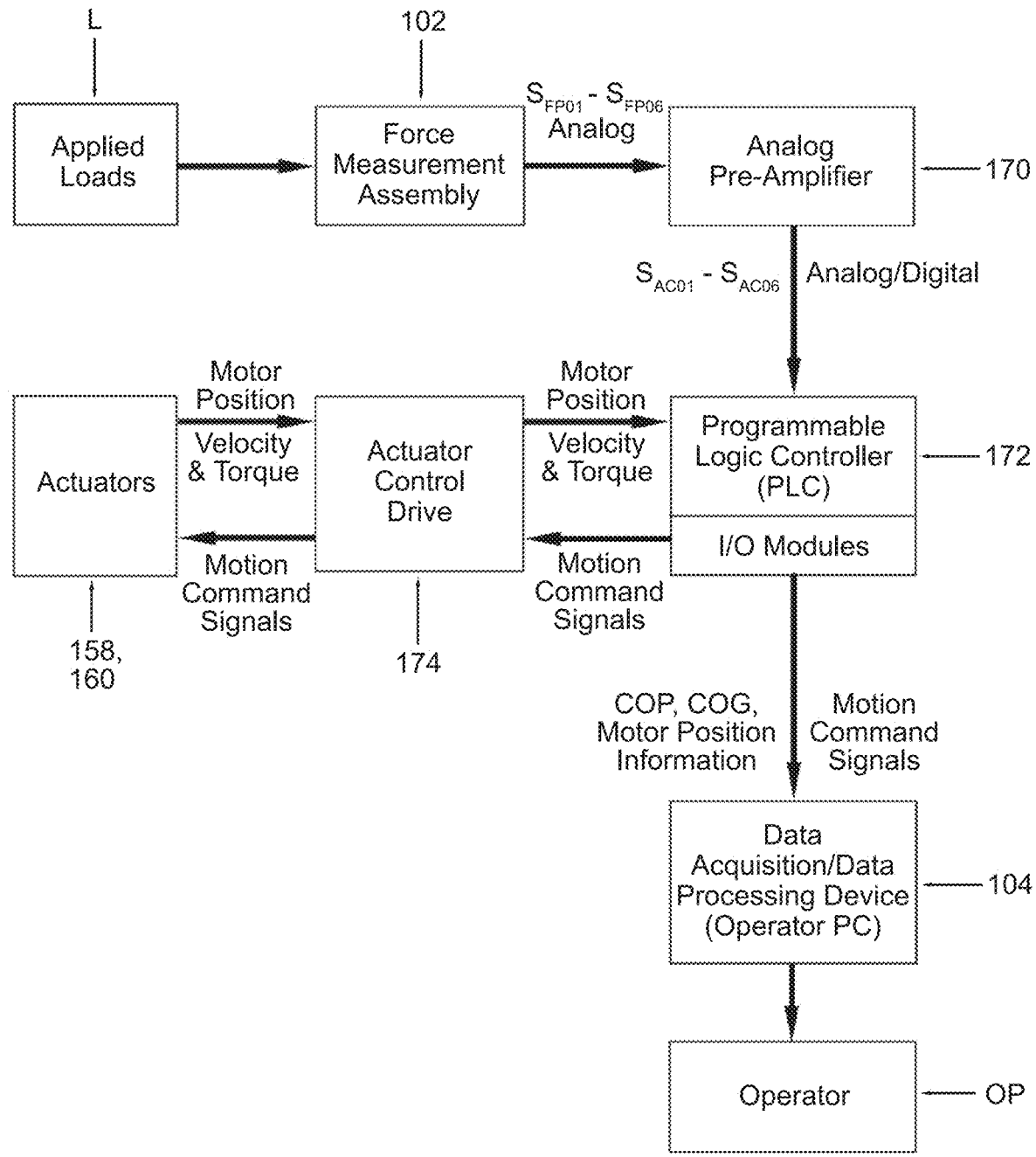
FIG. 12 is a block diagram illustrating data manipulation operations and motion control operations carried out by the force measurement system, according to an embodiment of the invention.

FIG. 12 graphically illustrates the acquisition and processing of the load data and the control of the actuator assemblies 158, 160 carried out by the exemplary force measurement system 100. Initially, as shown in FIG. 12, a load L is applied to the force measurement assembly 102 by a subject disposed thereon. The load is transmitted from the first and second plate components 110, 112 to its respective set of pylon-type force transducers or force transducer beams. As described above, in one embodiment of the invention, each plate component 110, 112 comprises four (4) pylon-type force transducers 154 disposed thereunder. Preferably, these pylon-type force transducers 154 are disposed near respective corners of each plate component 110, 112. In a preferred embodiment of the invention, each of the pylon-type force transducers includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the first and second plate components 110, 112. For each plurality of strain gages disposed on the pylon-type force transducers, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 154 disposed under each plate component 110, 112 output a total of three (3) analog output voltages (signals). In some embodiments, the three (3) analog output voltages from each plate component 110, 112 are then transmitted to an analog preamplifier board 170 in the base assembly 106 for pre-conditioning (i.e., signals $S_{FPO1}$-$S_{FPO6}$ in FIG. 12). The preamplifier board is used to increase the magnitudes of the transducer analog output voltages. After which, the analog force plate output signals $S_{APO1}$-$S_{APO6}$ are transmitted from the analog preamplifier 170 to the programmable logic controller (PLC) 172 of the base assembly 106. In the programmable logic controller (PLC) 172, analog force plate output signals $S_{APO1}$-$S_{APO6}$ are converted into forces, moments, centers of pressure (COP), and/or a center of gravity (COG) for the subject. Then, the forces, moments, centers of pressure (COP), subject center of gravity (COG), and/or sway angle for the subject computed by the programmable logic controller 172 are transmitted to the data acquisition/data processing device 104 (operator computing device 104) so that they can be utilized in reports displayed to an operator OP. Also, in yet another embodiment, the preamplifier board 170 additionally could be used to convert the analog voltage signals into digital voltage signals (i.e., the preamplifier board 170 could be provided with an analog-to-digital converter). In this embodiment, digital voltage signals would be transmitted to the programmable logic controller (PLC) 172 rather than analog voltage signals.

Figure 5:
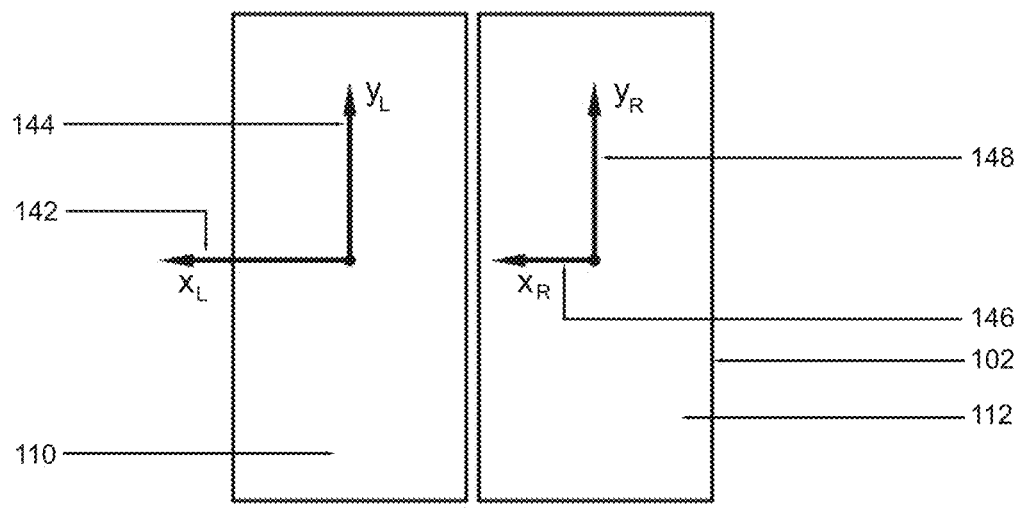
FIG. 5 is a diagrammatic top view of one force measurement assembly used in the force measurement system with exemplary coordinate axes superimposed thereon, according to an embodiment of the invention, wherein the force measurement assembly is in the form of a dual force plate.

When the programmable logic controller 172 receives the voltage signals $S_{ACO1}$-$S_{ACO6}$, it initially transforms the signals into output forces and/or moments by multiplying the voltage signals $S_{ACO1}$-$S_{ACO6}$ by a calibration matrix (e.g., $F_{Lz}$, $M_{Lx}$, $M_{Ly}$, $F_{Rz}$, $M_{Rx}$, $M_{Ry}$). After which, the the center of pressure for each foot of the subject (i.e., the x and y coordinates of the point of application of the force applied to the measurement surface by each foot) are determined by the programmable logic controller 172. Referring to FIG. 5, which depicts a top view of the measurement assembly 102, it can be seen that the center of pressure coordinates ($x_{P_L}$, $y_{P_L}$) for the first plate component 110 are determined in accordance with x and y coordinate axes 142, 144. Similarly, the center of pressure coordinates ($x_{P_R}$, $y_{P_R}$) for the second plate component 112 are determined in accordance with x and y coordinate axes 146, 148. If the force transducer technology described in U.S. Pat. No. 8,544,347 is employed, it is to be understood that the center of pressure coordinates ($x_{P_L}$, $y_{P_L}$, $x_{P_R}$, $x_{P_R}$) can be computed in the particular manner described in that application.

Figure 7:
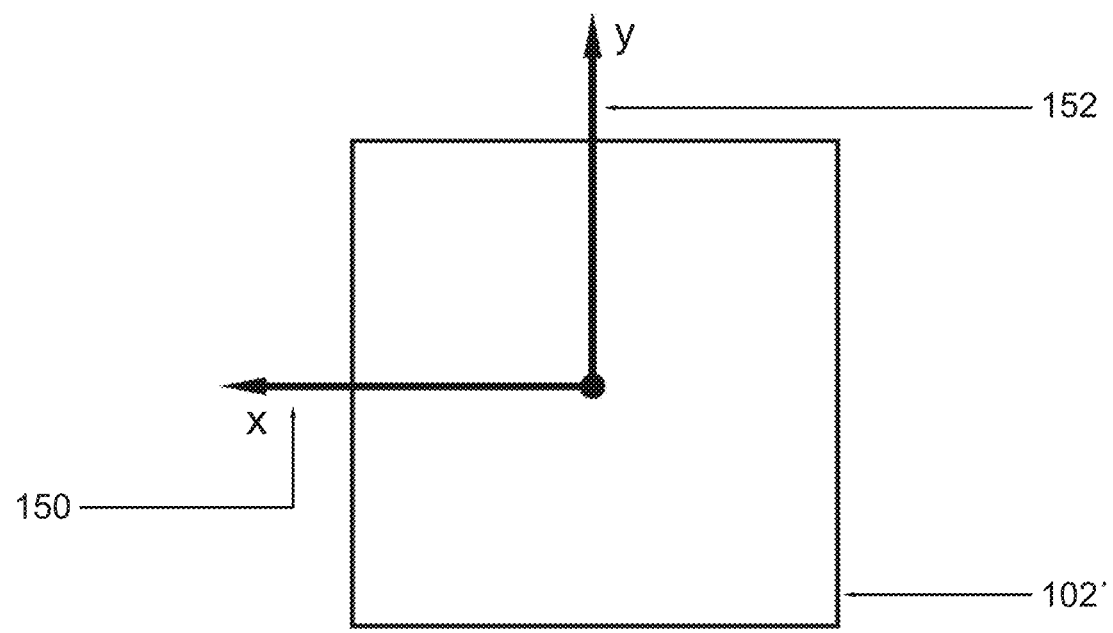
FIG. 7 is a diagrammatic top view of another force measurement assembly used in the force measurement system with exemplary coordinate axes superimposed thereon, according to an embodiment of the invention, wherein the force measurement assembly is in the form of a single force plate.

As explained above, rather than using a measurement assembly 102 having first and second plate components 110, 112, a force measurement assembly 102' in the form of a single force plate may be employed (see FIGS. 6 and 7, which illustrate a single force plate). As discussed hereinbefore, the single force plate comprises a single measurement surface on which both of a subject's feet are placed during testing. As such, rather than computing two sets of center of pressure coordinates (i.e., one for each foot of the subject), the embodiments employing the single force plate compute a single set of overall center of pressure coordinates ($x_P$, $y_P$) in accordance with x and y coordinate axes 150, 152.

In one exemplary embodiment, the programmable logic controller 172 in the base assembly 106 determines the vertical forces $F_{Lz}$, $F_{Rz}$ exerted on the surface of the first and second force plates by the feet of the subject and the center of pressure for each foot of the subject, while in another exemplary embodiment, the output forces of the data acquisition/data processing device 104 include all three (3) orthogonal components of the resultant forces acting on the two plate components 110, 112 (i.e., $F_{Lx}$, $F_{Ly}$, $F_{Lz}$, $F_{Rx}$, $F_{Ry}$, $F_{Rz}$) and all three (3) orthogonal components of the moments acting on the two plate components 110, 112 (i.e., $M_{Lx}$, $M_{Ly}$, $M_{Lz}$, $M_{Rx}$, $M_{Ry}$, $M_{Rz}$). In yet other embodiments of the invention, the output forces and moments of the data acquisition/data processing device 104 can be in the form of other forces and moments as well.

In the illustrated embodiment, the programmable logic controller 172 converts the computed center of pressure (COP) to a center of gravity (COG) for the subject using a Butterworth filter. For example, in one exemplary, non-limiting embodiment, a second-order Butterworth filter with a 0.75 Hz cutoff frequency is used. In addition, the programmable logic controller 172 also computes a sway angle for the subject using a corrected center of gravity (COG') value, wherein the center of gravity (COG) value is corrected to accommodate for the offset position of the subject relative to the origin of the coordinate axes (142, 144, 146, 148) of the force plate assembly 102. For example, the programmable logic controller 172 computes the sway angle for the subject in the following manner:

$$\theta = \sin^{-1}\left(\frac{COG'}{0.55h}\right) - 2.3° \quad (1)$$

where:
  θ: sway angle of the subject;
  COG': corrected center of gravity of the subject; and
  h: height of the center of gravity of the subject.

Now, referring again to the block diagram of FIG. 12, the manner in which the motion of the force measurement assembly 102 is controlled will be explained. Initially, an operator OP inputs one or more motion commands at the operator computing device 104 (data acquisition/data processing device 104) by utilizing one of the user input devices 132, 134. Once, the one or more motion commands are processed by the operator computing device 104, the motion command signals are transmitted to the programmable logic controller 172. Then, after further processing by the programmable logic controller 172, the motion command signals are transmitted to the actuator control drive 174. Finally, the actuator control drive 174 transmits the direct-current (DC) motion command signals to the first and second actuator assemblies 158, 160 so that the force measurement assembly 102, and the subject disposed thereon, can be displaced in the desired manner. The actuator control drive 174 controls the position, velocity, and torque of each actuator motor.

In order to accurately control the motion of the force measurement assembly 102, a closed-loop feedback control routine may be utilized by the force measurement system 100. As shown in FIG. 12, the actuator control drive 174 receives the position, velocity, and torque of each actuator motor from the encoders provided as part of each actuator assembly 158, 160. Then, from the actuator control drive 174, the position, velocity, and torque of each actuator motor is transmitted to the programmable logic controller 172, wherein the feedback control of the first and second actuator assemblies 158, 160 is carried out. In addition, as illustrated in FIG. 12, the position, velocity, and torque of each actuator motor is transmitted from the programmable logic controller 172 to the operator computing device 104 so that it is capable of being used to characterize the movement of the subject on the force measurement assembly 102 (e.g., the motor positional data and/or torque can be used to compute the sway of the subject). Also, the rotational and translational positional data that is received from first and second actuator assemblies 158, 160 can be transmitted to the operator computing device 104.

Next, the electrical single-line diagram of FIG. 13, which schematically illustrates the power distribution system for the base assembly 106, will be explained. As shown in this figure, the building power supply is electrically coupled to an isolation transformer 176 (also refer to FIG. 3). In one exemplary embodiment, the isolation transformer 176 is a medical-grade isolation transformer that isolates the electrical system of the base assembly 106 from the building electrical system. The isolation transformer 176 greatly minimizes any leakage currents from the building electrical system, which could pose a potential safety hazard to a subject standing on the metallic base assembly 106. The primary winding of the isolation transformer 176 is electrically coupled to the building electrical system, whereas the secondary winding of isolation transformer 176 is electrically coupled to the programmable logic controller 172 (as schematically illustrated in FIG. 13).

Referring again to FIG. 13, it can be seen that the programmable logic controller 172 is electrically coupled to the actuator control drive 174 via an emergency stop (E-stop) switch 138. As explained above, in one embodiment, the emergency stop switch 138 is in the form of a red pushbutton that can be easily pressed by a user of the force measurement system 100 (e.g., a subject on the force measurement assembly 102 or an operator) in order to quasi-instantaneously stop the displacement of the force measurement assembly 102. Because the emergency stop switch 138 is designed to fail open, the emergency stop switch 138 is a fail-safe means of aborting the operations (e.g., the software operations) performed by the programmable logic controller 172. Thus, even if the programmable logic controller 172 fails, the emergency stop switch 138 will not fail, thereby cutting the power to the actuator control drive 174 so that the force measurement assembly 102 remains stationary (i.e., the brakes on the actuator assemblies 158, 160 will engage, and thus, prevent any intentional movement thereof). Also, in one embodiment, the emergency stop switch assembly 138 includes a reset button for re-enabling the operation of the actuator control drive 174 after it is has been shut down by the emergency stop switch.

Figure 13:
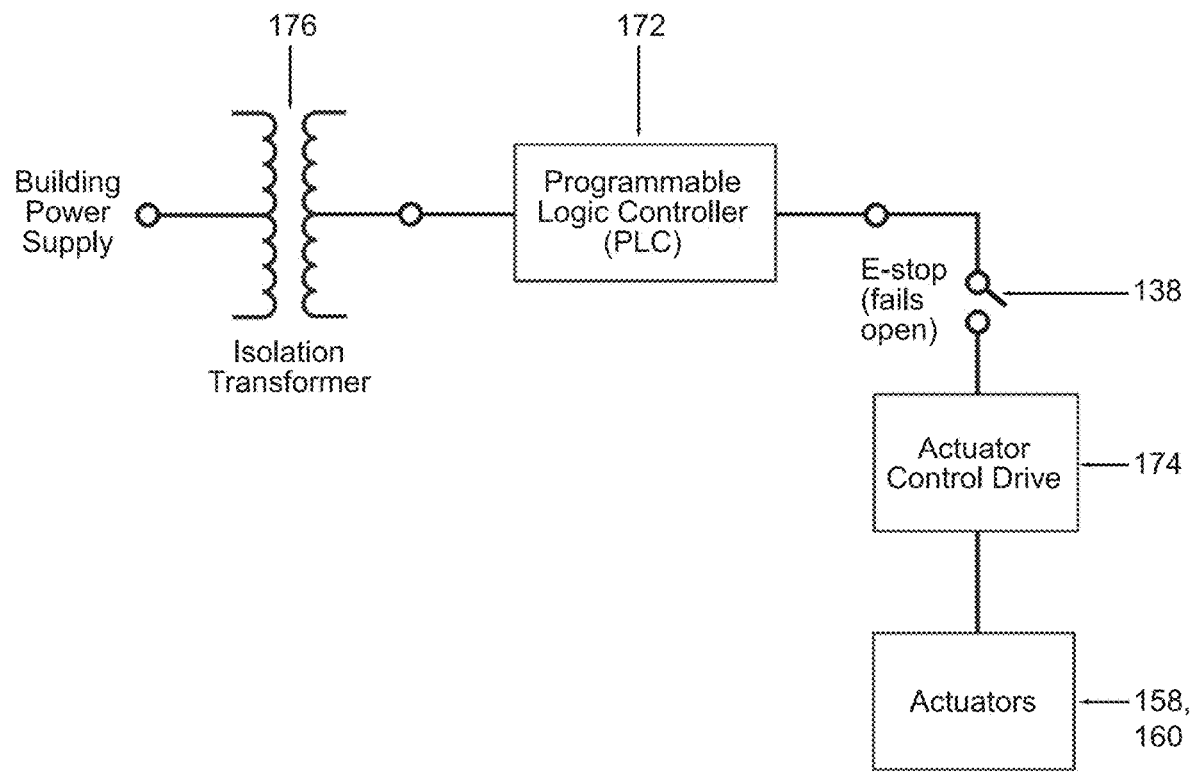
FIG. 13 is a single-line diagram of the base assembly electrical power system, according to an embodiment of the invention.

As shown in FIG. 13, the first and second actuator assemblies 158, 160 are powered by the actuator control drive 174. While not explicitly shown in FIG. 13, the electrical system of the base assembly 106 may further include a power entry module that includes a circuit breaker (e.g., a 20 A circuit breaker) and a filter. Also, the electrical system of the base assembly 106 may additionally include an electromagnetic interference (EMI) filter that reduces electrical noise so as to meet the requirements of the Federal Communications Commission (FCC).

Now, specific functionality of the immersive virtual reality environment of the force measurement system 100 will be described in detail. It is to be understood that the aforedescribed functionality of the immersive virtual reality environment of the force measurement system 100 can be carried out by the data acquisition/data processing device 104 (i.e., the operator computing device) utilizing software, hardware, or a combination of both hardware and software. For example, the data acquisition/data processing device 104 can be specially programmed to carry out the functionality described hereinafter. In one embodiment of the invention, the computer program instructions necessary to carry out this functionality may be loaded directly onto an internal data storage device 104c of the data acquisition/data processing device 104 (e.g., on a hard drive thereof) and subsequently executed by the microprocessor 104a of the data acquisition/data processing device 104. Alternatively, these computer program instructions could be stored on a portable computer-readable medium (e.g., a flash drive, a floppy disk, a compact disk, etc.), and then subsequently loaded onto the data acquisition/data processing device 104 such that the instructions can be executed thereby. In one embodiment, these computer program instructions are embodied in the form of a virtual reality software program executed by the data acquisition/data processing device 104. In other embodiments, these computer program instructions could be embodied in the hardware of the data acquisition/data processing device 104, rather than in the software thereof. It is also possible for the computer program instructions to be embodied in a combination of both the hardware and the software.

Figure 52:
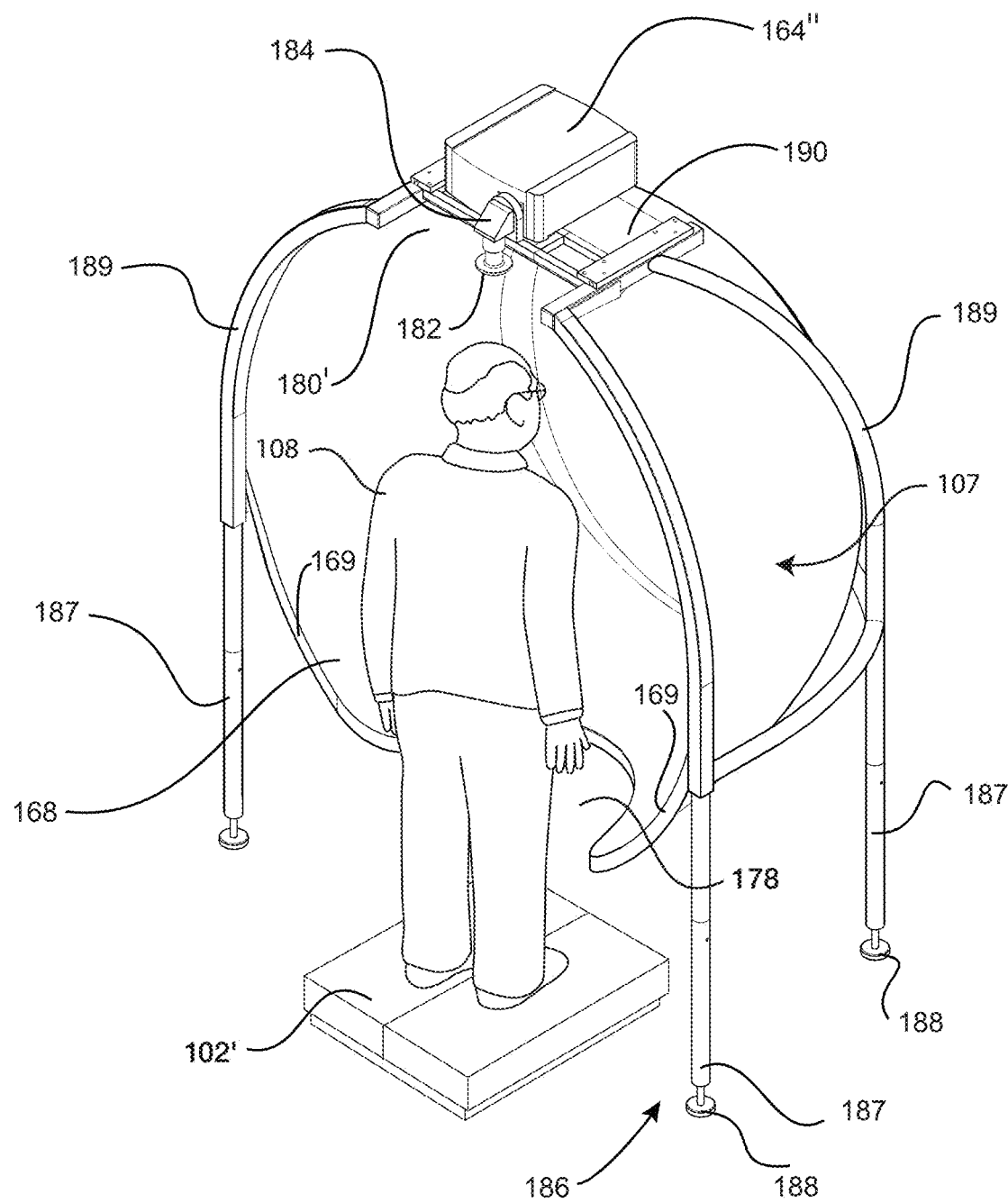
FIG. 52 is a perspective view of a subject disposed on a static force measurement assembly and positioned within an immersive subject visual display device, according to yet another alternative embodiment of the invention.

In alternative embodiments of the invention, a force measurement assembly 102 in the form of a static force plate (i.e., the force plate surface is stationary and is not displaced relative to the floor or ground) can be used with the immersive virtual reality environment described herein. Such a static force plate does not have any actuators or other devices that translate or rotate the force measurement surface(s) thereof. For example, as shown in FIG. 52, the static force plate 102' is disposed beneath the semi-circular cutout 178 of the generally hemispherical projection screen 168 of the visual display device 107. As depicted in FIG. 52, the static force plate 102' is vertically aligned with the semi-circular cutout 178 in the bottom portion of the generally hemispherical projection screen 168 (i.e., when a subject 108 stands on the static force plate 102', his or her legs pass through the semi-circular cutout 178 in the bottom portion of the generally hemispherical projection screen 168 so that he or she is able to become fully immersed in the simulated environment created by the scenes displayed on the screen 168). As described in detail hereinafter, the data acquisition/data processing device of the force measurement system illustrated in FIG. 52 may be programmed to perturb the visual input of the subject 108 during the performance of a balance test or training routine by manipulating the scenes on the output screen 168 of the visual display device 107. During the performance of the balance test or training routine while the subject is disposed on the static force plate 102', the data acquisition/data processing device may be further programmed to utilize the output forces and/or moments computed from the output data of the static force plate 102' in order to assess a response of the subject to the visual stimuli on the generally hemispherical projection screen 168 of the visual display device 107. For example, to assess the response of the subject 108 during the performance of the balance test or training routine, the output forces and/or moments determined using the static force plate 102' may be used to determine any of the scores or parameters (i)-(viii) described below in conjunction with the embodiment illustrated in FIG. 53.

As described above, in one or more embodiments of the invention, one or more virtual reality scenes are projected on the generally hemispherical projection screen 168 of the subject visual display device 107 so that the visual perception of a subject can be effectively altered during a test being performed using the force measurement system 100 (e.g., a balance test). In order to illustrate the principles of the invention, the immersive virtual reality environment of the force measurement system 100 will be described in conjunction with an exemplary balance assessment protocol, namely the Sensory Organization Test ("SOT"). Although, those of ordinary skill in the art will readily appreciate that the immersive virtual reality environment of the force measurement system 100 can be utilized with various other assessment protocols as well. For example, the force measurement system 100 could also include protocols, such as the Center of Gravity ("COG") Alignment test, the Adaptation Test ("ADT"), the Limits of Stability ("LOS") test, the Weight Bearing Squat test, the Rhythmic Weight Shift test, and the Unilateral Stance test. In addition, the immersive virtual reality environment and the displaceable force measurement assembly 102 of the force measurement system 100 can be used with various forms of training, such as closed chain training, mobility training, quick training, seated training, and weight shifting training. These training categories have customizable training options, including a variety of scenes that create immersivity. A brief description of each of these five categories of training will be provided hereinafter.

Closed chain training requires users to specify hip, knee, ankle, or lower back for target training. The training exercises associated with closed chain training are designed to gradually increase the amount of flexibility and to increase the overall amount of difficulty.

Mobility training starts with elements from seated training and progresses up through a full stepping motion. One goal of this training series is to help a patient coordinate the sit to stand movement and to help the patient regain control of normal activities of daily living.

Quick Training is designed to meet the basic needs of training in a quick and easy to set up interface. A variety of different trainings can be chosen that range from simple stand still with the cursor in the center target to FIG. 8 motions. In the illustrative embodiment, a variety of different scenes may be used when performing Quick Training (e.g., the fountain scene 1030 of FIG. 71 and the airport lounge scene 1050 of FIG. 72 may be used when performing Quick Training). In the fountain scene 1030 of FIG. 71, there is motion at the center of the scene 1030 with water flowing, unrelated to any movement of the subject. Additionally, the airport lounge scene 1050 of FIG. 72 incorporates horizontal and vertical lines to enhance the subject's perception of depth within the scene 1050 and provide cues for motion.

Seated training is performed while in a seated position. Seated training is typically performed using a twelve (12) inch block as a base together with a four (4) inch block, a foam block, or a rocker board placed on top of the twelve (12) inch block. These training exercises help a subject or patient begin to explore their base of support as well as coordinate core stability.

Weight shifting training involves leaning or moving in four different directions: forward, backward, left, or right. Combined with movements on top of different surfaces, the goal of the weight shifting training is to get people more comfortable with moving beyond their comfort levels through challenging them to hit targets placed close together initially, and then moving them outward toward their theoretical limits.

Figure 22:
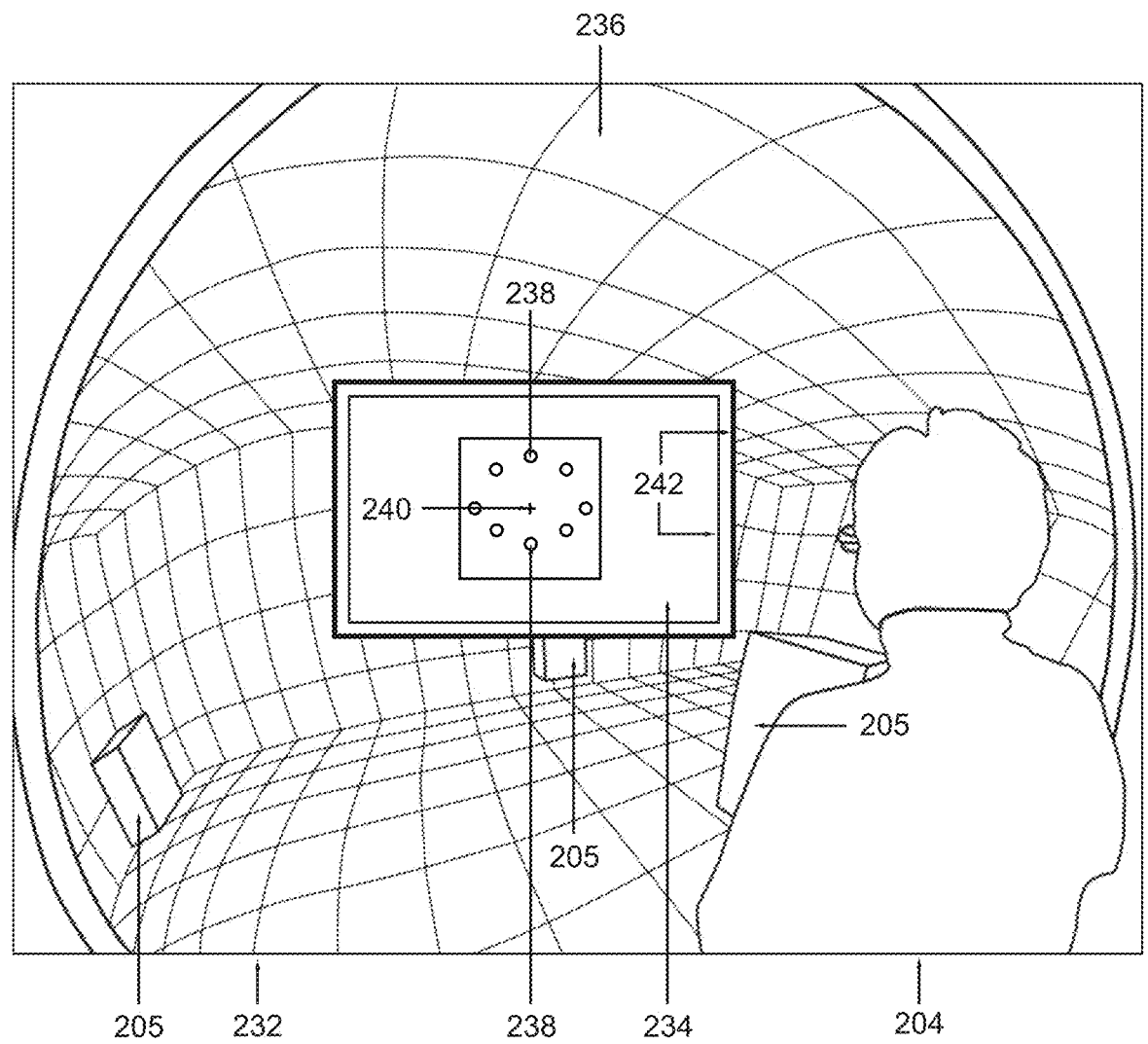
FIG. 22 is a first variation of a training screen image displayed on the subject visual display device of the force measurement system, according to an embodiment of the invention.

In general, each training protocol may utilize a series of targets or markers that are displayed on the screen 168 of the subject visual display device 107. The goal of the training is for the subject or patient 108 to move a displaceable visual indicator (e.g., a cursor) into the stationary targets or markers that are displayed on the screen 168. For example, as shown in the screen image 232 of FIG. 22, the output screen 168 of the subject visual display device 107 may be divided into a first, inner screen portion 234, which comprises instructional information for a subject 204 performing a particular test or training protocol, and a second outer screen portion 236, which comprises a displaceable background or one or more virtual reality scenes that are configured to create a simulated environment for the subject 204. As shown in FIG. 22, a plurality of targets or markers 238 (e.g., in the form of circles) are displayed on the first, inner screen portion 234. In addition, a displaceable visual indicator or cursor 240 is also displayed on the first, inner screen portion 234. The data acquisition/data processing device 104 controls the movement of the visual indicator 240 towards the plurality of stationary targets or markers 238 by using the one or more computed numerical values determined from the output signals of the force transducers associated with the force measurement assembly 102. In the illustrated embodiment, the first, inner screen portion 234 is provided with a plain white background.

In an illustrative embodiment, the one or more numerical values determined from the output signals of the force transducers associated with the force measurement assembly 102, 102' comprise the center of pressure coordinates ($x_P$, $y_P$) computed from the ground reaction forces exerted on the force plate assembly 102 by the subject. For example, with reference to the force plate coordinate axes 150, 152 of FIG. 7, when a subject leans to the left on the force measurement assembly 102' (i.e., when the x-coordinate $x_P$ of the center of pressure is positive), the cursor 240 displayed on the inner screen portion 234 is displaced to the left. Conversely, when a subject leans to the right on the force measurement assembly 102' (i.e., when the x-coordinate $x_P$ of the center of pressure is negative in FIG. 7), the cursor 240 on the inner screen portion 234 is displaced to the right. When a subject leans forward on the force measurement assembly 102' (i.e., when the y-coordinate $y_P$ of the center of pressure is positive in FIG. 7), the cursor 240 displayed on the inner screen portion 234 is upwardly displaced on the inner screen portion 234. Conversely, when a subject leans backward on the force measurement assembly 102' (i.e., when the y-coordinate $y_P$ of the center of pressure is negative in FIG. 7), the cursor 240 displayed on the inner screen portion 234 is downwardly displaced on the inner screen portion 234. In the training scenario illustrated in FIG. 22, the subject 204 may be instructed to move the cursor 240 towards each of the plurality of targets or markers 238 in succession. For example, the subject 204, may be instructed to move the cursor 240 towards successive targets 238 in a clockwise fashion (e.g., beginning with the topmost target 238 on the first, inner screen portion 234).

As illustrated in FIG. 22, a virtual reality scenario is displayed on the second outer screen portion 236 of the output screen 168 of the subject visual display device 107. The virtual reality scenario in FIG. 22 comprises a three-dimensional checkerboard room. As shown in FIG. 22, the three-dimensional checkerboard room comprises a plurality of three-dimensional boxes or blocks 205 in order to give the subject 204 a frame of reference for perceiving the depth of the room (i.e., the boxes or blocks 205 enhance the depth perception of the subject 204 with regard to the virtual room). In one or more embodiments, the data acquisition/data processing device 104 is configured to generate a motion profile for the selective displacement of the virtual reality scenario. The data acquisition/data processing device 104 may generate the motion profile for the virtual reality scenario (e.g., the three-dimensional checkerboard room) in accordance with any one of: (i) a movement of the subject on the force measurement assembly (e.g., by using the center of pressure coordinates ($x_P$, $y_P$)), (ii) a displacement of the force measurement assembly 102 by one or more actuators (e.g., by using the motor positional data and/or torque from the first and second actuator assemblies 158, 160), and (iii) a predetermined velocity set by a system user (e.g., the virtual reality scenario may be displaced inwardly at a predetermined velocity, such as 5 meters per second). In an alternative embodiment, the subject could be instructed to adapt to a pseudorandom movement of the displaceable force measurement assembly 102 and/or the pseudorandom movement of the virtual reality scenario. Displacing the virtual reality scene inwardly on the visual display device 107 inhibits the sensory ability, namely the visual flow, of the subject by creating artificial visual inputs from which he or she must differentiate from his or her actual surroundings.

In other embodiments, rather than comprising a virtual reality scenario, the second outer screen portion 236 of the output screen 168 may comprise a displaceable background (e.g., a background comprising a plurality of dots). For either the virtual reality scenario or the displacement background, the data acquisition/data processing device 104 is configured to displace the image displayed on the outer screen portion 236 using a plurality of different motion profiles. For example, when a displaceable background is displayed in the outer screen portion 236, the displaceable background may be displaced, or scrolled, left-to-right, right-to-left, top-to-bottom, or bottom-to-top on the output screen 168. In addition, the data acquisition/data processing device 104 may be configured to rotate the displaceable background about a central axis in any of the pitch, roll, or yaw direction (i.e., an axis passing centrally through the output screen 168, such as along radius line R1 in FIG. 10, rotation in the roll direction). Moreover, the data acquisition/data processing device 104 may be configured to adjust the position of the central axis, about which the displaceable background rotates, based upon a subject height input value so that the central axis is approximately disposed at the eye level of the subject. It is to be understood that any of these motion profiles described in conjunction with the displaceable background also can be applied to the virtual reality scenario by the data acquisition/data processing device 104. Preferably, the data acquisition/data processing device 104 is also specially programmed so as to enable a system user (e.g., a clinician) to selectively choose the manner in which the displaceable background is displaced during the training routines (i.e., the data acquisition/data processing device 104 is preferably provided with various setup options that allow the clinician to determine how the displaceable background moves during the training routines described herein). Also, preferably, the data acquisition/data processing device 104 is specially programmed so as to enable a system user (e.g., a clinician) to selectively choose from a plurality of different displaceable backgrounds that can be interchangeably used during various training routines.

In FIG. 22, the inner screen portion 234 is depicted with a border 242, which separates the inner screen portion 234 from the second outer screen portion 236. However, it is to be understood that, in other embodiments of the invention, the border 242 may be omitted. Also, in some embodiments, the data acquisition/data processing device 104 is specially programmed so as to enable a system user (e.g., a clinician) to selectively choose whether or not the inner screen portion 234 with the patient instructional information displayed thereon is displaced in accordance with the movement of the subject on the displaceable force measurement assembly 102.

Figure 23:
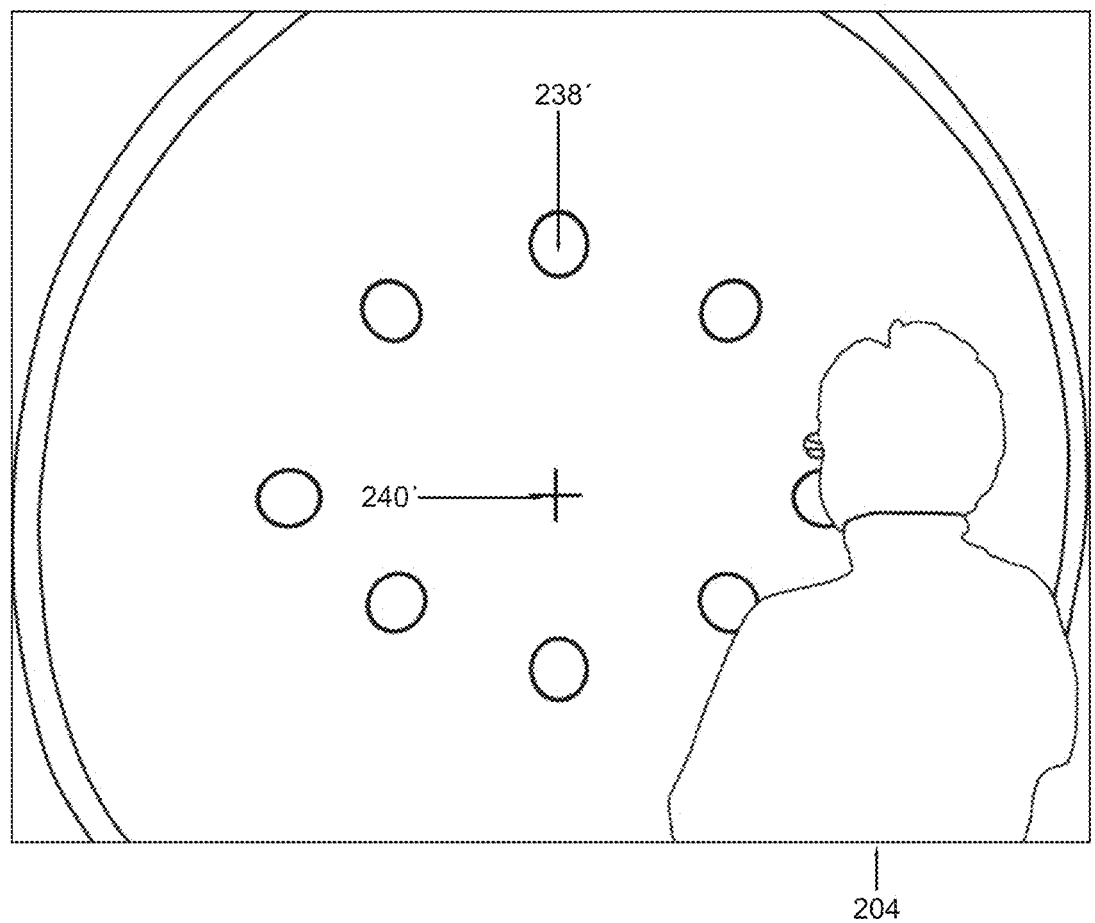
FIG. 23 is a second variation of a training screen image displayed on the subject visual display device of the force measurement system, according to an embodiment of the invention.

In another embodiment, with reference to FIG. 23, it can be seen that only instructional information for a subject 204 may be displayed on the output screen 168 of the subject visual display device 107. As shown in this figure, a plurality of enlarged targets or markers 238' (e.g., in the form of circles) and an enlarged displaceable visual indicator or cursor 240' are displayed on the output screen 168. As described above, during the execution of the training protocol, the subject 204 is instructed to move the cursor 240' into each of the plurality targets or markers 238' in successive progression. In FIG. 23, the plurality of targets or markers 238' and the displaceable visual indicator or cursor 240' are displaced on a plain white background that is not moving.

In yet another embodiment, the configuration of the output screen 168 of the subject visual display device 107 could be similar to that which is depicted in FIG. 22, except that the plurality of targets or markers 238 and the displaceable visual indicator or cursor 240 could be superimposed directly on the displaceable background, rather than being separated therefrom in the inner screen portion 234. Thus, unlike in FIG. 22, where the targets 238 and the cursor 240 are superimposed on a plain white background, the targets 238 and the cursor 240 would be displayed directly on the displaceable background. In some scenarios, the targets 238 would be stationary on the output screen 168 of the subject visual display device 107, while in other scenarios, the targets 238 could be displaced on the output screen 168 of the subject visual display device 107 while the subject 204 is undergoing training.

In still another embodiment, the data acquisition/data processing device 104 is specially programmed with a plurality of options that can be changed in order to control the level of difficulty of the training. These options may include: (i) pacing (i.e., how fast a patient must move from target 238, 238' to target 238, 238'), (ii) the percentage of limits of stability (which changes the spacing of the targets 238, 238', (iii) percent weight bearing (i.e., the targets 238, 238' can be adjusted in accordance with the percentage of a subject's weight that is typically placed on his or her right leg as compared to his or her left leg so as to customize the training for a particular subject, i.e., to account for a disability, etc.), and (iv) accessories that can placed on the plate surface (i.e., type of surface to stand on (e.g., solid or foam), size of box to step on/over, etc.). In addition, the data acquisition/data processing device 104 can be specially programmed to adjust the magnitude of the response of the displaceable force measurement assembly 102 and the virtual reality environment on the screen 168. For example, while a subject is undergoing training on the system 100, the displacement of the virtual reality environment on the screen 168 could be set to a predetermined higher or lower speed. Similarly, the speed of rotation and/or translation of the displaceable force measurement assembly 102 could be set to predetermined higher or lower speed.

Figure 24:
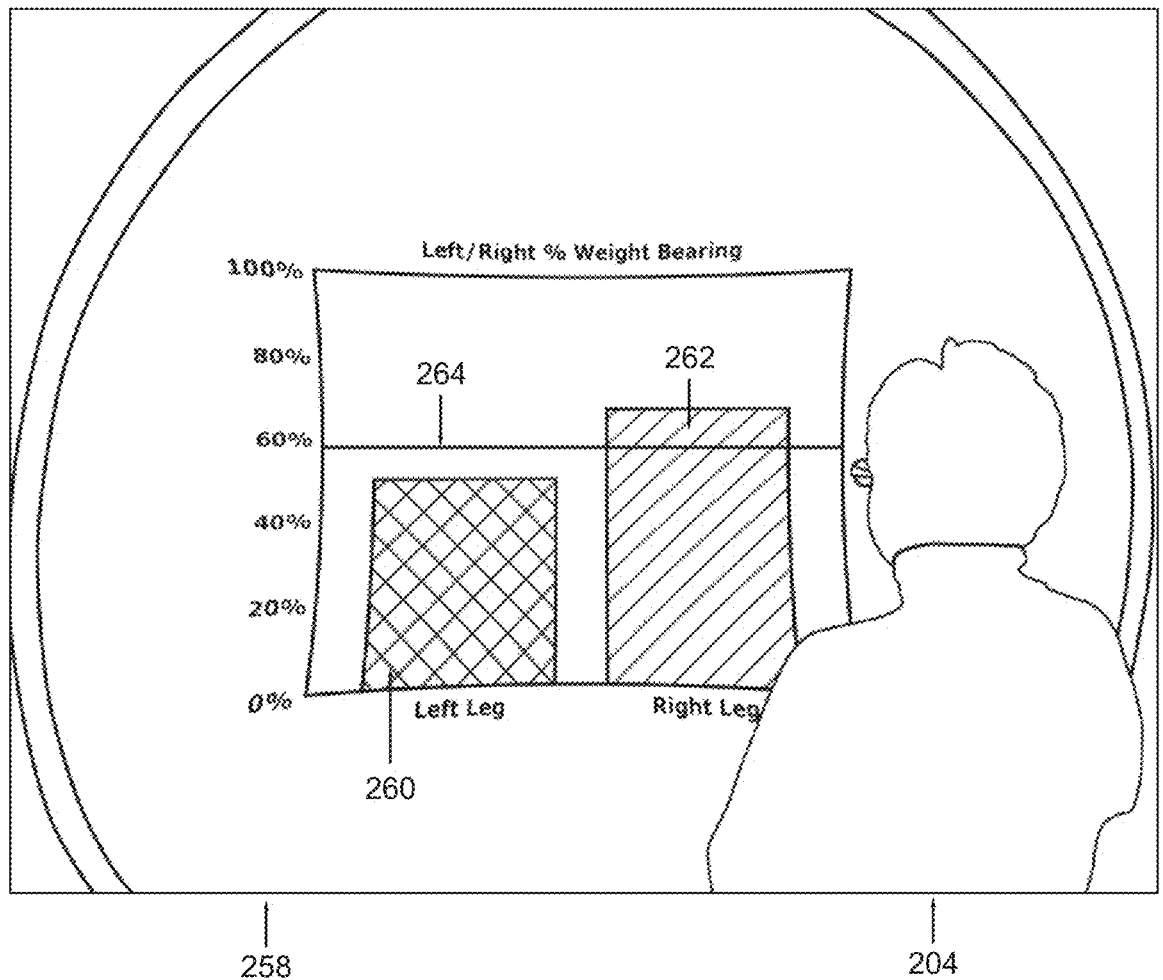
FIG. 24 is a third variation of a training screen image displayed on the subject visual display device of the force measurement system, according to an embodiment of the invention.

In yet another embodiment, the data acquisition/data processing device 104 is configured to compute the vertical forces $F_{Lz}$, $F_{Rz}$ exerted on the surface of the first and second force plate components 110, 112 by the respective feet of the subject, or alternatively, to receive these computed values for $F_{Lz}$, $F_{Rz}$ from the programmable logic controller 172. In this embodiment, with reference to the screen image 258 of FIG. 24, first and second displaceable visual indicators (e.g., in the form of adjacent displaceable bars 260, 262) are displayed on the output screen 168 of the subject visual display device 107. As shown in FIG. 24, the first displaceable bar 260 represents the percentage of a subject's total body weight that is disposed on his or her left leg, whereas the second displaceable bar 262 represents the percentage of a subject's total body weight that is disposed on his or her right leg. In FIG. 24, because this is a black-and-white image, the different colors (e.g., red and green) of the displaceable bars 260, 262 are indicated through the use of different hatching patterns (i.e., displaceable bar 260 is denoted using a crisscross type hatching pattern, whereas displaceable bar 262 is denoted using a diagonal hatching pattern). The target percentage line 264 in FIG. 24 (e.g., a line disposed at 60% of total body weight) gives the subject 204 a goal for maintaining a certain percentage of his body weight on a prescribed leg during the performance of a particular task. For example, the subject 204, may be instructed to move from a sit-to-stand position while being disposed on the dual force measurement assembly 102. While performing the sit-to-stand task, the subject 204 is instructed to maintain approximately 60% of his or her total body weight on his or her left leg, or alternatively, maintain approximately 60% of his or her total body weight on his or her right leg. During the performance of this task, the data acquisition/data processing device 104 controls the respective positions of the displaceable bars 260, 262 using the computed values for the vertical forces $F_{Lz}$, $F_{Rz}$ (i.e., the bars 260, 262 are displayed on the output screen 168 in accordance with the values for the vertical forces $F_{Lz}$, $F_{Rz}$ determined over the time period of the sit-to-stand task task). If the subject is able to maintain approximately the percentage weight goal on his or her prescribed leg, then the displaceable bar 260, 262 for that leg (either right or left) will continually oscillate in close proximity to the target percentage line 264.

For the left bar 260 displayed in FIG. 24, the percentage weight for the left leg is computed as follows:

$$\% \, W_L = \left( \frac{F_{Z_L}}{F_{Z_L} + F_{Z_R}} \right) * 100\% \qquad (2)$$

where:
%~$W_L$: percentage of total body weight disposed on subject's left leg;
$F_{Z_L}$: vertical force on subject's left leg (e.g., in Newtons); and
$F_{Z_R}$: vertical force on subject's right leg (e.g., in Newtons).

For the right bar 262 displayed in FIG. 24, the percentage weight for the right leg is computed as follows:

$$\% \, W_R = \left( \frac{F_{Z_R}}{F_{Z_L} + F_{Z_R}} \right) * 100\% \qquad (3)$$

where:
%~$W_R$: percentage of total body weight disposed on subject's right leg;

$F_{Z_L}$: vertical force on subject's left leg (e.g., in Newtons); and $F_{Z_R}$: vertical force on subject's right leg (e.g., in Newtons).

People maintain their upright posture and balance using inputs from somatosensory, vestibular and visual systems. In addition, individuals also rely upon inputs from their somatosensory, vestibular and visual systems to maintain balance when in other positions, such as seated and kneeling positions. During normal daily activity, where dynamic balance is to be maintained, other factors also matter. These factors are visual acuity, reaction time, and muscle strength. Visual acuity is important to see a potential danger. Reaction time and muscle strength are important to be able to recover from a potential fall. During the performance of the Sensory Organization Test ("SOT"), certain sensory inputs are taken away from the subject in order to determine which sensory systems are deficient or to determine if the subject is relying too much on one or more of the sensory systems. For example, the performance of the SOT protocol allows one to determine how much a subject is relying upon visual feedback for maintaining his or her balance.

Figure 14:
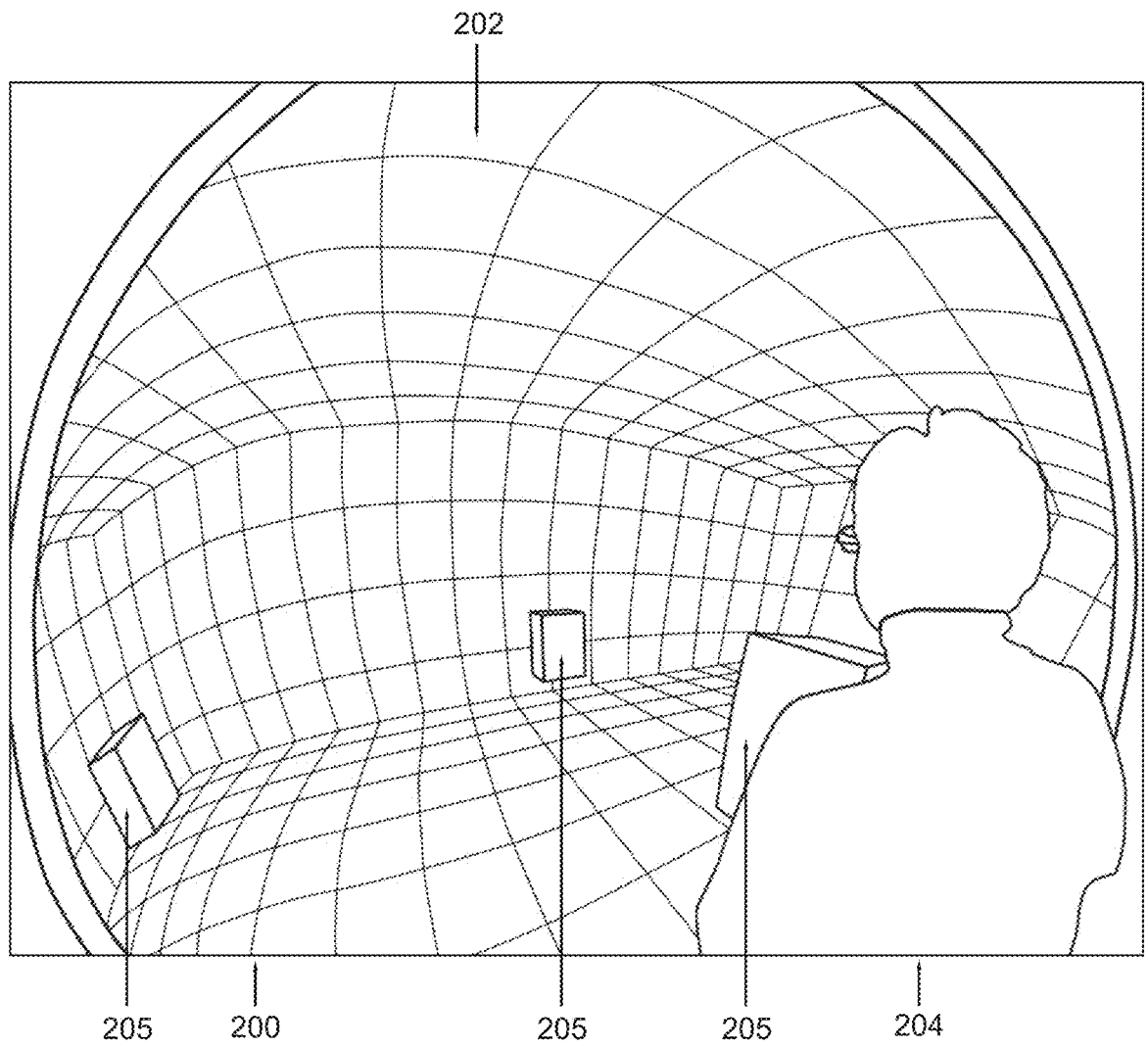
FIG. 14 is a first example of a virtual reality scene displayed on the subject visual display device of the force measurement system, according to an embodiment of the invention.

In one embodiment, the SOT protocol comprises six conditions under which a subject is tested (i.e., six test stages). In accordance with the first sensory condition, a subject simply stands in stationary, upright position on the force plate assembly 102 with his or her eyes open. During the first condition, a stationary virtual reality scene is projected on the generally hemispherical projection screen 168 of the subject visual display device 107, and the force plate assembly 102 is maintained in a stationary position. For example, the virtual reality scene displayed on the generally hemispherical projection screen 168 may comprise a checkerboard-type enclosure or room (e.g., see FIG. 14), or some other appropriate scene with nearfield objects (e.g., boxes or blocks 205). In the illustrated embodiment, the virtual reality scene is in the form of a three-dimensional image, and the nature of the scene will remain consistent throughout the performance of the SOT protocol. As shown in the screen image 200 of FIG. 14, a subject 204 is disposed in an immersive virtual reality environment 202 comprising a three-dimensional checkerboard room. As shown in FIG. 14, the three-dimensional checkerboard room comprises a plurality of three-dimensional boxes or blocks 205 in order to give the subject 204 a frame of reference for perceiving the depth of the room (i.e., the boxes or blocks 205 enhance the depth perception of the subject 204 with regard to the virtual room).

In accordance with the second sensory condition of the SOT protocol, the subject is blindfolded so that he or she is unable to see the surrounding environment. Similar to the first condition, the force plate assembly 102 is maintained in a stationary position during the second condition of the SOT test. By blindfolding the subject, the second condition of the SOT effectively removes the visual feedback of the subject.

During the third condition of the SOT protocol, like the first and second conditions, the force plate assembly 102 remains in a stationary position. However, in accordance with the third sensory condition of the test, the virtual reality scene displayed on the generally hemispherical projection screen 168 is moved in sync with the sway angle of the subject disposed on the force plate assembly 102. For example, when the subject leans forward on the force plate assembly 102, the virtual reality scene displayed on the screen 168 is altered so as to appear to the subject to be inwardly displaced on the output screen 168. Conversely, when the subject leans backward on the force plate assembly 102, the virtual reality scene is adjusted so as to appear to the subject to be outwardly displaced on the screen 168. As in the first condition, the eyes of the subject remain open during the third condition of the SOT protocol.

In accordance with the fourth sensory condition of the SOT protocol, the force plate assembly 102 and the subject disposed thereon is displaced (e.g., rotated), while the eyes of the subject remain open. The force plate assembly 102 is displaced according to the measured sway angle of the subject (i.e., the rotation of the force plate assembly 102 is synchronized with the computed sway angle of the subject). During the fourth condition, similar to the first condition, a stationary virtual reality scene is projected on the generally hemispherical projection screen 168 of the subject visual display device 107.

During the fifth condition of the SOT protocol, like the second condition thereof, the subject is blindfolded so that he or she is unable to see the surrounding environment. However, unlike during the second condition, the force plate assembly 102 does not remain stationary, rather the force plate assembly 102 and the subject disposed thereon is displaced (e.g., rotated). As for the fourth condition, the force plate assembly 102 is displaced according to the measured sway angle of the subject (i.e., the rotation of the force plate assembly 102 is synchronized with the computed sway angle of the subject). As was described above for the second condition of SOT protocol, by blindfolding the subject, the fifth condition of the SOT test effectively removes the visual feedback of the subject.

Lastly, during the sixth sensory condition of the SOT protocol, like the fourth and fifth conditions, the force plate assembly 102 and the subject disposed thereon is displaced (e.g., rotated). Although, in accordance with the sixth sensory condition of the test, the virtual reality scene displayed on the generally hemispherical projection screen 168 is also moved in sync with the sway angle of the subject disposed on the force plate assembly 102. As previously described for the fourth and fifth conditions, the displacement of the force plate assembly 102 is governed by the measured sway angle of the subject (i.e., the rotation of the force plate assembly 102 is synchronized with the computed sway angle of the subject). In an exemplary embodiment, when the subject is forwardly displaced on the force plate assembly 102 during the sixth condition of the SOT protocol, the virtual reality scene displayed on the screen 168 is altered so as to appear to the subject to be inwardly displaced on the output screen 168. Conversely, when the subject is rearwardly displaced on the force plate assembly 102, the virtual reality scene is adjusted so as to appear to the subject to be outwardly displaced on the screen 168. As in the fourth condition, the eyes of the subject remain open during the sixth condition of the SOT protocol.

Figure 47:
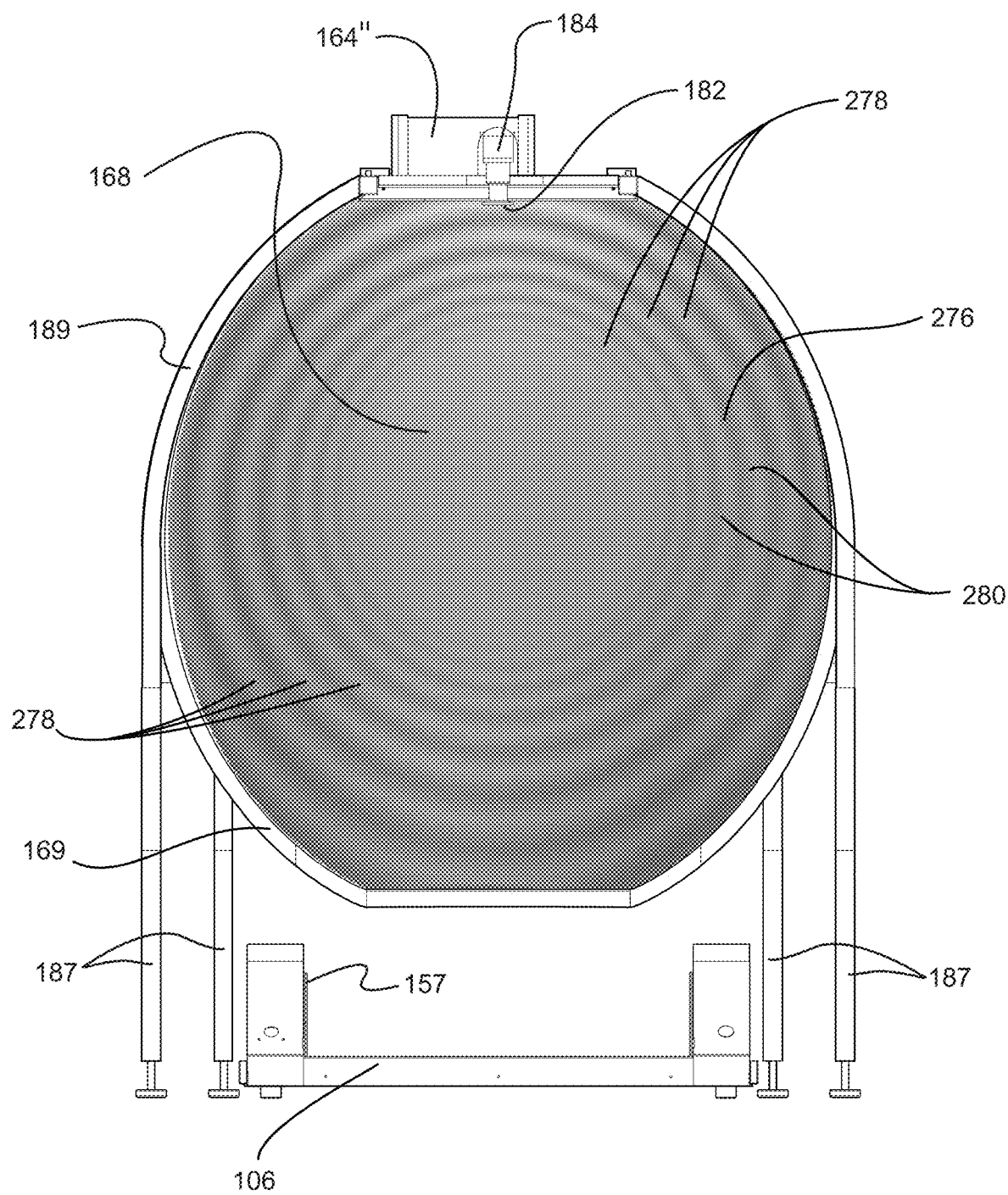
FIG. 47 is a first variation of a screen image comprising a plurality of concentric bands displayed on the subject visual display device of the force measurement system, according to an embodiment of the invention, wherein the plurality of concentric bands are generally circular in shape.
Figure 48:
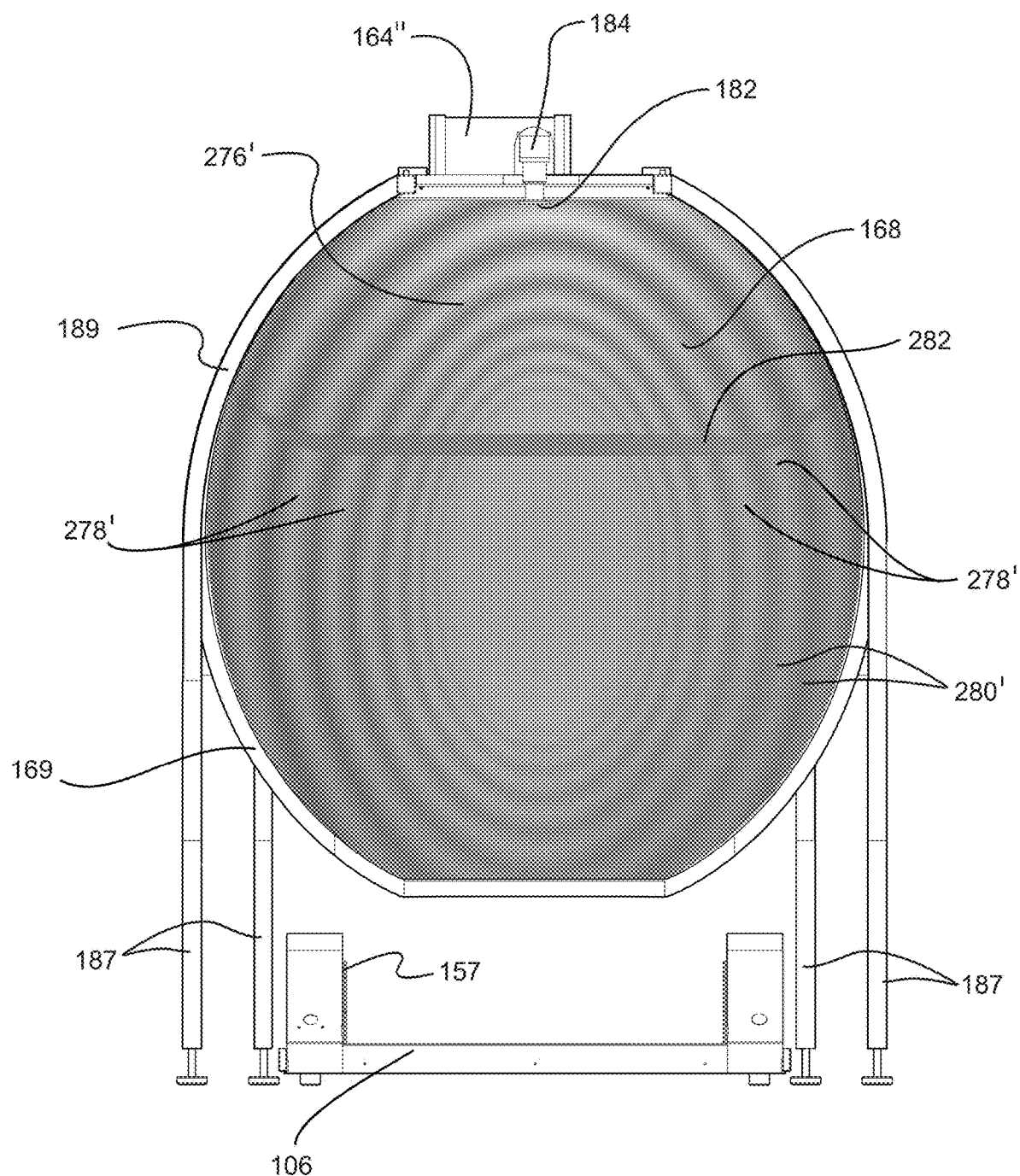
FIG. 48 is a second variation of a screen image comprising a plurality of generally concentric bands displayed on the subject visual display device of the force measurement system, according to an embodiment of the invention, wherein the plurality of concentric bands are generally elliptical or oval in shape.

During the performance of the SOT protocol, the scene or screen image displayed on the generally hemispherical projection screen 168 may also comprise one of the images illustrated in FIGS. 47 and 48. Initially, turning to FIG. 47, it can be seen that the screen image 276 on the hemispherical projection screen 168 comprises a plurality of substantially concentric bands 278 that are configured to create a disorienting visual stimuli for the subject disposed on the force measurement assembly 102. The specially programmed data acquisition/data processing device 104 of the force measurement system 100 generates the screen image 276 of FIG. 47, and the projector 164" projects the generated image onto the screen 168. As depicted in FIG. 47, it can be seen that each of the plurality of substantially concentric bands 278 comprise blurred edge portions without any clearly defined boundary lines so that the subject is unable to establish a particular focal point of reference on the output screen 168. In other words, each band or ring 278 comprises a gradient-type edge portion 280 that is very diffuse in nature, and does not comprise any hard line transitions. As shown in FIG. 47, the plurality of substantially concentric bands 278 generated by the specially programmed data acquisition/data processing device 104 of the force measurement system 100 are three-dimensionally arranged on the screen 168 so as to create a three-dimensional tunnel effect for the subject. Advantageously, because the blurred or gradient-type edge portions 280 of the band or rings 278 do not include any clearly defined boundary lines or fixation points, the subject is unable to establish a particular focal point of reference on the output screen 168. When a subject is performing conditions three and six of the SOT protocol, it is desired that the subject believe that he or she is not moving, when in fact, he or she is actually moving on the surface of the force measurement assembly 102. Advantageously, the absence of all hard lines and defined points in the screen image 276 of FIG. 47 eliminates the frame of reference that the subject would otherwise utilize to visually detect their movement on the force measurement assembly 102, and thus greatly enhances the effectiveness of the SOT protocol. The screen image 276 of FIG. 47 enhances the effectiveness of the SOT protocol by precluding the visual input normally available from a defined reference point or line on the screen in front of the subject.

While each of the bands or rings 278 in the screen image 276 of FIG. 47 is generally circular in shape, it is to be understood that the invention is not so limited. Rather, other suitable shapes may be used for the bands or rings 278 as well. For example, in other embodiments of the invention, the bands or rings generated by the one or more data processing devices, and projected on the hemispherical projection screen 168, may comprise one or more of the following other configurations: (i) a plurality of elliptical concentric bands or rings, (ii) a plurality of rectangular concentric bands or rings, (iii) a plurality of square concentric bands or rings, and (iv) a plurality of concentric bands or rings having generally straight side portions with rounded corner portions.

In an exemplary embodiment, when the plurality of concentric bands or rings have generally straight side portions with rounded corner portions, the straight side portion of each band or ring may comprise one-third (⅓) of its overall height or width, while the radius of each rounded corner portion may comprise one-third (⅓) of its overall height or width. As such, in the exemplary embodiment, the straight side portion of each band or ring comprises one-third (⅓) of its overall height or width, the first rounded corner portion comprises one-third (⅓) of its overall height or width, and the second rounded corner portion comprises the remaining one-third (⅓) of its overall height or width. However, in other embodiments, it is to be understood that straight side portions and the rounded corner portions may comprise other suitable ratios of the overall height or width of band or rings.

Next, turning to FIG. 48, it can be seen that the screen image 276' on the hemispherical projection screen 168 comprises a plurality of substantially concentric bands 278', which are similar in many respects to those depicted in FIG. 47, except that the bands 278' in FIG. 48 have a different overall shape. In particular, the plurality of concentric bands or rings 278' in FIG. 48 are generally elliptical or oval in shape, rather than circular in shape. As was described above for the image 276 of FIG. 47, the data acquisition/data processing device 104 of the force measurement system 100 is specially programmed to generate the screen image 276' of FIG. 48, and the projector 164" projects the generated image onto the screen 168. Like the bands or rings 278 of FIG. 47, the concentric bands or rings 278' of FIG. 48 also comprise gradient-type edge portions 280' without any clearly defined boundary lines so that the subject is unable to establish a particular focal point of reference on the output screen 168. In addition, the substantially concentric bands 278' of FIG. 48 are three-dimensionally arranged on the screen 168 so as to create a three-dimensional tunnel effect for the subject. As was explained above for the screen image of FIG. 47, the absence of all hard lines and defined points in the screen image 276' of FIG. 48 eliminates the frame of reference that the subject would otherwise utilize to visually detect their movement on the force measurement assembly 102, and thus greatly enhances the effectiveness of the SOT protocol. In some embodiments, the concentric bands 278' in FIG. 48 are provided with an elliptical or oval shape in order to emulate a passageway of a building (i.e., so the subject viewing the screen image 276' has the illusion that he or she is traveling down a hallway or passageway of a building). Also, in some embodiments, the screen image 276' of FIG. 48, as well as the screen image 276 of FIG. 47, is rotated about a central axis in any one of the pitch, roll, or yaw direction (i.e., an axis passing centrally through the output screen 168, such as along radius line R1 in FIG. 10, rotation in the roll direction) during the performance of the SOT protocol. The movement of the screen image 276, 276' may also be synchronized with the movement of the subject such that the screen image 276, 276' is rotated and inwardly or outwardly displaced on the screen in sync with a sway angle of the subject (e.g., when the subject leans forward on the force plate, the image is rotated downwardly and displaced into the screen, and is oppositely displaced when the subject leans backward of the force plate).

Referring again to FIG. 48, it can be seen that the screen image 276' also comprises a horizontal line 282 disposed laterally across the plurality of concentric bands or rings 278'. That is, the horizontal line 282 laterally intersects the plurality of concentric bands or rings 278'. As shown in FIG. 48, the horizontal line 282 is disposed closer to the top of each elliptically-shaped band or ring 278', than the bottom of each elliptically-shaped band or ring 278', so as to be generally aligned with the line of sight of a subject of average height. In one or more embodiments, the horizontal line 282 is utilized as a visual reference line for the subject during the performance of conditions one, two, four, and five of the SOT protocol (i.e., the conditions of the SOT protocol during which the screen image on the hemispherical projection screen 168 is not displaced). In these one or more embodiments, the horizontal line 282 is configured to be selectively turned on and off by the specially programmed data acquisition/data processing device 104 of the force measurement system 100 so that it is capable of being displayed during conditions one, two, four, and five of the SOT protocol (i.e., when the screen image is not displaced), but then turned off during conditions three and six of the SOT protocol (i.e., when the screen image is displaced).

In addition, while the screen images 276, 276' of FIGS. 47 and 48 are particularly suitable for use in the SOT protocol, it is to be understood that these the screen images 276, 276' may be utilized in conjunction with other balance and postural stability tests and protocols as well. For example, the screen images 276, 276' of FIGS. 47 and 48 may also be employed in the Adaptation Test ("ADT") and the Motor Control Test ("MCT"), while testing the balance of a subject or patient.

In another embodiment, the data acquisition/data processing device 104 of the force measurement system 100 may be specially programmed to execute a modified version of the SOT protocol wherein two or more of the six conditions of the protocol are combined with one another so as to more accurately and efficiently perform the test. The SOT protocol described above comprises six separate conditions (i.e., discrete sub-tests), each of which are performed for a predetermined period of time (e.g., each of the six conditions of the SOT protocol may be performed for approximately 20 seconds). In the modified version of the SOT protocol that will be described hereinafter, the displacement velocity (e.g., gain) of the screen background image is gradually incremented over time by the data acquisition/data processing device 104 from an initial static condition to a final dynamic condition. At the final dynamic condition, the screen image on the hemispherical projection screen 168 is displaced at a velocity that is equal to, or greater than the subject's movement (e.g., the displacement velocity of the screen image may be synchronized with the subject's computed sway angle velocity or it may be greater than the subject's sway angle velocity). Rather than the plurality of discrete conditions or sub-tests that are utilized in the SOT protocol explained above, the modified version of the SOT protocol that will be described hereinafter utilizes a continuum of different test conditions that continually vary over the time duration of the SOT protocol. Advantageously, the modified protocol allows the SOT testing to be performed more efficiently because, if it is determined that the subject is successfully performing the protocol as the velocity of the screen image is continually increased, the testing can simply be stopped after a shorter period (i.e., the test may be able to be stopped after 20 seconds, 30 seconds, etc.).

The modified version of the SOT protocol may initially comprise generating, by using the specially programmed data acquisition/data processing device 104 of the force measurement system 100, one or more screen images (e.g., screen images 276, 276') that are displayed on the hemispherical projection screen 168. At the commencement of the SOT protocol, the one or more screen images are displayed on the output screen 168 in an initial static condition wherein the one or more images are generally stationary (i.e., the images are not moving on the screen 168). Subsequent to the initial static condition, the one or more images are displaced on the output screen 168 in accordance with a velocity value that incrementally increases over time as the SOT protocol progresses (e.g., the velocity value of the one or more images may be incremented by a predetermined amount every five (5) seconds so that the velocity value gets progressively higher as the SOT protocol progresses). The displacement of the one or more images on the output screen 168 may comprise, for example, left-to-right displacement, right-to-left displacement, top-to-bottom displacement, and/or bottom-to-top displacement on the screen 168. The displacement of the one or more images on the output screen 168 also may comprise displacements corresponding to: (i) a medial-lateral direction of the subject, (ii) an anterior-posterior direction of the subject, and/or (iii) a superior-inferior direction of the subject. In addition, the data acquisition/data processing device 104 of the force measurement system 100 may be specially programmed to rotate the displaceable image(s) about a central axis in any of the pitch, roll, or yaw direction (i.e., an axis passing centrally through the output screen 168, such as along radius line R1 in FIG. 10, rotation in the roll direction) during the SOT protocol. As such, the image velocity value that is incrementally increased during the modified SOT protocol may comprise a linear velocity value or an angular velocity value. While the modified SOT protocol is being performed, and the screen image is gradually being displaced at an incrementally higher velocity, the performance of the subject or patient is evaluated in order to assess a postural stability of the subject (e.g., by evaluating the subject's center-of-pressure, center-of-gravity, and/or sway angle over time).

Figure 46:
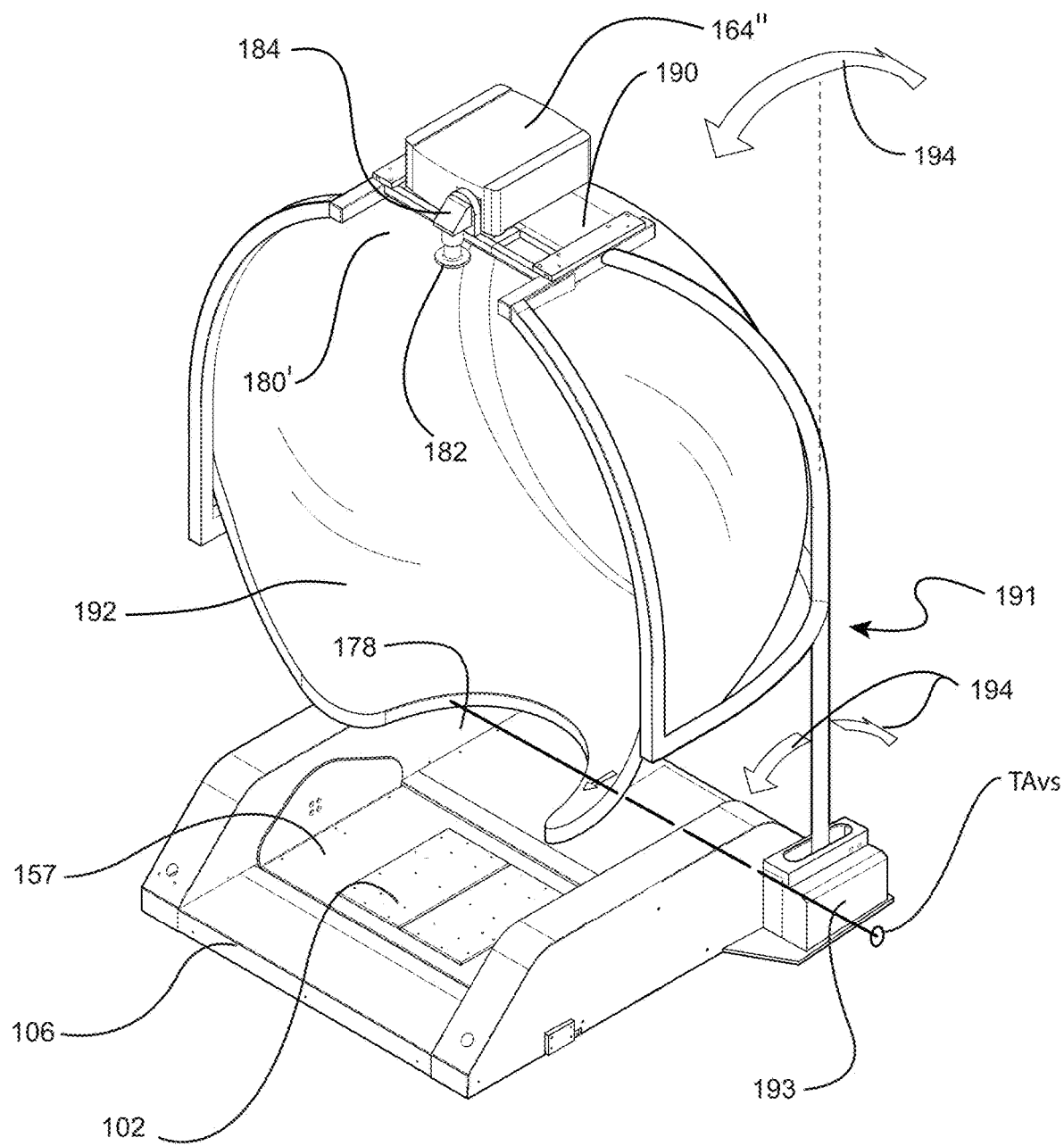
FIG. 46 is a perspective view of yet another alternative force measurement system comprising a displaceable visual surround device, a base assembly, and displaceable force measurement assembly, according to an embodiment of the invention.

As an alternative to displacing one or images on the screen 168 during the performance of the modified SOT protocol, it is to be understood that a displaceable visual surround device, which at least partially circumscribes three sides of a subject (i.e., three sides of a torso of a subject), may be employed. In particular, with reference to FIG. 46, the visual surround device 191 may comprise visual surround portion 192 that is displaceable by means of one or more actuators in an actuator device 193 that are operatively coupled to the specially programmed data acquisition/data processing device 104 of the force measurement system 100. In this alternative embodiment, the one or more data processing devices generate a motion profile for the visual surround device 191, rather than generating a motion profile for a displaceable image on the screen 168. At the commencement of the SOT protocol, the visual surround portion 192 of the visual surround device 191 is maintained in an initial static condition wherein the visual surround portion 192 is generally stationary. Subsequent to the initial static condition, the visual surround portion 192 is displaced by the one or more actuators in the actuator device 193 in accordance with a velocity value that incrementally increases over time as the SOT protocol progresses (e.g., the displacement velocity value of the visual surround portion 192 may be incremented by a predetermined amount every five (5) seconds so that the velocity value gets progressively higher as the SOT protocol progresses). Similar to that which was described above for the displaceable screen images, the displacement the visual surround portion 192 may comprise, for example, left-to-right displacement, right-to-left displacement, top-to-bottom displacement, and/or bottom-to-top displacement, depending on the quantity and the placement of the actuators. The displacement of the visual surround portion 192 also may comprise displacements corresponding to: (i) a medial-lateral direction of the subject, (ii) an anterior-posterior direction of the subject, and/or (iii) a superior-inferior direction of the subject. In addition, the data acquisition/data processing device 104 of the force measurement system 100 may be specially programmed to rotate the visual surround portion 192 about a central axis in any of the pitch, roll, or yaw direction (i.e., an axis passing centrally through the visual surround portion 192, rotation in the roll direction) during the SOT protocol. As such, as was described above for the displaceable screen images, the velocity value of the visual surround portion 192 that is incrementally increased during the modified SOT protocol may comprise a linear velocity value or an angular velocity value. While the modified SOT protocol is being performed, and the visual surround portion 192 is gradually being displaced at an incrementally higher velocity, the performance of the subject or patient is evaluated in order to assess a postural stability of the subject (e.g., by evaluating the subject's center-of-pressure, center-of-gravity, and/or sway angle over time). Referring again to FIG. 46, it can be seen that, in the illustrated embodiment, the visual surround portion 192 is rotationally displaced (i.e., as indicated by curved arrows 194) about a transverse horizontal axis $TA_{VS}$.

Similar to that described above for the displacement of the screen image, the displacement velocity (e.g., gain) of the visual surround portion 192 may be gradually incremented over time from an initial static condition to a final dynamic condition. At the final dynamic condition, the visual surround portion 192 is displaced at a velocity that is equal to, or greater than the subject's movement (e.g., the displacement velocity of the visual surround portion 192 may be synchronized with the subject's computed sway angle velocity or it may be greater than the subject's sway angle velocity). For example, in the illustrated embodiment of FIG. 46, the angular velocity of the visual surround portion 192 about the transverse axis $TA_{VS}$ may be equal to the subject's sway angle velocity at the final dynamic condition.

In the modified SOT protocol, the force measurement assembly 102, and the subject disposed thereon, may be incrementally displaced in a manner similar to that described above for the screen image on the screen 168 and the visual surround portion 192. That is, the second actuator assembly 160 may be used to rotate the force measurement assembly 102, and the subject disposed thereon, at an incrementally higher angular velocity during the modified SOT protocol (see FIG. 2). At the commencement of the SOT protocol, the force measurement assembly 102, and the subject disposed thereon, are maintained in an initial static condition wherein the force measurement assembly 102 and the subject are stationary. Subsequent to the initial static condition, the force measurement assembly 102, and the subject disposed thereon, are rotated in accordance with a velocity value that incrementally increases over time as the SOT protocol progresses (e.g., the angular velocity value of the force measurement assembly 102 and the subject may be incremented by a predetermined amount every five (5) seconds so that the velocity value gets progressively higher as the SOT protocol progresses). While the modified SOT protocol is being performed, and the force measurement assembly 102 carrying the subject is gradually being displaced at an incrementally higher angular velocity, the performance of the subject or patient is evaluated in order to assess a postural stability of the subject (e.g., by evaluating the subject's center-of-pressure, center-of-gravity, and/or sway angle over time).

Similar to that described above for the displacement of the screen image and the visual surround portion 192, the rotational velocity (e.g., gain) of the force measurement assembly 102 carrying the subject may be gradually incremented over time from an initial static condition to a final dynamic condition. At the final dynamic condition, the force measurement assembly 102 carrying the subject is displaced at an angular velocity that is equal to, or greater than the subject's movement (e.g., the displacement velocity of the screen image may be synchronized with the subject's computed sway angle velocity or it may be greater than the subject's sway angle velocity). During the performance of the modified SOT protocol, the displacement velocity of either the screen image or the visual surround portion 192 may be generally equal to the angular displacement velocity of the force measurement assembly 102 and the subject (i.e., the force measurement assembly 102 and the subject disposed thereon may be displaced using an angular velocity that is synchronized with the displacement velocity of either the screen image or the visual surround portion 192).

Advantageously, because the velocity of the screen image, the visual surround portion 192, and/or the force measurement assembly 102 carrying the subject are incrementally increased during the performance of the modified SOT protocol, the SOT protocol is capable of being performed in a far more efficient manner. That is, rather than laboriously executing six separate conditions for fixed time durations, the protocol conditions are combined with one another so that it takes far less time to determine the actual performance of the subject. In one or more embodiments, the data acquisition/data processing device 104 of the force measurement system 100 may be specially programmed to determine the time duration of the SOT protocol in accordance with a quasi real-time assessment of the postural stability of the subject (e.g., by evaluating the subject's center-of-pressure, center-of-gravity, and/or sway angle over time). As such, when an accurate assessment of the subject's performance is obtained, the modified SOT protocol is simply concluded.

As explained above, the modified version of the SOT protocol combines two or more conditions with one another so as to more accurately and efficiently perform the test. For example, the first SOT condition described above may be combined with the third SOT condition. Similarly, the fourth SOT condition described above may be combined with the six SOT condition, while the second condition (blindfolded subject, stationary force measurement assembly 102) may be combined with the fifth SOT condition (blindfolded subject, displaced force measurement assembly 102). Also, in some embodiments, three conditions of the SOT protocol may be combined with one another. For example, the first, third, and sixth conditions of the SOT protocol may be combined with one another so that either the displacement velocity of the screen image or visual surround portion 192 is simultaneously incremented together with the angular displacement velocity of the force measurement assembly 102 and the subject disposed thereon. In one exemplary embodiment of the modified SOT protocol, the combined first, third, and sixth conditions of the SOT protocol may be performed initially, and then the combined second and fifth conditions may be performed thereafter. Also, because the subject's performance is evaluated in quasi real-time during the performance of the modified SOT protocol, the data acquisition/data processing device 104 of the force measurement system 100 may be specially programmed so as to automatically combine different sequences of conditions with one another based upon the subject's performance during the modified SOT protocol. Also, the data acquisition/data processing device 104 of the force measurement system 100 may be specially programmed so as to allow the system operator (e.g., a clinician) to select different conditions to be combined with one another while the subject or patient is executing the modified SOT protocol. That is, the system operator may monitor the subject's performance during the execution of the modified SOT protocol, and then select a particular sequence of conditions based upon that performance.

During the performance of the modified SOT protocol, it is to be understood that the screen images 276, 276', which were described in conjunction with FIGS. 47 and 48 above, may be displayed on the generally hemispherical projection screen 168 while one or more of the conditions are being performed. For example, the screen images 276, 276' of FIGS. 47 and 48 may be utilized during the performance of any combination of the first, third, fourth, and sixth conditions.

Also, in one or more alternative embodiments, during the performance of the balance test (e.g., the SOT protocol or modified SOT protocol described above), the subject or patient 108 may be outfitted with augmented reality glasses (i.e., reality-altering glasses) in order to perturb the subject's visual input during the performance of the balance test. For example, in these embodiments, the screen images 276, 276' of FIGS. 47 and 48 may be displayed using the augmented reality glasses (i.e., reality-altering glasses), rather than on the generally hemispherical projection screen 168. The augmented reality glasses may comprise one or more high-resolution liquid-crystal (LCD) displays (e.g., two (2) LCD displays) that generate a large virtual screen image (e.g., 60" to 80" virtual screen viewed from 10 feet) for the user, wherein the augmented reality glasses are capable of displaying both two-dimensional (2D) and three-dimensional (3D) video for the user thereof. The augmented reality glasses may further comprise one or more discrete video graphics array (VGA) cameras (e.g., two (2) VGA cameras) for capturing both two-dimensional (2D) and three-dimensional (3D) stereoscopic video images of the environment surrounding the user. In addition, the augmented reality glasses may comprise an inertial measurement unit (IMU) integrated therein, which comprises three (3) accelerometers, three (3) gyroscopes, and three (3) magnetometers for tracking the head movement of the user so that the user's current head direction and angle of view may be determined. Also, the augmented reality glasses may comprise one or more interfaces (e.g., high-definition multimedia interface (HDMI) or a suitable wireless interface) that operatively connect the augmented reality glasses to an external data processing device (e.g., data acquisition/data processing device 104 or 330). It is to be understood that the augmented reality glasses worn by the subject or patient 108 during the performance of a balance test (e.g., the SOT protocol or modified SOT protocol) could achieve the same effect described above with regard to the images of FIGS. 47 and 48. Also, the augmented reality glasses may be worn by the subject or patient 108 while performing the modified SOT protocol described above so that the one or more images, which are displaced at incrementally higher velocities during the performance of the protocol, are displaced on a virtual output screen projected in front of the subject.

Also, in one or more alternative embodiments, the reality-altering glasses worn by the subject or patient 108 may be designed such that the subject or patient 108 has no direct view of the surrounding environment. That is, the only view that the subject or patient 108 has of the surrounding environment is the view projected on the one or more visual display devices of the reality-altering glasses (i.e., the reality-altering glasses may be in the form of virtual reality glasses).

In these one or more alternative embodiments, the data acquisition/data processing device 330 may be specially programmed to alter, displace, or both alter and displace one or more video images of an environment surrounding the subject so that, when the one or more video images are displayed to the subject on the one or more visual displays of the augmented reality glasses, the one or more video images no longer depict an accurate representation of the environment surrounding the subject so as to perturb a visual input of the subject. For example, the data acquisition/data processing device 330 may be specially programmed to laterally, vertically, or rotationally displace the images of the environment surrounding the subject so that, when they are viewed by the subject using the one or more visual displays of the augmented reality glasses, the images of the environment are skewed relative to the actual environmental setting. As such, after being altered by the data acquisition/data processing device 330, the images of the environment surrounding the subject, as viewed by the subject through the augmented reality glasses, are visually distorted relative to the actual environment that the subject would see if he or she were looking directly at the environment and not wearing the augmented reality glasses. Thus, the manipulation of the images of the environment by the data acquisition/data processing device 330 results in the conveyance of a distorted view of reality to the subject, thereby perturbing the visual input of the subject.

In addition, in one or more alternative embodiments, it is to be understood that the augmented reality glasses may be used alone to perturb the subject's visual input, or in combination with a force measurement assembly (e.g., force measurement assembly 102 described herein). For example, the augmented reality glasses may be used to perturb the subject's visual input while the subject 108 is simultaneously displaced on the force measurement assembly 102 during the performance of a balance test, such as the SOT protocol or modified SOT protocol described herein.

Figure 51A:
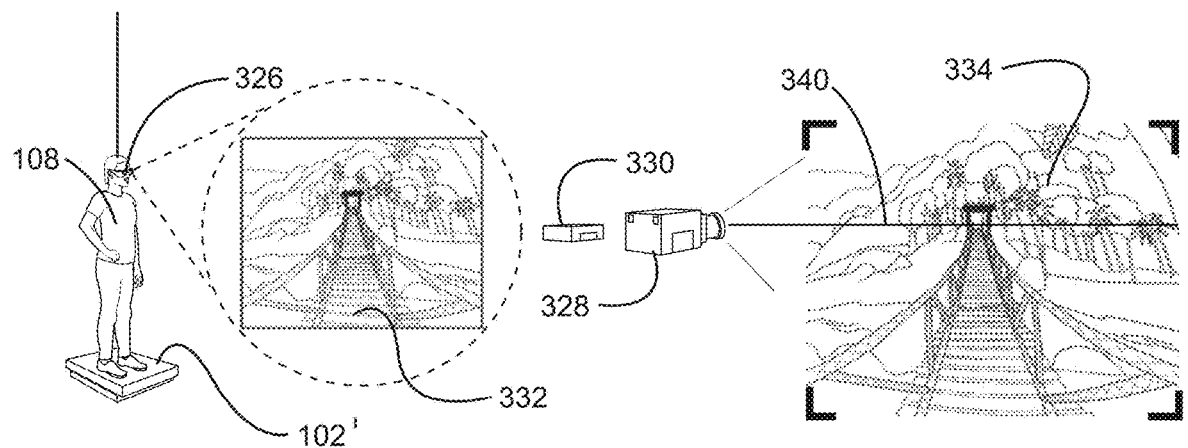
FIG. 51A is a first diagrammatic view of a subject wearing augmented reality glasses and disposed on a force measurement assembly, wherein the subject is disposed in an upright position on the force measurement assembly, and the image of the scenery viewed by the subject through the augmented reality glasses generally matches the actual view of the scenery captured by the camera(s) of the augmented reality glasses.
Figure 51B:
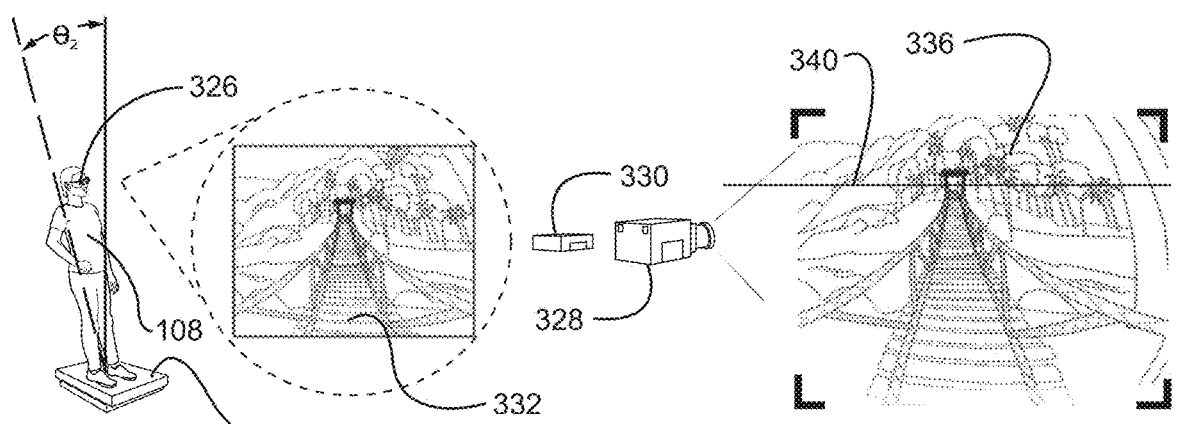
FIG. 51B is a second diagrammatic view of a subject wearing augmented reality glasses and disposed on a force measurement assembly, wherein the subject is in a rearwardly disposed sway angle position on the force measurement assembly, and the image of the scenery viewed by the subject through the augmented reality glasses has been modified so that it does not match that the actual view of the scenery captured by the camera(s) of the augmented reality glasses.
Figure 51C:
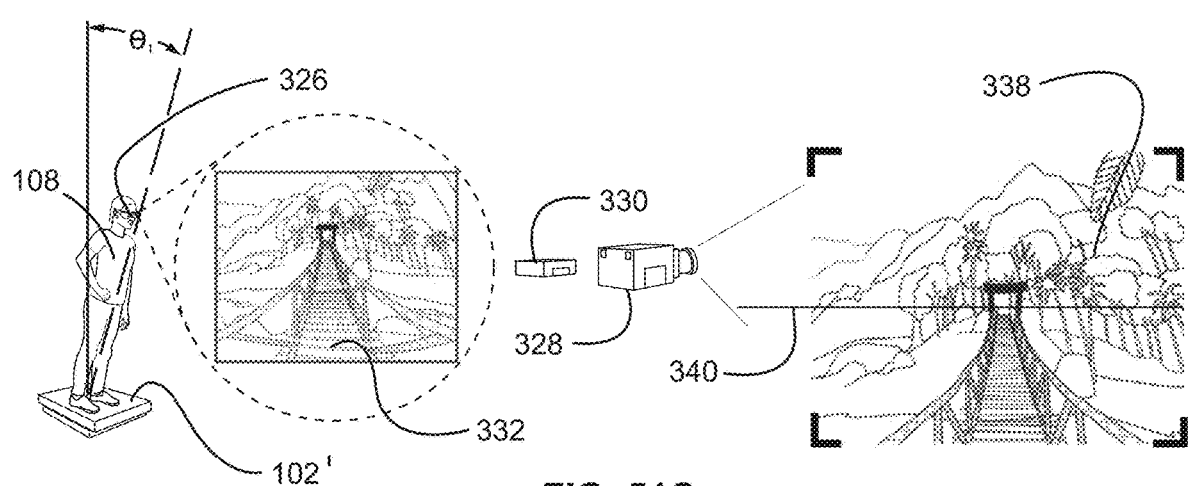
FIG. 51C is a third diagrammatic view of a subject wearing augmented reality glasses and disposed on a force measurement assembly, wherein the subject is in a forwardly disposed sway angle position on the force measurement assembly, and the image of the scenery viewed by the subject through the augmented reality glasses has been modified so that it does not match that the actual view of the scenery captured by the camera(s) of the augmented reality glasses.

In these one or more alternative embodiments, the data acquisition/data processing device 330 may also be specially programmed to perform the functionality that is illustrated in FIGS. 51A-51C. Initially, with reference to FIG. 51A, it can be seen that a subject 108 wearing augmented reality glasses 326 is disposed on a force measurement assembly 102' (i.e., a force plate) in a generally upright position (i.e., so that a vertical reference axis passing through the subject 108 is perpendicular to the top surface of the force plate 102). In the configuration of FIG. 51A, the screen image 332 that is viewed by the subject 108 through the augmented reality glasses 326 matches the actual view of the scenery 334 that is captured by the one or more cameras 328 of the augmented reality glasses 326. That is, in FIG. 51A, the scenery that is disposed in front of the one or more cameras 328 of the augmented reality glasses 326, and in front of the subject 108, is not altered by the data acquisition/data processing device 330 that is operatively coupled to the augmented reality glasses 326. A reference line 340 is superimposed on each of the screen images 334, 336, 338 in FIGS. 51A, 51B, 51C in order to more clearly illustrate the manner in which the image captured by the camera 328 is shifted when the subject 108 is in the sway angle $\theta_1$, $\theta_2$ positions on the force plate 102'.

Next, turning to FIG. 51B, it can be seen that the subject 108 who is wearing the augmented reality glasses 326 and is disposed on the force measurement assembly 102' (i.e., a force plate) is disposed in a rearwardly inclined sway angle position. That is, as illustrated in FIG. 51B, the longitudinal reference axis passing through the subject 108 is disposed at a rearward angle $\theta_2$ relative to a vertical reference axis that is disposed perpendicular to the force plate top surface. In the configuration of FIG. 51B, the screen image 332 that is viewed by the subject 108 through the augmented reality glasses 326 does not match the actual view of the scenery 336 that is captured by the one or more cameras 328 of the augmented reality glasses 326. Rather, in the scenario illustrated by FIG. 51B, the data acquisition/data processing device 330 that is operatively coupled to the augmented reality glasses 326 is specially programmed to alter the actual view captured by the one or more cameras 328 of the augmented reality glasses 326 so that subject 108 sees the exact same view through the glasses 326 that he would see if he were standing in a straight upright position on the force plate 102' (i.e., in the standing position of FIG. 51A). As such, by using the data acquisition/data processing device 330 to alter the actual view of the surrounding scenery that is captured by the one or more cameras 328 of the augmented reality glasses 326, the augmented reality system creates the illusion to the subject 108 that he has not moved at all (i.e., the subject's visual sense of perception is altered so that he is unable to perceive that he is disposed in a rearwardly inclined position). In the scenario of FIG. 51B, in order to make the screen image 332 that is viewed by the subject 108 through the augmented reality glasses 326 match the upright position image of FIG. 51A, the data acquisition/data processing device 330 is specially programmed to slightly enlarge and downwardly rotate the actual view of the scenery captured by the one or more cameras 328 of the augmented reality glasses 326 so as to correct for the rearwardly inclined orientation of the subject 108. In the FIG. 51B scenario, in order to determine the magnitude of the magnification and the downward rotation angle of the actual view of the scenery captured by the one or more cameras 328, the data acquisition/data processing device 330 may initially determine the center of pressure (COP) for the subject 108 from the force measurement assembly 102'. Then, in the manner described above, the data acquisition/data processing device 330 may determine the center of gravity (COG) for the subject based upon the center of pressure. After which, the sway angle $\theta_2$ may be determined for the subject 108 using the center of gravity (COG) in the manner described above (e.g., see equation (1) above). Finally, once the sway angle $\theta_2$ is determined for the subject 108, the displacement angle and magnification of the image of the surrounding environment displayed to the subject 108 using the augmented reality or reality-altering glasses 326 may be determined using geometric relationships between the sway angle $\theta_2$ of the subject 108 and the displacement angle of the video image of the surrounding environment captured by the one or more cameras 328 of the reality-altering glasses 326 (e.g., the sway angle $\theta_2$ of the subject 108 is generally equal to the displacement angle of the video image).

In an alternative embodiment, rather than enlarging and downwardly rotating the actual view of the scenery captured by the one or more cameras 328 of the reality-altering glasses 326, the data acquisition/data processing device 330 is specially programmed to capture an initial image of the environment surrounding the subject before the subject displaces his or her body into the rearwardly inclined sway angle position (i.e., while the subject is still standing in a straight upright position of FIG. 51A). Then, once the subject has displaced his or her body into the rearwardly inclined sway angle position of FIG. 51B, the data acquisition/data processing device 330 is specially programmed to display the initial image to the subject using the one or more visual displays of the reality-altering glasses 326 so as to create the illusion to the subject 108 that he or she is still in the straight upright position of FIG. 51A.

Next, turning to FIG. 51C, it can be seen that the subject 108 who is wearing the augmented reality glasses 326 and is disposed on the force measurement assembly 102' (i.e., a force plate) is disposed in a forwardly inclined sway angle position. That is, as illustrated in FIG. 51C, the longitudinal reference axis passing through the subject 108 is disposed at a forward angle $\theta_1$ relative to a vertical reference axis that is disposed perpendicular to the force plate top surface. In the configuration of FIG. 51C, the screen image 332 that is viewed by the subject 108 through the augmented reality glasses 326 does not match the actual view of the scenery 338 that is captured by the one or more cameras 328 of the augmented reality glasses 326. Rather, in the scenario illustrated by FIG. 51C, the data acquisition/data processing device 330 that is operatively coupled to the augmented reality glasses 326 is specially programmed to alter the actual view captured by the one or more cameras 328 of the augmented reality glasses 326 so that subject 108 sees the exact same view through the glasses 326 that he would see if he were standing in a straight upright position on the force plate 102' (i.e., in the standing position of FIG. 51A). As such, as described above with respect to FIG. 51B, by using the data acquisition/data processing device 330 to alter the actual view of the surrounding scenery that is captured by the one or more cameras 328 of the augmented reality glasses 326, the augmented reality system creates the illusion to the subject 108 that he has not moved at all (i.e., the subject's visual sense of perception is altered so that he is unable to perceive that he is disposed in a forwardly inclined position). In the scenario of FIG. 51C, in order to make the screen image 332 that is viewed by the subject 108 through the augmented reality glasses 326 match the upright position image of FIG. 51A, the data acquisition/data processing device 330 is specially programmed to slightly decrease and upwardly rotate the actual view of the scenery captured by the one or more cameras 328 of the augmented reality glasses 326 so as to correct for the forwardly inclined orientation of the subject 108. In the FIG. 51C scenario, similar to that described above for the FIG. 51B scenario, in order to determine the magnitude of the demagnification and the upward rotation angle of the actual view of the scenery captured by the one or more cameras 328, the data acquisition/data processing device 330 may initially determine the center of pressure (COP) for the subject 108 from the force measurement assembly 102'. Then, in the manner described above, the data acquisition/data processing device 330 may determine the center of gravity (COG) for the subject based upon the center of pressure. After which, the sway angle $\theta_1$ may be determined for the subject 108 using the center of gravity (COG) in the manner described above (e.g., see equation (1) above). Finally, once the sway angle $\theta_1$ is determined for the subject 108, the displacement angle and demagnification of the image of the surrounding environment displayed to the subject 108 using the augmented reality or reality-altering glasses 326 may be determined using geometric relationships between the sway angle $\theta_1$ of the subject 108 and the displacement angle of the video image of the surrounding environment captured by the one or more cameras 328 of the reality-altering glasses 326 (e.g., the sway angle $\theta_1$ of the subject 108 is generally equal to the displacement angle of the video image).

In an alternative embodiment, rather than decreasing and upwardly rotating the actual view of the scenery captured by the one or more cameras 328 of the reality-altering glasses 326, data acquisition/data processing device 330 is specially programmed to capture an initial image of the environment surrounding the subject before the subject displaces his or her body into the forwardly inclined sway angle position (i.e., while the subject is still standing in a straight upright position of FIG. 51A). Then, once the subject has displaced his or her body into the forwardly inclined sway angle position of FIG. 51C, the data acquisition/data processing device 330 is specially programmed to display the initial image to the subject using the one or more visual displays of the reality-altering glasses 326 so as to create the illusion to the subject 108 that he or she is still in the straight upright position of FIG. 51A.

Rather than using the stationary-type force measurement assembly 102' depicted in FIGS. 51A-51C, it is to be understood that, in one or more other embodiments, the displaceable force measurement assembly 102 described above may alternatively be used during the balance test described above, wherein the subject's visual input is perturbed using the reality-altering glasses 326. In these one or more other embodiments, because the displaceable force measurement assembly 102 is movably coupled to the base assembly 106, the rearwardly and forwardly inclined angular positions of the subject 108 (as shown in FIGS. 51B and 51C, respectively) may be achieved by rotating the force measurement assembly 102 with the subject 108 disposed thereon in accordance with a predetermined angle to achieve the forward and rearward angular displacements.

Figure 53:
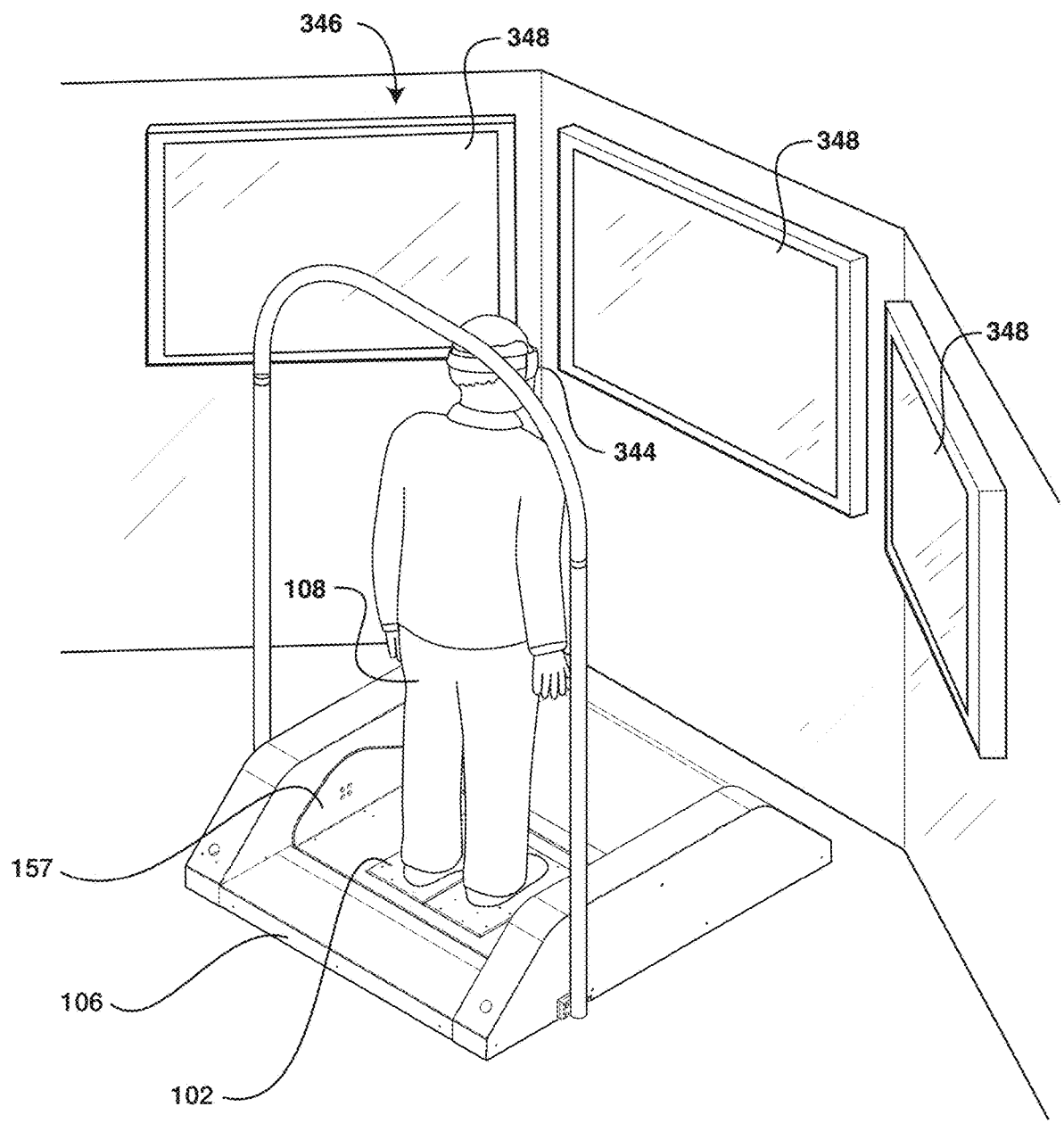
FIG. 53 is a perspective view of a subject wearing a head-mounted visual display device disposed on a displaceable force measurement assembly, according to still another alternative embodiment of the invention.

Further, in one or more alternative embodiments, the subject or patient 108 may be outfitted with another type of head-mounted visual display device that is different than the augmented reality glasses depicted in FIGS. 51A-51C. For example, as shown in FIG. 53, the subject 108 disposed on the base assembly 106 with displaceable force measurement assembly 102 may be outfitted with a head-mounted visual display device 344 with an output screen that at least partially circumscribes the head of the subject 108 such that the output screen of the head-mounted visual display device 344 engages enough of the peripheral vision of the subject 108 such that the subject 108 becomes immersed in the simulated environment created by the scenes displayed on the output screen. In one or more embodiments, the head-mounted visual display device may comprise a virtual reality headset or an augmented reality headset that has a wrap-around shape in order to at least partially circumscribe the head of the subject 108. The base assembly 106 and the displaceable force measurement assembly 102 depicted in FIG. 53 have the same constituent components and functionality as described above. In the embodiment of FIG. 53, similar to that described above, the displaceable force measurement assembly 102 may be operatively connected to a programmable logic controller (PLC) 172 and a data acquisition/data processing device 104. In this embodiment, the programmable logic controller (PLC) 172 and/or the data acquisition/data processing device 104 may be programmed to displace the force measurement assembly 102 so as to perturb a somatosensory or proprioceptive input of the subject 108 during the performance of a balance test (e.g., the Sensory Organization Test, the Adaptation Test, or the Motor Control Test) or training routine where one or more sensory inputs of the subject are modified. During the performance of a balance test or training routine where the force measurement assembly 102 is displaced, the data acquisition/data processing device 104 may be further programmed to utilize the output forces and/or moments computed from the output data of the force measurement assembly 102 in order to assess a response of the subject 108 to the displacement of the force measurement assembly 102. For example, to assess the response of the subject 108 during the performance of the balance test or training routine, the output forces and/or moments determined using the force measurement assembly 102 may be used to determine: (i) a quantitative score of the subject's sway during the trials of the test or training routine (e.g., see sway angle calculations described above), (ii) the type of strategy used by the subject 108 to maintain his or her balance (e.g., hip or ankle strategy) during the trials of the test or training routine, (iii) the changes in the center of gravity of the subject 108 during the trials of the test or training routine (e.g., refer to center of gravity determination described above), (iv) one or more quantitative sensory scores indicative of which sensory system(s) are impaired (i.e., indicative of whether one or more of the somatosensory, vestibular and visual systems are impaired), (v) the latency time of the subject 108 (e.g., the amount of time that it takes for the subject 108 to respond to a translational or rotational perturbation of the force measurement assembly 102), (vi) the weight symmetry of the subject 108 (i.e., how much weight is being placed on the right leg versus the left leg), (vii) the amount of force that the subject 108 is able to exert in order to bring his or her body back to equilibrium after a perturbation (e.g., the amount of force exerted by the subject 108 in response to a translational or rotational perturbation of the force measurement assembly 102), and (viii) the sway energy of the subject 108 in response to a perturbation (e.g., the anterior-posterior sway of the subject 108 in response to a translational or rotational perturbation of the force measurement assembly 102).

In one or more embodiments, the head-mounted visual display device 344 may have an organic light-emitting diode (OLED) display or liquid crystal display (LCD) with a resolution of at least 2160 pixels in the horizontal direction by 1200 pixels in the vertical direction (or 1080 by 1200 pixel resolution for each eye of the subject). Also, in one or more embodiments, the head-mounted visual display device 344 may have a refresh rate of at least 59 Hertz, or alternatively, at least 90 Hertz. In one or more further embodiments, the head-mounted visual display device 344 may have a refresh rate between approximately 59 Hertz and approximately 240 Hertz, inclusive (or between 59 Hertz and 240 Hertz, inclusive). Moreover, in one or more embodiments, the display latency or display time lag of the head-mounted visual display device 344 (i.e., amount of time that it takes for the pixels of the display to update in response to the head movement of the user) is between approximately 50 milliseconds and approximately 70 milliseconds, inclusive (or between 50 milliseconds and 70 milliseconds, inclusive). In one or more further embodiments, the head-mounted visual display device 344 may have a display latency or display time between approximately 10 milliseconds and approximately 50 milliseconds, inclusive (or between 10 milliseconds and 50 milliseconds, inclusive). Furthermore, in one or more embodiments, the data acquisition/data processing device 104 that is operatively coupled to the head-mounted visual display device 344 may execute a machine learning algorithm for predictive tracking of the subject's head movement so as to predict how the subject is going to move and pre-render the correct image for that view, thereby significantly decreasing the display latency or display time lag.

Also, in one or more embodiments, the head-mounted visual display device 344 may have a horizontal field of view of at least 50 degrees and a vertical field of view of at least 50 degrees. More particularly, in one or more further embodiments, the head-mounted visual display device 344 may have a horizontal field of view of at least 110 degrees and a vertical field of view of at least 90 degrees. In yet one or more further embodiments, the head-mounted visual display device 344 may have a horizontal field of view of at least 210 degrees and a vertical field of view of at least 130 degrees. In still one or more further embodiments, the head-mounted visual display device 344 may have a horizontal field of view between approximately 100 degrees and approximately 210 degrees, inclusive (or between 100 degrees and 210 degrees, inclusive), and a vertical field of view between approximately 60 degrees and approximately 130 degrees, inclusive (or between 60 degrees and 130 degrees, inclusive). Advantageously, maximizing the horizontal and vertical fields of view results in a more immersive experience for the subject because a greater portion of the subject's peripheral vision is covered.

In one or more embodiments, the head-mounted visual display device 344 may be operatively coupled to the data acquisition/data processing device 104 by one or more wired connections. For example, the video signal(s) for the head-mounted visual display device 344 may be transmitted using a high-definition multimedia interface (HDMI) cable and the data signal(s) for the head-mounted visual display device 344 may be transmitted using a Universal Serial Bus (USB) cable. The head-mounted visual display device 344 may also include a wired power connection. In one or more alternative embodiments, the head-mounted visual display device 344 may be operatively coupled to the data acquisition/data processing device 104 using a wireless connection rather than hardwired connection(s).

In one or more embodiments, in order to effectively handle the data processing associated with the head-mounted visual display device 344, the data acquisition/data processing device 104 coupled to the head-mounted visual display device 344 may have a high performance microprocessor, one or more high performance graphics cards, and sufficient random-access memory (RAM). For example, in an illustrative embodiment, the data acquisition/data processing device 104 coupled to the head-mounted visual display device 344 may have an Intel® Core i5 processor or greater, one or more NVIDIA® GeForce 900 series graphics processing units (GPU) or a higher series GPU, and eight (8) gigabytes of random-access memory (RAM) or greater.

In one or more embodiments, the head-mounted visual display device 344 may incorporate an integral inertial measurement unit (IMU) with an accelerometer, magnetometer, and gyroscope for sensing the head movement of the subject. Also, the head-mounted visual display device 344 may include optical-based outside-in positional tracking for tracking the position and orientation of the head-mounted visual display device 344 in real time. The optical-based outside-in positional tracking may include remote optical photosensors that detect infrared light-emitting diode (LED) markers on the head-mounted visual display device 344, or conversely, remote infrared light-emitting diode (LED) beams that are detected by photosensors on the head-mounted visual display device 344.

In one or more embodiments, the head-mounted visual display device 344 may be formed using lightweight materials (e.g., lightweight polymeric materials or plastics) so as to minimize the weight of the head-mounted visual display device 344 on the subject.

Referring again to FIG. 53, it can be seen that the force measurement system illustrated therein may also be provided with a wall-mounted visual display device 346 comprising a plurality of flat display screens 348 arranged or joined together in a concave arrangement so as to at least partially circumscribe the three sides of the torso of the subject 108. As such, rather than using the head-mounted visual display device 344, the scenes creating the simulated environment for the subject 108 may be displayed on the plurality of flat display screens 348 in FIG. 53. In an alternative embodiment, rather than using the plurality of flat display screens 348 arranged or joined together in the concave arrangement of FIG. 53, a continuously curved display screen may be used to display the immersive scenes to the subject 108, the curved display screen engaging enough of the peripheral vision of the subject 108 such that the subject 108 becomes immersed in the simulated environment. In another alternative embodiment, rather than using the plurality of flat display screens 348 arranged or joined together in the concave arrangement of FIG. 53 or a continuously curved display screen, a wall-mounted flat display screen may be used to display the immersive scenes to the subject 108. While in the aforedescribed alternative embodiments, these other visual display screens may be used with the base assembly 106 and the displaceable force measurement assembly 102 depicted in FIG. 53, it is to be understood that these other wall-mounted visual displays do not have an immersive effect that is equivalent to the generally hemispherical projection screen 168 described above because the subject 108 is not as encapsulated by these alternative visual displays (i.e., these alternative visual displays lack the wraparound side portions and wraparound top and bottom portions that are provided by the generally hemispherical projection screen 168).

As described above in conjunction with the preceding embodiments, the data acquisition/data processing device 104 of the force measurement system illustrated in FIG. 53 may further perturb the visual input of the subject 108 during the performance of the balance test or training routine by manipulating the scenes on the output screen of the visual display device. Also, in the embodiment of FIG. 53, and the other embodiments described above, the force measurement system may further comprise an eye movement tracking device configured to track eye movement and/or eye position of the subject 108 while the subject 108 performs the balance test or training routine (e.g., the eye movement tracking device 312 described hereinafter in conjunction with FIG. 50). In this embodiment, the eye movement tracking device outputs one or more eye tracking signals to the data acquisition/data processing device 104, and the data acquisition/data processing device 104 utilizes the eye tracking signals in order to assess a response of the subject 108 to the perturbed visual input (i.e., by measuring the eye movement of the subject 108 in response to a displaced image on the output screen of the visual display device). In one or more embodiments, the eye movement tracking device may be incorporated into the head-mounted visual display device 344 depicted in FIG. 53.

In yet one or more alternative embodiments of the invention, a force measurement assembly 102' in the form of a static force plate, such as that illustrated in FIG. 52, may be used with the head-mounted visual display device 344, rather than the displaceable force measurement assembly 102 and base assembly 106 of FIG. 53. Similar to that described above in conjunction with the preceding embodiments, the data acquisition/data processing device of the static force plate system may perturb the visual input of the subject during the performance of the balance test or training routine by manipulating the scenes on the output screen of the head-mounted visual display device 344. During the performance of the balance test or training routine while the subject is disposed on the static force plate, the data acquisition/data processing device may be further programmed to utilize the output forces and/or moments computed from the output data of the static force plate in order to assess a response of the subject to the visual stimuli on the output screen of the head-mounted visual display device 344. For example, to assess the response of the subject 108 during the performance of the balance test or training routine, the output forces and/or moments determined using the force measurement assembly 102 may be used to determine any of the scores or parameters (i)-(viii) described above in conjunction with the embodiment illustrated in FIG. 53.

In one or more embodiments, the data acquisition/data processing device 104 coupled to the head-mounted visual display device 344 is programmed to generate one or more scenes of a simulated and/or augmented environment displayed on the head-mounted visual display device 344, and further generate one or more clinician screens (e.g., one or more screens with test results) that are displayed on an additional visual display device visible to a clinician (e.g., operator visual display device 130 in FIG. 1). In these one or more embodiments, the one or more scenes of the simulated and/or augmented environment that are displayed on the head-mounted visual display device 344 comprise a plurality of targets or markers (e.g., the plurality of targets or markers 238' in FIG. 23) and at least one displaceable visual indicator (e.g., the displaceable visual indicator or cursor 240' in FIG. 23), and the data acquisition/data processing device 104 is programmed to control the movement of the at least one displaceable visual indicator 240' towards the plurality of targets or markers 238' based upon one or more computed numerical values (e.g., the center of pressure coordinates) determined using the output forces and/or moments of the force measurement assembly 102.

Figure 16:
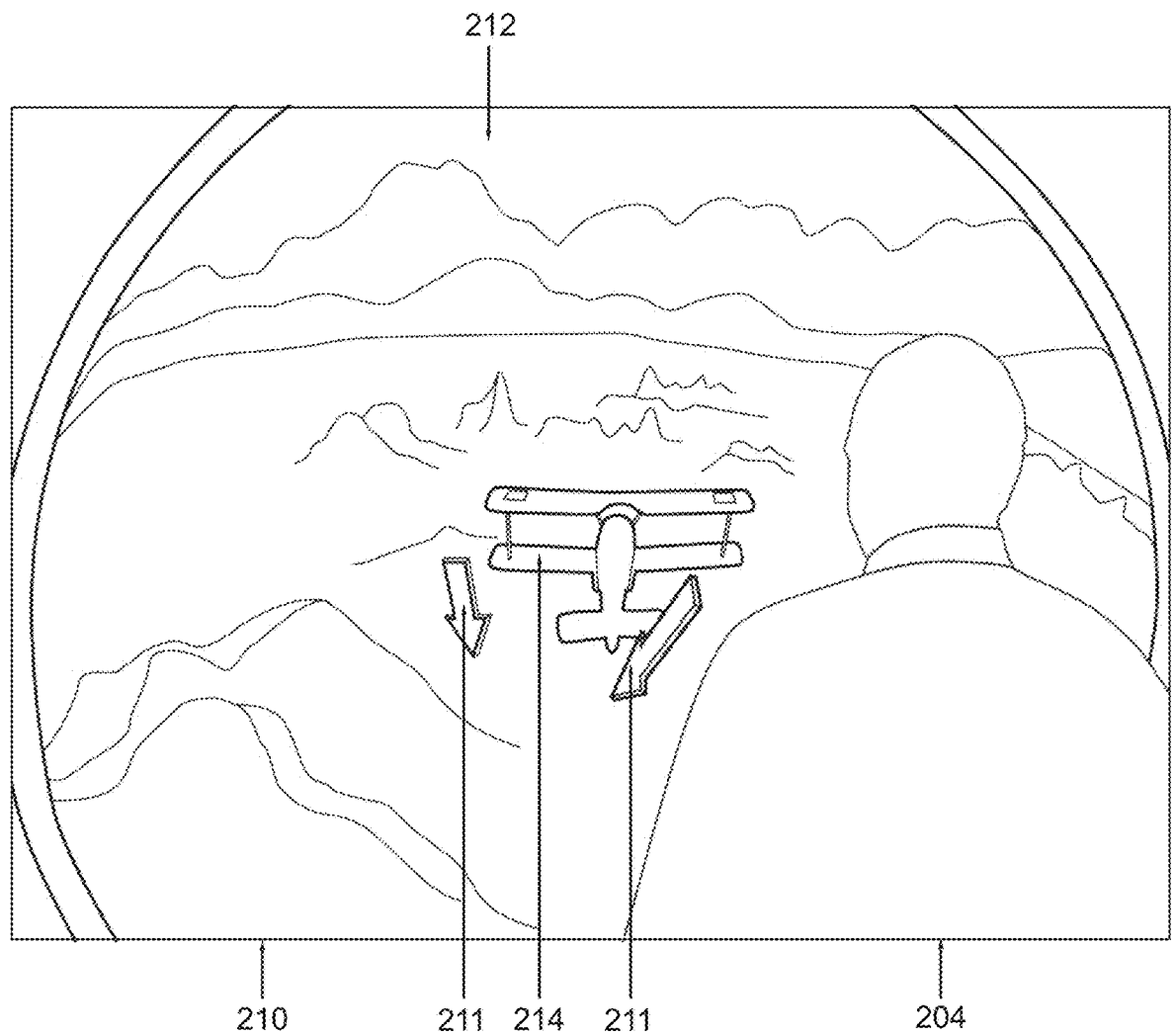
FIG. 16 is a first variation of an interactive game displayed on the subject visual display device of the force measurement system, according to an embodiment of the invention.
Figure 17:
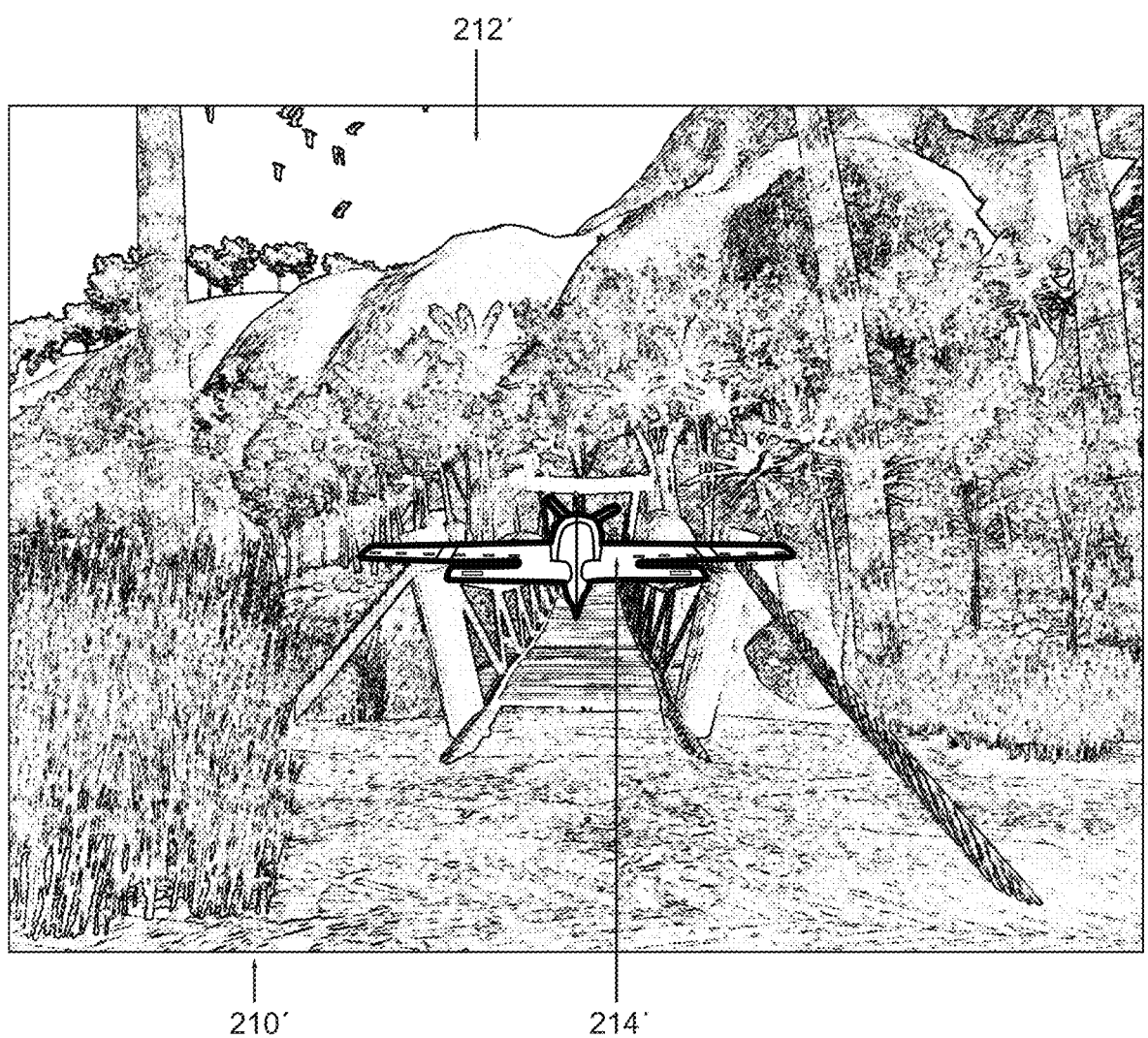
FIG. 17 is a second variation of an interactive game displayed on the subject visual display device of the force measurement system, according to an embodiment of the invention, wherein a game element is in a first position.
Figure 18:
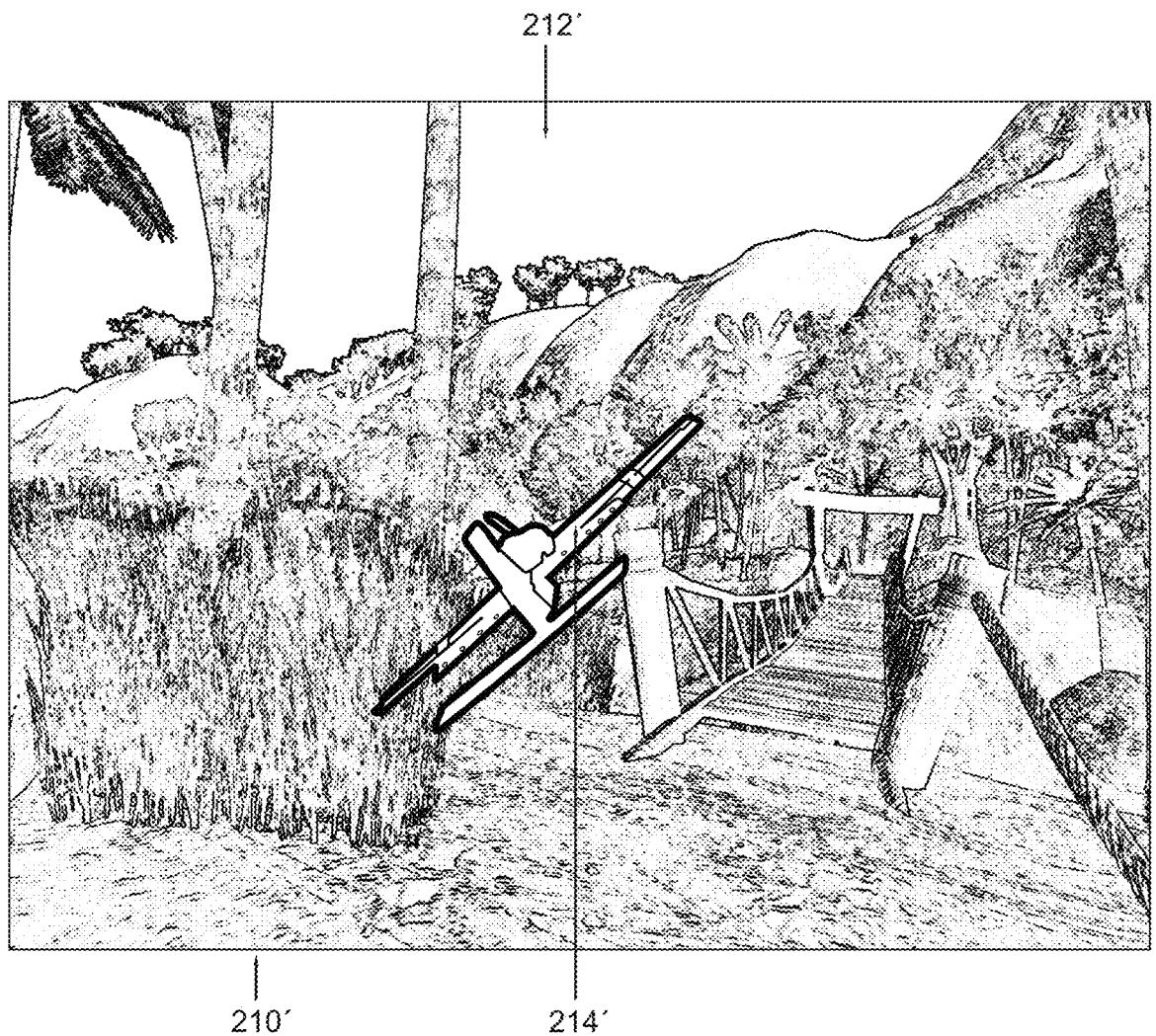
FIG. 18 is a second variation of an interactive game displayed on the subject visual display device of the force measurement system, according to an embodiment of the invention, wherein the game element is in a second position.
Figure 19:
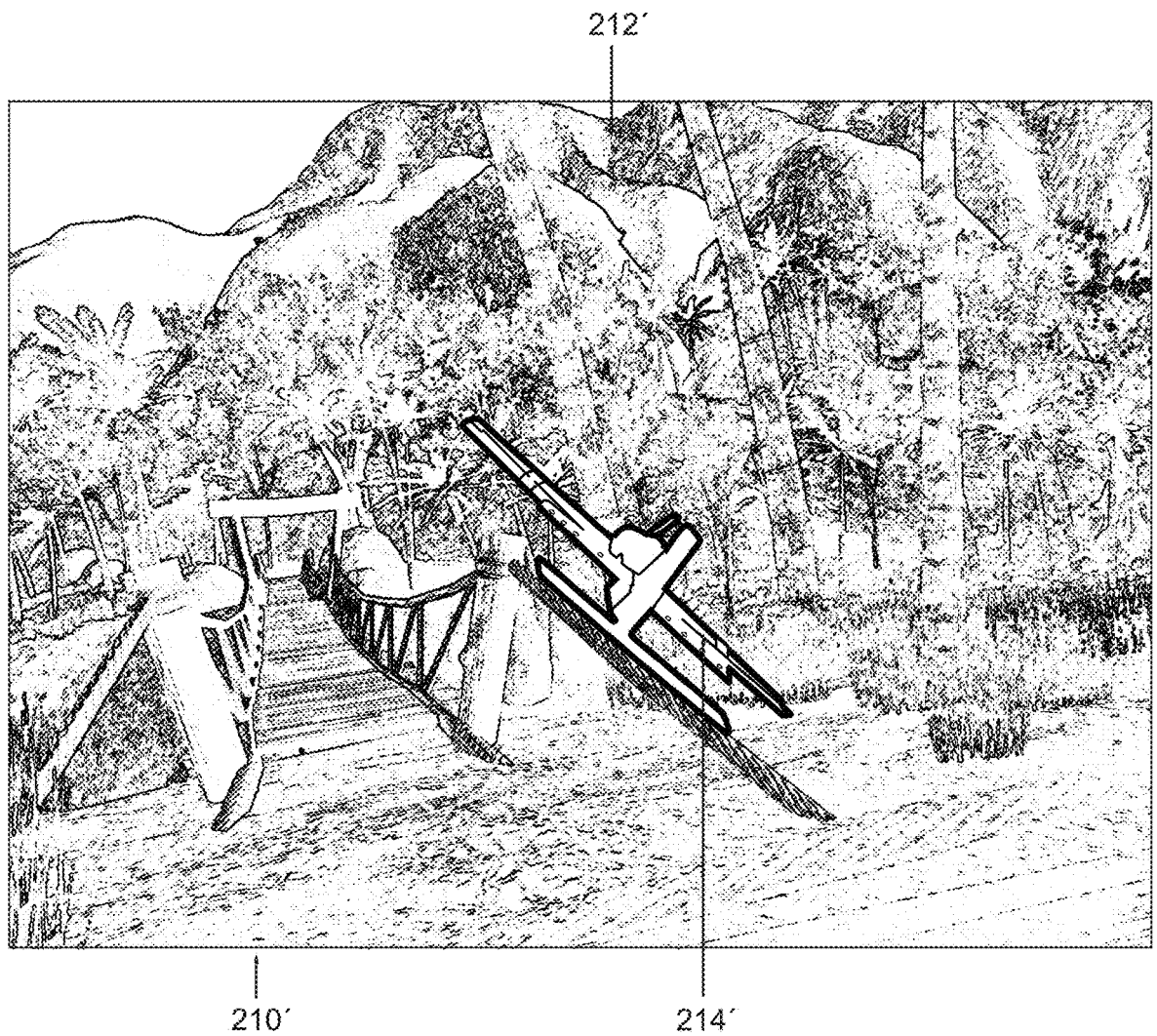
FIG. 19 is a second variation of an interactive game displayed on the subject visual display device of the force measurement system, according to an embodiment of the invention, wherein the game element is in a third position.
Figure 20:
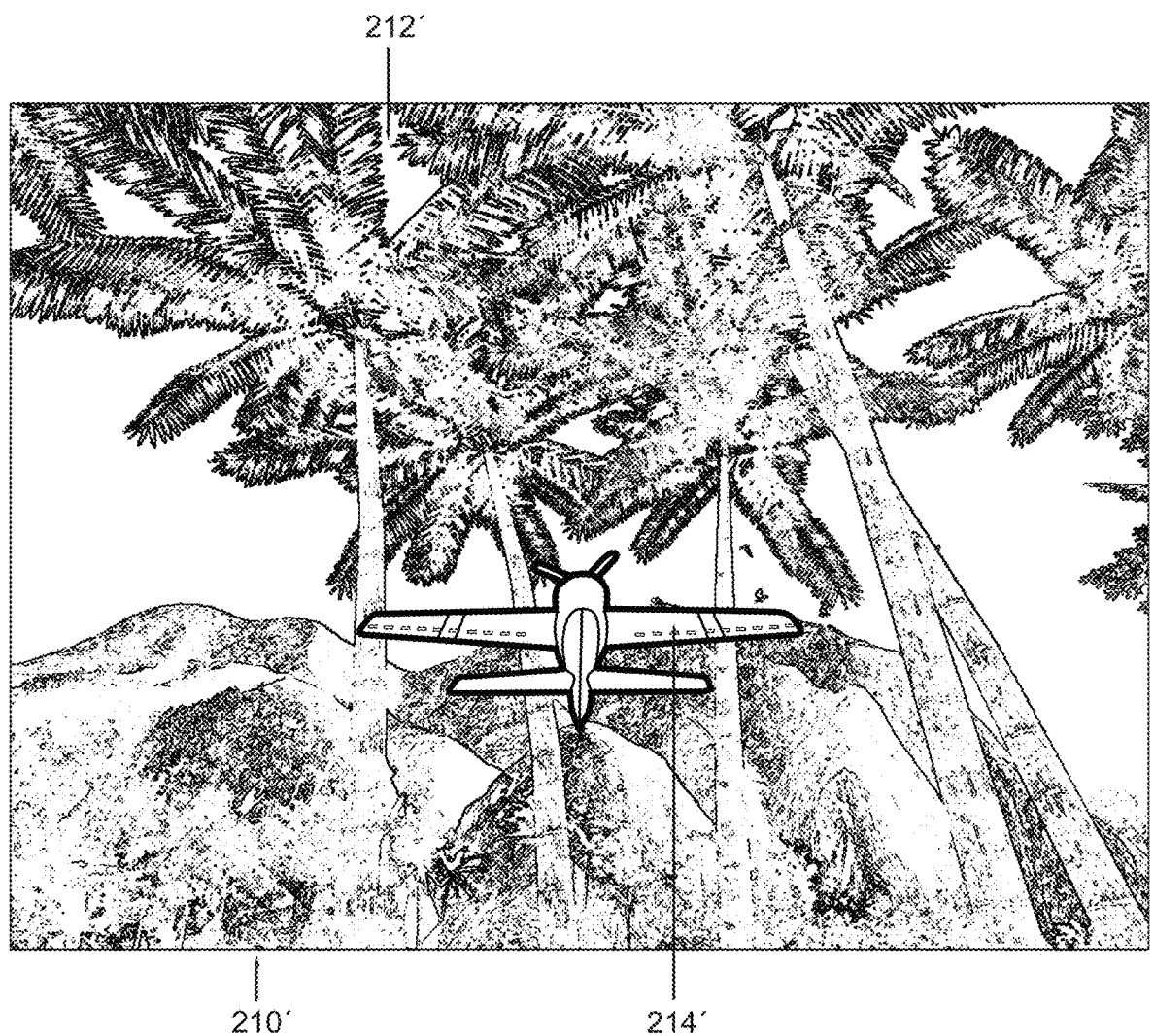
FIG. 20 is a second variation of an interactive game displayed on the subject visual display device of the force measurement system, according to an embodiment of the invention, wherein the game element is in a fourth position.
Figure 21:
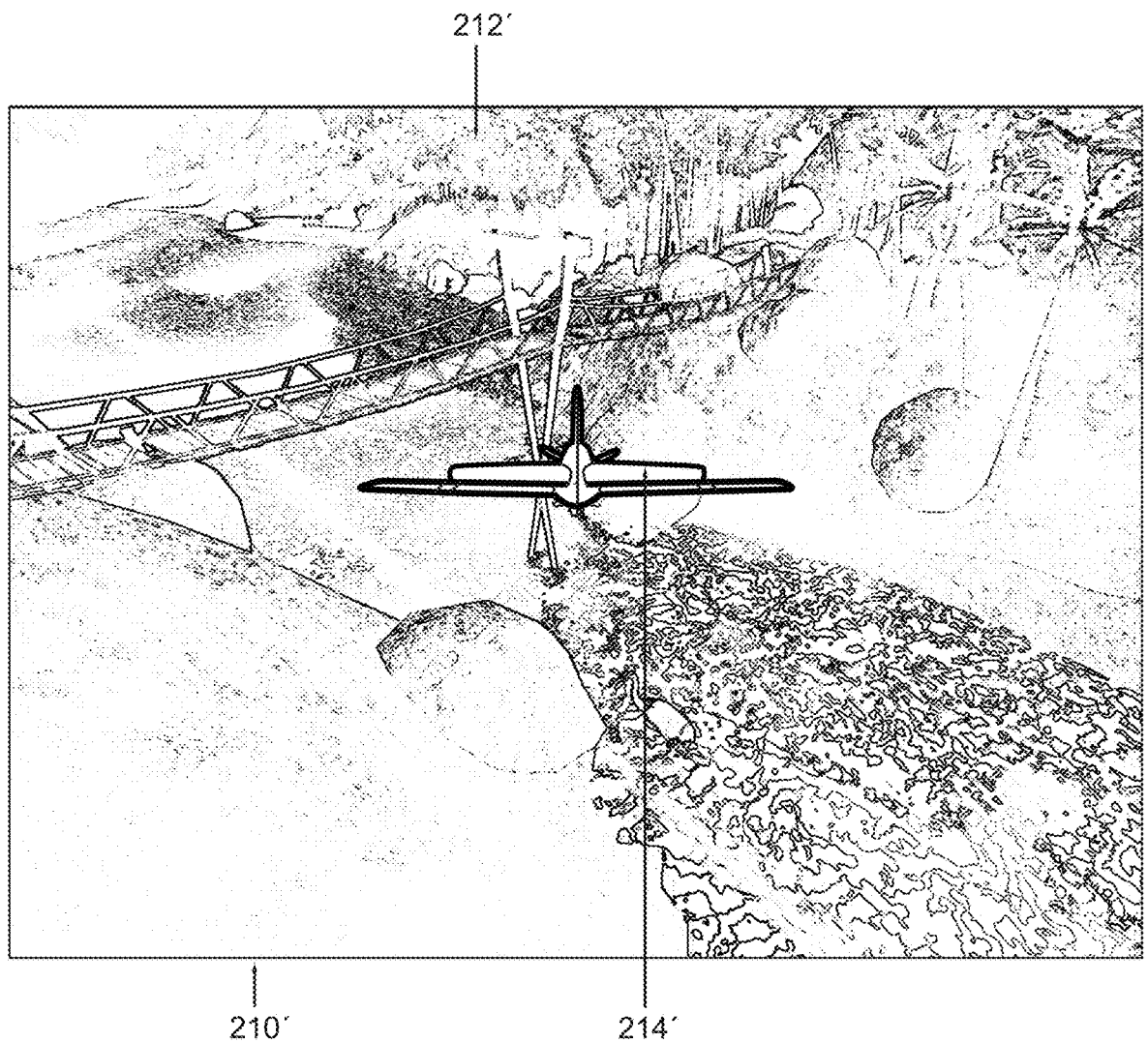
FIG. 21 is a second variation of an interactive game displayed on the subject visual display device of the force measurement system, according to an embodiment of the invention, wherein the game element is in a fifth position.

In further embodiments of the invention, the data acquisition/data processing device 104 is configured to control the movement of a game element of an interactive game displayed on the immersive subject visual display device 107 by using one or more numerical values determined from the output signals of the force transducers associated with the force measurement assembly 102. Referring to screen images 210, 210', 218 illustrated in FIGS. 16-21 and 27, it can be seen that the game element may comprise, for example, an airplane 214, 214' that can be controlled in a virtual reality environment 212, 212' or a skier 222 that is controlled in a virtual reality environment 220. With particular reference to FIG. 16, because a subject 204 is disposed within the confines of the generally hemispherical projection screen 168 while playing the interactive game, he or she is completely immersed in the virtual reality environment 212. FIG. 16 illustrates a first variation of this interactive game, whereas FIGS. 17-21 illustrate a second variation of this interactive game (e.g., each variation of the game uses a different airplane 214, 214' and different scenery). Although FIGS. 17-21 depict generally planar images, rather than a concave image projected on a generally hemispherical screen 168 as shown in FIG. 16, it is to be understood that the second variation of the interactive game (FIGS. 17-21) is equally capable of being utilized on a screen that at least partially surrounds a subject (e.g., a generally hemispherical projection screen 168). In the first variation of the interactive airplane game illustrated in FIG. 16, arrows 211 can be provided in order to guide the subject 204 towards a target in the game. For example, the subject 204 may be instructed to fly the airplane 214 through one or more targets (e.g., rings or hoops) in the virtual reality environment 212. When the airplane is flown off course by the subject 204, arrows 211 can be used to guide the subject 204 back to the general vicinity of the one or more targets.

Figure 25:
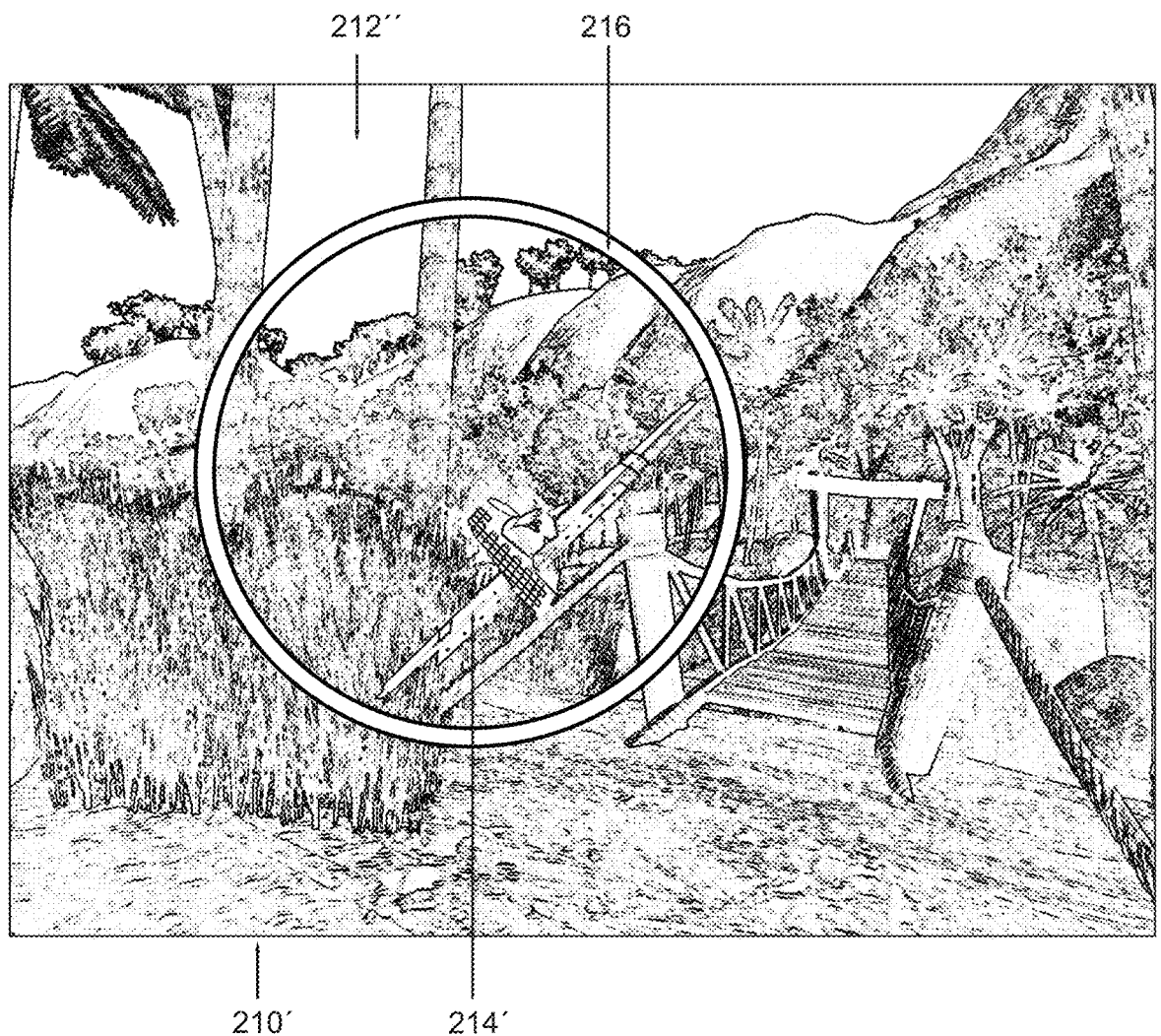
FIG. 25 is a third variation of an interactive game displayed on the subject visual display device of the force measurement system, according to an embodiment of the invention, wherein the interactive game is provided with one or more targets and a game element is in a first position.
Figure 26:
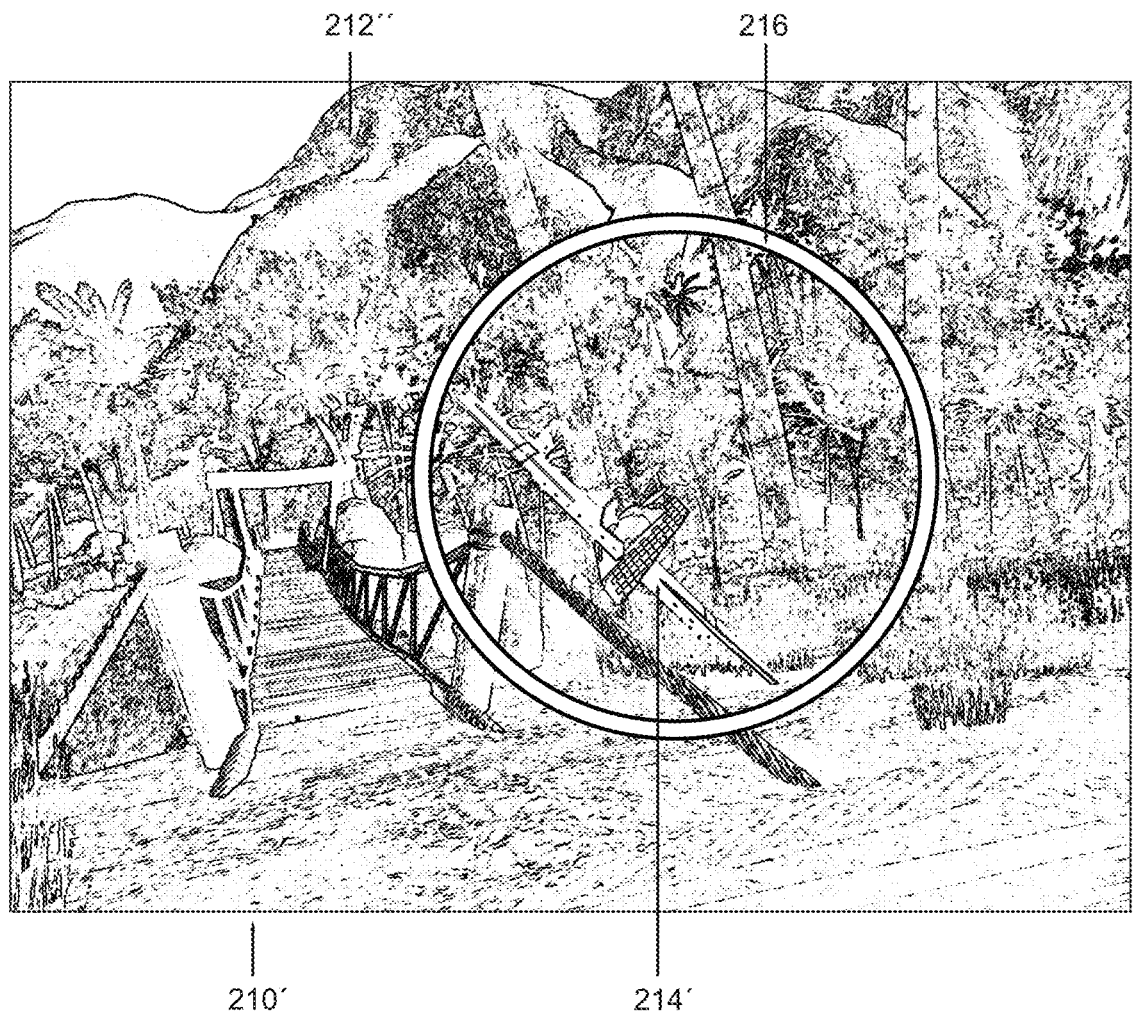
FIG. 26 is a third variation of an interactive game displayed on the subject visual display device of the force measurement system, according to an embodiment of the invention, wherein the interactive game is provided with one or more targets and the game element is in a second position.
Figure 27:
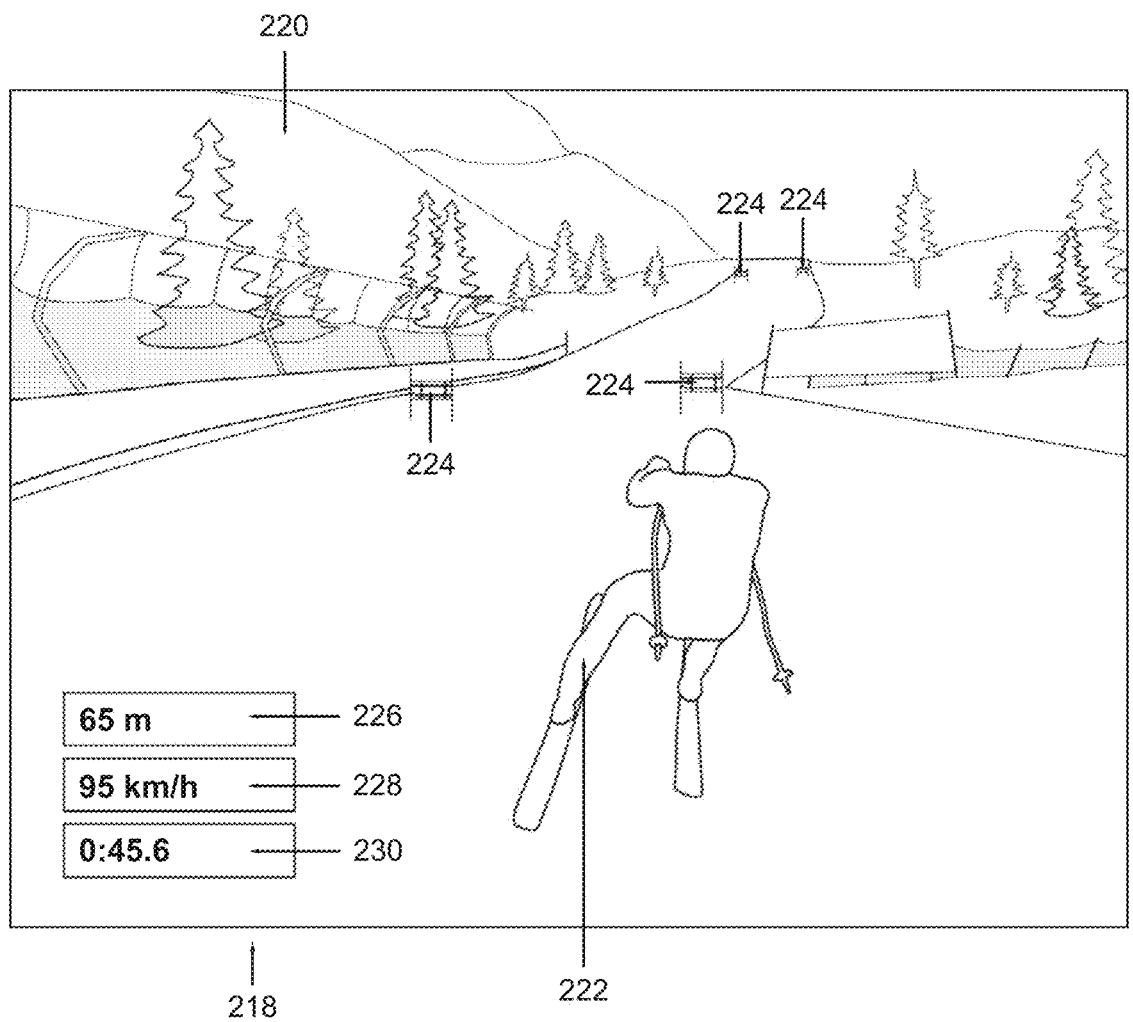
FIG. 27 is another example of an interactive game displayed on the subject visual display device of the force measurement system, according to an embodiment of the invention, wherein the interactive game is in the form of an interactive skiing game.

With reference to FIGS. 25 and 26, a target in the form of a ring or hoop 216 is illustrated in conjunction with the second variation of the interactive airplane game. In this virtual reality scenario 212", a subject is instructed to fly the airplane 214' through the ring 216. In FIG. 25, the airplane 214' is being displaced to the left by the subject through the ring 216, whereas, in FIG. 26, the airplane 214' is being displaced to the right by the subject through the ring 216. Advantageously, the airplane simulation game is a type of training that is more interactive for the patient. An interactive type of training, such as the airplane simulation game, improves patient compliance by more effectively engaging the subject in the training. In addition, in order to further increase patient compliance, and ensure that the subject exerts his or her full effort, a leaderboard with scores may be utilized in the force measurement system 100. To help ensure subject performance comparisons that are fair to the participants, separate leaderboards may be utilized for different age brackets.

In some embodiments, the position of the rings or hoops 216 in the virtual reality scenario 212" could be selectively displaceable in a plurality of different positions by a user or operator of the system 100. For example, the data acquisition/data processing device 104 could be specially programmed with a plurality of predetermined difficulty levels for the interactive airplane game. A novice difficulty level could be selected by the user or operator of the system 100 for a subject that requires a low level of difficulty. Upon selecting the novice difficulty level, the rings or hoops 216 would be placed in the easiest possible locations within the virtual reality scenario 212". For a subject requiring a higher level of difficulty, the user or operator of the system 100 could select a moderate difficulty level, wherein the rings or hoops 216 are placed in locations that are more challenging than the locations used in the novice difficulty level. Finally, if a subject requires a maximum level of difficulty, the user or operator could select a high difficulty level, wherein the rings or hoops 216 are placed in extremely challenging locations in the virtual reality scenario 212". In addition, in some embodiments, the position of the rings or hoops 216 in the virtual reality scenario 212" could be randomly located by the data acquisition/data processing device 104 so that a subject undergoing multiple training sessions using the interactive airplane game would be unable to memorize the locations of the rings or hoops 216 in the scenario 212", thereby helping to ensure the continued effectiveness of the training.

In yet a further embodiment of the invention, the interactive type of subject or patient training may comprise an interactive skiing game. For example, as illustrated in the screen image 218 of FIG. 27, the immersive virtual reality environment 220 may comprise a scenario wherein the subject controls a skier 222 on a downhill skiing course. Similar to the interactive airplane game described above, the interactive skiing game may comprise a plurality of targets in the forms of gates 224 that the subject is instructed to contact while skiing the downhill course. To make the interactive skiing game even more engaging for the subject, a plurality of game performance parameters may be listed on the screen image, such as the total distance traveled 226 (e.g., in meters), the skier's speed 228 (e.g., in kilometers per hour), and the skier's time 230 (e.g., in seconds).

In an illustrative embodiment, the one or more numerical values determined from the output signals of the force transducers associated with the force measurement assembly 102 comprise the center of pressure coordinates $(x_P, y_P)$ computed from the ground reaction forces exerted on the force plate assembly 102 by the subject. For example, with reference to the force plate coordinate axes 150, 152 of FIG. 7, when a subject leans to the left on the force measurement assembly 102' (i.e., when the x-coordinate $x_P$ of the center of pressure is positive), the airplane 214' in the interactive airplane game is displaced to the left (see e.g., FIG. 18) or the skier 222 in the interactive skiing game is displaced to the left (see e.g., FIG. 27). Conversely, when a subject leans to the right on the force measurement assembly 102' (i.e., when the x-coordinate $x_P$ of the center of pressure is negative in FIG. 7), the airplane 214' in the interactive airplane game is displaced to the right (see e.g., FIG. 19) or the skier 222 in the interactive skiing game is displaced to the right (see e.g., FIG. 27). When a subject leans forward on the force measurement assembly 102' (i.e., when the y-coordinate $y_P$ of the center of pressure is positive in FIG. 7), the altitude of the airplane 214' in the interactive airplane game is increased (see e.g., FIG. 20) or the speed of the skier 222 in the interactive skiing game is increased (see e.g., FIG. 27). Conversely, when a subject leans backward on the force measurement assembly 102' (i.e., when the y-coordinate $y_P$ of the center of pressure is negative in FIG. 7), the altitude of the airplane 214' in the interactive airplane game is decreased (see e.g., FIG. 21) or the speed of the skier 222 in the interactive skiing game is decreased (see e.g., FIG. 27).

Figure 32:
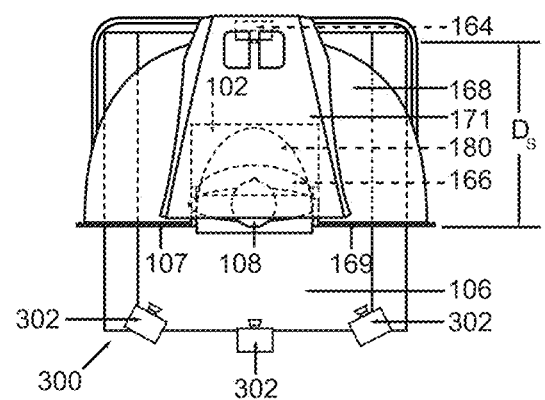
FIG. 32 is a diagrammatic top view of a force and motion measurement system having a motion acquisition/capture system, according to an embodiment of the invention, wherein the motion acquisition/capture system is illustrated with the base assembly, the immersive subject visual display device, and a subject having a plurality of markers disposed thereon.
Figure 33:
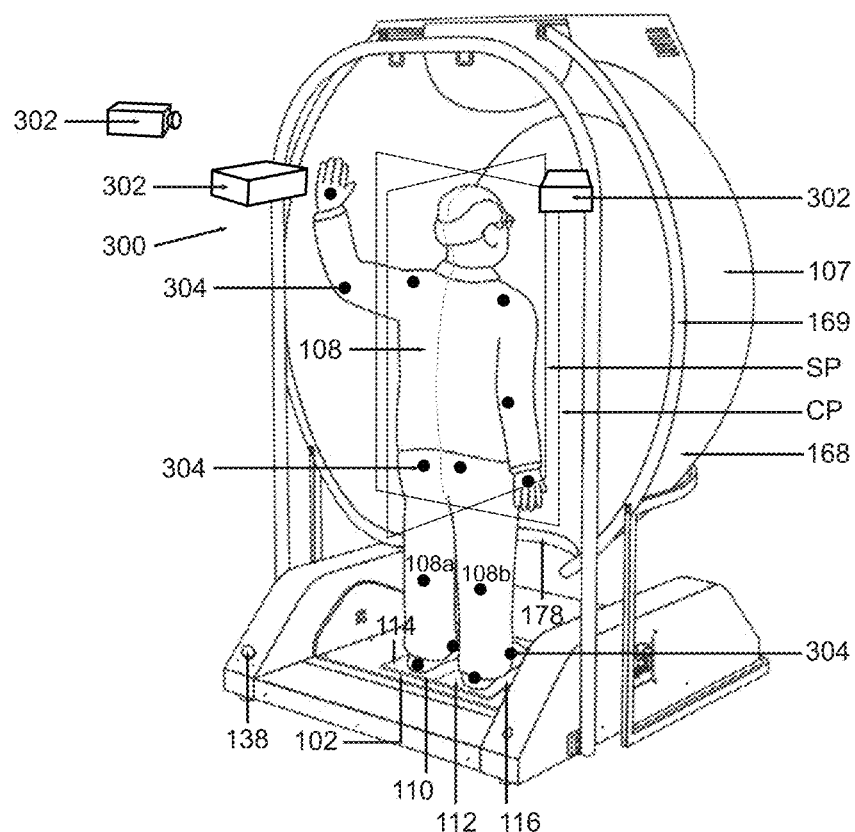
FIG. 33 is a perspective view of a force and motion measurement system having a motion acquisition/capture system, according to an embodiment of the invention, wherein the motion acquisition/capture system is illustrated with the base assembly, the immersive subject visual display device, and a subject having a plurality of markers disposed thereon.

In still a further embodiment, a force and motion measurement system is provided that includes both the force measurement system 100 described above together with a motion detection system 300 that is configured to detect the motion of one or more body gestures of a subject (see FIGS. 32 and 33). For example, during a particular training routine, a subject may be instructed to reach for different targets on the output screen 168. While the subject reaches for the different targets on the output screen 168, the motion detection system 300 detects the motion of the subject's body gestures (e.g., the motion detection system 300 tracks the movement of one of the subject's arms while reaching for an object on the output screen 168). As shown in FIG. 33, a subject 108 is provided with a plurality of markers 304 disposed thereon. These markers 304 are used to record the position of the limbs of the subject in 3-dimensional space. A plurality of cameras 302 are disposed in front of the subject visual display device 107 (and behind the subject 108), and are used to track the position of the markers 304 as the subject moves his or her limbs in 3-dimensional space. While three (3) cameras are depicted in FIGS. 32 and 33, one of ordinary skill in the art will appreciate that more or less cameras can be utilized, provided that at least two cameras 302 are used. In one embodiment of the invention, the subject has a plurality of single markers applied to anatomical landmarks (e.g., the iliac spines of the pelvis, the malleoli of the ankle, and the condyles of the knee), or clusters of markers applied to the middle of body segments. As the subject 108 executes particular movements on the force measurement assembly 102, and within the hemispherical subject visual display device 107, the data acquisition/data processing device 104 calculates the trajectory of each marker 304 in three (3) dimensions. Then, once the positional data is obtained using the motion detection system 300 (i.e., the motion acquisition/capture system 300), inverse kinematics can be employed in order to determine the joint angles of the subject 108.

Figure 50:
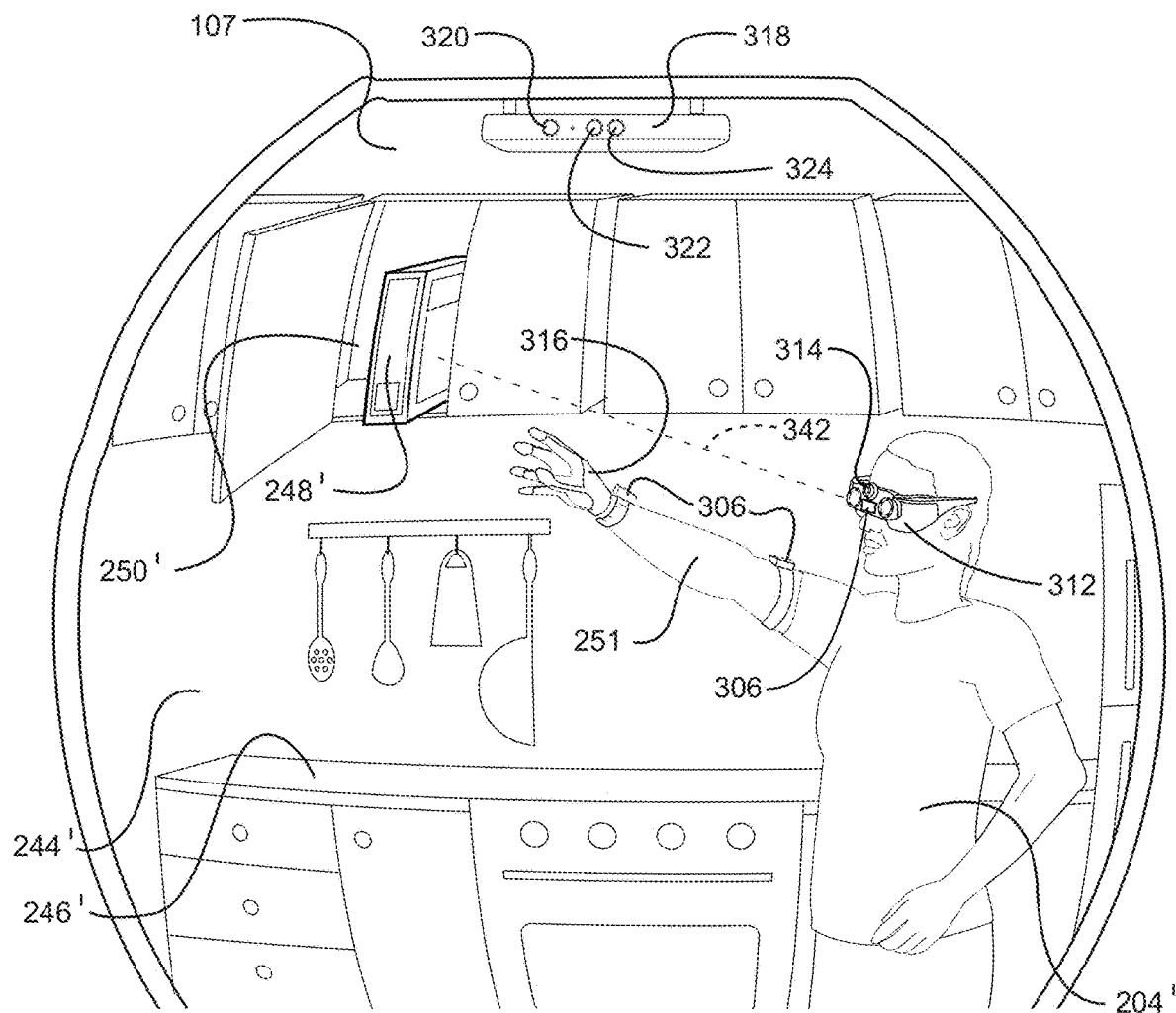
FIG. 50 is a perspective view of a subject interacting with a virtual reality scene displayed on the subject visual display device of the force measurement system, wherein the subject is outfitted with an eye movement tracking device having a field-of-view camera and an inertial measurement unit attached thereto.

While the motion detection system 300 described above employs a plurality of markers 304, it is to be understood that the invention is not so limited. Rather, in another embodiment of the invention, a markerless motion detection/motion capture system is utilized. The markerless motion detection/motion capture system uses a plurality of high speed video cameras to record the motion of a subject without requiring any markers to be placed on the subject. Both of the aforementioned marker and markerless motion detection/motion capture systems are optical-based systems. In one embodiment, the optical motion detection/motion capture system 300 utilizes visible light, while in another alternative embodiment, the optical motion detection/motion capture system 300 employs infrared light (e.g., the system 300 could utilize an infrared (IR) emitter to project a plurality of dots onto objects in a particular space as part of a markless motion capture system). For example, as shown in FIG. 50, a motion capture device 318 with one or more cameras 320, one or more infrared (IR) depth sensors 322, and one or more microphones 324 may be used to provide full-body three-dimensional (3D) motion capture, facial recognition, and voice recognition capabilities. It is also to be understood that, rather than using an optical motion detection/capture system, a suitable magnetic or electro-mechanical motion detection/capture system can also be employed in the system 100 described herein.

Figure 37:
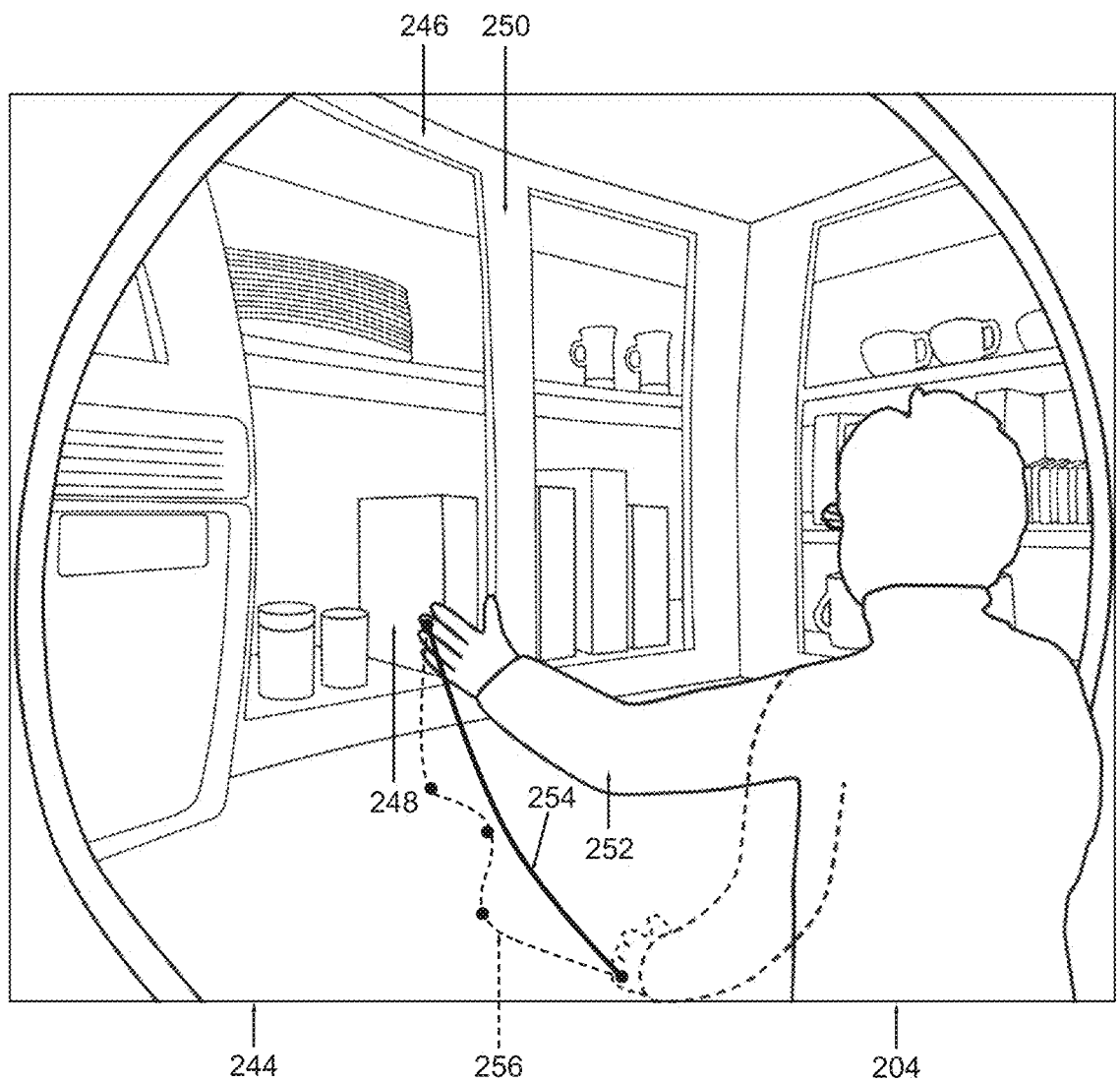
FIG. 37 is a third example of a virtual reality scene displayed on the subject visual display device of the force measurement system, according to an embodiment of the invention.

In some embodiments, the motion detection system 300, which is shown in FIGS. 32 and 33, is used to determine positional data (i.e., three-dimensional coordinates) for one or more body gestures of the subject 108 during the performance of a simulated task of daily living. The one or more body gestures of the subject 108 may comprise at least one of: (i) one or more limb movements of the subject, (ii) one or more torso movements of the subject, and (iii) a combination of one or more limb movements and one or more torso movements of the subject 108. In order to simulate a task of daily living, one or more virtual reality scenes can be displayed on the subject visual display device 107. One such exemplary virtual reality scene is illustrated in FIG. 37. As illustrated in the screen image 244 of FIG. 37, the immersive virtual reality environment 246 simulating the task of daily living could comprise a scenario wherein a subject 204 is removing an object 248 (e.g., a cereal box) from a kitchen cabinet 250. While the subject 204 is performing this simulated task, the data acquisition/data processing device 104 could quantify the performance of the subject 204 during the execution of the task (e.g., removing the cereal box 248 from the kitchen cabinet 250) by analyzing the motion of the subject's left arm 252, as measured by the motion detection system 300. For example, by utilizing the positional data obtained using the motion detection system 300, the data acquisition/data processing device 104 could compute the three-dimensional (3-D) trajectory of the subject's left arm 252 through space. The computation of the 3-D trajectory of the subject's left arm 252 is one exemplary means by which the data acquisition/data processing device 104 is able to quantify the performance of a subject during the execution of a task of daily living. At the onset of the training for a subject 204, the 3-D trajectory of the subject's left arm 252 may indicate that the subject 204 is taking an indirect path (i.e., a zigzag path or jagged path 256 indicated using dashed lines) in reaching for the cereal box 248 (e.g., the subject's previous injury may be impairing his or her ability to reach for the cereal box 248 in the most efficient manner). However, after the subject 204 has been undergoing training for a continuous period of time, the 3-D trajectory of the subject's left arm 252 may indicate that the subject 204 is taking a more direct path (i.e., an approximately straight line path 254) in reaching for the cereal box 248 (e.g., the training may be improving the subject's ability to reach for the cereal box 248 in an efficient fashion). As such, based upon a comparison of the subject's left arm trajectory paths, a physical therapist treating the subject or patient 204 may conclude that the subject's condition is improving over time. Thus, advantageously, the motion detection system 300 enables a subject's movement to be analyzed during a task of daily living so that a determination can be made as to whether or not the subject's condition is improving.

Figure 34:
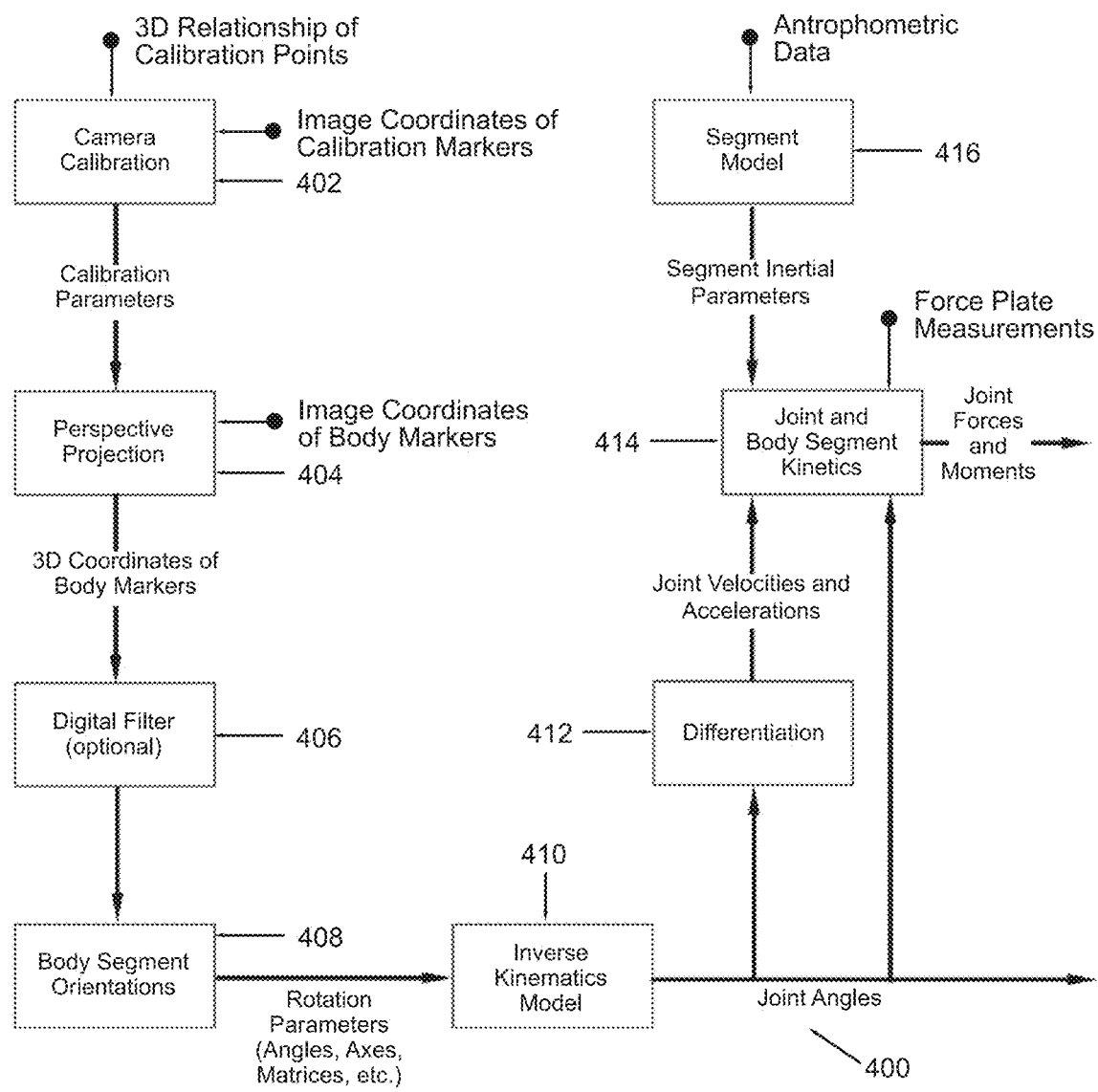
FIG. 34 is a block diagram illustrating a calculation procedure for the joint angles, velocities, and accelerations, and a calculation procedure for the joint forces and moments, both of which are carried out by the force and motion measurement system according to an embodiment of the invention.

Moreover, in other embodiments, the motion detection system 300 may also be used to determine the forces and/or moments acting on the joints of a subject 108. In particular, FIG. 34 diagrammatically illustrates an exemplary calculation procedure 400 for the joint angles, velocities, and accelerations carried out by the force and motion measurement system that includes the motion detection system 300 depicted in FIGS. 32 and 33. Initially, as shown in block 402 of FIG. 34, the plurality of cameras 302 are calibrated using the image coordinates of calibration markers and the three-dimensional (3-D) relationship of calibration points such that a plurality of calibration parameters are generated. In one exemplary embodiment of the invention, the calibration of the plurality of cameras 302 is performed using a Direct Linear Transformation ("DLT") technique and yields eleven (11) DLT parameters. However, it is to be understood that, in other embodiments of the invention, a different technique can be used to calibrate the plurality of cameras 302. Then, in block 404, the perspective projection of the image coordinates of the body markers 304 is performed using the calibration parameters so that the image coordinates are transformed into actual three-dimensional (3-D) coordinates of the body markers 304. Because the digitization of the marker images involves a certain amount of random error, a digital filter is preferably applied to the three-dimensional (3-D) coordinates of the markers to remove the inherent noise in block 406. Although, it is to be understood that the use of a digital filter is optional, and thus is omitted in some embodiments of the invention. In block 408, local coordinate systems are utilized to determine the orientation of the body segments relative to each other. After which, in block 410, rotational parameters (e.g., angles, axes, matrices, etc.) and the inverse kinematics model are used to determine the joint angles. The inverse kinematics model contains the details of how the angles are defined, such as the underlying assumptions that are made regarding the movement of the segments relative to each other. For example, in the inverse kinematics model, the hip joint could be modeled as three separate revolute joints acting in the frontal, horizontal, and sagittal plane, respectively. In block 412, differentiation is used to determine the joint velocities and accelerations from the joint angles. Although, one of ordinary skill in the art will appreciate that, in other embodiments of the invention, both differentiation and analytical curve fitting could be used to determine the joint velocities and accelerations from the joint angles.

In addition, FIG. 34 diagrammatically illustrates the calculation procedure for the joint forces and moments that is also carried out by the force and motion measurement system, which comprises the force measurement system 100 and motion detection system 300 of FIGS. 32-33. Referring again to this figure, antrophometric data is applied to a segment model in block 416 in order to determine the segment inertial parameters. By using the segment inertial parameters together with the joint velocities and accelerations and the force plate measurements, joint and body segment kinetics are used in block 414 to determine the desired joint forces and moments. In a preferred embodiment of the invention, Newton-Euler Formulations are used to compute the joint forces and moments. However, it is to be understood that the invention is not so limited. Rather, in other embodiments of the invention, the kinetics analysis could be carried out using a different series of equations. In order to more clearly illustrate the requisite calculations for determining the joint forces and moments, the determination of the joint reaction forces and joint moments of the subject will be explained using an exemplary joint of the body.

In particular, the computation of the joint reaction forces and joint moments of the subject will be described in reference to an exemplary determination of the forces and moments acting on the ankle. The force measurement assembly 102 is used to determine the ground reaction forces and moments associated with the subject being measured. These ground reaction forces and moments are used in conjunction with the joint angles computed from the inverse kinematics analysis in order to determine the net joint reaction forces and net joint moments of the subject. In particular, inverse dynamics is used to calculate the net joint reaction forces and net joint moments of the subject by using the computed joint angles, angular velocities, and angular accelerations of a musculoskeletal model, together with the ground reaction forces and moments measured by the force measurement assembly 102.

Figure 35:
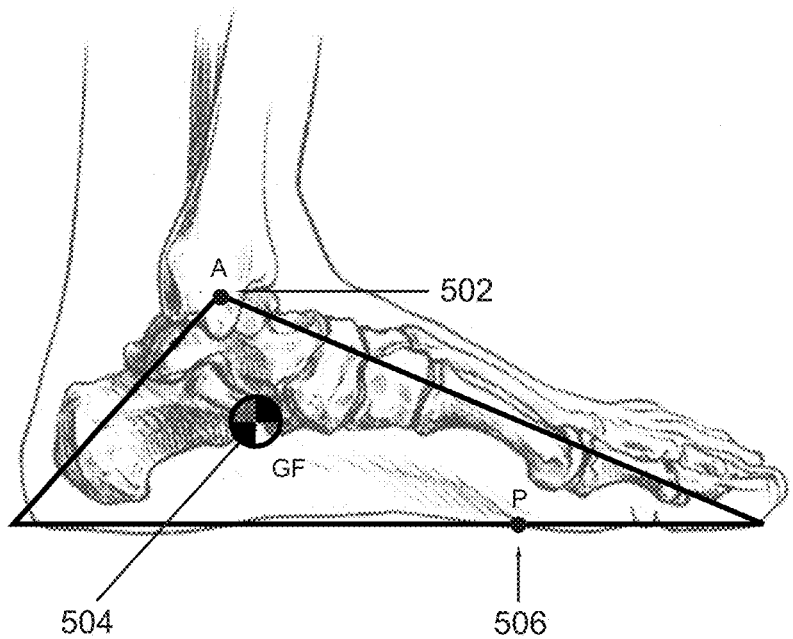
FIG. 35 is a diagrammatic view of a human foot and its typical bone structure with certain elements of the free body diagram of FIG. 36 superimposed thereon, according to an exemplary embodiment of the invention.
Figure 36:
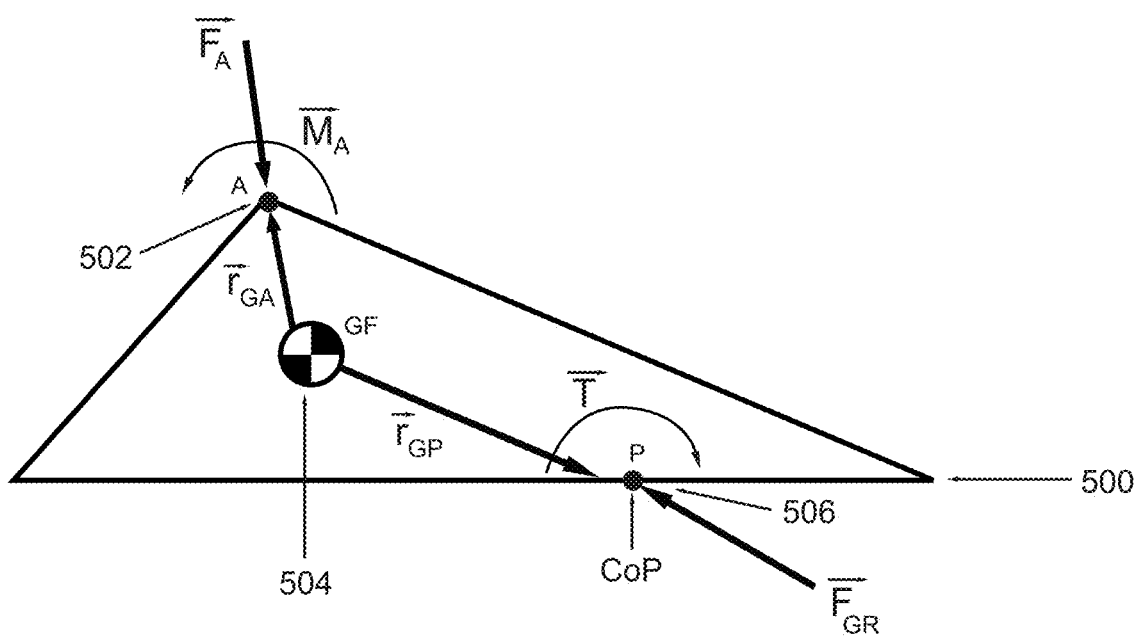
FIG. 36 is a free body diagram that diagrammatically represents the forces and moments acting on the ankle joint according to an exemplary embodiment of the invention.

An exemplary calculation of the forces and moments at the ankle joint will be explained with reference to the foot diagram of FIG. 35 and the free body diagram 500 depicted in FIG. 36. In FIGS. 35 and 36, the ankle joint 502 is diagrammatically represented by the point "A", whereas the gravitational center 504 of the foot is diagrammatically represented by the circular marker labeled "GF". In this figure, the point of application for the ground reaction forces $\vec{F}_{Gr}$ (i.e., the center of pressure 506) is diagrammatically represented by the point "P" in the free body diagram 500. The force balance equation and the moment balance equation for the ankle are as follows:

$$m_F \cdot \vec{a}_{GF} = \vec{F}_{Gr} + \vec{F}_A \quad (4)$$

$$\vec{J}_F \cdot \dot{\vec{\omega}}_F + \vec{\omega}_F \times \vec{J}_F \vec{\omega}_F = \vec{M}_A + \vec{T} + (\vec{r}_{GA} \times \vec{F}_A) + (\vec{r}_{GP} \times \vec{F}_{Gr}) \quad (5)$$

where:
- $m_F$: mass of the foot
- $\vec{a}_{GF}$: acceleration of the gravitational center of the foot
- $\vec{F}_{Gr}$: ground reaction forces
- $\vec{F}_A$: forces acting on the ankle
- $\vec{J}_F$: rotational inertia of the foot
- $\dot{\vec{\omega}}_F$: angular acceleration of the foot
- $\vec{\omega}_F$: angular velocity of the foot
- $\vec{M}_A$: moments acting on the ankle
- $\vec{T}$: torque acting on the foot
- $\vec{r}_{GA}$: position vector from the gravitational center of the foot to the center of the ankle
- $\vec{r}_{Gr}$: position vector from the gravitational center of the foot to the center of pressure In above equations (4) and (5), the ground reaction forces $\vec{F}_{Gr}$ are equal in magnitude and opposite in direction to the externally applied forces $\vec{F}_{that}$ the body exerts on the supporting surface through the foot (i.e., $\vec{F}_{Gr} = -\vec{F}_e$).

Then, in order to solve for the desired ankle forces and moments, the terms of equations (4) and (5) are rearranged as follows:

$$\vec{F}_A = m_F \cdot \vec{a}_{GF} - \vec{F}_{Gr} \quad (6)$$

$$\vec{M}_A = \vec{J}_F \cdot \dot{\vec{\omega}}_F + \vec{\omega}_F \times \vec{J}_F \vec{\omega}_F - \vec{T} - (\vec{r}_{GA} \times \vec{F}_A) - (\vec{r}_{GP} \times \vec{F}_{Gr}) \quad (7)$$

By using the above equations, the magnitude and directions of the ankle forces and moments can be determined. The net joint reaction forces and moments for the other joints in the body can be computed in a similar manner.

Figure 49:
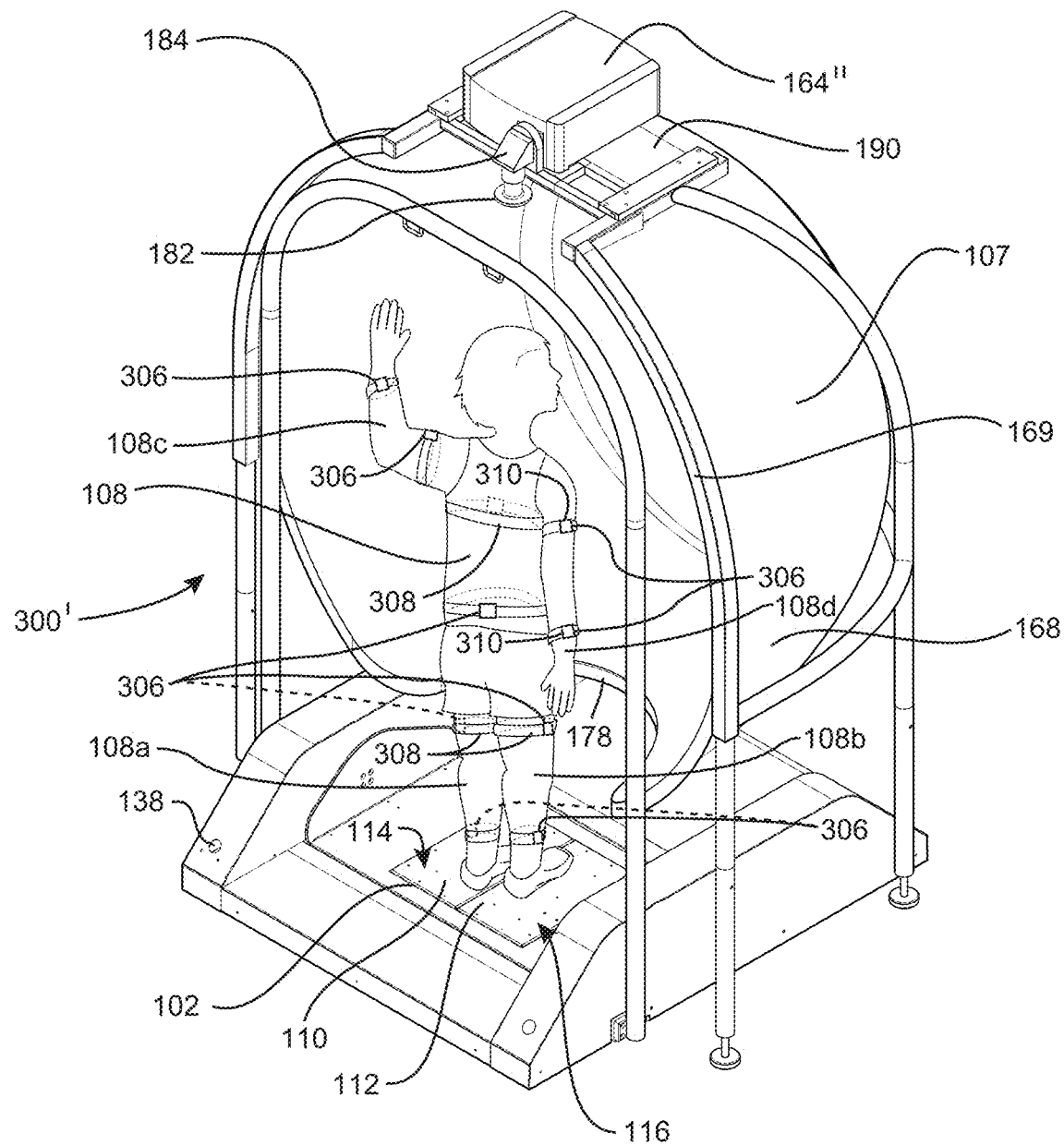
FIG. 49 is a perspective view of a force and motion measurement system having a motion detection system, according to an embodiment of the invention, wherein the motion detection system comprises a plurality of inertial measurement units (IMUs) for detecting the motion of the subject.

In an alternative embodiment, the motion detection system that is provided in conjunction with the force measurement system 100 may comprise a plurality of inertial measurement units (IMUs), rather than taking the form of a marker-based or markerless motion capture system. As described above for the motion detection system 300, the IMU-based motion detection system 300' may be used to detect the motion of one or more body gestures of a subject (see e.g., FIG. 49). As shown in FIG. 49, a subject or patient 108 may be provided with a plurality of inertial measurement units 306 disposed thereon. The one or more body gestures of the subject 108 may comprise one or more limb movements of the subject, one or more torso movements of the subject, or a combination of one or more limb movements and one or more torso movements of the subject.

As shown in FIG. 49, a subject or patient 108 may be outfitted with a plurality of different inertial measurement units 306 for detecting motion. In the illustrative embodiment, the subject 108 is provided with two (2) inertial measurement units 306 on each of his legs 108a, 108b (e.g., on the side of his legs 108a, 108b). The subject is also provided with two (2) inertial measurement units 306 on each of his arms 108c, 108d (e.g., on the side of his arms 108c, 108d). In addition, the subject 108 of FIG. 49 is provided with an inertial measurement unit 306 around his waist (e.g., with the IMU located on the back side of the subject 108), and another inertial measurement unit 306 around his or her chest (e.g., with the IMU located on the front side of the subject 108 near his sternum). In the illustrated embodiment, each of the inertial measurement units 306 is operatively coupled to the data acquisition/data processing device 104 by wireless means, such as Bluetooth, or another suitable type of personal area network wireless means.

In the illustrated embodiment of FIG. 49, each of the inertial measurement units 306 is coupled to the respective body portion of the subject 108 by a band 308. As shown in FIG. 49, each of the inertial measurement units 306 comprises an IMU housing 310 attached to an elastic band 308. The band 308 is resilient so that it is capable of being stretched while being placed on the subject 108 (e.g., to accommodate the hand or the foot of the subject 108 before it is fitted in place on the arm 108c, 108d or the leg 108a, 108b of the subject 108). The band 308 can be formed from any suitable stretchable fabric, such as neoprene, spandex, and elastane. Alternatively, the band 308 could be formed from a generally non-stretchable fabric, and be provided with latching means or clasp means for allowing the band 308 to be split into two portions (e.g., the band 308 could be provided with a snap-type latching device).

In other embodiments, it is possible to attach the inertial measurement units 306 to the body portions of the subject 108 using other suitable attachment means. For example, the inertial measurement units 306 may be attached to a surface (e.g., the skin or clothing item of the subject 108 using adhesive backing means. The adhesive backing means may comprise a removable backing member that is removed just prior to the inertial measurement unit 306 being attached to a subject 108 or object. Also, in some embodiments, the adhesive backing means may comprise a form of double-sided bonding tape that is capable of securely attaching the inertial measurement unit 306 to the subject 108 or another object.

In one or more embodiments, each inertial measurement unit 306 may comprise a triaxial (three-axis) accelerometer sensing linear acceleration $\vec{a}\,'$, a triaxial (three-axis) rate gyroscope sensing angular velocity $\vec{\omega}\,'$, a triaxial (three-axis) magnetometer sensing the magnetic north vector $\vec{n}\,'$, and a central control unit or microprocessor operatively coupled to each of accelerometer, gyroscope, and the magnetometer. In addition, each inertial measurement unit 306 may comprise a wireless data interface for electrically coupling the inertial measurement unit 306 to the data acquisition/data processing device 104.

In one or more embodiments, the motion of the subject 108 may be detected by the plurality of inertial measurement units 306 while one or more images are displayed on the hemispherical projection screen 168 of the subject visual display device 107. The one or more images that are displayed on the screen 168 may comprise one or more simulated tasks, interactive games, training exercises, or balance tests. The data acquisition/data processing device 104 is specially programmed to quantify the performance of a subject 108 during the execution of the one or more simulated tasks, interactive games, training exercises, or balance tests by analyzing the motion of the one or more body gestures of the subject 108 detected by the plurality of inertial measurement units 306.

For example, as described above with regard to the motion detection system 300, the inertial measurement units 306 of the motion detection system 300' may be used to determine positional data (i.e., three-dimensional coordinates) for one or more body gestures of the subject 108 during the performance of a simulated task of daily living. In order to simulate a task of daily living, one or more virtual reality scenes can be displayed on the subject visual display device 107. One such exemplary virtual reality scene is illustrated in FIG. 50. As illustrated in the screen image 244' of FIG. 50, the immersive virtual reality environment 246' simulating the task of daily living could comprise a scenario wherein a subject 204' is pointing and/or grabbing towards an object 248' (e.g., a cereal box) that he is about ready to grasp from a kitchen cabinet 250'. While the subject 204' is performing this simulated task, the data acquisition/data processing device 104 may quantify the performance of the subject 204' during the execution of the task (e.g., reaching for, and removing the cereal box 248' from the kitchen cabinet 250') by analyzing the motion of the subject's right arm 251, as measured by the motion detection system 300'. For example, by utilizing the positional data obtained using the motion detection system 300' (with inertial measurement units (IMUs) 306), the data acquisition/data processing device 104 may compute the three-dimensional (3-D) position and orientation of the subject's right arm 251 in space. The computation of the 3-D position and orientation of the subject's right arm 251 is one exemplary means by which the data acquisition/data processing device 104 is able to quantify the performance of a subject during the execution of a task of daily living. Thus, advantageously, the motion detection system 300' enables a subject's movement to be quantified and analyzed during a task of daily living.

Next, an illustrative manner in which the data acquisition/data processing device 104 of the force measurement system 100 performs the inertial measurement unit (IMU) calculations will be explained in detail. In particular, this calculation procedure will describe the manner in which the orientation and position of one or more body portions (e.g., limbs) of a subject 108, 204' could be determined using the signals from the plurality of inertial measurement units (IMUs) 306 of the motion detection system 300'. As explained above, in one or more embodiments, each inertial measurement unit 306 includes the following three triaxial sensor devices: (i) a three-axis accelerometer sensing linear acceleration $\vec{a}\,'$, (ii) a three-axis rate gyroscope sensing angular velocity $\vec{\omega}\,'$, and (iii) a three-axis magnetometer sensing the magnetic north vector $\vec{n}\,'$. Each inertial measurement unit 306 senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}$ (t) and position $\vec{R}$ (t) in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement units (IMUs) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}$ (t) is obtained by single integration of the angular velocity as follows:

$$\vec{\theta}(t) = \vec{\theta}_0 + \int_0^t \vec{\omega}(t)dt \qquad (8)$$

$$\vec{\theta}(t) = \vec{\theta}_0 + \int_0^t \vec{\Theta}(t)\vec{\omega}(t)dt \qquad (9)$$

where $\vec{\Theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{a(t) - \vec{g}\}dt \qquad (10)$$

$$\vec{v}(t) = \vec{v}_0 + \int_0^t \{\vec{\Theta}(t)[\vec{a}'(t) + 2\vec{\omega}' \times \vec{z}'(t)] - \vec{g}\}dt \qquad (11)$$

where $2\vec{\omega}' \times \vec{z}'(t)$ is the Coriolis term, and where the local linear velocity is given by the following equation:

$$\vec{v}'(t) = \vec{\Theta}^{-1}(t)\vec{v}(t) \qquad (12)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t)dt \qquad (13)$$

At the initial position, the IMU's local-to-global rotation's matrix has an initial value $\vec{\Theta}(0) \equiv \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\vec{\Theta}_0(\vec{n}', \vec{n})$ that are unconstrained in one component of rotation. The $\vec{\Theta}_0(\vec{g}', \vec{n}', \vec{g}, \vec{n})$ has many implementations, with the common one being the Kabsch algorithm. As such, using the calculation procedure described above, the data acquisition/data processing device 104 of the force measurement system 100 may determine the orientation $\vec{\theta}$ (t) and position $\vec{R}$ (t) of one or more body portions of the subject 108, 204'. For example, the orientation of a limb of the subject 108, 204' (e.g., the right arm 251 of the subject 204' in FIG. 50) may be determined by computing the orientation $\vec{\Theta}(t)$ and position $\vec{R}(t)$ of two points on the limb of the subject 108, 204' (i.e., at the respective locations of two inertial measurement units (IMUs) 306 disposed on the limb of the subject 108, 204').

Referring again to FIG. 50, it can be seen that the subject 204' is also provided with an eye movement tracking device 312 that is configured to track the eye movement and/or eye position of the subject 204' (i.e., the eye movement, the eye position, or the eye movement and the eye position of the subject 204') while he performs the one or more simulated tasks, interactive games, training exercises, or balance tests. The eye movement tracking device 312 may be utilized in conjunction with the motion detection system 300'. For example, in the virtual reality environment 246' of FIG. 50, the eye movement tracking device 312 may be used to determine the eye movement and/or eye position of the subject 204' while he performs the one or more simulated tasks, interactive games, training exercises, or balance tests. The eye movement tracking device 312 may be in the form of the eye movement tracking devices described in U.S. Pat. Nos. 6,113,237 and 6,152,564, the entire disclosures of which are incorporated herein by reference. The eye movement tracking device 312 is configured to output one or more first signals that are representative of the detected eye movement and/or eye position of the subject 204' (e.g., the saccadic eye movement of the subject). As explained above, the eye movement tracking device 312 may be operatively connected to the input/output (I/O) module of the programmable logic controller 172, which in turn, is operatively connected to the data acquisition/data processing device 104. As will be described in more detail hereinafter, referring again to FIG. 50, a head position detection device (i.e., an inertial measurement unit 306) may also be provided on the head of the subject 204' so that a head position of the subject 204' is capable of being determined together with the eye movement and/or eye position of the subject 204' determined using the eye movement tracking device 312. The head position detection device 306 is configured to output one or more second signals that are representative of the detected position of the head of the subject 204'. As such, using the one or more first output signals from the eye movement tracking device 312 and the one or more second output signals from head position detection device 306, the data acquisition/data processing device 104 may be specially programmed to determine one or more gaze directions of the subject 204' (as diagrammatically indicated by dashed line 342 in FIG. 50) during the performance of the one or more simulated tasks, interactive games, training exercises, or balance tests. In addition, as will be described in further detail hereinafter, the data acquisition/data processing device 104 may be further configured to compare the one or more gaze directions of the subject 204' to the position of one or more objects (e.g., cereal box 248') in the one or more scene images of the at least one visual display device so as to determine whether or not the eyes of the subject 204' are properly directed at the object 248' (e.g., cereal box) that is about to be grasped by the subject 204'.

In one or more embodiments, the data acquisition/data processing device 104 determines the one or more gaze directions of the subject 204' as a function of the eye angular position ($\Theta_E$) of the subject 204' determined by the eye movement tracking device 312 and the angular position of the subject's head ($\Theta_H$) determined by the head position detection device 306. More particularly, in one or more embodiments, the data acquisition/data processing device 104 is specially programmed to determine the one or more gaze directions of the subject 204' by computing the algebraic sum of the eye angular position ($\Theta_E$) of the subject 204' (as determined by the eye movement tracking device 312) and the angular position ($\Theta_H$) of the subject's head (as determined by the head position detection device 306).

In addition, the data acquisition/data processing device 104 may be specially programmed to determine a position of one or more objects (e.g., the cereal box 248' in FIG. 50) in the one or more scene images 244' of the visual display device. Once the position of the one or more objects on the screen of the visual display device are determined, the data acquisition/data processing device 104 may be further specially programmed to compare the one or more gaze directions of the subject 204' (as detected from the output of the eye movement tracking device 312 and head position detection device 306) to the position of one or more objects on the screen of visual display device (e.g., by using a ray casting technique to project the imaginary sight line 342 in FIG. 50 determined from the output of the eye movement tracking device 312 and head position detection device 306) towards one or more objects (e.g., the cereal box 248') in a virtual world. That is, one or more objects (e.g., the cereal box 248') displayed on the visual display device may be mapped into the virtual environment so that an intersection or collision between the projected sight line 342 and the one or more objects may be determined. Alternatively, or in addition to, comparing the one or more gaze directions of the subject to the position of one or more objects on the screen, the data acquisition/data processing device 104 may be specially programmed to compute a time delay between a movement of the one or more objects (e.g., the cereal box 248') in the one or more scene images of the visual display device and a change in the gaze direction of the subject 204'. For example, the data acquisition/data processing device 104 may be specially programmed to move or displace the object across the screen, then subsequently determine how much time elapses (e.g., in seconds) before the subject changes his or her gaze direction in response to the movement of the object. In an exemplary scenario, a clinician may instruct a patient to continually direct his or her eyes at a particular object on the screen. When the object is displaced on the screen, the time delay (or reaction time of the subject) would be a measure of how long it takes the subject to change the direction of his or her eyes in response to the movement of the object on the screen (i.e., so the subject is still staring at that particular object).

When utilizing the eye movement tracking device 312, the data acquisition/data processing device 104 may be specially programmed to assess a performance of the subject 204' while performing one or more simulated tasks, interactive games, training exercises, or balance tests using the comparison of the one or more gaze directions of the subject 204' to the position of one or more objects or the computed time delay of the subject 204'. For example, if the comparison between the one or more gaze directions of the subject 204' to the position of one or more objects reveals that there is a large distance (e.g., 10 inches or more) between the projected sight line 342 of the subject's gaze direction and the position determined for the one or more objects on the screen of the visual display device, then the data acquisition/data processing device 104 may determine that the performance of the subject 204' during the one or more simulated tasks, interactive games, training exercises, or balance tests is below a baseline normative value (i.e., below average performance). Conversely, if the comparison between the one or more gaze directions of the subject 204' to the position of one or more objects reveals that there is a small distance (e.g., 3 inches or less) between the projected sight line 342 of the subject's gaze direction and the position determined for the one or more objects on the screen of the visual display device, then the data acquisition/data processing device 104 may determine that the performance of the subject 204' during the one or more simulated tasks, interactive games, training exercises, or balance tests is above a baseline normative value (i.e., above average performance). Similarly, if the computed time delay between a movement of the one or more objects on the screen of the visual display device and a change in the subject's gaze direction is large (e.g., a large time delay of 1 second or more), then the data acquisition/data processing device 104 may determine that the performance of the subject 204' during the one or more simulated tasks, interactive games, training exercises, or balance tests is below a baseline normative value (i.e., below average performance). Conversely, if the computed time delay between a movement of the one or more objects on the screen of the visual display device and a change in the subject's gaze direction is small (e.g., a small time delay of 0.25 seconds or less), then the data acquisition/data processing device 104 may determine that the performance of the subject 204' during the one or more simulated tasks, interactive games, training exercises, or balance tests is above a baseline normative value (i.e., above average performance).

Also, as illustrated in FIG. 50, the subject 204' is provided with a scene camera 314 mounted to the eye movement tracking device 312 so that one or more video images of an environment surrounding the subject may be captured, as the one or more gaze directions of the subject 204' are determined using the output of the eye movement tracking device 312 and head position detection device 306. The scene camera 314 records the environment surrounding the subject 204' in relation to a video being captured by a forward facing head-mounted camera. Similar to the eye movement tracking device 312, the scene camera 314 may be operatively connected to the input/output (I/O) module of the programmable logic controller 172, which in turn, is operatively connected to the data acquisition/data processing device 104. As such, using the one or more output signals from the scene camera 314, the data acquisition/data processing device 104 may be specially programmed to utilize the one or more video images captured by the scene camera in a virtual reality environment 246' displayed on the visual display device 107 during the performance of the one or more simulated tasks, interactive games, training exercises, or balance tests. For example, in one or more embodiments, the scene camera 314 may be used to add to the imagery in a virtual reality environment in which the subject 204' is immersed. In one or more alternative embodiments, the scene camera 314 may be used to capture the gaze position of the subject 204' while he or she interacts in a virtual reality environment (e.g., the virtual reality environment 246' in FIG. 50).

Turning once again to FIG. 50, it can be seen that the head position detection device (i.e., the inertial measurement unit 306) is disposed on the head of the subject 204' so that a head position and orientation of the subject 204' is capable of being determined together with the eye movement and/or eye position of the subject 204' determined using the eye movement tracking device 312, and the one or more video images of an environment surrounding the subject 204' determined using the scene camera 314. As such, using the one or more output signals from the head-mounted inertial measurement unit 306, the data acquisition/data processing device 104 may be specially programmed to calculate the head position and orientation of the subject 204' during the performance of the one or more simulated tasks, interactive games, training exercises, or balance tests (i.e., by using the calculation procedure described above for the IMUs 306). For example, in the virtual reality environment 246' of FIG. 50, the head-mounted inertial measurement unit 306 may be used to determine whether or not the head of the subject 204' is properly pointing toward the object 248' (e.g., cereal box) that is about to be grasped by the subject 204'.

In addition, as shown in FIG. 50, the subject 204' may also be provided with an instrumented motion capture glove 316 on his right hand in order to detect one or more finger motions of the subject while the subject performs the one or more simulated tasks, interactive games, training exercises, or balance tests. The instrumented motion capture glove 316 may comprise a plurality of different sensor devices, which may include a plurality of finger flexion or bend sensors on each finger, a plurality of abduction sensors, one or more palm-arch sensors, one or more sensors measuring thumb crossover, one or more wrist flexion sensors, and one or more wrist abduction sensors. The sensor devices of the instrumented motion capture glove 316 may be attached to an elastic material that fits over the hand of the subject 204', which permits the subject 204' to manipulate his hand without any substantial decrease in mobility due the instrumented glove 316. The instrumented motion capture glove 316 outputs a plurality of signals that are representative of the detected finger movement of the subject 204'. The instrumented motion capture glove 316 may be operatively connected to the data acquisition/data processing device 104 of the force measurement system 100. The data acquisition/data processing device 104 may be specially programmed to determine the finger positions and orientations of the subject during the performance of the one or more simulated tasks, interactive games, training exercises, or balance tests using the plurality of signals outputted by the instrumented motion capture glove 316 (e.g., by executing calculations similar to those described above for the IMUs). In the illustrated embodiment, the instrumented motion capture glove 316 is operatively connected to the data acquisition/data processing device 104 by wireless means, such as Bluetooth, or another suitable type of personal area network wireless means.

In a further embodiment, a measurement and analysis system is provided that generally includes a visual display device together with an eye movement tracking device 312 and a data acquisition/data processing device 104. The eye movement tracking device 312 functions in the same manner described above with regard to the preceding embodiments. In addition, the measurement and analysis system may also comprise the scene camera 314 and the head-mounted inertial measurement unit 306 explained above.

In yet a further embodiment, a measurement and analysis system is provided that generally includes a visual display device having an output screen, the visual display device configured to display one or more scene images on the output screen so that the images are viewable by a subject; an object position detection system, the object position detection system configured to detect a position of a body portion of a subject 108, 204' and output one or more first signals representative of the detected position; and a data acquisition/data processing device 104 operatively coupled to the visual display device and the object position detection system. In this further embodiment, the object position detection system may comprise one or more of the following: (i) one or more inertial measurement units 306 (e.g., see FIGS. 49 and 50), (ii) a touchscreen interface of the visual display device 130 (e.g., see FIG. 1), (iii) one or more infrared (IR) sensing devices 322 (e.g., see FIG. 50), and (iv) one or more cameras (e.g., see FIGS. 32 and 33).

In this further embodiment, the data acquisition/data processing device 104 is specially programmed to receive the one or more first signals that are representative of the position of the body portion (e.g., an arm) of the subject 108, 204' and to compute the position, orientation, or both the position and orientation, of the body portion (e.g., the arm) of the subject 108, 204' using the one or more first signals. For example, the data acquisition/data processing device 104 may be specially programmed to determine the position and orientation of an arm 251 of the subject 108, 204' using the output signals from a plurality of inertial measurement units 306 attached along the length of the subject's arm (e.g., as illustrated in FIG. 50). As explained above, the positional coordinates of the subject's arm may be initially determined relative to a local coordinate system, and then subsequently transformed to a global coordinate system. In addition, the data acquisition/data processing device 104 may be specially programmed to determine a position of one or more objects (e.g., the cereal box 248' in FIG. 50) in the one or more scene images 244' of the visual display device. For example, the pixel coordinates (x pixels by y pixels) defining the position of the object (e.g., the cereal box 248') on the screen may be transformed into dimensional coordinates (e.g., x inches by y inches) using the physical size of the screen (e.g., 40 inches by 30 inches). As such, the position of the object (e.g., the cereal box 248') on the screen may be defined in terms of a global coordinate system having an origin at the center of the visual display device. Also, the positional coordinates of the subject's arm may be transformed such that they are also defined in accordance with the same global coordinate system having its origin at the center of the visual display device.

Once the position and/or orientation of the body portion (e.g., the arm) of the subject 108, 204' and the position of the one or more objects on the screen of the visual display device are defined relative to the same coordinate system, the data acquisition/data processing device 104 may be further specially programmed to compute a difference value between the computed position and/or orientation of the body portion (e.g., the arm) of the subject and the position determined for the one or more objects on the screen of the visual display device. For example, the data acquisition/data processing device 104 may compute a distance value between the coordinates of the arm of the subject and the coordinates of the one or more objects on the screen in order to assess how close the subject's arm is to the intended object (e.g., the cereal box 248') on the screen (e.g., to determine if he or she is pointing at, or reaching for, the correct object on the screen). Alternatively, or in addition to, computing the difference value, the data acquisition/data processing device 104 may be specially programmed to compute a time delay between a movement of the one or more objects on the screen of the visual display device and a movement of the body portion (e.g., an arm) of the subject. For example, the data acquisition/data processing device 104 may be specially programmed to move or displace the object across the screen, then subsequently determine how much time elapses (e.g., in seconds) before the subject moves his or her arm in response to the movement of the object. In an exemplary scenario, a clinician may instruct a patient to continually point to a particular object on the screen. When the object is displaced on the screen, the time delay (or reaction time of the subject) would be a measure of how long it takes the subject to move his or her arm in response to the movement of the object on the screen (i.e., so the subject is still pointing at that particular object).

In this further embodiment, the data acquisition/data processing device 104 may be specially programmed to utilize a ray casting technique in order to project an imaginary arm vector of the subject 204', the orientation and position of which may be determined using the output signal(s) from one or more inertial measurement units 306 on the arm of the subject 204' (see FIG. 50), towards one or more objects (e.g., the cereal box 248') in a virtual world. That is, one or more objects (e.g., the cereal box 248') displayed on the visual display device may be mapped into the virtual environment so that an intersection or collision between the projected arm vector and the one or more objects may be determined. As such, in one exemplary scenario, the data acquisition/data processing device 104 is capable of determining whether or not a subject 204' is correctly pointing his or her arm in the direction of a particular object (e.g., cereal box 248') on the screen of the visual display device.

Also, in this further embodiment, the data acquisition/data processing device 104 may be specially programmed to assess a performance of the subject 204' while performing one or more simulated tasks, interactive games, training exercises, or balance tests using the computed difference value or the computed time delay of the subject 204'. For example, if the computed difference value between the calculated position and/or orientation of the body portion (e.g., the arm) of the subject and the position determined for the one or more objects on the screen of the visual display device is large (i.e., a large distance of 20 inches or more), then the data acquisition/data processing device 104 may determine that the performance of the subject 204' during the one or more simulated tasks, interactive games, training exercises, or balance tests is below a baseline normative value (i.e., below average performance). Conversely, if the computed difference value between the calculated position and/or orientation of the body portion (e.g., the arm) of the subject and the position determined for the one or more objects on the screen of the visual display device is small (i.e., a small distance of 3 inches or less), then the data acquisition/data processing device 104 may determine that the performance of the subject 204' during the one or more simulated tasks, interactive games, training exercises, or balance tests is above a baseline normative value (i.e., above average performance). Similarly, if the computed time delay between a movement of the one or more objects on the screen of the visual display device and a movement of the body portion (e.g., an arm) of the subject is large (i.e., a large time delay of 1 second or more), then the data acquisition/data processing device 104 may determine that the performance of the subject 204' during the one or more simulated tasks, interactive games, training exercises, or balance tests is below a baseline normative value (i.e., below average performance). Conversely, if the computed time delay between a movement of the one or more objects on the screen of the visual display device and a movement of the body portion (e.g., an arm) of the subject is small (i.e., a small time delay of 0.2 seconds or less), then the data acquisition/data processing device 104 may determine that the performance of the subject 204' during the one or more simulated tasks, interactive games, training exercises, or balance tests is above a baseline normative value (i.e., above average performance).

Also, in one or more other embodiments, the measurement and analysis system described above may further comprise a force measurement assembly (e.g., force measurement assembly 102) configured to receive a subject. In addition, in one or more other embodiments, the measurement and analysis system may additionally include the instrumented motion capture glove described in detail above.

Figure 38:
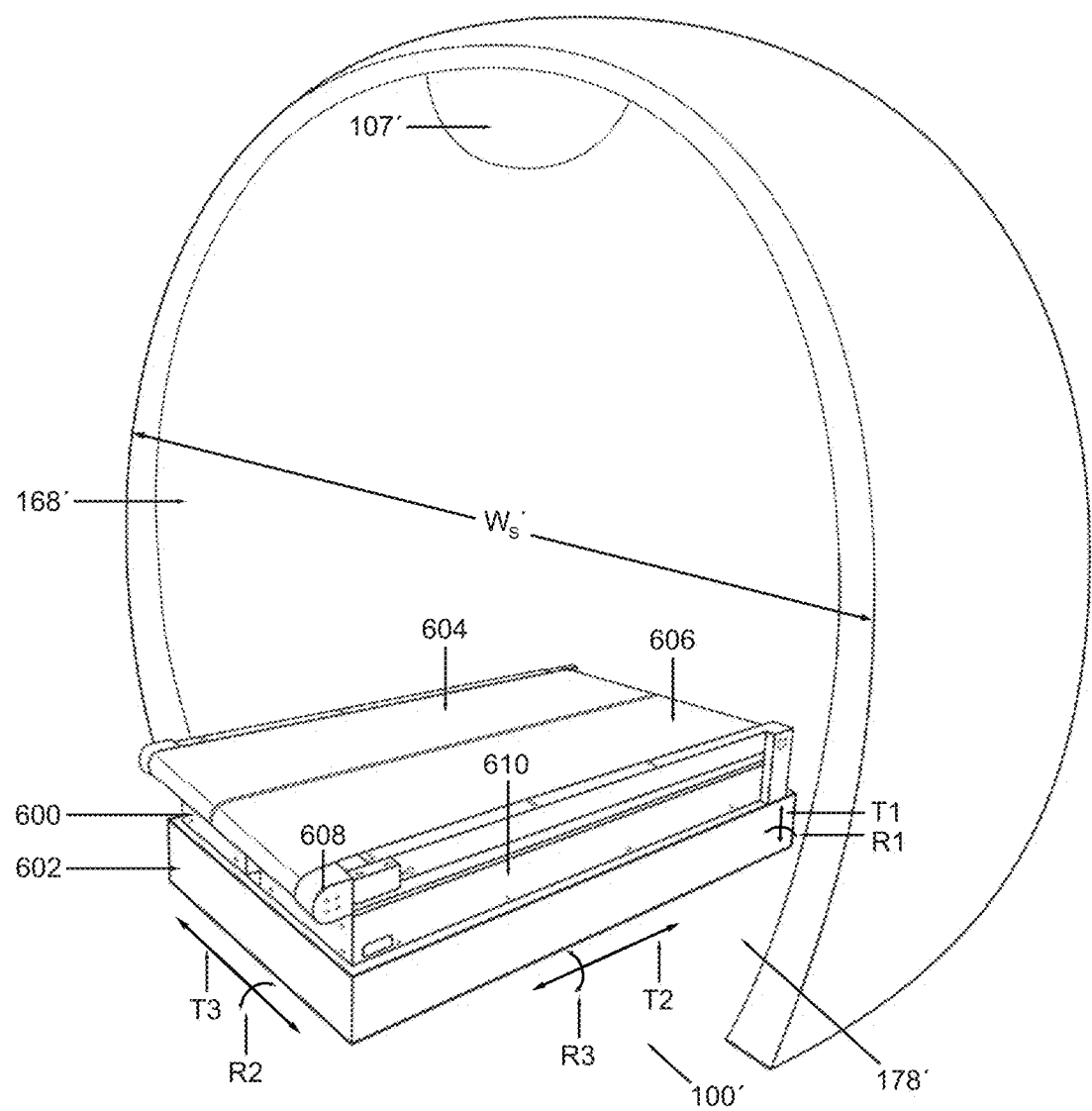
FIG. 38 is a diagrammatic perspective view of an alternative force measurement system comprising an instrumented treadmill and an enlarged hemispherical projection screen, according to an embodiment of the invention.

In yet a further embodiment, a modified version of the force measurement system 100' may comprise a force measurement device 600 in the form of an instrumented treadmill. Like the force measurement assemblies 102, 102' described above, the instrumented treadmill 600 is configured to receive a subject thereon. Refer to FIG. 38, it can be seen that the subject visual display device 107' is similar to that described above, except that the screen 168' of the subject visual display device 107' is substantially larger than the screen 168 utilized in conjunction with the force measurement system 100 (e.g., the diameter of the screen 168' is approximately two (2) times larger that of the screen 168). In one exemplary embodiment, the projection screen 168' has a width $W_S$' lying in the range between approximately one-hundred and eighty (180) inches and approximately two-hundred and forty (240) inches (or between one-hundred and eighty (180) inches and two-hundred and forty (240) inches). Also, rather than being supported on a floor surface using the screen support structure 167 explained above, the larger hemispherical screen 168' of FIG. 38 rests directly on the floor surface. In particular, the peripheral edge of the semi-circular cutout 178', which is located at the bottom of the screen 168', rests directly on the floor. The hemispherical screen 168' of FIG. 38 circumscribes the instrumented treadmill 600. Because the other details of the subject visual display device 107' and the data acquisition/data processing device 104 are the same as that described above with regard to the aforementioned embodiments, no further description of these components 104, 107' will be provided for this embodiment.

As illustrated in FIG. 38, the instrumented treadmill 600 is attached to the top of a motion base 602. The treadmill 600 has a plurality of top surfaces (i.e., a left and right rotating belt 604, 606) that are each configured to receive a portion of a body of a subject (e.g., the left belt of the instrumented treadmill 600 receives a left leg 108*a* of a subject 108, whereas the right belt 606 of the instrumented treadmill 600 receives a right leg 108*b* of the subject 108). In a preferred embodiment, a subject 108 walks or runs in an upright position atop the treadmill 600 with the feet of the subject contacting the top surfaces of the treadmill belts 604, 606. The belts 604, 606 of the treadmill 600 are rotated by one or more electric actuator assemblies 608, which generally comprise one or more electric motors. Similar to the force measurement assemblies 102, 102' described above, the instrumented treadmill 600 is operatively connected to the data acquisition/data processing device 104 by an electrical cable. While it is not readily visible in FIG. 38 due to its location, the force measurement assembly 610, like the force measurement assemblies 102, 102', includes a plurality of force transducers (e.g., four (4) pylon-type force transducers) disposed below each rotating belt 604, 606 of the treadmill 600 so that the loads being applied to the top surfaces of the belts 604, 606 can be measured. Similar to that described above for the force measurement assembly 102, the separated belts 604, 606 of the instrumented treadmill 600 enables the forces and/or moments applied by the left and right legs 108*a*, 108*b* of the subject 108 to be independently determined. The arrows T1, T2, T3 disposed adjacent to the motion base 602 in FIG. 38 schematically depict the displaceable nature (i.e., the translatable nature) of the instrumented treadmill 600, which is effectuated by the motion base 602, whereas the curved arrows R1, R2, R3 in FIG. 38 schematically illustrate the ability of the instrumented treadmill 600 to be rotated about a plurality of different axes, the rotational movement of the instrumented treadmill 600 being generated by the motion base 602.

Figure 39A:
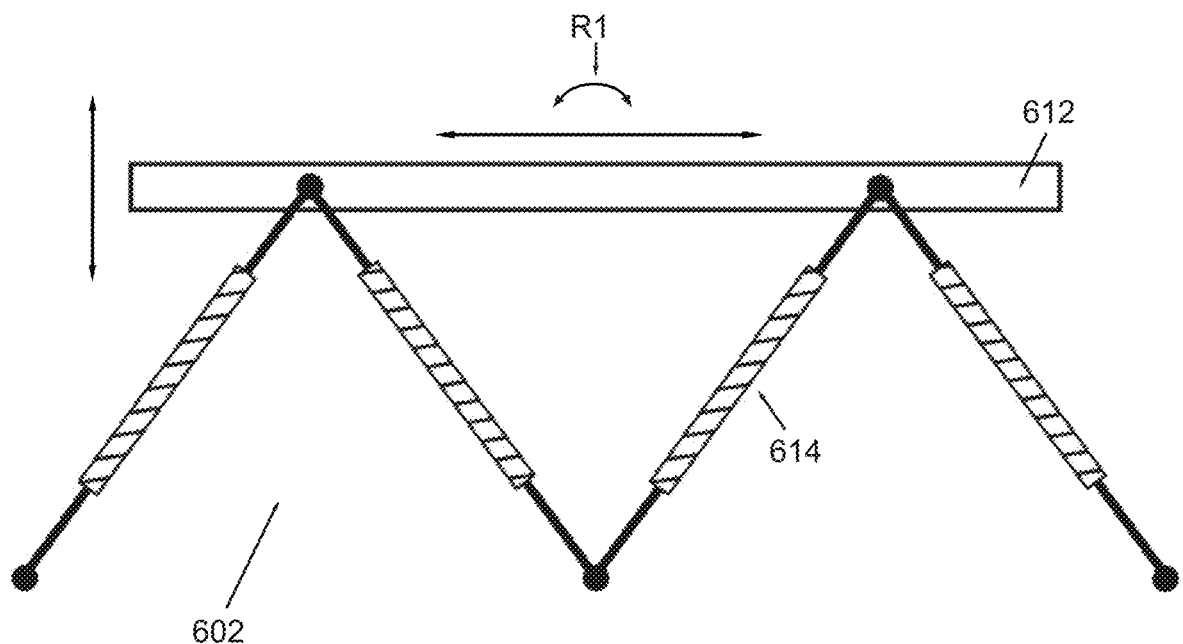
FIG. 39A is a schematic side view of a motion base according to an embodiment of the invention.
Figure 39B:
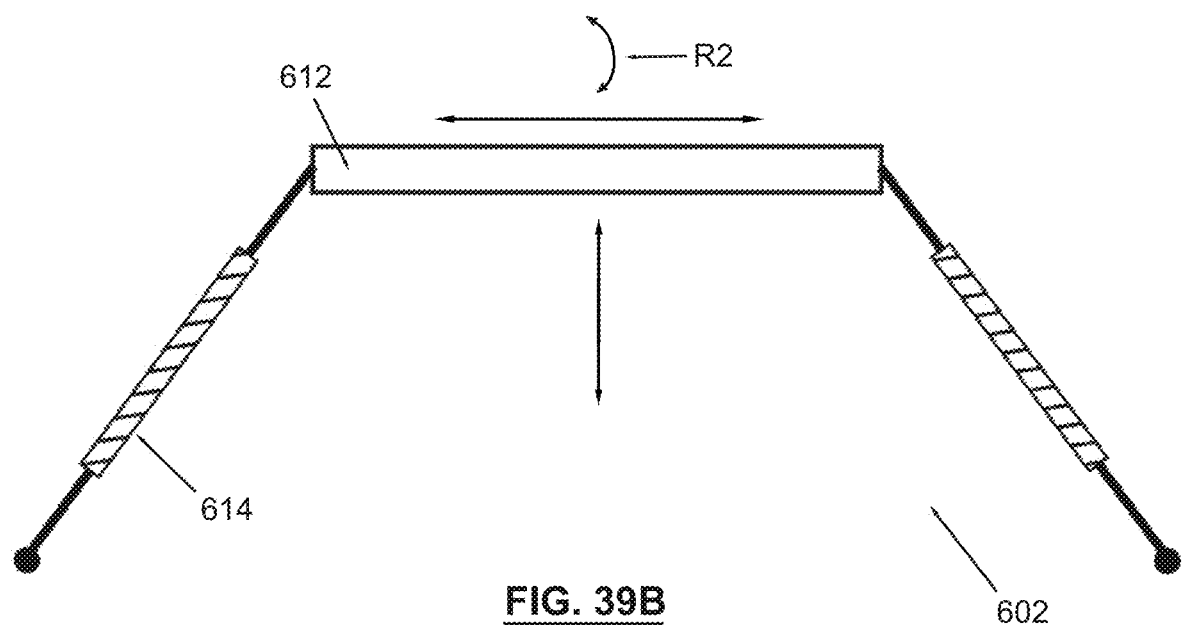
FIG. 39B is a schematic front view of a motion base according to an embodiment of the invention.

The primary components of the motion base 602 are schematically depicted in FIGS. 39A and 39B. As depicted in these figures, the motion base 602 comprises a movable top surface 612 that is preferably displaceable (i.e., translatable, as represented by straight arrows) and rotatable (as illustrated by curved arrows R1, R2) in 3-dimensional space by means of a plurality of actuators 614. In other words, the motion base 602 is preferably a six (6) degree-of-freedom motion base. The instrumented treadmill 600 is disposed on the movable top surface 612. The motion base 602 is used for the dynamic testing of subjects when, for example, the subject is being tested, or is undergoing training, in a virtual reality environment. While the motion base 602 is preferably translatable and rotatable in 3-dimensional space, it is to be understood that the present invention is not so limited. Rather, motion bases 602 that only are capable of 1 or 2 dimensional motion could be provided without departing from the spirit and the scope of the claimed invention. Also, motion bases 602 that are only capable of either linear motion or rotational motion are encompassed by the present invention.

Figure 45:
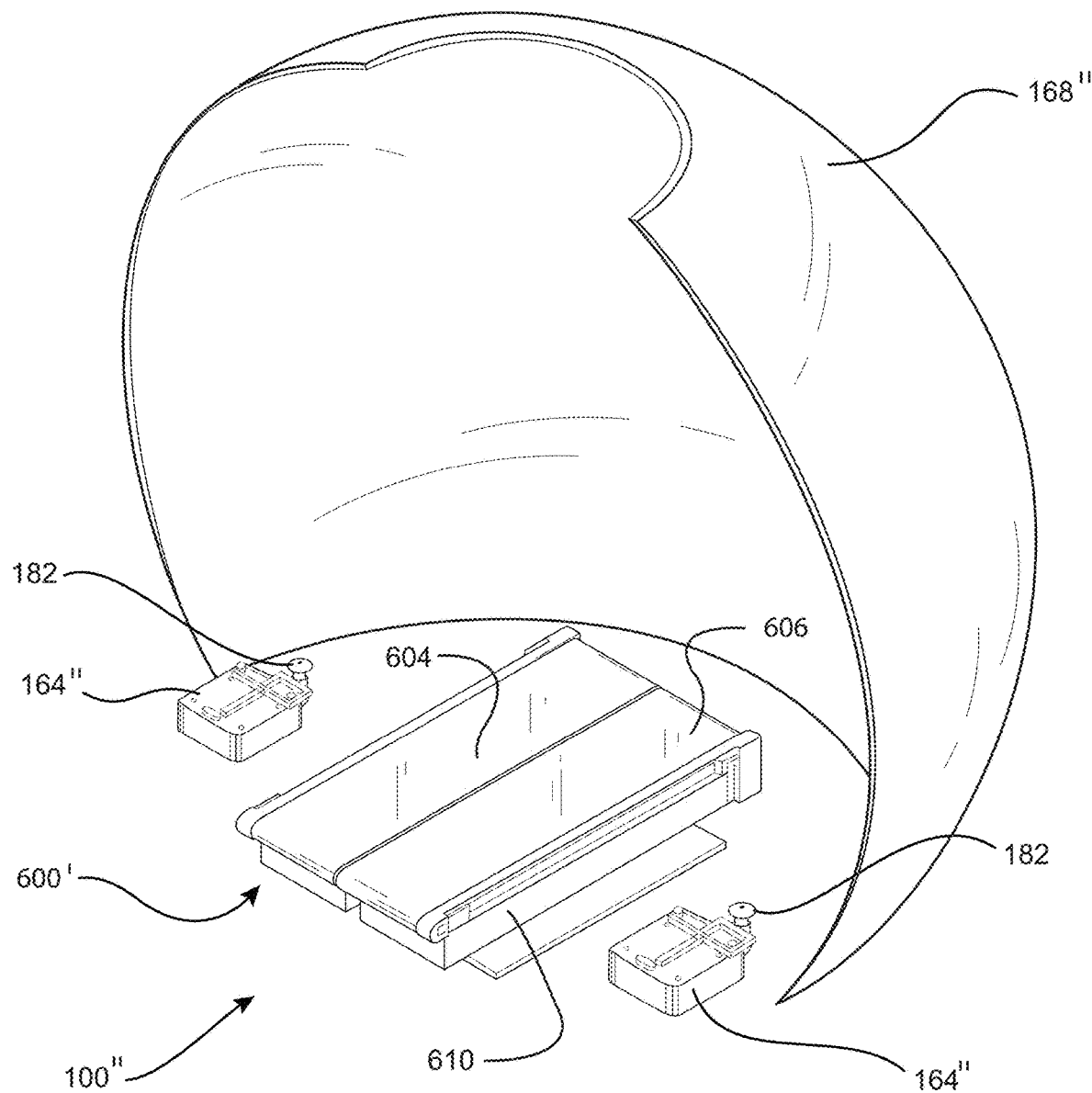
FIG. 45 is a diagrammatic perspective view of another alternative force measurement system comprising an instrumented treadmill and an enlarged hemispherical projection screen wherein two projectors with respective fisheye lens are disposed in the front of the visual display device, according to an embodiment of the invention.

Another modified version of the force measurement system 100", which comprises a force measurement device 600' in the form of an instrumented treadmill, is illustrated in FIG. 45. Similar to the instrumented treadmill in FIG. 38, the instrumented treadmill of FIG. 45 comprises left and right rotating belts 604, 606 and a force measurement assembly 610 disposed underneath the treadmill belts 604, 606. The force measurement system 100" of FIG. 45 is similar in many respects to the force measurement system 100' of FIG. 38, except that the projector arrangement is different from that of the FIG. 38 embodiment. In particular, in the embodiment of FIG. 45, two (2) projectors 164", each having a respective fisheye-type lens 182, are used to project an image onto the generally hemispherical projection screen 168". As illustrated in FIG. 45, each of the projectors 164" generally rests on the top surface of the floor, and has a fisheye-type lens 182 that is angled upward at an approximately 90 degree angle. Similar to that described above with regard to FIGS. 30 and 31, the projectors 164" with the fisheye-type lenses 182 project intersecting light beams onto the generally hemispherical projection screen 168". Advantageously, the use of two projectors 164" with fisheye-type lenses 182, rather than just a single projector 164" with a fisheye lens 182, accommodates the larger diameter projection screen 168" that is utilized with the instrumented treadmill 600', and it also has the added benefit of removing shadows that are cast on the output screen 168" by the subject 108 disposed on the force measurement assembly 600'.

In still a further embodiment of the invention, the virtual reality environment described herein may include the projection of an avatar image onto the hemispherical projection screen 168 of the subject visual display device 107. For example, as illustrated in the screen image 266 of FIG. 40, the immersive virtual reality environment 268 may comprise a scenario wherein an avatar 270 is shown walking along a bridge 207. The avatar image 270 on the screen 168 represents and is manipulated by the subject 108 disposed on the force measurement assembly 102 or the instrumented treadmill 600. The animated movement of the avatar image 270 on the screen 168 is controlled based upon the positional information acquired by the motion acquisition/capture system 300 described above, as well as the force and/or moment data acquired from the force measurement assembly 102 or the instrumented treadmill 600. In other words, an animated skeletal model of the subject 108 is generated by the data acquisition/data processing device 104 using the acquired data from the motion capture system 300 and the force measurement assembly 102 or the instrumented treadmill 600. The data acquisition/data processing device 104 then uses the animated skeletal model of the subject 108 to control the movement of the avatar image 270 on the screen 168.

Figure 40:
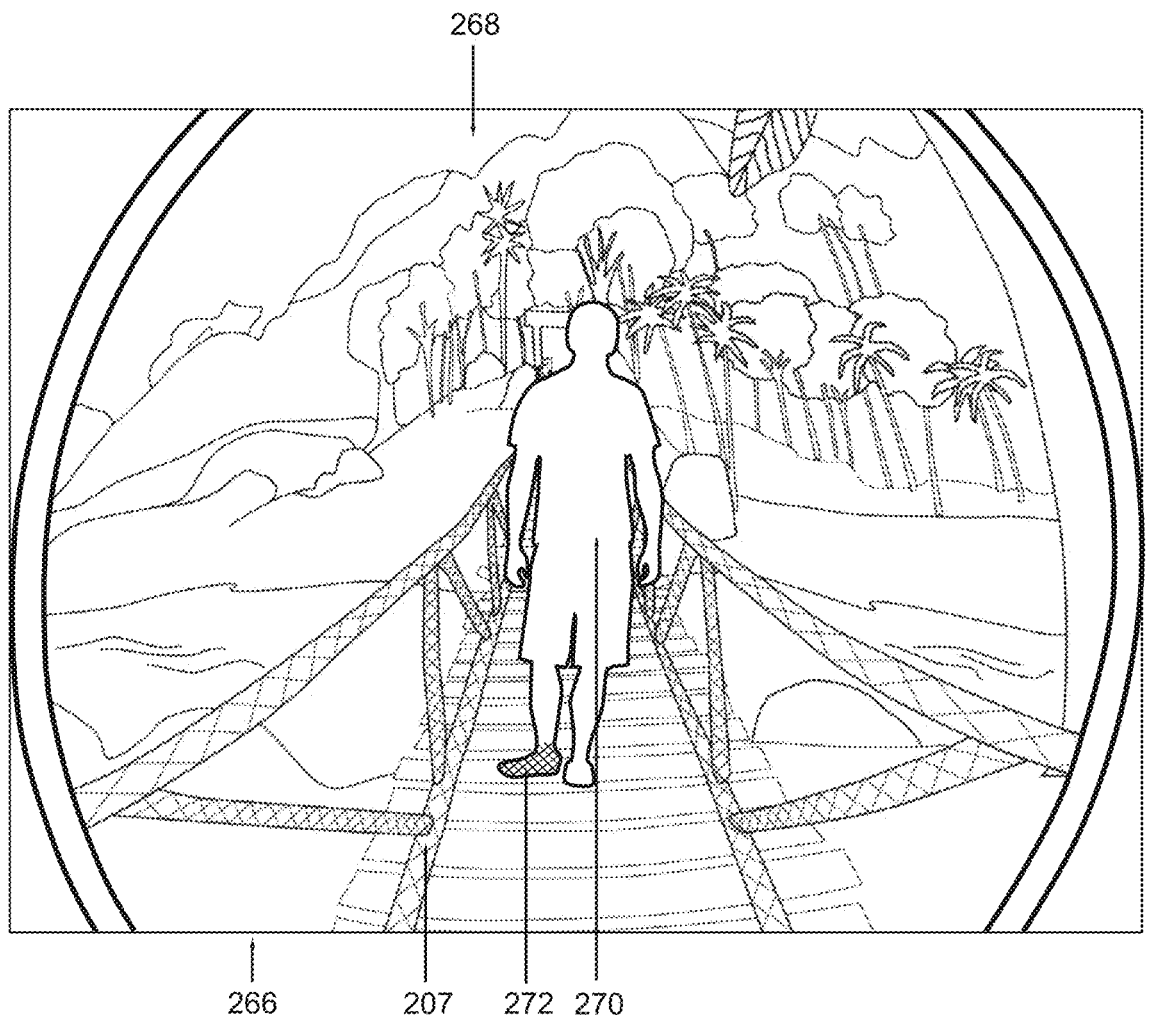
FIG. 40 is a fourth example of a virtual reality scene displayed on the subject visual display device of the force measurement system, wherein the virtual reality scene comprises an avatar, according to an embodiment of the invention.

The avatar image 270 illustrated in the exemplary virtual reality scenario of FIG. 40 has a gait disorder. In particular, it can be seen that the left foot 272 of the avatar 270 is positioned in an abnormal manner, which is indicative of the subject 108 who is controlling the avatar 270 having a similar disorder. In order to bring this gait abnormality to the attention of the subject 108 and the clinician conducting the evaluation and/or training of the subject, the left foot 272 of the avatar 270 is shown in a different color on the screen 168 (e.g., the left foot turns "red" in the image in order to clearly indicate the gait abnormality). In FIG. 40, because this is a black-and-white image, the different color (e.g., red) of the left foot 272 of the avatar 270 is indicated using a hatching pattern (i.e., the avatar's left foot 272 is denoted using crisscross type hatching). It is to be understood that, rather than changing the color of the left foot 272, the gait abnormality may indicated using other suitable means in the virtual reality environment 268. For example, a circle could be drawn around the avatar's foot 272 to indicate a gait disorder. In addition, a dashed image of an avatar having normal gait could be displayed on the screen 168 together with the avatar 270 so that the subject 108 and the clinician could readily ascertain the irregularities present in the subject's gait, as compared to a virtual subject with normal gait.

Figure 41:
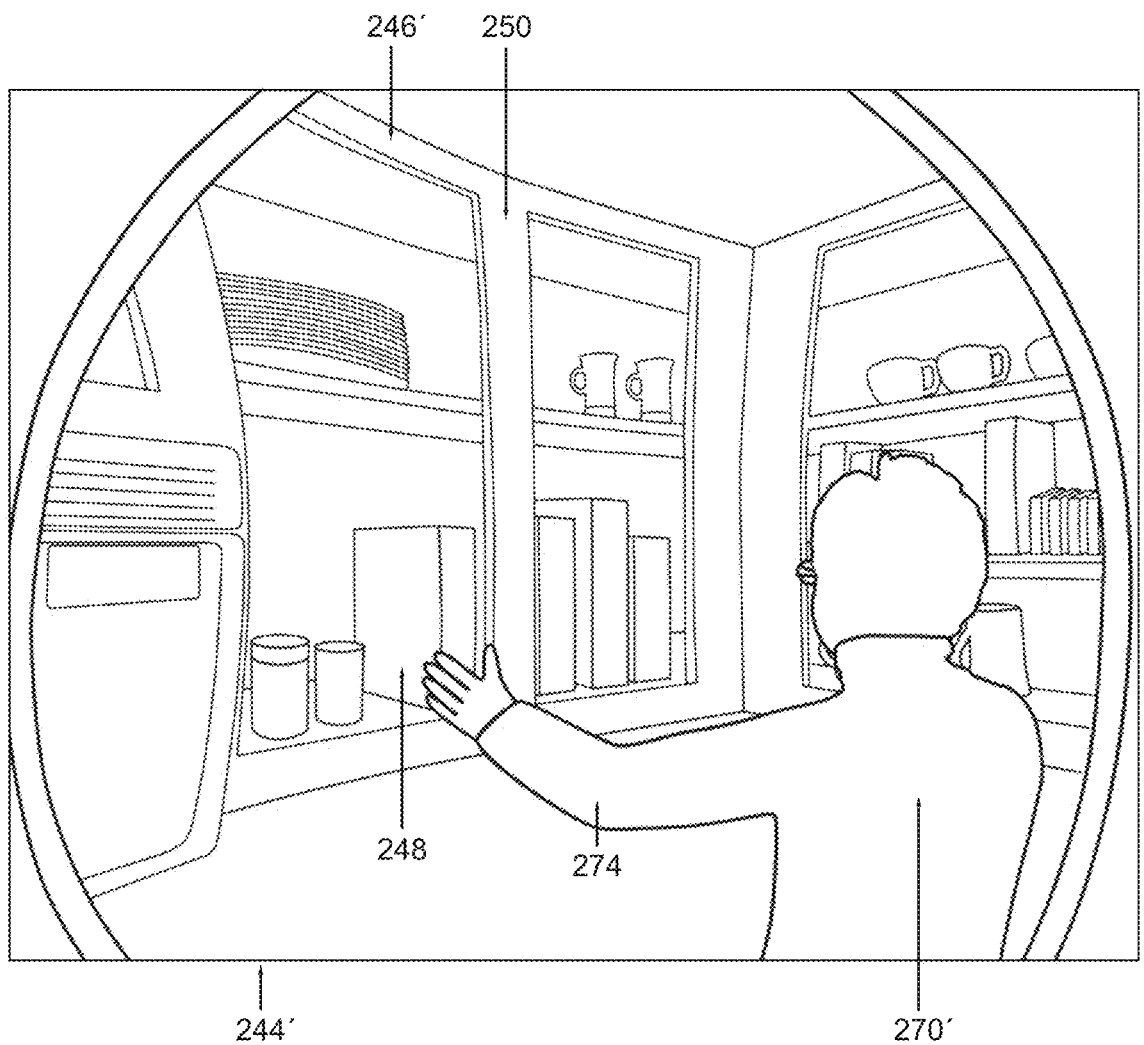
FIG. 41 is a fifth example of a virtual reality scene displayed on the subject visual display device of the force measurement system, wherein the virtual reality scene comprises another avatar, according to an embodiment of the invention.

In FIG. 41, another virtual reality environment utilizing an avatar 270' is illustrated. This figure is similar in some respects to FIG. 37 described above, except that the avatar 270' is incorporated into the virtual reality scenario. As shown in the screen image 244' of FIG. 41, the immersive virtual reality environment 246' simulates a task of daily living comprising a scenario wherein the avatar 270', which is controlled by the subject 108, is removing an object 248 (e.g., a cereal box) from a kitchen cabinet 250. Similar to that described above in conjunction with FIG. 40, the avatar image 270' on the screen 168 represents and is manipulated by the subject 108 disposed on the force measurement assembly 102 or the instrumented treadmill 600. The animated movement of the avatar image 270' on the screen 168 is controlled based upon the positional information acquired by the motion acquisition/capture system 300 described above, as well as the force and/or moment data acquired from the force measurement assembly 102 or the instrumented treadmill 600. In other words, the manner in which the avatar 270' removes cereal box 248 from the kitchen cabinet 250 is controlled based upon the subject's detected motion. Similar to that explained above for FIG. 40, a disorder in a particular subject's movement may be animated in the virtual reality environment 246' by making the avatar's left arm 274 turn a different color (e.g., red). As such, any detected movement disorder is brought to the attention of the subject 108 and the clinician conducting the evaluation and/or training of the subject. In this virtual reality scenario 246', the cameras 302 of the motion acquisition/capture system 300 may also be used to detect the head movement of the subject 108 in order to determine whether or not the subject is looking in the right direction when he or she is removing the cereal box 248 from the kitchen cabinet 250. That is, the cameras 302 may be used to track the direction of the subject's gaze. It is also to be understood that, in addition to the cameras 302 of FIGS. 32 and 33, a head-mounted camera on the subject 108 may be used to track the subject's gaze direction. The head-mounted camera could also be substituted for one or more of the cameras in FIGS. 32 and 33.

In yet further embodiments of the invention incorporating the avatar 270, 270' on the screen 168, the data acquisition/data processing device 104 is specially programmed so as to enable a system user (e.g., a clinician) to selectively choose customizable biofeedback options in the virtual reality scenarios 246' and 268. For example, the clinician may selectively choose whether or not the color of the avatar's foot or arm would be changed in the virtual reality scenarios 246', 268 so as to indicate a disorder in the subject's movement. As another example, the clinician may selectively choose whether or not the dashed image of an avatar having normal gait could be displayed on the screen 168 together with the avatar 270, 270' so as to provide a means of comparison between a particular subject's gait and that of a "normal" subject. Advantageously, these customizable biofeedback options may be used by the clinician to readily ascertain the manner in which a particular subject deviates from normal movement(s), thereby permitting the clinician to focus the subject's training on the aspects of the subject's movement requiring the most correction.

In other further embodiments of the invention, the force measurement system 100 described herein is used for assessing the visual flow of a particular subject, and at least in cases, the impact of a subject's visual flow on the vestibular systems. In one or more exemplary embodiments, the assessment of visual flow is concerned with determining how well a subject's eyes are capable of tracking a moving object.

In still further embodiments, the force measurement system 100 described herein is used for balance sensory isolation, namely selectively isolating or eliminating one or more pathways of reference (i.e., proprioceptive, visual, and vestibular). As such, it is possible to isolate the particular deficiencies of a subject. For example, the elderly tend to rely too heavily upon visual feedback in maintaining their balance. Advantageously, tests performed using the force measurement system 100 described herein could reveal an elderly person's heavy reliance upon his or her visual inputs. In yet further embodiments, the virtual reality scenarios described above may include reaction time training and hand/eye coordination training (e.g., catching a thrown ball, looking and reaching for an object, etc.). In order to effectively carry out the reaction time training routines and the hand/eye coordination training routines, the system 100 could be provided with the motion capture system 300 described above, as well as eye movement tracking system for tracking the eye movement (gaze) of the subject or patient.

Figure 56:
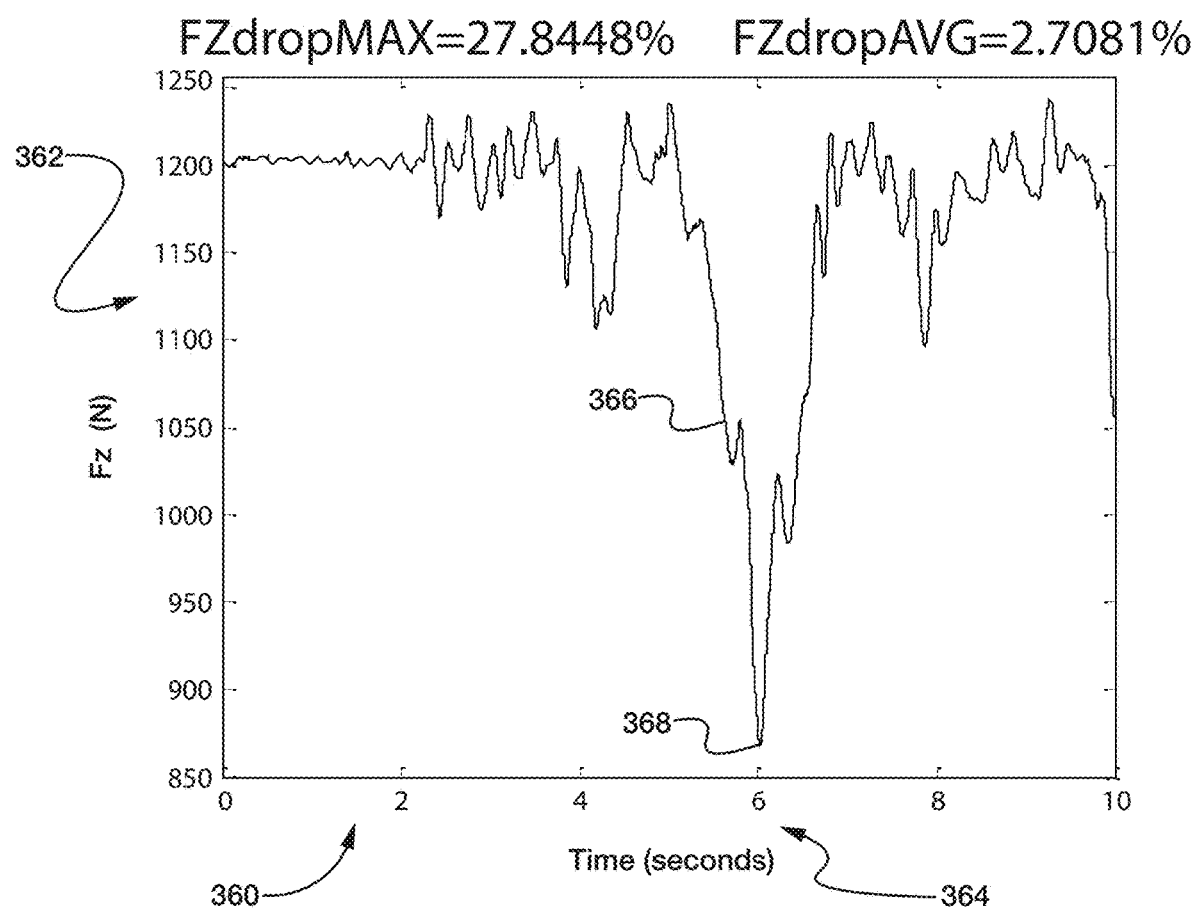
FIG. 56 is a graph illustrating a vertical force curve generated during the performance of a test trial where a subject is pulling on the harness while standing still, according to an embodiment of the invention.
Figure 57:
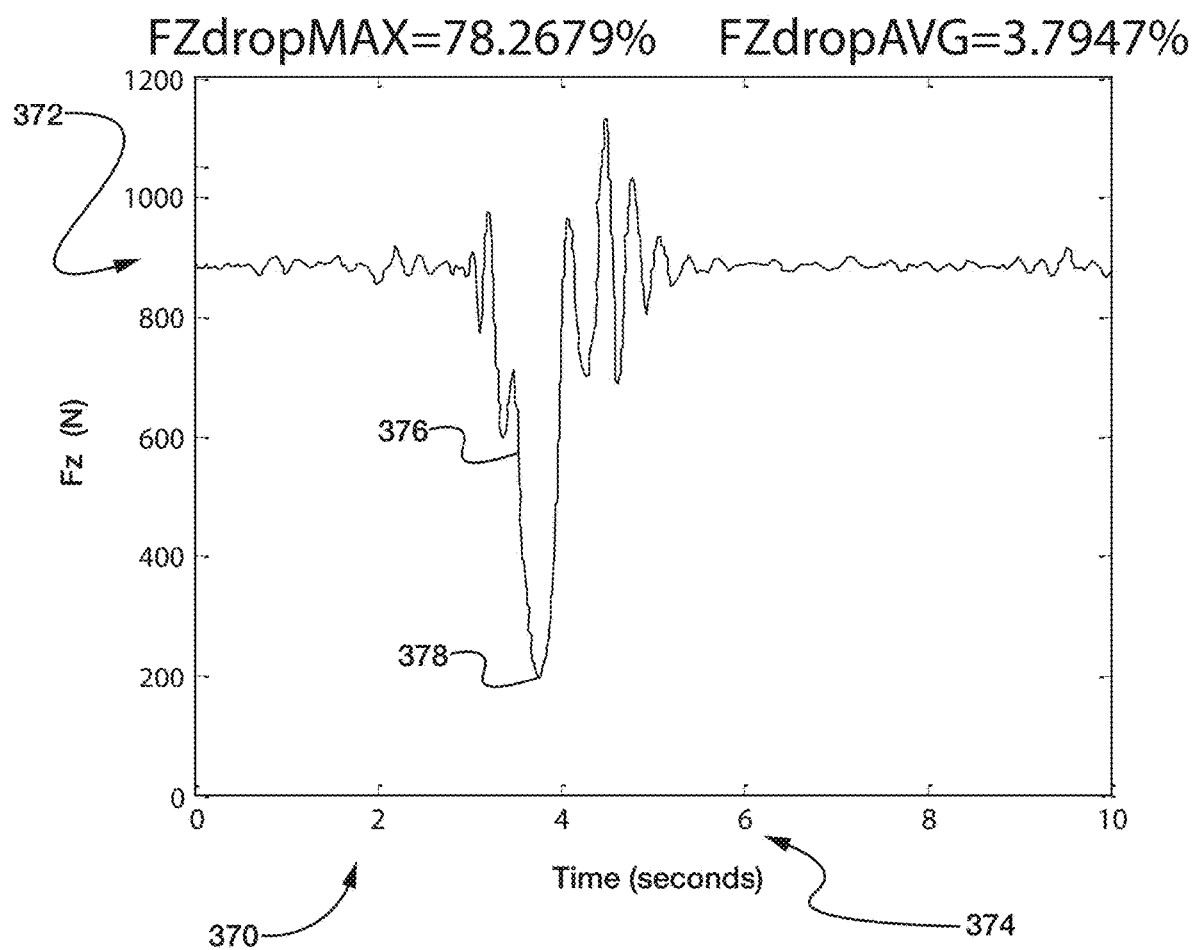
FIG. 57 is a graph illustrating a vertical force curve generated during the performance of a test trial where a subject steps off the force measurement assembly with one foot, and places his or her foot back onto the force measurement assembly, according to another embodiment of the invention.
Figure 58:
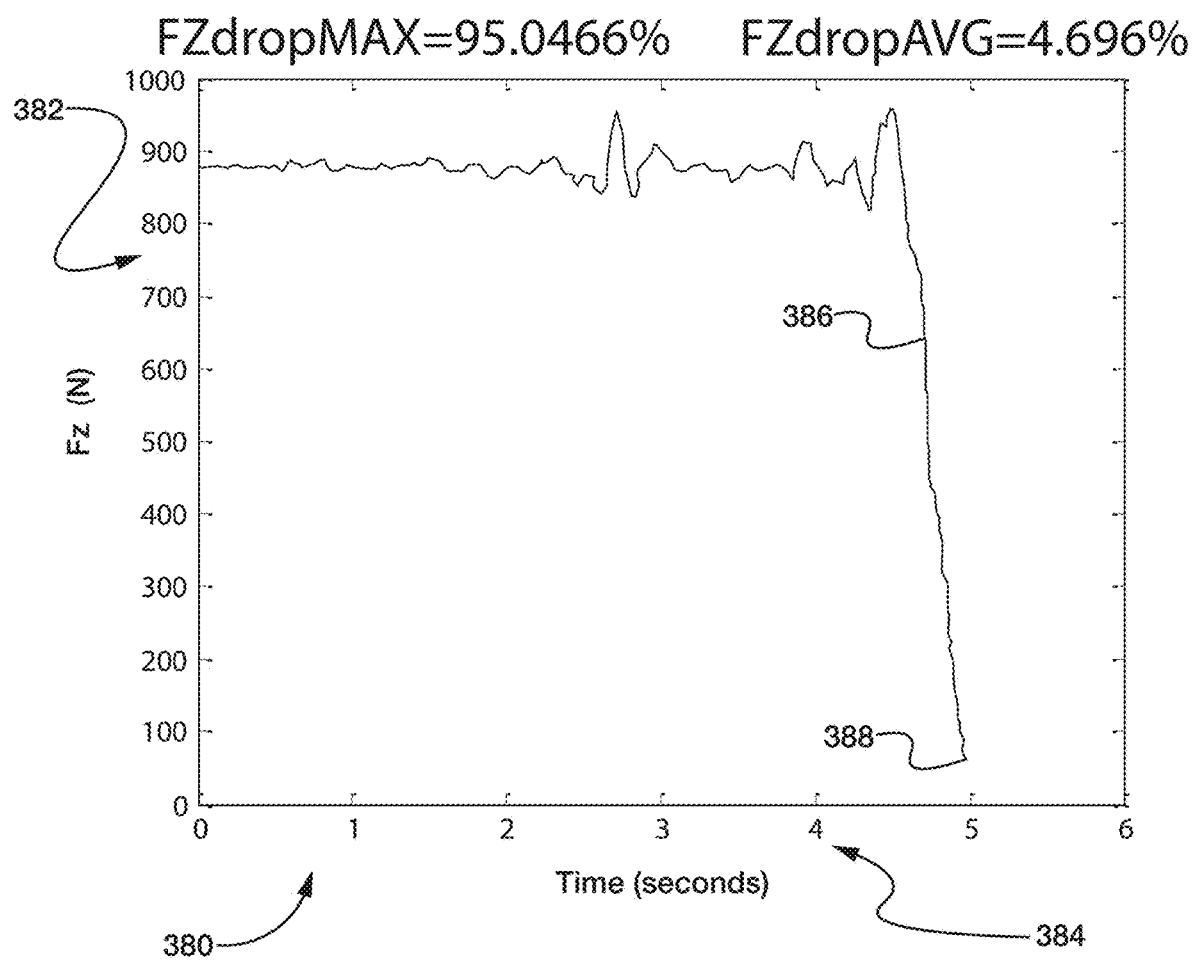
FIG. 58 is a graph illustrating a vertical force curve generated during the performance of a test trial where a subject steps off the force measurement assembly with both feet, and does not return to the force measurement assembly, according to another embodiment of the invention.

In yet further embodiments, the data acquisition/data processing device 104 of the force measurement system 100 is programmed to determine a presence of a measurement error resulting from a portion of the load from the at least one portion of the body of the subject 108 being applied to an external object rather than the intended top surfaces 114, 116 of the force measurement assembly 102. As illustrated in the graphs of FIGS. 56-58, the data acquisition/data processing device 104 may be configured to determine the presence of the measurement error by computing a maximum drop in the vertical component ($F_Z$) of the output force for a predetermined duration of time. Also, as illustrated in the graphs of FIGS. 56-58, the data acquisition/data processing device 104 may be configured to determine the presence of the measurement error by computing an average drop in the vertical component ($F_Z$) of the output force for a predetermined duration of time. For example, a vertical force curve (i.e., an $F_Z$ curve) generated for a test trial where the subject 108 is pulling on the harness 352 while standing still is illustrated in FIG. 56. As shown in this figure, the y-axis 362 of the graph 360 is the vertical component ($F_Z$) of the output force in Newtons (N), while the x-axis 364 of the graph 360 is the time in seconds (sec). In the graph 360 of FIG. 56, it can be seen that the vertical force curve 366 has a minimum point at 368. As another example, a vertical force curve (i.e., an $F_Z$ curve) generated for a test trial where the subject 108 steps off the force measurement assembly 102 with one foot, and places his or her foot back onto the force measurement assembly 102, is illustrated in FIG. 57. As shown in this figure, the y-axis 372 of the graph 370 is the vertical component ($F_Z$) of the output force in Newtons (N), while the x-axis 374 of the graph 370 is the time in seconds (sec). In the graph 370 of FIG. 57, it can be seen that the vertical force curve 376 has a minimum point at 378. As yet another example, a vertical force curve (i.e., an $F_Z$ curve) generated for a test trial where the subject 108 steps off the force measurement assembly 102 with both feet, but does not return to the force measurement assembly 102, is illustrated in FIG. 58. As shown in this figure, the y-axis 382 of the graph 380 is the vertical component ($F_Z$) of the output force in Newtons (N), while the x-axis 384 of the graph 380 is the time in seconds (sec). In the graph 380 of FIG. 58, it can be seen that the vertical force curve 386 has a minimum point and endpoint at 388 where the subject 108 steps off the force measurement assembly 102 with both feet.

Figure 54:
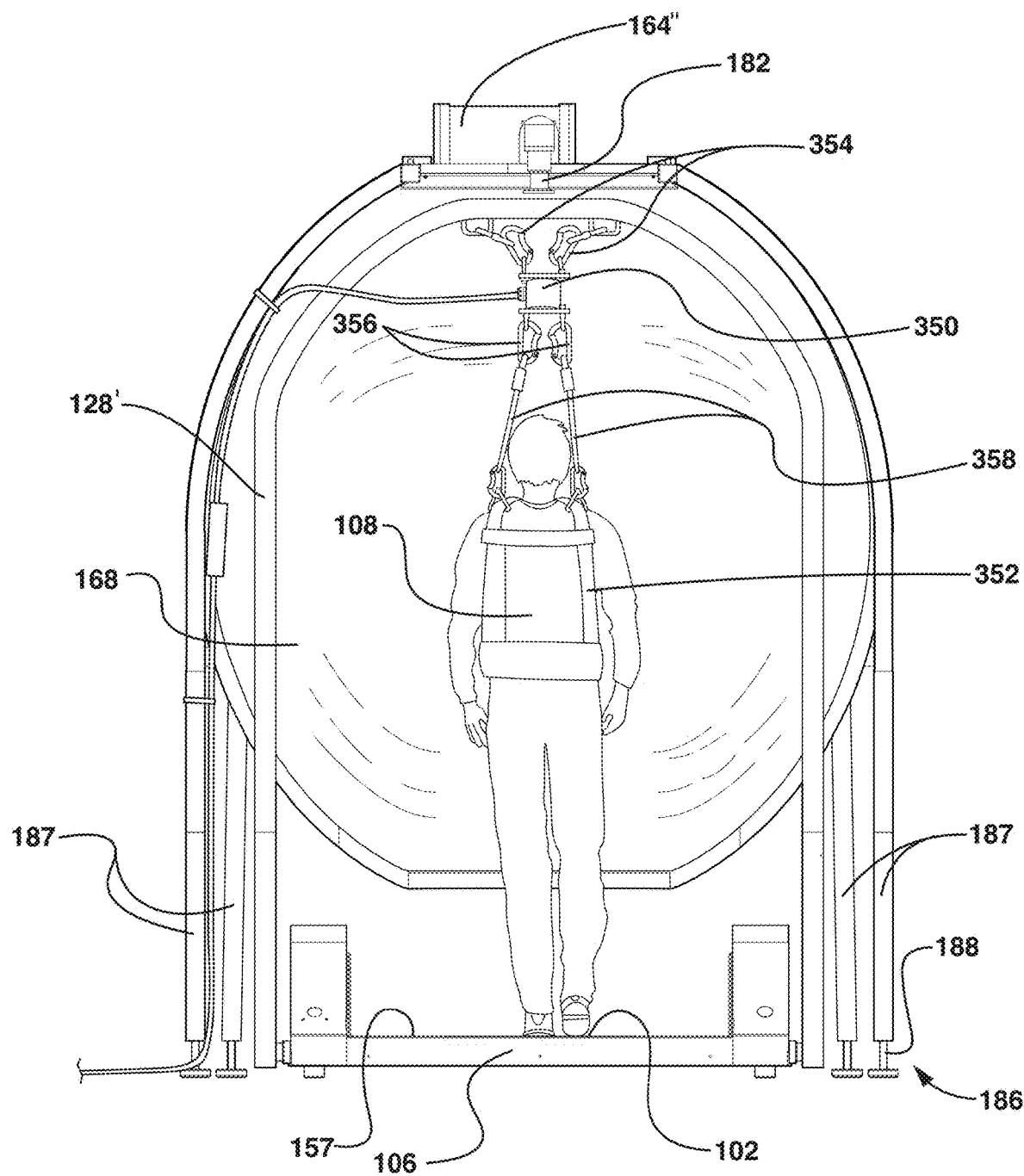
FIG. 54 is a perspective view of the base assembly and the immersive subject visual display device of the force measurement system according to yet another alternative embodiment of the invention, wherein the system is further provided with a subject harness connected to a force sensor.
Figure 55:
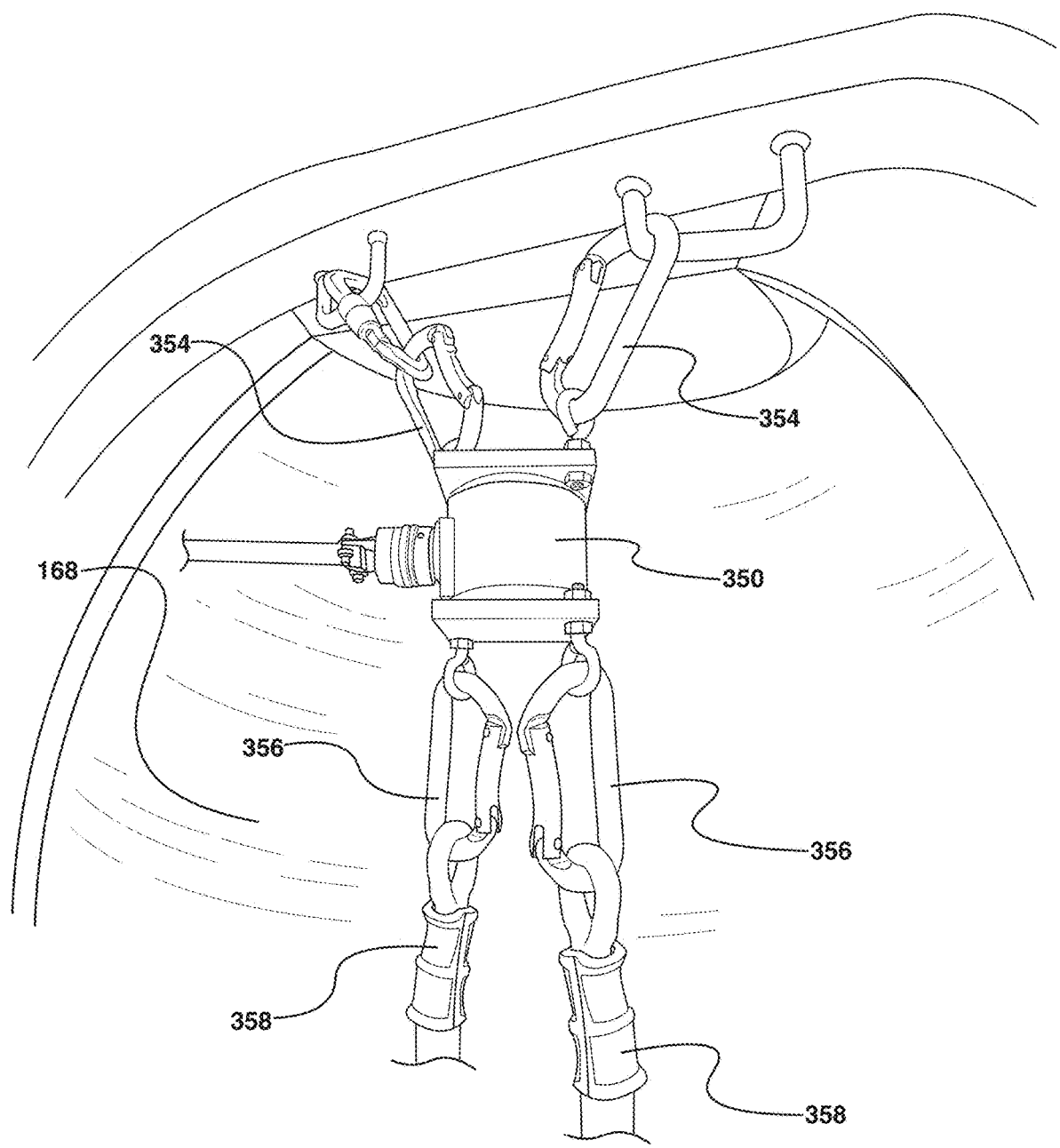
FIG. 55 is an enlarged portion of the perspective view depicted in FIG. 54, wherein the harness force sensor is illustrated together with the upper and lower harness connectors.

In these further embodiments, the force measurement system 100 may further comprise an external force sensor (i.e., a load transducer) configured to measure a force exerted on an external object by the subject. The external force sensor (i.e., a load transducer) is operatively coupled to the data acquisition/data processing device 104 of the force measurement system 100 so that the load data acquired by the external force sensor (i.e., a load transducer) may be transmitted to the data acquisition/data processing device 104. When the external force sensor is used to measure the force exerted on the external object by the subject, the data acquisition/data processing device 104 may be configured to determine the presence of the measurement error by determining whether the force measured by the external force sensor is greater than a predetermined threshold value (e.g., greater than 10 Newtons). In the illustrative embodiment, with reference to FIG. 54, the external object on which the subject 108 is exerting the force may comprise a safety harness 352 worn by the subject 108 to prevent the subject from falling, and the safety harness 352 may be provided with the external force sensor 350 (see FIGS. 54 and 55). As shown in FIGS. 54 and 55, the external force sensor 350 may be connected between the harness support structure 128' and the safety harness 352. More particularly, in the illustrative embodiment, the top of the external force sensor 350 is connected to the harness support structure 128' by the upper harness connectors 354, and the bottom of the external force sensor 350 is connected to the harness ropes 358 by the lower harness connectors 356. The safety harness 352 is suspended from the lower harness connectors 356 by the harness ropes 358. Also, in the illustrative embodiment, with reference now to FIG. 42, another external object on which the subject 108 is exerting the force may comprise stationary portions 122a, 122b of the base assembly 106 of the force measurement system 100, and the stationary portions 122a, 122b of the base assembly 106 may be provided with respective external force sensors 390, 392 for measuring the forces exerted thereon by the subject 108. In the illustrative embodiment, the data acquisition/data processing device 104 is further configured to classify the type of action by the subject 108 that results in the subject 108 exerting the force on the external object (e.g., on the harness 352 or the stationary portions 122a, 122b of the base assembly 106). For example, in the illustrative embodiment, the type of action by the subject 108 that results in the subject 108 exerting the force on the external object is selected from the group consisting of: (i) pulling on a safety harness 352, (ii) stepping at least partially off the top surfaces 114, 116 of the force measurement assembly 102, and (iii) combinations thereof.

In these further embodiments, the data acquisition/data processing device 104 is further configured to generate an error notification on the output screen of the operator visual display device 130 when the data acquisition/data processing device 104 determines the presence of the measurement error. In addition, the data acquisition/data processing device 104 may be further configured to classify the type of action by the subject 108 that results in the portion of the load being applied to the external object (e.g., the harness 352 or the stationary portion 122a, 122b of the base assembly 106). The error notification generated on the output screen of the operator visual display device 130 by the data acquisition/data processing device 104 may include the classification of the type of action by the subject 108 that results in the portion of the load being applied to the external object.

In these further embodiments, the data acquisition/data processing device 104 may compute the normalized maximum drop in the vertical component ($F_Z$dropMAX) of the output force during a test trial by using the following equation:

$$F_Z dropMAX = \frac{(StartMean\ F_Z - Min\ F_Z)}{StartMean\ F_Z} \quad (14)$$

where:
StartMean $F_Z$: mean value of the vertical force ($F_Z$) for the first 500 milliseconds of the trial; and
Min $F_Z$: minimum value of the vertical force ($F_Z$) for the trial.

For example, for the vertical force curve 366 depicted in FIG. 56, the $F_Z$dropMAX value is approximately 27.8% for the trial in which the subject 108 is pulling on the harness 352 while standing still. As another example, for the vertical force curve 376 depicted in FIG. 57, the $F_Z$dropMAX value is approximately 78.3% for the trial in which the subject 108 steps off the force measurement assembly 102 with one foot, and then places his or her foot back onto the force measurement assembly 102. As yet another example, for the vertical force curve 386 depicted in FIG. 58, the $F_Z$dropMAX value is approximately 95.0% for the trial in which the subject 108 steps off the force measurement assembly 102 with both feet, and does not return to the force measurement assembly 102.

In these further embodiments, the data acquisition/data processing device 104 may compute the normalized average drop in the vertical component ($F_Z$dropAVG) of the output force during a test trial by using the following equation:

$$F_Z dropAVG = \frac{(StartMean\ F_Z - Mean\ F_Z)}{StartMean\ F_Z} \quad (15)$$

where:
StartMean $F_Z$: mean value of the vertical force ($F_Z$) for the first 500 milliseconds of the trial; and
Mean $F_Z$: mean value of the vertical force ($F_Z$) from 501 milliseconds to the end of the trial.

For example, for the vertical force curve 366 depicted in FIG. 56, the $F_Z$dropAVG value is approximately 2.7% for the trial in which the subject 108 is pulling on the harness 352 while standing still. As another example, for the vertical force curve 376 depicted in FIG. 57, the $F_Z$dropAVG value is approximately 3.8% for the trial in which the subject 108 steps off the force measurement assembly 102 with one foot, and then places his or her foot back onto the force measurement assembly 102. As yet another example, for the vertical force curve 386 depicted in FIG. 58, the $F_Z$dropAVG value is approximately 4.7% for the trial in which the subject 108 steps off the force measurement assembly 102 with both feet, and does not return to the force measurement assembly 102.

In these further embodiments, the data acquisition/data processing device 104 may be configured to generate an error notification on the output screen of the operator visual display device 130 based upon comparing the $F_Z$dropMAX and $F_Z$dropAVG values computed for a particular trial to predetermined threshold values. For example, the data acquisition/data processing device 104 may be configured to determine if the $F_Z$dropMAX value computed for a particular trial is greater than 0.50 and if the $F_Z$dropAVG value computed for a particular trial is greater than 0.02. When the data acquisition/data processing device 104 determines that the $F_Z$dropMAX value is greater than 0.50 and the $F_Z$dropAVG value is greater than 0.02 (i.e., both of these two conditions are true), the error notification outputted by the data acquisition/data processing device 104 on the operator visual display device 130 may indicate that the subject has likely fallen during the trial (e.g., by outputting a message on the screen, such as "Subject has most likely fallen during trial, it is suggested that trial be repeated."). However, if the data acquisition/data processing device 104 determines that the $F_z$dropAVG value computed for a particular trial is greater than 0.01, but at least one of the preceding two conditions is not true (i.e., the $F_z$dropMAX value is not greater than 0.50 and/or the $F_z$dropAVG value is not greater than 0.02), then the error notification outputted by the data acquisition/data processing device 104 on the operator visual display device 130 may indicate that the subject has likely pulled on the harness 352 (e.g., by outputting a message on the screen, such as "Subject has most likely pulled on harness, it is suggested that trial be repeated."). Otherwise, if the data acquisition/data processing device 104 determines that the first set criteria are not satisfied (i.e., $F_z$dropMAX value is less than 0.50 and/or $F_z$dropAVG value is less than 0.02) and the second criteria are not satisfied (i.e., $F_z$dropAVG value is less than 0.01), then no error notification will be outputted by the data acquisition/ data processing device 104 on the operator visual display device 130 because, based on the computed $F_z$dropMAX and $F_z$dropAVG values, it appears to have been a good trial.

In still further embodiments, the data acquisition/data processing device 104 of the force measurement system is programmed to determine a type of balance strategy that the subject is using to maintain his or her balance on the force measurement assembly. In these further embodiments, the type of balance strategy determined by the data acquisition/ data processing device 104 is selected from the group consisting of: (i) an ankle strategy, (ii) a hip strategy, (iii) a step strategy, and (iv) combinations thereof. As will be described hereinafter, the data acquisition/data processing device 104 may determine the type of balance strategy that the subject is using to maintain his or her balance on the force measurement assembly by using output data from a variety of different devices. In one or more of these further embodiments, the force measurement assembly may be in the form of a force plate or a balance plate (e.g., the displaceable force plate 102 depicted in FIG. 44 or the static force plate 102' depicted in FIG. 52). When the force measurement assembly is in the form of the displaceable force plate 102 depicted in FIG. 44, the force measurement system further includes the base assembly 106 described above, which has a stationary portion and a displaceable portion. In this arrangement, as described above, the force measurement assembly 102 forms a part of the displaceable portion of the base assembly 106, and the force measurement system additionally comprises a plurality of actuators 158, 160 coupled to the data acquisition/data processing device 104. As explained above, the first actuator 158 is configured to translate the displaceable portion of the base assembly 106, which includes the force measurement assembly 102, relative to the stationary portion of the base assembly 106, while the second actuator 160 is configured to rotate the force measurement assembly 102 about a transverse rotational axis TA relative to the stationary portion of the base assembly 106.

In these further embodiments, the best type of balance strategy that can be employed by the subject depends on the particular task that the subject is being asked to perform. That is, for one particular task, an ankle balance strategy may be the best strategy for the subject to use, while for another particular task, a hip balance strategy may be the best strategy for the subject to use. For other tasks, a step balance strategy may be the best option for the subject. For example, because the ankle balance strategy does not offer as much opportunity to change the subject's center of gravity, it is not the best balance option for all situations. Also, a particular subject may have physical limitations that affect his or her balance strategy (e.g., an older person with stiff joints may have a significantly harder time using an ankle balance strategy as compared to a younger person with more flexible joints).

In one or more other further embodiments, the force measurement assembly may be in the form of an instrumented treadmill 600 (see FIG. 38), rather than a force measurement assembly 102, 102'.

In one or more of these further embodiments, the data acquisition/data processing device 104 is programmed to determine the type of balance strategy that the subject is using to maintain his or her balance on the force measurement assembly based upon one or more of the output forces and/or moments determined from the one or more signals of the force measurement assembly (i.e., the one or more signals of the force measurement assembly 102, 102' or instrumented treadmill 600). In these further embodiments, the one or more output forces and/or moments used by the data acquisition/data processing device 104 to determine the type of balance strategy comprise one or more shear forces, one or more vertical forces, or one or more moments used to compute the center of pressure of the subject. For example, when the data acquisition/data processing device 104 utilizes the shear force or a parameter based on the shear force to determine the type of balance strategy, a shear force approximately equal to zero is representative of an all ankle strategy by the subject, whereas a shear force that is equal to a substantial non-zero value is indicative of a hip strategy by the subject. In such a case, if the shear force measured by the force measurement assembly is greater than a predetermined magnitude, then the subject is using his or her hips, rather than his or her ankles, to maintain balance. The data acquisition/data processing device 104 may determine if the subject 108 uses a step balance strategy by evaluating the center of pressure of the subject 108 determined from the force measurement assembly (i.e., a step by the subject 108 will be evident by a characteristic change in the center of pressure of the subject).

In another one or more of these further embodiments, the force measurement system may further comprise a motion capture system with one or more motion capture devices configured to detect the motion of the subject 108 (e.g., the marker-based motion capture system 300 with cameras 302 depicted in FIGS. 32 and 33). In these further embodiments, the motion capture system 300 is operatively coupled to the data acquisition/data processing device 104, and the data acquisition/data processing device 104 is programmed to determine the type of balance strategy that the subject 108 is using to maintain his or her balance on the force measurement assembly based upon the output data from the one or more motion capture devices of the motion capture system (i.e., the limb movements of the subject determined from the motion capture data). For example, when the data acquisition/data processing device 104 utilizes the motion capture system to determine the type of balance strategy, the images captured by the motion capture system are indicative of whether the subject 108 is using a hip strategy or an ankle strategy to maintain his or her balance.

In yet another one or more of these further embodiments, the force measurement system may further comprise at least one camera (e.g., at least one web camera) configured to capture the motion of the subject 108. In these further embodiments, the camera is operatively coupled to the data acquisition/data processing device 104, and the data acquisition/data processing device 104 is programmed to determine the type of balance strategy that the subject 108 is using to maintain his or her balance on the force measurement assembly based upon the output data from the at least one camera. For example, when the data acquisition/data processing device 104 utilizes the at least one camera (e.g., at least one web camera) to determine the type of balance strategy, a vision model (e.g., PoseNet) that employs a convolutional neural network (CNN) may be used to estimate the balance strategy of the subject by estimating the locations of the key body joints of the subject 108. In one or more of these further embodiments, a markerless motion capture system comprising a plurality of cameras (e.g., a plurality of web cameras) may be mounted on elements of the force measurement system in order to capture the motion of the subject in a variety of different planes. For example, with reference to FIG. 44, a first camera may be mounted on the screen 168 facing the subject in order to capture the coronal plane of the subject. A second camera may be mounted on the first side bar of the harness support structure 128' (see FIG. 54), and angled in a direction facing the subject so as to capture the sagittal plane of the subject from a first side. A third camera may be mounted on the second side bar of the harness support structure 128' (see FIG. 54), and angled in a direction facing the subject so as to capture the sagittal plane of the subject from a second side.

In still another one or more of these further embodiments, the force measurement system may further comprise one or more inertial measurement units (e.g., one or more inertial measurement units 306 as depicted in FIG. 49) configured to detect the motion of the subject 108. In these further embodiments, the one or more inertial measurement units 306 are operatively coupled to the data acquisition/data processing device 104, and the data acquisition/data processing device 104 is programmed to determine the type of balance strategy that the subject 108 is using to maintain his or her balance on the force measurement assembly based upon the output data from the one or more inertial measurement units 306. For example, when the data acquisition/data processing device 104 utilizes one or more inertial measurement units 306 to determine the type of balance strategy, a first one of the inertial measurement units 306 may be mounted on the torso of the subject 108, a second one of the inertial measurement units 306 may be mounted near a hip of the subject 108, and a third one of the inertial measurement units 306 may be mounted near an ankle of the subject 108 (e.g., refer to FIG. 49).

In yet another one or more of these further embodiments, the force measurement system may further comprise a radar-based sensor configured to detect the posture of the subject 108. In these further embodiments, the radar-based sensor is operatively coupled to the data acquisition/data processing device 104, and the data acquisition/data processing device 104 is programmed to determine the type of balance strategy that the subject 108 is using to maintain his or her balance on the force measurement assembly based upon the output data from the radar-based sensor. For example, when the data acquisition/data processing device 104 utilizes the radar-based sensor to determine the type of balance strategy, the radar-based sensor may be mounted on one of the side bars of the harness support structure 128' (see FIG. 54), and angled in a direction facing the subject so as to capture the sagittal plane of the subject from a side. As one example, the radar-based sensor may utilize a miniature radar chip to detect touchless gesture or pose interactions, such as in the Google® *Soli* device.

In still another one or more of these further embodiments, the force measurement system may further comprise an infrared sensor configured to detect the posture of the subject 108. In these further embodiments, the infrared sensor is operatively coupled to the data acquisition/data processing device 104, and the data acquisition/data processing device 104 is programmed to determine the type of balance strategy that the subject 108 is using to maintain his or her balance on the force measurement assembly based upon the output data from the infrared sensor. For example, as described above, the infrared sensor may be part of a motion detection/motion capture system that employs infrared light (e.g., the system could utilize an infrared (IR) emitter to project a plurality of dots onto objects in a particular space as part of a markless motion capture system). As shown in the exemplary system of FIG. 50, the motion detection/motion capture system employing infrared light may comprise one or more cameras 320, one or more infrared (IR) depth sensors 322, and one or more microphones 324 to provide full-body three-dimensional (3D) motion capture, facial recognition, and voice recognition capabilities.

In these further embodiments where the balance strategy of the subject 108 is determined, the force measurement system further comprises at least one visual display device having an output screen (e.g., the subject visual display device 107 and/or operator visual display device 130 described above and depicted in FIG. 1). In these further embodiments, the data acquisition/data processing device 104 is configured to generate a visual indicator (e.g., see the virtual representation 394 in FIGS. 59 and 60) indicative of the type of balance strategy that the subject is using to maintain his or her balance, and to display the visual indicator 394 in the one or more images 396, 397 on the output screen of the at least one visual display device.

In these further embodiments where the balance strategy of the subject 108 is determined, the force measurement system further comprises one or more user input devices, such as the keyboard 132 and/or mouse 134 depicted in FIG. 1 and described above. In these further embodiments, the user input device 132, 134 is configured to output an input device signal based upon an input by a user, and the data acquisition/data processing device 104 is configured to set a parameter related to the balance strategy of the subject 108 based upon the input by the user entered using the user input device 132, 134. Also, in these further embodiments, the data acquisition/data processing device 104 is further programmed to generate and display visual feedback to the subject 108 on the output screen of the at least one visual display device based upon the parameter entered by the user. For example, the clinician may set a goal for a particular angle of displacement of the subject's hip angle $\theta_H$ or the subject's ankle angle $\Theta_A$, and then a line may be displayed on the subject visual display device that denotes that particular angle. As the subject displaces his or her body on the force measurement assembly, the virtual representation 394 of the subject on the force plate surface 398 disposed in the screen image 396, 397 may be displaced in accordance with the subject's movement so that the subject 108 is able to visualize the virtual representation 394 of him or her approach the line marking his or her joint angle displacement goal.

In these further embodiments, the visual feedback provided to the subject 108 regarding his or her balance strategy may be provided in conjunction with a balance assessment and training regime. First of all, an assessment may be performed on the subject to determine if there are particular weaknesses in the balance strategy of the subject. For example, as described above, a motion capture system may be used to determine the hip and ankle joint angles $\Theta_H$, $\theta_A$ of the subject in the sagittal plane. Secondly, based on the results of the balance assessment, a balance training program for the subject may be developed. For example, the balance training program may involve scenarios that would require the subject to use each one of the three balance strategies (i.e., the ankle strategy, the hip strategy, and the step strategy) depending on the scenario. During the training, the clinician may use the visual feedback functionality of the force measurement system in order to set the required range of motion for the subject (e.g., the angular range of displacement for the hip joint angle and/or the ankle joint angle of the subject). Then, during the training, the visual feedback may be modified when the subject reaches a certain target angular displacement (e.g., the line displayed on the subject visual display device that denotes a particular goal angle may be shifted to another rotational position once the goal is achieved). The data acquisition/data processing device 104 of the force measurement system may be programmed to perform all of the above-described assessment and training functionality.

Figure 59:
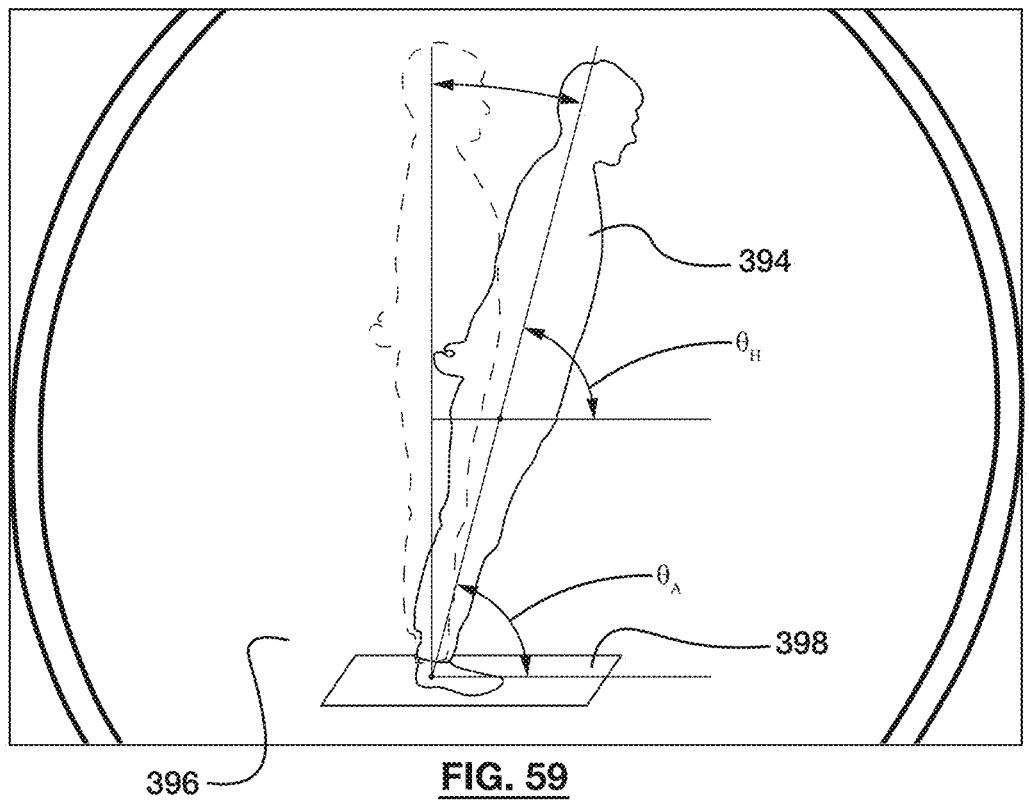
FIG. 59 is an example of a screen image displayed on the visual display device of the force measurement system, wherein a virtual representation of the subject is depicted using an ankle balance strategy, according to an embodiment of the invention.
Figure 60:
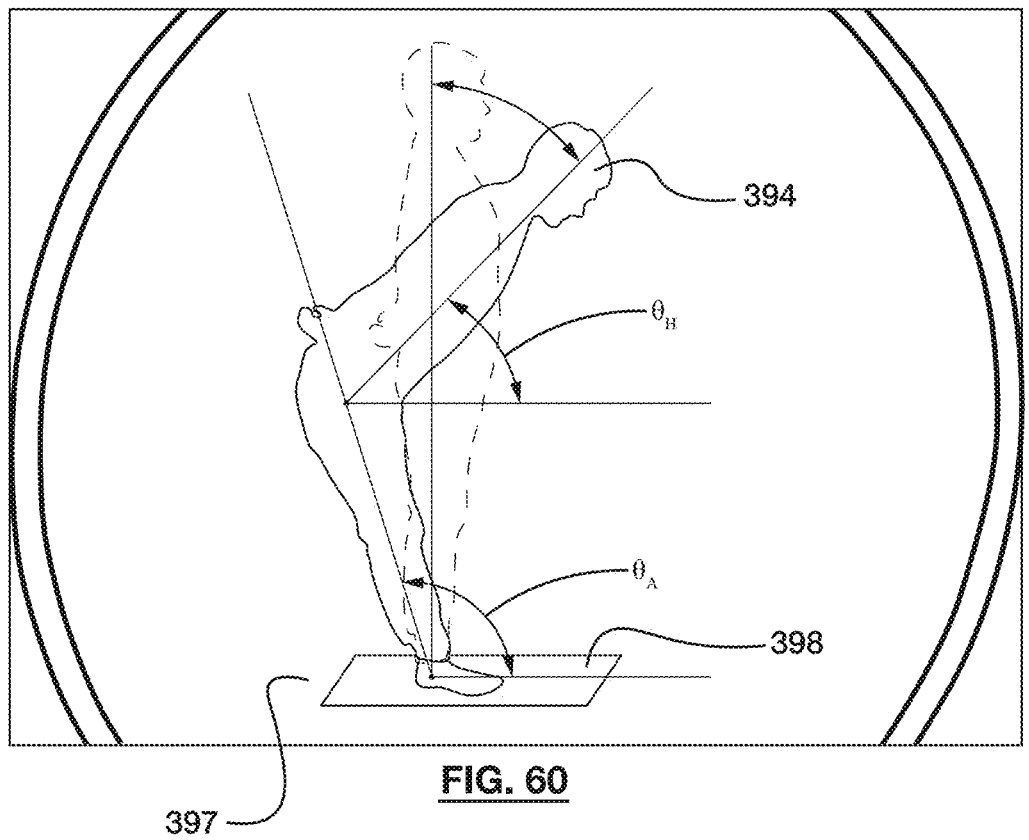
FIG. 60 is an example of a screen image displayed on the visual display device of the force measurement system, wherein a virtual representation of the subject is depicted using a combination hip and ankle balance strategy, according to an embodiment of the invention.

In FIG. 59, a first exemplary screen image 396 on the subject visual display device 107 is illustrated. In the screen image 396 of FIG. 59, the virtual representation 394 of the subject is depicted using an ankle balance strategy where the hip joint angle $\theta_H$ is approximately equal to the ankle joint angle $\Theta_A$. In FIG. 60, a second exemplary screen image 397 on the subject visual display device 107 is illustrated. In the screen image 397 of FIG. 60, the virtual representation 394 of the subject is depicted using a combination hip and ankle balance strategy where the hip joint angle $\theta_H$ is not equal to the ankle joint angle $\Theta_A$. In general, when the hip joint angle $\theta_H$ is equal or approximately equal to the ankle joint angle $\Theta_A$, then an ankle balance strategy is being used by the subject. Conversely, when the hip joint angle $\theta_H$ and the ankle joint angle $\theta_A$ are different, then a hip balance strategy is being used by the subject.

In still further embodiments, the data acquisition/data processing device 104 of the force measurement system is programmed to determine a difference between a center of pressure and a center of mass for the subject from output force and/or moment data, and the one or more data processing devices are additionally programmed to determine the fall risk of the subject based upon the difference between the center of pressure and the center of mass for the subject. For example, a large difference between the center of pressure and the center of mass for a subject will typically be indicative of a high fall risk. Conversely, if the difference between the center of pressure and the center of mass for a subject is small, then the fall risk of the subject is low. In one or more of these further embodiments, the data acquisition/data processing device 104 may determine the difference between a center of pressure and a center of mass for the subject from output force and/or moment data generated by a force measurement assembly. The force measurement assembly may be in the form of a force plate or a balance plate (e.g., the displaceable force plate 102 depicted in FIG. 44 or the static force plate 102' depicted in FIG. 52). When the force measurement assembly is in the form of the displaceable force plate 102 depicted in FIG. 44, the force measurement system further includes the base assembly 106 described above, which has a stationary portion and a displaceable portion. In this arrangement, as described above, the force measurement assembly 102 forms a part of the displaceable portion of the base assembly 106, and the force measurement system additionally comprises a plurality of actuators 158, 160 coupled to the data acquisition/data processing device 104. As explained above, the first actuator 158 is configured to translate the displaceable portion of the base assembly 106, which includes the force measurement assembly 102, relative to the stationary portion of the base assembly 106, while the second actuator 160 is configured to rotate the force measurement assembly 102 about a transverse rotational axis TA relative to the stationary portion of the base assembly 106.

In these further embodiments, the data acquisition/data processing device 104 may be configured to determine the difference between the center of pressure and the center of mass for the subject by using a combination of a high pass filter and a low pass filter on center of pressure data determined from the output force and/or moment data. For example, in one exemplary, non-limiting embodiment, a low pass filter with a 0.75 Hz cutoff frequency and a high pass filter with a 10.0 Hz cutoff frequency are applied to the center of pressure data in order to determine the difference between the center of pressure and the center of mass. The high pass filter eliminates the signal noise associated with the center of pressure data. Alternatively, in another example, the center of pressure and the center of mass may be computed separately, and then the difference between the center of pressure and the center of mass can be computed.

In one or more of these further embodiments, the data acquisition/data processing device 104 is configured to determine the difference between the center of pressure and the center of mass for the subject while the subject is standing stationary on the top surface of the force measurement assembly. Alternatively, in one or more other ones of these further embodiments, the data acquisition/data processing device 104 is configured to determine the difference between the center of pressure and the center of mass for the subject while the subject is displacing his or her body (e.g., swaying in the medial-lateral direction and/or superior-inferior direction) while standing on the top surface of the force measurement assembly.

In one or more other further embodiments, the force measurement assembly may be in the form of an instrumented treadmill 600 (see FIG. 38), rather than a force measurement assembly 102, 102'.

In one or more of these further embodiments, the data acquisition/data processing device 104 is programmed to determine the center of pressure data and the center of mass data based upon one or more of the output forces and/or moments determined from the one or more signals of the force measurement assembly (i.e., the one or more signals of the force measurement assembly 102, 102' or instrumented treadmill 600).

In these further embodiments, the data acquisition/data processing device 104 of the force measurement system is further programmed to determine one or more balance parameters of the subject from the output force and/or moment data while the subject is stepping onto the top surface of the force measurement assembly and/or stepping off the top surface of the force measurement assembly. The one or more balance parameters of the subject determined by the data acquisition/data processing device 104 include a displacement of a center of pressure for at least one foot of the subject (e.g., for the left foot of the subject, for the right foot of the subject, or for both the right and left feet of the subject). The center of pressure may be computed by the data acquisition/data processing device 104 in the manner described above with regard to FIGS. 5 and 7. During the transitional period when the subject is stepping onto the top surface of the force measurement assembly and/or stepping off the top surface of the force measurement assembly, the center of pressure will be displaced over a boundary edge of the force measurement assembly. In these further embodiments, the displacement of the center of pressure for the one or more feet of the subject may be used to predict the fall risk of the subject. For example, if the displacement path of the center of pressure for the subject is erratic with many jagged fluctuations, then the subject may have a high risk of falling. Conversely, if the displacement path of the center of pressure for the subject is generally smooth without many jagged fluctuations, then the subject may have a low risk of falling.

In these further embodiments, when the subject is stepping onto the top surface of the force measurement assembly and/or stepping off the top surface of the force measurement assembly, the one or more balance parameters of the subject determined by the data acquisition/data processing device 104 may further include a weight distribution on each foot of the subject quantified by a percentage of the subject's total body weight on each foot (e.g., 60% of total body weight being placed on the right leg versus 40% of total body weight being placed on the left leg) and/or weight symmetry between the feet of the subject (e.g., approximately symmetric weight distribution or asymmetric weight distribution). In these further embodiments, the data acquisition/data processing device 104 utilizes the vertical force ($F_Z$) measured by the force measurement assembly to determine the weight distribution on each foot of the subject and/or weight symmetry between the feet of the subject (i.e., the vertical force is used to get the weight of the subject on each foot). In these further embodiments, the data acquisition/data processing device 104 also utilizes the vertical force ($F_Z$) as a measure of stabilization of the subject (e.g., a shift in the weight of the subject from one foot to the other foot is indicative of the stability of the subject). In these further embodiments, the weight distribution on each foot of the subject and/or weight symmetry between the feet of the subject may be used to predict the fall risk of the subject. For example, if the weight distribution of the subject is highly asymmetric between the feet of the subject, then the subject may have a high risk of falling. Conversely, if the weight distribution of the subject is nearly symmetric between the feet of the subject, then the subject may have a low risk of falling.

In these further embodiments, when the subject is stepping onto the top surface of the force measurement assembly and/or stepping off the top surface of the force measurement assembly, the one or more balance parameters of the subject determined by the data acquisition/data processing device 104 may further include a time duration for the subject to reach a stable position on the force measurement assembly. For example, when the subject is stepping onto the top surface of the force measurement assembly, it may take the subject approximately 2 to 10 seconds after the second foot of the subject reaches the force measurement assembly to reach a stable position on the force measurement assembly. When the subject is stepping off the top surface of the force measurement assembly, the stability of the subject is considered after the subject lifts his or her first foot off the force measurement assembly. The data acquisition/data processing device 104 may be configured to determine that the stable position of the subject on the force measurement assembly has been reached when a displacement of a center of pressure for the subject remains within a predetermined sway envelope (e.g., the center of pressure does not move outside the boundary of a circular or elliptical sway envelope while the subject is standing on the force measurement assembly). A sway envelope for a subject with a balance disorder is typically larger than for a normal subject. Measurements taken during the stabilization phase of the subject (e.g., the approximately 2 to 10 second time period) are indicative of the subject's overall stability and likelihood of falling. In these further embodiments, the time duration for the subject to reach a stable position may be used to predict the fall risk of the subject. For example, if the subject takes a long time to reach a stable position, then the subject may be instable and have a high risk of falling. Conversely, if the subject only takes a short period of time to reach a stable position, then the subject may have a low risk of falling.

In these further embodiments, the data acquisition/data processing device 104 may be configured to determine the one or more balance parameters of the subject while the subject is either stepping onto the top surface of the force measurement assembly for a body weight measurement (e.g., during a physical exam where the subject is being weighed) or stepping off the top surface of the force measurement assembly after the body weight measurement (e.g., during the physical exam where the subject is being weighed). The vertical force ($F_Z$) measured by the force measurement assembly is used to determine the weight of the subject.

In these further embodiments, the data acquisition/data processing device 104 may be further configured to determine a fall risk of the subject by inputting one or more of the above-described balance parameters (i.e., difference between the center of pressure and the center of mass for the subject, displacement of the center of pressure, weight distribution on each foot, and/or time duration for the subject to reach a stable position) into a trained neural network (e.g., trained convolutional neural network (CNN), and then predicting the fall risk of the subject based upon each of these balance parameters (e.g., the trained neural network can be trained so as to determine normal and abnormal values for the balance parameters, as well as to apply weights to the balance parameters based upon their correlation with a fall risk of the subject).

Figure 61:
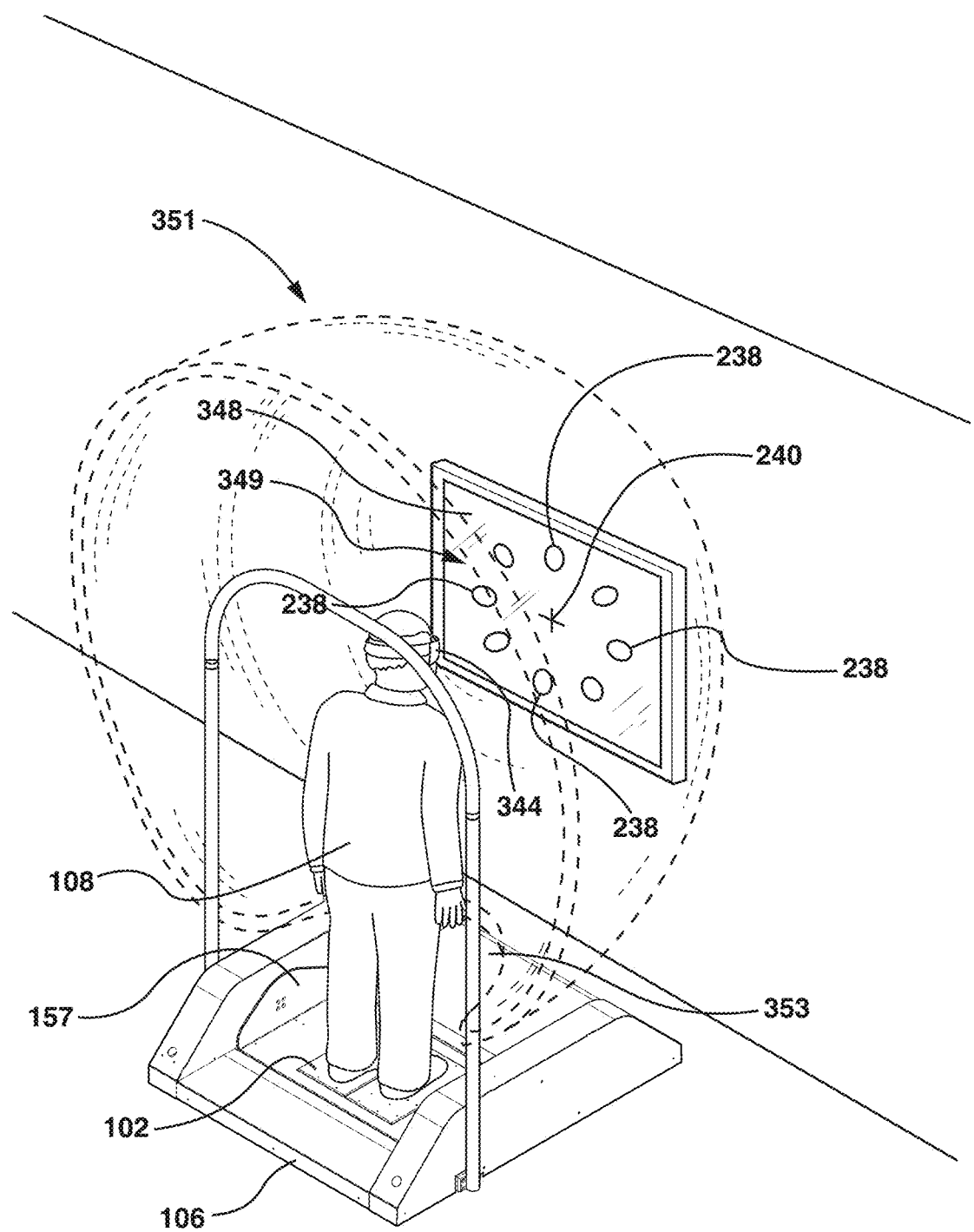
FIG. 61 is a perspective view of a subject disposed on a displaceable force measurement assembly while wearing a head-mounted visual display device that creates a virtual screen surround around a flat visual display device, according to yet another alternative embodiment of the invention.
Figure 62:
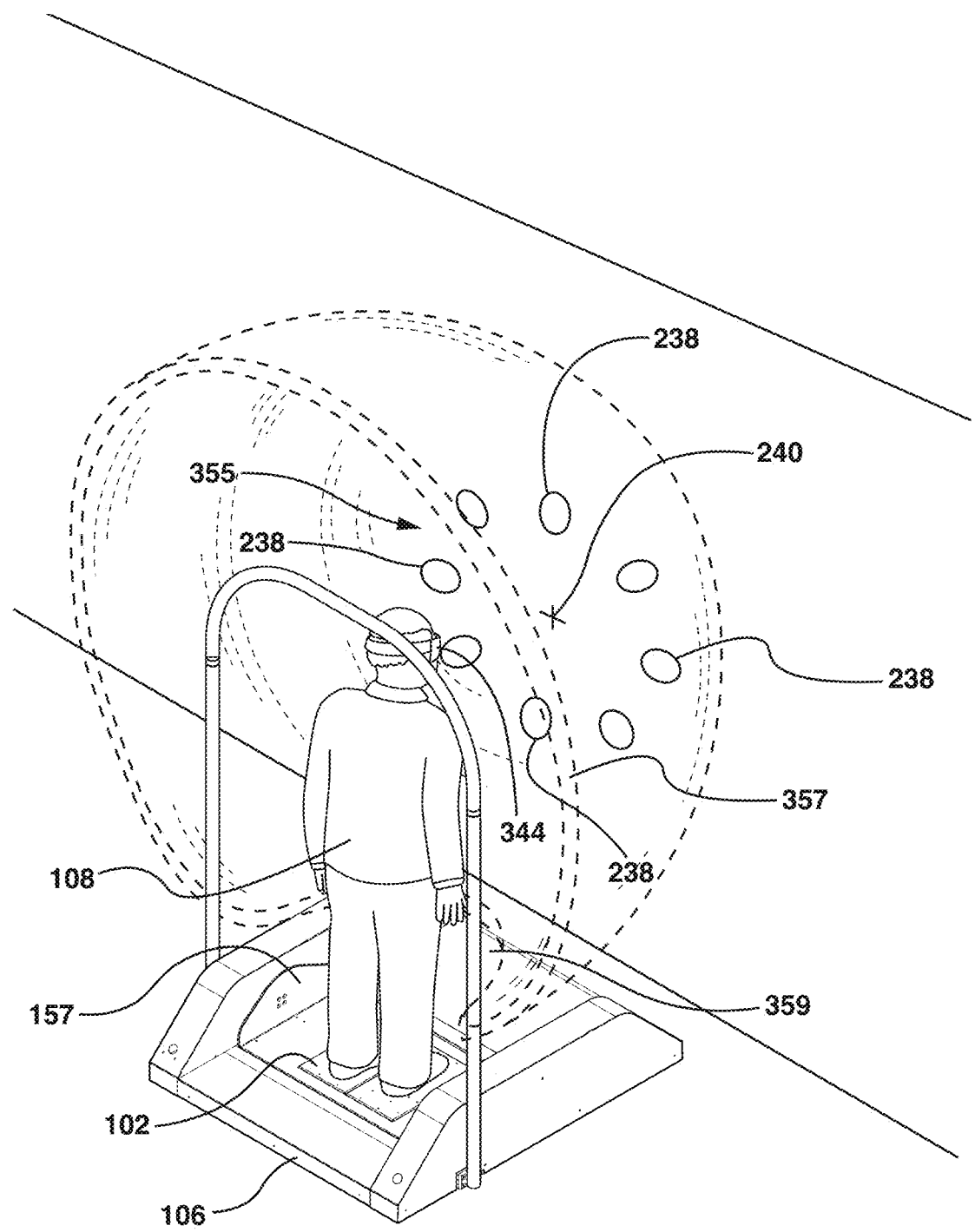
FIG. 62 is a perspective view of a subject disposed on a displaceable force measurement assembly while wearing a head-mounted visual display device that creates a virtual visual display device with a virtual screen surround, according to still another alternative embodiment of the invention.

In yet further embodiments, referring to FIGS. 61 and 62, the force measurement system generally comprises a force measurement assembly 102 configured to receive a subject 108, at least one visual display device 344, 348, the at least one visual display device 344, 348 configured to display one or more images; and one or more data processing devices 104 operatively coupled to the force measurement assembly 102 and the at least one visual display device 344, 348. In these further embodiments, as shown in FIGS. 61 and 62, the one or more data processing devices 104 are further configured to generate a first image portion 349, 355 and display the first image portion 349, 355 using the at least one visual display device 344, 348, and to generate a second image portion 351, 357 and display the second image portion 351, 357 using the at least one visual display device 344. The first image portion 349, 355 displayed using the at least one visual display device 344, 348 comprises a primary screen image for viewing by the subject 108, and the second image portion 351, 357 displayed using the at least one visual display device 344 comprises a virtual screen surround configured to at least partially circumscribe three sides of a torso of the subject 108 and to substantially encompass a peripheral vision of the subject 108.

As shown in FIGS. 61 and 62, in the illustrative embodiments, the force measurement assembly 102 is in the form of a force plate or a balance plate. Although, in other embodiments, the force measurement assembly may be in the form of an instrumented treadmill (e.g., the instrumented treadmill 600, 600' shown in FIGS. 38 and 45). Also, in the embodiments of FIGS. 61 and 62, the force measurement system further includes the base assembly 106 described above, which has a stationary portion and a displaceable portion. In this arrangement, as described above, the force measurement assembly 102 forms a part of the displaceable portion of the base assembly 106, and the force measurement system additionally comprises a plurality of actuators 158, 160 coupled to the one or more data processing devices 104. As explained above, the first actuator 158 is configured to translate the displaceable portion of the base assembly 106, which includes the force measurement assembly 102, relative to the stationary portion of the base assembly 106, while the second actuator 160 is configured to rotate the force measurement assembly 102 on the rotatable carriage assembly 157 about a transverse rotational axis TA relative to the stationary portion of the base assembly 106 (see e.g., FIGS. 3, 42, and 43).

Now, with reference to FIG. 61, in one further embodiment, the at least one visual display device 344, 348 comprises a first visual display device 348 and a second visual display device 344. In the embodiment of FIG. 61, it can be seen that the first visual display device comprises a flat display screen 348. In other embodiments, the first visual display device may alternatively comprise a curved display screen. As shown in FIG. 61, the first image portion 349 with the primary screen image is displayed on the flat display screen 348 of the first visual display device. In the embodiment of FIG. 61, it can be seen that the second visual display device is in the form of a head-mounted visual display device 344. For example, in the embodiment of FIG. 61, the head-mounted visual display device 344 may comprise an augmented reality headset that is capable of supplementing real-world objects, such as the flat display screen 348, with computer-generated virtual objects. The head-mounted visual display device 344 may have the headset performance parameters described above (e.g., the aforedescribed field of view range, refresh rate range, and display latency range). As shown in FIG. 61, the second image portion 351 with the virtual screen surround is displayed using the head-mounted visual display device 344. Advantageously, similar to the physical dome-shaped projection screen 168 described above, the virtual screen surround 351 is capable of creating an immersive environment for the subject 108 disposed on the force measurement assembly 102 (i.e., the virtual screen surround 351 engages enough of the subject's peripheral vision such that the subject becomes, and remains immersed in the primary screen image that is being displayed on the flat display screen 348).

Next, with reference to FIG. 62, in another further embodiment, the at least one visual display device comprises the head-mounted visual display device 344 without a physical display device. As shown in FIG. 62, the first image portion 355 with the primary screen image is displayed using the head-mounted visual display device 344. In FIG. 62, the second image portion with the virtual screen surround 357 is additionally displayed using the head-mounted visual display device 344. In the embodiment of FIG. 62, the head-mounted visual display device 344 may comprise a virtual reality headset that generates entirely virtual objects or an augmented reality headset that is capable of supplementing real-world objects with computer-generated virtual objects.

In the embodiments of FIGS. 61 and 62, it can be seen that the virtual screen surround 351, 357 generated by the one or more data processing devices 104 and displayed by the at least one visual display device 344 comprises a virtual cutout 353, 359 configured to receive a portion of the body of the subject 108 therein. Similar to that described above for the cutout 178 in the physical dome-shaped projection screen 168, the semi-circular virtual cutout 353, 359 permits the subject 108 to be substantially circumscribed by the generally hemispherical virtual screen surround 351, 357 on three sides. Also, in the embodiments of FIGS. 61 and 62, the virtual screen surround 351, 357 generated by the one or more data processing devices 104 and displayed by the at least one visual display device 344 has a concave shape. More specifically, in the illustrative embodiments of FIGS. 61 and 62, the virtual screen surround 351, 357 generated by the one or more data processing devices 104 and displayed by the at least one visual display device 344, 348 has a hemispherical shape.

In addition, as shown in the embodiments of FIGS. 61 and 62, the primary screen image 349, 355 in the first image portion may comprise a subject test screen or subject training screen with a plurality of targets or markers 238 (e.g., in the form of circles) and a displaceable visual indicator or cursor 240. As described above, the one or more data processing devices 104 control the movement of the visual indicator 240 towards the plurality of stationary targets or markers 238 based upon output data determined from the output signals of the force transducers associated with the force measurement assembly 102. For example, in one testing or training scenario, the subject 108 may be instructed to move the cursor 240 towards each of the plurality of targets or markers 238 in succession. For example, the subject 108 may be instructed to move the cursor 240 towards successive targets 238 in a clockwise fashion (e.g., beginning with the topmost target 238 in the primary screen image 349, 355).

In one or more other embodiments, rather than comprising a subject test screen or subject training screen, the primary screen image 349, 355 in the first image portion displayed by the at least one visual display device 344, 348 may alternatively comprise one of: (i) an instructional screen for the subject, (ii) a game screen, and (iii) an immersive environment or virtual reality environment.

In these further embodiments, the virtual screen surround 351, 357 depicted in FIGS. 61 and 62 may be displaced by the one or more data processing devices 104 in order to compensate for the movement of the head of the subject 108. For example, a head position detection device (e.g., an inertial measurement unit 306 as depicted in FIG. 50) may be provided on the head of the subject 108 in order to measure the position of the head of the subject 108, and then the one or more data processing devices 104 may adjust the position of the virtual screen surround 351, 357 in accordance with the subject's head position so that the virtual screen surround 351, 357 always substantially encompasses a peripheral vision of the subject regardless of the gazing direction of the subject 108. In other words, the virtual screen surround 351, 357 rotates with the head of the subject 108 so that the subject 108 is always generally gazing at the center portion of the virtual screen surround 351, 357 (i.e., the one or more data processing devices 104 displace the virtual screen surround 351, 357 to track the position of the subject's head).

In other embodiments, rather than an inertial measurement unit, the head position measurement device for measuring the head position of the subject 108 may comprise one or more of the following: (i) a video camera, (ii) an infrared sensor, (iii) an ultrasonic sensor, and (iv) a markerless motion capture device.

Also, in these further embodiments, the one or more data processing devices 104 may be programmed to activate or turn "on" the virtual screen surround 351, 357 in FIGS. 61 and 62 when the weight of the subject 108 is detected on the force measurement assembly 102 (e.g., when the force measurement assembly 102 detects a vertical force $F_Z$ that meets or exceeds a predetermined threshold value, for example, $F_Z \geq 200$ Newtons). Conversely, the one or more data processing devices 104 may be programmed to deactivate or turn "off" the virtual screen surround 351, 357 in FIGS. 61 and 62 when the weight of the subject 108 is not detected on the force measurement assembly 102 (e.g., when the force measurement assembly 102 detects a vertical force $F_Z$ that is less than a predetermined threshold value, for example, $F_Z < 200$ Newtons). Also, the one or more data processing devices 104 may be programmed to deactivate or turn "off" the virtual screen surround 351, 357 in FIGS. 61 and 62 if it is determined that the subject 108 has likely fallen during testing or training (e.g., when the one or more processing devices 104 determine that the $F_Z$dropMAX value is greater than 0.50 and the $F_Z$dropAVG value is greater than 0.02 as explained above).

In addition, in these further embodiments, the one or more data processing devices 104 may be programmed to visually indicate when the subject 108 is placing an excessive amount of weight (e.g., greater than 60% of his or her body weight) on one of his or her feet compared to the other of his or her feet. For example, when the subject 108 in FIGS. 61 and 62 is placing an excessive amount of the weight (e.g., greater than 60% of his or her body weight) on his left foot as detected by the first plate component 110 (i.e., the left plate component 110) of the dual force plate 102, the one or more data processing devices 104 may be programmed to make the left half of the virtual screen surround 351, 357 brighter and/or change the color of the left half of the virtual screen surround 351, 357 (e.g., change the color to "red"). Similarly, in this example, when the subject 108 in FIGS. 61 and 62 is placing an excessive amount of the weight (e.g., greater than 60% of his or her body weight) on his right foot as detected by the second plate component 112 (i.e., the right plate component 112) of the dual force plate 102, the one or more data processing devices 104 may be programmed to make the right half of the virtual screen surround 351, 357 brighter and/or change the color of the right half of the virtual screen surround 351, 357 (e.g., change the color to "red").

Figure 15:
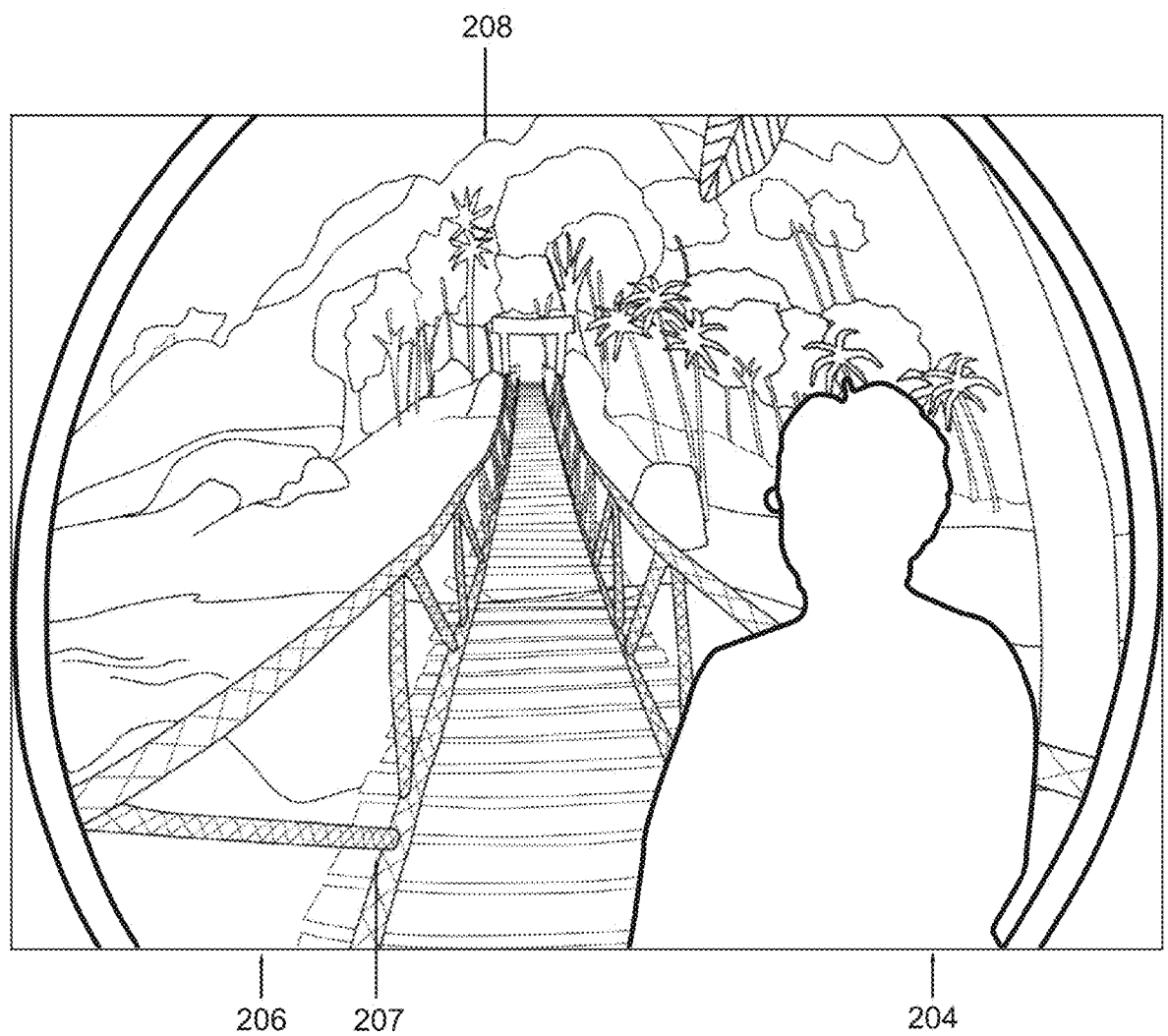
FIG. 15 is a second example of a virtual reality scene displayed on the subject visual display device of the force measurement system, according to an embodiment of the invention.

In these further embodiments, the data acquisition/data processing device 104 may be further programmed to generate a virtual representation of the subject and a visual element with which the virtual representation of the subject is able to interact, and to display the virtual representation of the subject and the visual element in the one or more images on the output screen of the at least one visual display device (e.g., the subject visual display device 107). For example, as described above with regard to FIG. 41, a virtual representation of the subject (e.g., an avatar 270') may interact with a visual element (e.g., a cereal box 248 in a kitchen cabinet 250) in a virtual reality scene. As another example, as illustrated in FIG. 15, a virtual representation of the subject 204 may interact with another type a visual element (e.g., a bridge 207) in a virtual reality scene. In these embodiments, the data acquisition/data processing device 104 may be further programmed to generate tactile feedback for the subject 108 using at least one of the first and second actuators 158, 160 on the base assembly 106 based upon the virtual representation of the subject interacting with the visual element in the one or more images on the output screen of the at least one visual display device (e.g., in the bridge scene 206, if the virtual representation of the subject 204 is walking up an incline on the bridge 207, the second actuator 160 may rotate the force measurement assembly 102 relative to the base assembly 106 so as to simulate the incline of the bridge 207 in the scene 206). In some of these embodiments, the visual element in the one or more images on the output screen of the at least one visual display device may comprise an obstacle disposed in a virtual walking path of the virtual representation of the subject, and the data acquisition/data processing device 104 may be programmed to generate the tactile feedback for the subject 108 using the at least one of the first and second actuators 158, 160 on the base assembly 106 when the virtual representation of the subject on the output screen collides with the obstacle disposed in the virtual walking path in the one or more images displayed on the at least one visual display device (e.g., in the bridge scene 206, if the virtual representation of the subject 204 collides with one of the sides of the bridge 207, the subject 108 will receive a slight jolt from one of the actuators 158, 160). As another example, if the virtual representation of the subject is walking down an endless grocery aisle and collides with a box in the grocery aisle, the first actuator 158 of the base assembly 106 may be used to provide a slight jolt to the subject 108 to indicate the collision.

Figure 63:
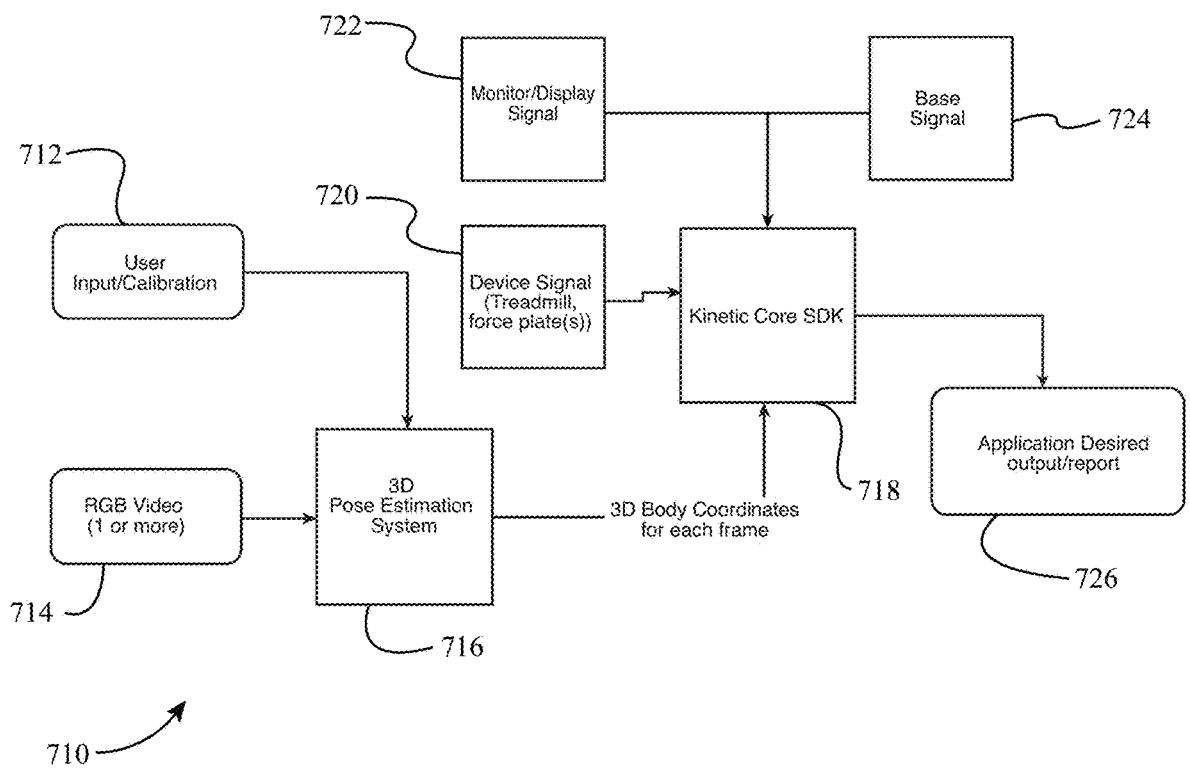
FIG. 63 is a schematic diagram of a first illustrative embodiment of biomechanical analysis system that utilizes a displaceable force measurement assembly.

Now, with reference to the block diagrams in FIGS. 63 and 64, several illustrative biomechanical analysis systems in which the aforedescribed force measurement assembly 102 or instrumented treadmill 600, 600' are used with a three-dimensional (3D) pose estimation system will be explained. In these one or more illustrative embodiments, the 3D pose estimation system may comprise the 3D pose estimation system described in U.S. Pat. No. 10,853,970, the entire disclosure of which is incorporated herein by reference. Initially, in the block diagram 710 of FIG. 63, it can be seen that the 3D pose estimation system 716 receives images of a scene from one or more RGB video cameras 714. The 3D pose estimation system 716 extracts the features from the images of the scene for providing inputs to a convolutional neural network. Then, the 3D pose estimation system 716 generates one or more volumetric heatmaps using the convolutional neural network, and applies a maximization function to the one or more volumetric heatmaps in order to obtain a three dimensional pose of one or more persons in the scene. As shown in FIG. 63, the 3D pose estimation system 716 determines one or more three dimensional coordinates of the one or more persons in the scene for each image frame, and outputs the three dimensional coordinates to a kinetic core software development kit (SDK). In addition, as shown in FIG. 63, user input and/or calibration parameters 712 may also be received as inputs to the 3D pose estimation system 716.

In the illustrative embodiment of FIG. 63, in addition to the three dimensional coordinates for each image frame from the 3D pose estimation system 716, the kinetic core SDK 718 may also receive one or more device signals 720 from one or more force plates and/or an instrumented treadmill and/or as inputs. For example, the instrumented treadmill and the one or more force plates may comprise the force measurement assembly 102 or the instrumented treadmill 600, 600' described above. In addition, as shown in FIG. 63, the kinetic core SDK 718 may receive a monitor/display signal 722 as an input (e.g., an input signal from a touch-screen display). Further, as shown in FIG. 63, the kinetic core SDK 718 may receive one or more motion base signals 724 (e.g., one or more signals from the base assembly 106 described above). Then, the kinetic core SDK 718 determines and outputs one or more biomechanical performance parameters in an application desired output/report 726 using the three dimensional coordinates from the 3D pose estimation system 716 and the one or more signals 720, 722, 724 from the connected devices. The illustrative biomechanical analysis system of FIG. 63 does not include trained CNN backpropagation, but another illustrative biomechanical analysis system that will be described hereinafter does include trained CNN backpropagation.

Next, referring to FIG. 64, a second illustrative biomechanical analysis system in which the pose estimation system may be utilized will be explained. With reference to the block diagram 730 of FIG. 64, it can be seen that the second illustrative biomechanical analysis system is similar in many respects to the first illustrative biomechanical analysis system described above. As such, for the sake of brevity, the features that the second illustrative biomechanical analysis system has in common with the first illustrative biomechanical analysis system will not be discussed because these features have already been explained above. Although, unlike the first illustrative biomechanical analysis system, the second illustrative biomechanical analysis system of FIG. 64 includes trained CNN backpropagation. More specifically, in the illustrative embodiment of FIG. 64, the kinetic core SDK 718 is operatively coupled to one or more trained convolutional neural networks (CNNs) 717, which in turn, are operatively coupled to the 3D pose estimation system 716 so that better accuracy may be obtained from the 3D pose estimation system 716. In the illustrative embodiment of FIG. 64, in addition to the three dimensional coordinates for each image frame from the 3D pose estimation system 64, the kinetic core SDK 718 receives the device signals 720, 722, 724 from the connected external devices. Then, the kinetic core SDK 718 determines and outputs one or more biomechanical performance parameters in a biomechanical output report 728 using the three dimensional coordinates from the 3D pose estimation system 716 and the signals 720, 722, 724 from the connected external device. As shown in FIG. 64, the biomechanical output report 728 may include annotated datasets and/or kinematic and kinetic profiles for the one or more persons in the scene.

Now, the user input/calibration 712, the kinetic core SDK 718, and the application output 726 and 728 of the illustrative biomechanical analysis systems 710 and 730 will be described in further detail. In the illustrative embodiments described above, some user input 712 from the system may augment the automatic system calibration tasks performed. One source of input may involve the user selecting the XY pixel location of the four force plate corners from multiple RBG video images. The locations can be triangulated from this information. Additional calibration may require the user to hold an object, such as a checkboard or Aruco pattern. The person holding the calibration target will then perform a sequence of tasks, moving the calibration target at the optimal angle to the respective cameras and to the optimal positions for calibration within the capture volume. Another form of calibration may involve having the user standing on the force plate in the capture volume. The system will capture the user rotating their body around the vertical axis with their arms at 45 degree and 90 degrees of shoulder abduction. The 3D pose estimation system 716 then calibrates based on the plausible parameters (lengths) of the subject's body segment's and combined shape.

Figure 64:
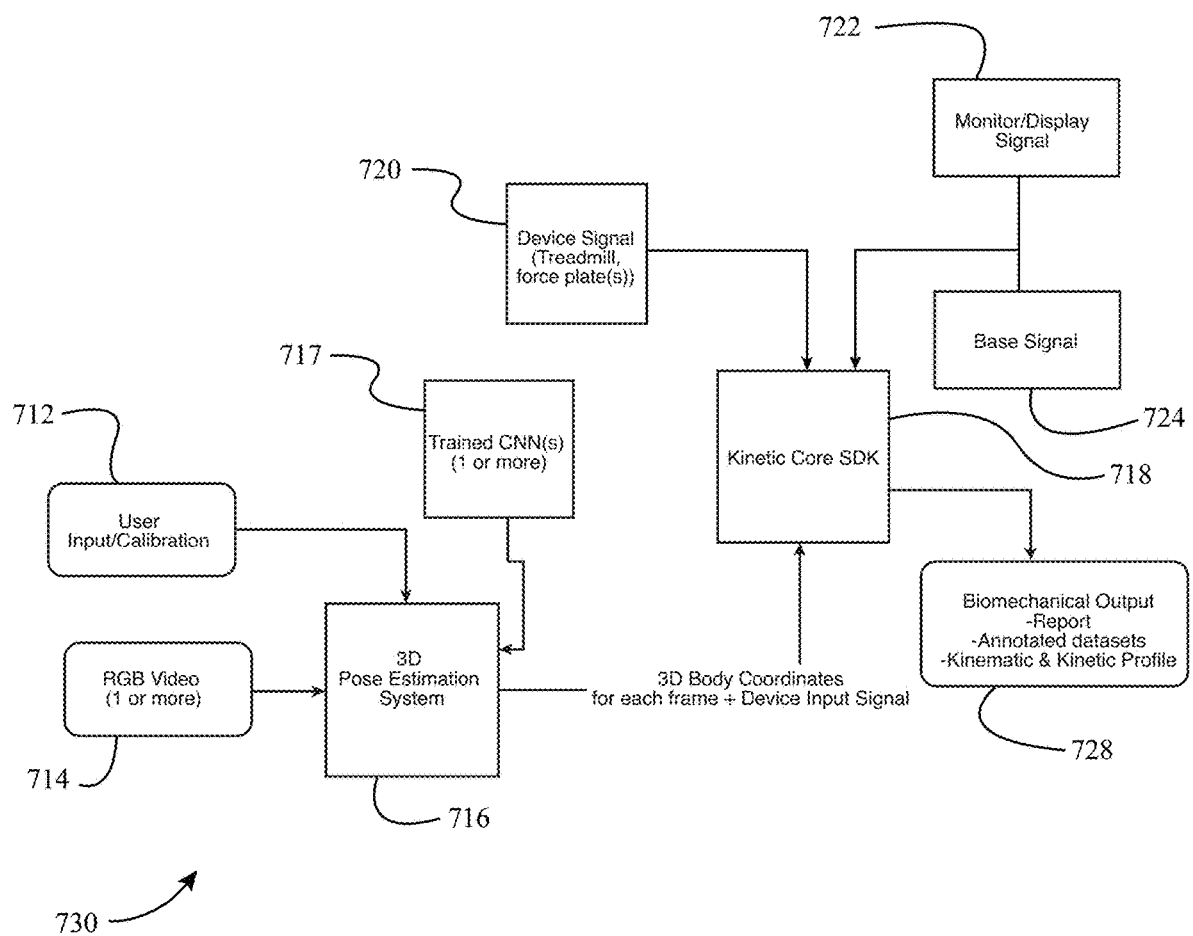
FIG. 64 is a schematic diagram of a second illustrative embodiment of biomechanical analysis system that utilizes a displaceable force measurement assembly.

In the illustrative embodiment of FIG. 64, there are one or more trained CNN modules 717 which are used to obtain better accuracy of the 3D pose estimation system 716. One of these models may be a "plausible physics" model. This model determined the plausibility of the estimated pose in the physical domain. In addition, this model may consider the temporal parameters of the physics, including: (i) body inertia, (ii) ground/floor contact in regards to foot position, (iii) body segment lengths, (iv) body segment angular velocities, and (v) joint ranges of motion. In the illustrative embodiment, an additional CNN may be applied for allowable human poses. This is a general model which will prevent unrealistic body representations and 3D reconstructions.

In the illustrative embodiments of FIGS. 63 and 64, the desired application output 726, 728 is a biomechanical analysis of the action's performed in the capture volume. This includes output, such as an annotated dataset in which calculated values, such as the rate of force development, maximum force, and other descriptors are displayed. A general report of the movement performed may also be generated and the algorithmically determined kinetic and kinematic insights from both traditional manually devised algorithms and insights derived from machine learned algorithms obtained from analysis of large datasets of similar movements.

The specific output is determined by the movement performed. As an example, analyzing a baseball swing is quite different than analyzing the balance of a subject after physical or visual perturbation. Each has its own key performance indicators (KPIs).

Using the key point information from the 3D pose estimation system 716 and the associated algorithms for movement specific analysis, the system becomes an "expert system" which is capable of diagnosing and providing rehabilitation and training interventions to improve the subject's performance during the tasks performed in the capture volume. This requires a large amount of training data, which is a recording of the actions performed in the capture space.

In the illustrative biomechanical analysis systems 710, 730 described above, the center of mass may be determined in order to guide the visual representation of the person in the visual scene. Other desired outputs may be trunk, knee, head position and hands position. With these variables' positions, angular and linear velocities can be calculated and essential for balance estimations can be provided. Also, for a functional force or balance plate where a subject can traverse the plate, the estimation of kinematic body segment position desired variables may be upper limb, trunk, hips, knees and ankle position. These variables would provide a gait analysis in combination with ground reaction force output provided by the force plate. The user can be required to walk, walk over a step or variables of it, plus other range of motion activities. The segment positions will provide linear and angular velocities and general kinematic outputs.

The illustrative biomechanical analysis systems 710, 730 may further include training models provided as part of the systems that enable the building of dynamic visual scenes. For example, when a participant uses the system 710, 730 for the first time, he or she is asked to walk on the treadmill or sway on the plate. Based on these movements the current kinematics/kinetics, COM movements, ground reaction forces are estimated. This is used to build scenes, for example if while walking the subject does not lift his foot enough, the obstacle height in the visual scene will be low at first. Different levels can then be built into the training protocol to progressively increase the obstacle height and encourage the person to lift his leg at a required height. In addition, with upper limb position a system user can perform dual task activities similar to daily life activities, where he or she would be walking or standing while pointing or grabbing objects. Such activities can be used as assessment and training as already proven by previous research.

In another illustrative biomechanical application, a therapist may review a captured video and force plate data, and write notes on the performance of the subject and any thoughts regarding their condition. Additionally, the expert may provide a review kinematic analysis while using the force plate data as additional information for making the decision. One key aspect of one biomechanical analysis system 710, 730 is determining the sway strategy of the patient. The kinematic information, derived from the 3D pose estimation system 716 is used by the therapist to determine a "sway strategy" or "balance strategy" of the patient. In the system, the subject is assumed to use an ankle strategy when regaining their balance in response to a known perturbation of the floor. The therapist may use the kinematic information to rate the strategy and determine if the amount of ankle versus hip movement is acceptable for the test. If deemed acceptable, the strategy employed by the subject and the therapist annotation (acceptable sway strategy or not) will be saved and used to train the algorithm. In time, the algorithm will provide instant feedback to the patient on the acceptability of the trial's sway strategy and provide a recommendation on how to improve the strategy (i.e.; focus on bending at the ankles and keep the torso upright, etc.). Also, the trunk and head position of the patient can offer a differential analysis to balance and how a patient performs a task. With the upper limb positions, a patient can perform tasks related to hand-eye coordination, ranges of motion, and dual tasks. These tasks are known for assessment and training in several types of population from neurological to orthopedic.

In one or more illustrative embodiments, the performance of the user suggestions on the sway strategy of the subsequent trial may be used to provide more useful recommendations. By grading the performance on the subsequent trial thousands of times, the machine learned algorithm learns what to suggest to the patient to obtain the desired result.

For a functional force or balance plate where a subject can traverse the plate, the 3D pose estimation system 716 may be used to estimate gait and upper body events during tasks, such as gait over obstacles, squats and range of motion activities. Aligning with the ground reaction forces provided by the force plate, a clinician will be able to determine not only body sway, but quantify errors in tasks, such as tandem gait.

In the illustrative biomechanical analysis systems 710, 730 described above, one or more data processing devices 104 may be configured to predict one or more balance parameters of the subject using the 3D pose estimation system 716. The one or more balance parameters predicted by the one or more data processing devices 104 may comprise at least one of: (i) a center of pressure, (ii) a center of mass, (iii) a center of gravity, (iv) a sway angle, and (v) a type of balance strategy. Also, the one or more data processing devices 104 of the illustrative biomechanical analysis systems 710, 730 may be further configured to provide feedback to the subject regarding his or her balance based upon the one or more predicted balance parameters of the subject determined using the 3D pose estimation system 716.

In one or more further illustrative embodiments, the biomechanical analysis systems 710, 730 may further include a sensory output device configured to generate sensory feedback for delivery to a system user. The sensory feedback may comprise at least one of a visual indicator, an audible indicator, and a tactile indicator. For example, the sensory output device may comprise one or more of the types of sensory output devices described in U.S. Pat. No. 9,414,784, the entire disclosure of which is incorporated herein by reference.

In one or more further illustrative embodiments, using the principles of inverse dynamics, the biomechanical analysis systems 710, 730 may further map the energy flow of the subject performing a balance activity in the capture space. The forces and torques occurring at each joint in the body may be determined by the kinematic positions and ground reaction forces (predicted and/or real) and mapped from the body segments and joints in contact with the force plate. Additionally, a temporal plausible physics algorithm may be used to correct for the inertia of the body segments from the previous body movements. Also, the biomechanical analysis systems 710, 730 may automatically calculate joint stresses using inverse dynamics. For example, the biomechanical analysis systems 710, 730 may automatically calculate the knee torque in one such application.

Figure 65:
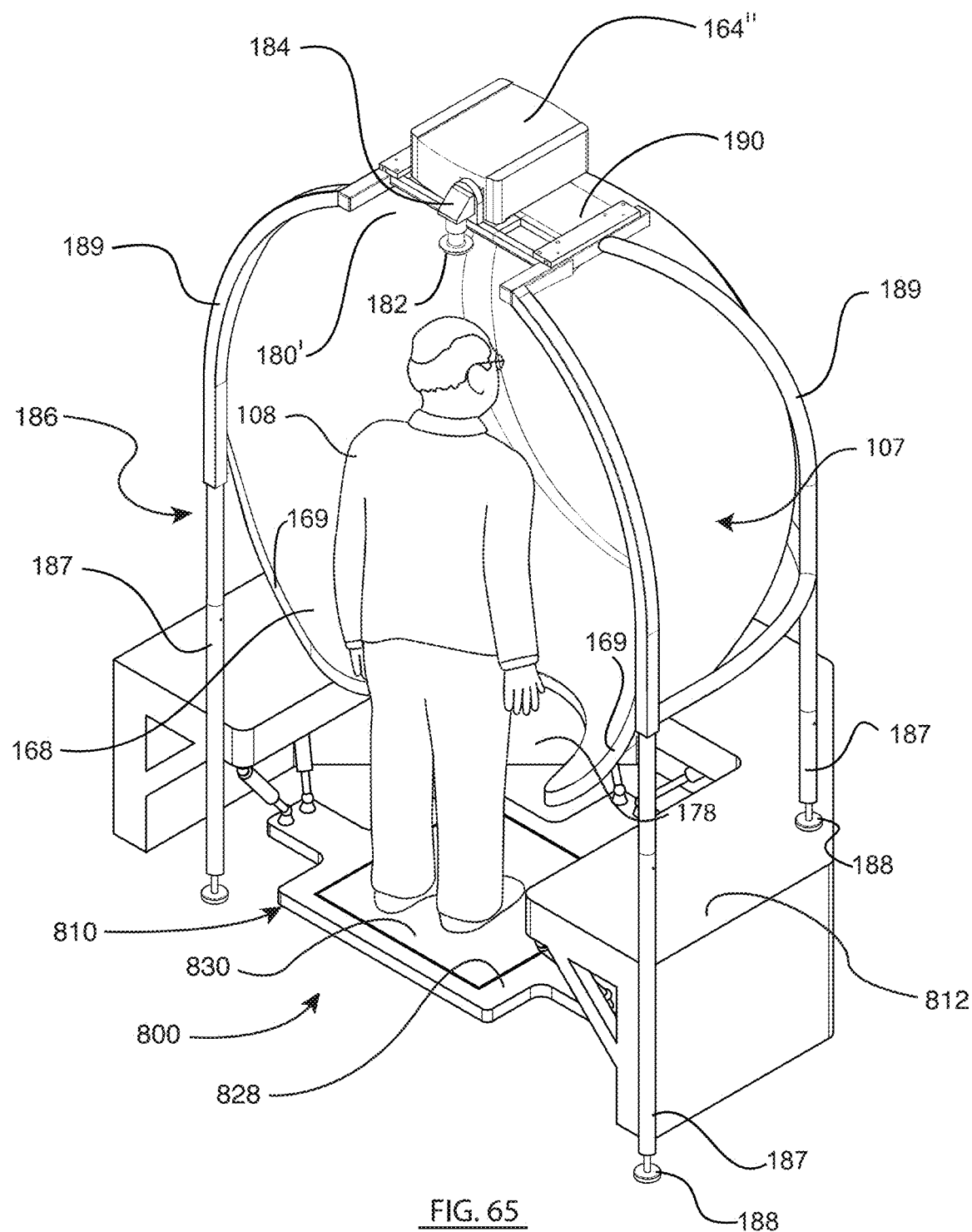
FIG. 65 is a perspective view of still another alternative force measurement system comprising a force plate mounted on a motion base and an immersive subject visual display device, according to an alternative embodiment of the invention.
Figure 66:
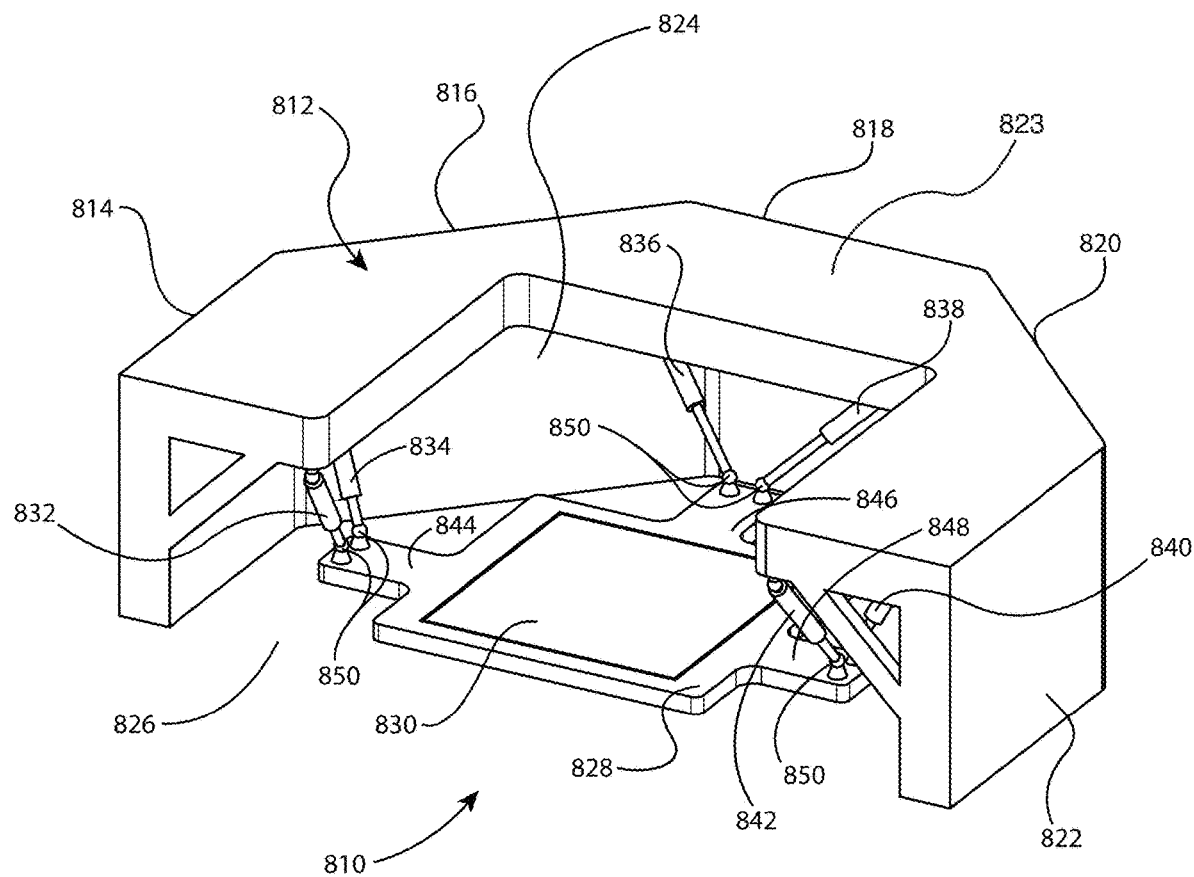
FIG. 66 is a perspective view of the motion base of the force measurement system of FIG. 65.

In still a further illustrative embodiment, with reference to FIGS. 65-66, a modified version of the force measurement system 800 may comprise a force plate 830 mounted on a displaceable platform 828 of a motion base assembly 810, an immersive visual display device 107, and one or more data processing devices 104 operatively coupled to the force plate 830, the actuation system of the motion base assembly 810, and the immersive visual display device 107. In this further embodiment, the one or more data processing devices 104 are configured to receive the one or more signals that are representative of the forces and/or moments being applied to the top surface of the force plate 830 by the subject, and to convert the one or more signals into output forces and/or moments. The one or more data processing devices 104 are further configured to selectively displace the force plate 830 using the actuation system of the motion base assembly 810. The motion base assembly 810 will be described in detail hereinafter. Because the details of the one or more data processing devices 104, the subject visual display device 107, and the force plate 830 are generally the same as that described above with regard to the aforementioned embodiments, no further description of these components 104, 107, and 830 will be provided for this embodiment.

Now, referring to FIG. 66, the components of the motion base assembly 810 will now be described in detail. As shown in FIG. 66, the motion base assembly 810 generally comprises a support structure 812, a displaceable carriage 828 coupled to the force plate 830; and an actuation system including a plurality of actuators 832, 834, 836, 838, 840, 842 operatively coupling the displaceable carriage 828 to the support structure 812. The plurality of actuators 832, 834, 836, 838, 840, 842 are configured to displace the displaceable carriage 828 relative to the support structure 812. As shown in FIGS. 65 and 66, the displaceable carriage 828 is suspended below a portion of the support structure 812 (i.e., the displaceable carriage 828 is suspension-mounted from the underside of the top wall 823 of the support structure 812). As depicted in FIG. 66, the displaceable carriage 828 of the motion base assembly 810 is preferably displaceable (i.e., translatable) and rotatable in 3-dimensional space by means of the plurality of actuators 832, 834, 836, 838, 840, 842. In other words, the motion base assembly 810 is preferably a six (6) degree-of-freedom motion base. In the illustrative embodiment, the motion base assembly 810 is used for the dynamic testing of subjects when, for example, the subject is being tested, or is undergoing training, in a virtual reality environment. Also, in the illustrative embodiment, the motion base assembly 810 is able to accommodate any type of perturbations as inputs (i.e., any type of perturbations generated by the one or more data processing devices 104. While the displaceable carriage 828 of the motion base assembly 810 is preferably translatable and rotatable in 3-dimensional space, it is to be understood that the motion base is not so limited. Rather, in alternative embodiments, the motion base assembly 810 is provided with lesser degrees of motion.

In the illustrative embodiment, as shown in FIG. 66, the support structure 812 of the motion base assembly 810 comprises a plurality of sidewalls 814, 816, 818, 820, 822 and a top wall 823 attached to the upper edges of the plurality of sidewalls 814, 816, 818, 820, 822. The top wall 823 of the support structure 812 defines an opening 824 for accommodating a subject 108 in a standing position on the force plate 830 (see FIG. 65). Also, as shown in the illustrative embodiment of FIG. 66, the support structure 812 of the motion base assembly 810 has an open back 826 for enabling the subject 108 to more easily get on and off the force plate 830. In the illustrative embodiment, the support structure 812 of the motion base assembly 810 generally has the shape of a half regular octagon where the sidewalls 814, 816, 818, 820, 822 of the support structure 812 form interior angles of approximately 135 degrees and exterior angles of approximately 45 degrees with one another. As shown in FIG. 66, the support structure 812 partially surrounds the displaceable carriage 828 in the illustrative embodiment.

Referring again to FIG. 66, in the illustrative embodiment, the displaceable carriage 828 is in a form of a displaceable platform suspended below a top portion of the support structure 812 (i.e., suspended below the top wall 823 of the support structure 812). In the illustrative embodiment, the displaceable carriage 828 is affixedly attached to the force plate 830 so that the force plate 830 is able to be displaced together with the displaceable carriage 828. In other alternative embodiments, other objects may be attached to the displaceable carriage 828 of the motion base assembly 810, such as an instrumented treadmill or other objects for which the displacement thereof is desired. For example, when the displaceable carriage 828 is being used to displace an instrumented treadmill, the structure of the displaceable carriage 828 may be modified accordingly to accommodate the increased size of the instrumented treadmill.

Next, with again reference to FIG. 66, the actuation system of the motion base assembly 810 will be described in detail. As shown in this figure, in the illustrative embodiment, the actuation system of the motion base assembly 810 generally comprises six (6) linear actuators 832, 834, 836, 838, 840, 842 configured to displace the displaceable carriage 828 and the force plate 830 supported thereon relative to the support structure 812 of the motion base assembly 810. In FIG. 66, it can be seen that each of the linear actuators 832, 834, 836, 838, 840, 842 is connected between an upper surface of the displaceable carriage (i.e., displaceable platform 828) and a lower surface of the top wall 823 of the support structure 812. More specifically, as shown in FIG. 66, the displaceable platform 828 is provided with three (3) protruding actuator connector portions 844, 846, 848 for accommodating the linear actuators 832, 834, 836, 838, 840, 842. The first and second linear actuators 832, 834 are connected between the first actuator connector portion 844 of the displaceable platform 828 and the lower surface of the top wall 823 of the support structure 812. The third and fourth linear actuators 836, 838 are connected between the second actuator connector portion 846 of the displaceable platform 828 and the lower surface of the top wall 823 of the support structure 812. The fifth and sixth linear actuators 840, 842 are connected between the third actuator connector portion 848 of the displaceable platform 828 and the lower surface of the top wall 823 of the support structure 812. In the illustrated embodiment, each of the linear actuators 832, 834, 836, 838, 840, 842 may be in a form of an electric cylinder, which is powered by an electric servo motor. However, in alternative embodiments, other types of linear actuators may be used in lieu of electric cylinders, such as hydraulic actuators or pneumatic actuators.

Turning again to FIG. 66, it can be seen that the upper end of each linear actuator 832, 834, 836, 838, 840, 842 of the actuation system is rotatably connected to the lower surface of the top wall 823 of the support structure 812 by means of an upper joint member having three rotational degrees of freedom. In the illustrative embodiment, the upper joint member rotatably coupling each linear actuator 832, 834, 836, 838, 840, 842 to the lower surface of the top wall 823 of the support structure 812 comprises an inline ball joint 850 or spherical joint 850 providing the three rotational degrees of freedom. Also, as best shown in FIG. 66, it can be seen that the lower end of each linear actuator 832, 834, 836, 838, 840, 842 of the actuation system is rotatably connected to the respective actuator connector portion 844, 846, 848 of the displaceable platform 828 by means of an lower joint member having three rotational degrees of freedom. In the illustrative embodiment, the lower joint member rotatably coupling each linear actuator 832, 834, 836, 838, 840, 842 to the respective actuator connector portion 844, 846, 848 of the displaceable platform 828 comprises an inline ball joint or spherical joint, like spherical joint 850, providing the three rotational degrees of freedom.

In further embodiments, the data acquisition/data processing device 104 of the force measurement system 100 is further programmed to receive the one or more input signals from the one or more user input devices 132, 134 based upon the one or more selections by the user (e.g., a clinician or operator OP), where a first one of the one or more selections by the user is a scene movement setting for the one or more scenes on the output screen of the at least one visual display 107, and a second one of the one or more selections by the user is a force measurement assembly movement setting for the force measurement assembly 102; display the one or more scenes on the output screen of the at least one visual display 107 based upon the scene movement setting selected by the user; and control the force measurement assembly 102 based upon the force measurement assembly movement setting selected by the user. While the functionality of these further embodiments is described with reference to the force measurement system 100 of FIG. 1, it is to be understood that this system functionality may be used in conjunction with other force measurement systems, such as the force measurement system 100' of FIG. 38 that comprises a force measurement device 600 in a form of an instrumented treadmill.

Figure 67:
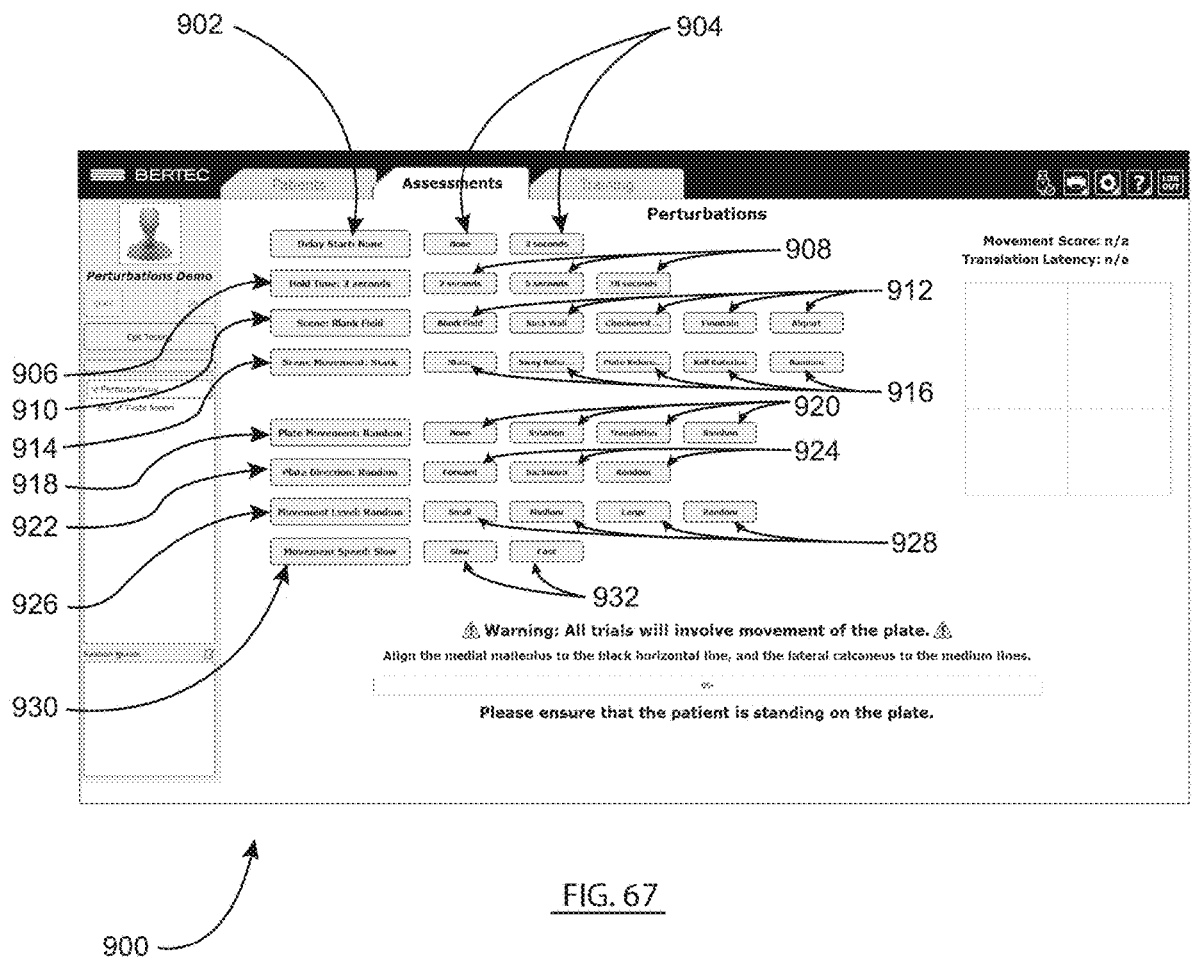
FIG. 67 is a screen image of a perturbation selection screen for enabling a user to select one or more desired perturbations, according to an embodiment of the invention.
Figure 68:
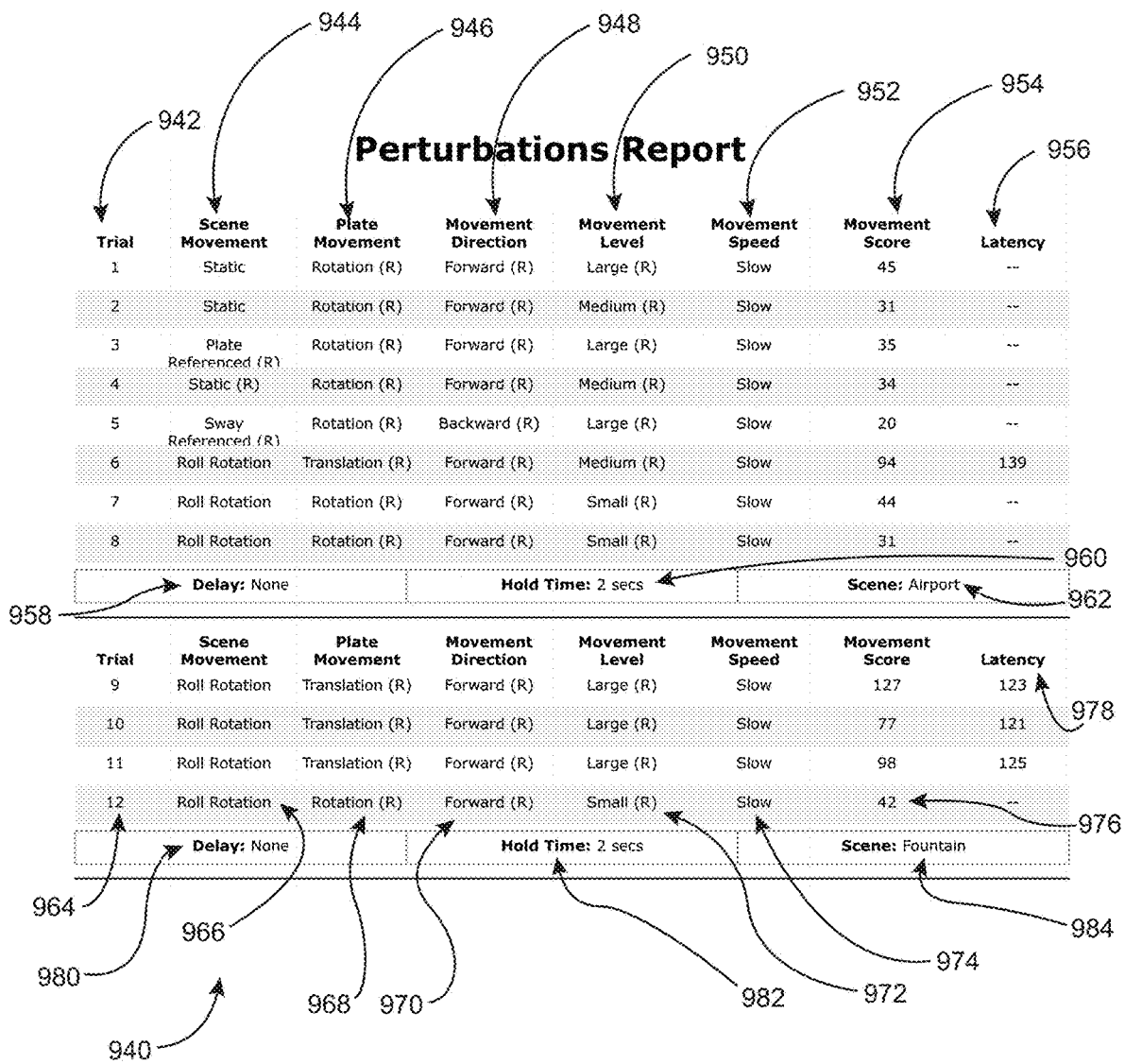
FIG. 68 is a screen image of a perturbation report information screen for displaying testing or training performance information regarding a subject, according to an embodiment of the invention.

Now, turning to FIGS. 67 and 68, in an illustrative embodiment, the data acquisition/data processing device 104 is programmed to generate a perturbation selection screen 900 (FIG. 67) for enabling a user to select one or more desired perturbations, and a perturbation report information screen 940 (FIG. 68) for displaying testing or training performance information regarding a subject. Referring initially to FIG. 67, it can be seen that the perturbation selection screen 900 includes a scene movement selection indicator 914 and a plurality of scene movement selectable choices 916. In the example of FIG. 67, the user has selected "Static" for the scene movement. In the illustrative embodiment, the scene movement setting selected by the user may be selected from the group consisting of: (i) static, with no scene movement, (ii) plate-referenced, where a movement of the one or more scenes mimics a movement of the force measurement assembly, (iii) sway-referenced, where a movement of the one or more scenes is based on a sway of the subject, (iv) roll rotation, where a movement of the one or more scenes is a predetermined angular displacement in a clockwise or counterclockwise direction, and (v) random, where a movement of the one or more scenes is random.

With reference again to FIG. 67, it can be seen that the perturbation selection screen 900 further includes a force plate movement selection indicator 918 and a plurality of force plate movement selectable choices 920. In the example of FIG. 67, the user has selected "Random" for the force plate movement. In the illustrative embodiment, the force plate movement setting or force measurement assembly movement setting selected by the user is selected from the group consisting of: (i) none, with no force measurement assembly movement, (ii) rotation, where the force measurement assembly is rotated, (iii) translation, where the force measurement assembly is translated, and (iv) random, where there is a random selection among the none, rotation, and translation settings.

As shown in FIG. 67, in the illustrative embodiment, the perturbation selection screen 900 further includes a force plate direction selection indicator 922 and a plurality of force plate direction selectable choices 924. In the example of FIG. 67, the user has selected "Random" for the force plate direction. In the illustrative embodiment, the force plate direction setting or force measurement assembly direction setting controls a direction of force plate or force measurement assembly movement. In the illustrative embodiment, the force measurement assembly direction setting selected by the user may be selected from the group consisting of: (i) forward, where the force measurement assembly is displaced in a forward direction, (ii) backward, where the force measurement assembly is displaced in a backward direction, and (iii) random, where there is a random selection between the forward and backward directions.

As also shown in FIG. 67, in the illustrative embodiment, the perturbation selection screen 900 further includes a movement level selection indicator 926 and a plurality of movement level selectable choices 928. In the example of FIG. 67, the user has selected "Random" for the movement level. In the illustrative embodiment, the movement level controls an amplitude of force measurement assembly movement and/or an amplitude of scene movement. In the illustrative embodiment, the movement level selected by the user may be selected from the group consisting of: (i) a first level, where the amplitude of the force measurement assembly or scene movement is the smallest, (ii) a second level, where the amplitude of the force measurement assembly or scene movement is at a medium level, (iii) a third level, where the amplitude of the force measurement assembly or scene movement is the highest, and (iv) random, where there is a random selection among the first level, second level, and third level.

Referring again to FIG. 67, in the illustrative embodiment, the perturbation selection screen 900 further includes a movement speed selection indicator 930 and a plurality of movement level selectable choices 932. In the example of FIG. 67, the user has selected "Slow" for the movement speed. In the illustrative embodiment, the force measurement assembly movement speed controls a speed of force measurement assembly movement and/or a speed of the scene movement. In the illustrative embodiment, the movement speed may be selected from the group consisting of: (i) a slow speed, where the speed of the force measurement assembly or scene is the smallest, (ii) a medium speed, where the speed of the force measurement assembly or scene is at a medium level, and (iii) a high speed, where the speed of the force measurement assembly or scene is the highest.

In the illustrative embodiment, the translational stimuli selection for the force plate movement or force measurement assembly movement results in the force platform moving forward or backward in the anteroposterior (AP) direction. In the perturbation training protocol, the amplitude of translation is selectable by the user among the following movement level options: small, medium, large (and random). The small, medium, and large options correspond to 4, 6, and 8 degrees of subject lean respectively. The distance that the force platform travels is calculated using both the degree of lean selected and the subject's height. Therefore, the platform distance traveled can be different for subjects of differing heights. However, the stimulus should induce the same lean angle for each subject in the same translation perturbation condition.

In the illustrative embodiment, the rotational stimuli selection for the force plate movement or force measurement assembly movement results in the force platform rotating forward or backward about the ankle joints in the AP plane. The amplitude of rotation is user-selectable among the same movement level options: small, medium, large (and random). The small, medium, and large options in the rotational setting correspond to 4, 6, and 8 degrees of force platform rotation, respectively. The angle that the force platform rotates in each condition remains consistent for all subjects regardless of patient height.

Additionally, in the illustrative embodiment, two types of speed are available for the force platform's motion in both rotational and translational movements. This option is called movement speed. The duration of force platform movement for the "Slow" speed option is 400 ms whereas the duration for "Fast" option is 250 ms. Force platform motions at faster speeds will require the patient to react faster to the perturbation. By incorporating higher speeds, clinicians can increase the challenge to the subject and ultimately improve performance.

In the illustrative embodiment, for trials where only the visual scene is moved, the clinician or operator OP can choose the "Static" option for the force platform motion. With this setting selected, the force platform would not move during the trial.

In the illustrative embodiment, in the "Static" setting for scene movement, the visual scene does not move. In the "Sway-Referenced" setting for scene movement, the visual scene motion mimics the subject's sway. That is, if the subject leans in one direction, the scene will move proportionally in the same direction to match the subject's lean. This setting is similar to the scene motion in conditions 3 and 6 in the Sensory Organization Test (SOT). In the "Plate-Referenced" setting for scene movement, the visual scene motion mimics the force platform motion. For example, if the force platform motion is a large fast forward translation, the visual scene will simultaneously make a large fast translation in the same direction. In the "Roll Rotation" setting for scene movement, the scene rotates 15 degrees clockwise or counterclockwise in the roll plane with the speed of 45 degrees per second. The direction of rotation is randomized. This visual perturbation will also happen in conjunction with the force platform motion. In addition to the above settings, the clinician or operator OP can select the scene to be "Blank", in which case scene motion will not be visible. The many scene movement profile options are designed to introduce visual stimuli that are sometimes consistent and sometimes contradictory to the information from other sensory mechanisms. The aim is to train the subject to effectively integrate the information from different sensory mechanisms.

Also, as shown in FIG. 67, in the illustrative embodiment, the perturbation selection screen 900 further includes a delay start time selection indicator 902 and a plurality of delay start time selectable choices 904 (e.g., "None" or "3 seconds"). In the example of FIG. 67, the user has selected "None" for the delay start time. In the illustrative embodiment, the delay start time is a time delay between a start of a trial and a start of movement of the force measurement assembly and/or scene, and the delay start time allows for data to be collected from the force measurement assembly prior to the movement of the force measurement assembly and/or scene.

Referring again to FIG. 67, in the illustrative embodiment, the perturbation selection screen 900 further includes a hold time selection indicator 906 and a plurality of delay start time selectable choices 908 (e.g., "2 seconds", "5 seconds", or "10 seconds"). In the example of FIG. 67, the user has selected "2 seconds" for the hold time. In the illustrative embodiment, the hold time is a time delay between an end of movement of the force measurement assembly and/or scene and an end of the trial, and the force measurement assembly and/or scene is configured to return to a home position after the hold time period has elapsed.

In the illustrative embodiment, in addition to the force platform motion profiles and visual motion profiles, the perturbations training allows the clinician or operator OP to select a Delay Start and a Hold Time. Delay Start is a feature that allows the system to collect 3 seconds of data from the force platform prior to perturbation occurring. This delay in platform motion does not affect scoring nor patient performance. Hold Time is another feature which influences the trial time as it is the time added to the trial after the perturbation has occurred. During this hold time, the force platform will remain in its final position after the perturbation and will not re-home until the hold time has elapsed. Similarly, during the hold time, the scene motion will remain visible until the hold time has elapsed. Hold Time can be between 2 seconds and 10 seconds. The option selected may influence patient performance based on duration and the perceived difficulty along with the other options selected in the training.

As also shown in FIG. 67, in the illustrative embodiment, the perturbation selection screen 900 further includes a scene selection indicator 910 and a plurality of scene selectable choices 912. In the example of FIG. 67, the user has selected "Blank Field" for the scene. In the illustrative embodiment, the scene may be selected from the group consisting of: (i) a rock wall, (ii) a checkered room, (iii) an airport, (iv) a fountain, and (v) a blank field.

Next, turning to FIG. 68, in the illustrative embodiment, it can be seen that the perturbation report information screen 940 includes a plurality of columns 942-956 and 964-978 displaying output data relating to the training routines performed for the subject. More specifically, in the example of FIG. 68, for trials 1-8, the report columns include a trial column 942, scene movement column 944, a plate movement column 946, a movement direction column 948, a movement level column 950, a movement speed column 952, a movement score column 954, and a latency column 956. Similarly, in the example of FIG. 68, for trials 9-13, the report columns include a trial column 964, scene movement column 966, a plate movement column 968, a movement direction column 970, a movement level column 972, a movement speed column 974, a movement score column 976, and a latency column 978. Referring again to the example of FIG. 68, for trials 1-8, the Time Delay selection 958 is set to "None", the Hold Time selection 960 is set to "2 seconds", and the Scene selection 962 is set to "Airport". In the example of FIG. 68, for trials 9-12, the Time Delay selection 980 is set to "None", the Hold Time selection 982 is set to "2 seconds", and the Scene selection 984 is set to "Fountain". During the perturbation training, the subject is instructed to maintain his or her balance with as little movement as possible during and after the perturbation.

In the illustrative embodiment, the perturbation results are quantified by the Movement Score (e.g., columns 954, 976 in FIG. 68). To determine the Movement Score, first the total COP path traveled in both anterior-posterior (AP) and mediolateral (ML) directions over the 2 seconds after the onset of subject response is determined. The average movement velocity is then determined by dividing the total path by 2 seconds. In order to compare the Movement Score across trials, the average velocity is divided by the velocity of the stimulus in order to get a score that is scaled for different stimuli. Higher movement scores indicate more subject movement. Scores can be compared to each other; however rotation movement scores are generally lower than translation movement scores. For translational perturbations, the latency in columns 956, 978 of FIG. 68 is also calculated (i.e., the amount of time that it takes for the subject to respond to a translational perturbation of the force measurement assembly 102). For rotational perturbations, the latency is minimal, and the response is almost immediate.

In the illustrative embodiment, the end-of-test report (e.g., the report depicted in FIG. 68) is compiled after completion of a test. This report will include the subject information, the settings from the test, and any data/metrics pertaining to the test. As described above, the perturbations training includes a Movement Score for all trials. Any trials which are translations will also include a Latency score.

In yet further embodiments, the data acquisition/data processing device 104 of the force measurement system 100 is further programmed to: (i) receive the one or more input signals from the one or more user input devices 132, 134 based upon the one or more selections by the user (e.g., a clinician or operator OP), where the one or more selections by the user include a scene parameter for one or more scenes on the output screen of the at least one visual display device; and then (ii) display the one or more scenes on the output screen of the subject visual display device 107 based upon the scene parameter selected by the user. While the functionality of these further embodiments is described with reference to the force measurement system 100 of FIG. 1, it is to be understood that this system functionality may be used in conjunction with other force measurement systems, such as the force measurement system 100' of FIG. 38 that comprises a force measurement device 600 in a form of an instrumented treadmill.

Figure 69:
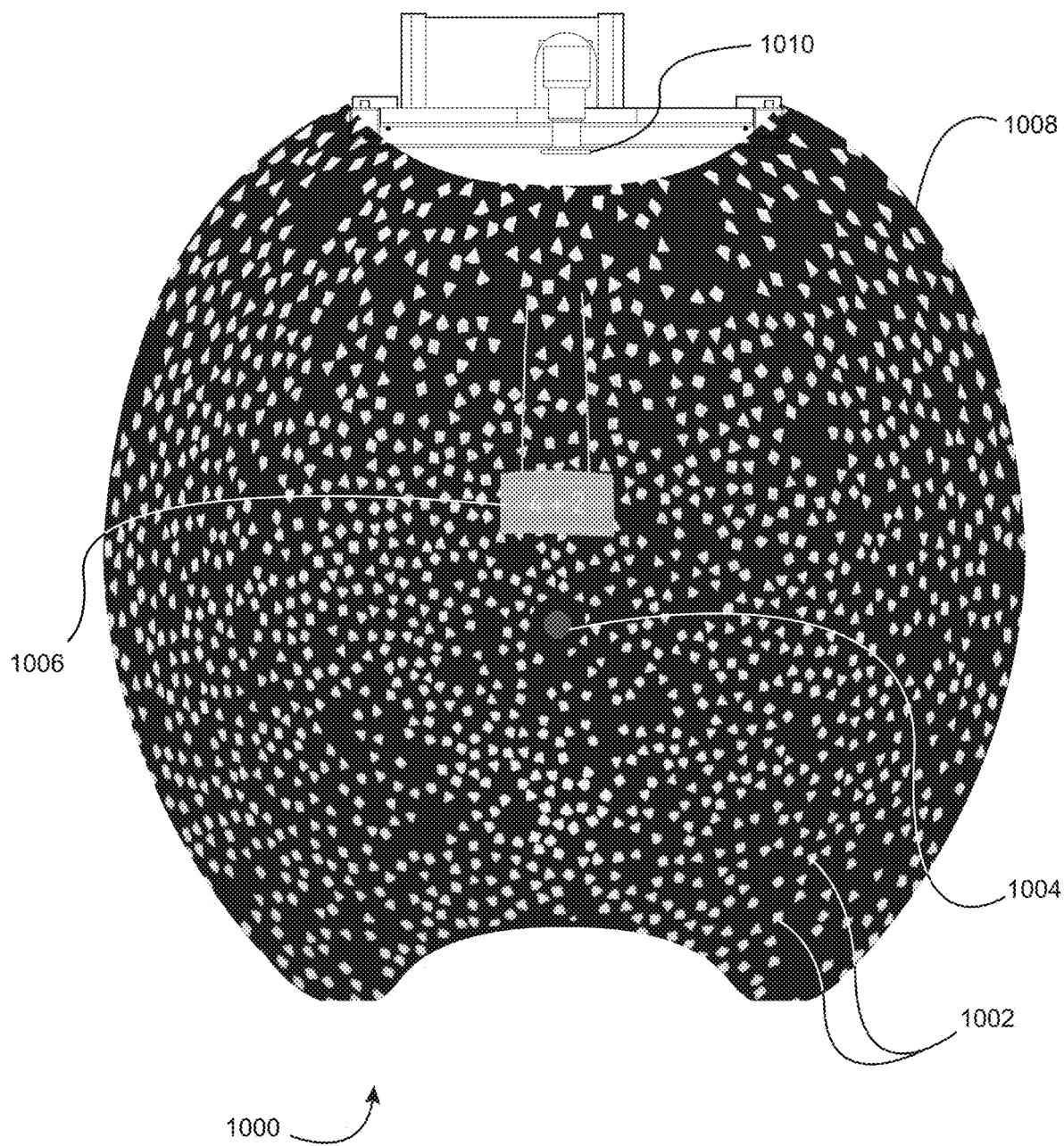
FIG. 69 is an exemplary optokinetic scene displayed on the subject visual display device of the force measurement system, according to an embodiment of the invention, wherein a cognitive task is superimposed on the optokinetic scene.

In these one or more further embodiments, the scene parameter selected by the user may be selected from the group consisting of: (i) a direction of movement of one or more objects being displaced in the one or more scenes, (ii)

a speed of movement of the one or more objects being displaced in the one or more scenes, and (iii) a density of the one or more objects being displaced in the one or more scenes. Also, in these one or more further embodiments, the one or more scenes displayed on the output screen of the subject visual display device 107 comprise at least one of: (i) a starfield, (ii) a fountain, (iii) an airport, and (iv) a checkered room. In these one or more further embodiments, the user can choose from different optokinetic flow protocol scenes that will be displayed to the subject. Also, the user can define the direction of the optokinetic movement (e.g., up, down, left, right), the speed of the optokinetic movement (e.g., speed ranges from 0-25 in increments of 5), the density of the optokinetic scene (e.g., low, medium, or high). For example, with reference to FIG. 69, the user can select a starfield scene 1000 to display on the dome-shaped projection screen 1008 with the image being projected thereon by the projector lens 1010. As shown in FIG. 69, the starfield scene 1000 incorporates a black background with small white pyramids 1002 layered on top of the black background that replicate stars. In the illustrative embodiment, the density of the stars 1002 in the scene 1000 is able to be adjusted by the user as well as the direction and speed of movement of the stars 1002. In FIG. 69, it can be seen that the starfield scene 1000 further comprises a circular dot 1004 near the middle of the screen image on which the subject may focus while he or she is standing on the force measurement assembly 102 of the force measurement system 100.

Also, in these one or more further embodiments, the data acquisition/data processing device 104 of the force measurement system 100 may be further programmed to generate and display a cognitive task on the output screen of the subject visual display device 107 with the one or more scenes; and determine whether the subject 108 is able to correctly perform the cognitive task when the one or more scenes are being displayed on the output screen. For example, referring again to FIG. 69, it can be seen that, in the illustrative embodiment, the cognitive task may comprise a sign 1006 drop down in the scene 1000, with the task presented on the sign 1006. In the illustrative embodiment, the cognitive task options include: (i) presenting a math task on the screen (e.g., a simple addition math task as shown in FIG. 69), and the subject gives the answer to the math problem; (ii) presenting a Stroop congruent task on the screen (e.g., a word that is a color is presented on the screen, and the text of the word is congruent with the color), and the subject is instructed to identify the word/color; and (iii) presenting a Stroop incongruent task on the screen (e.g., a word that is a color is presented on the screen, and the text of the word is a different color), and the subject is instructed to identify the text color, and not the word. As an example of a Stroop congruent task, the word displayed on the screen is "blue" and the text color is also blue. As an example of a Stroop incongruent task, the word is "blue" and the text color is green.

Figure 71:
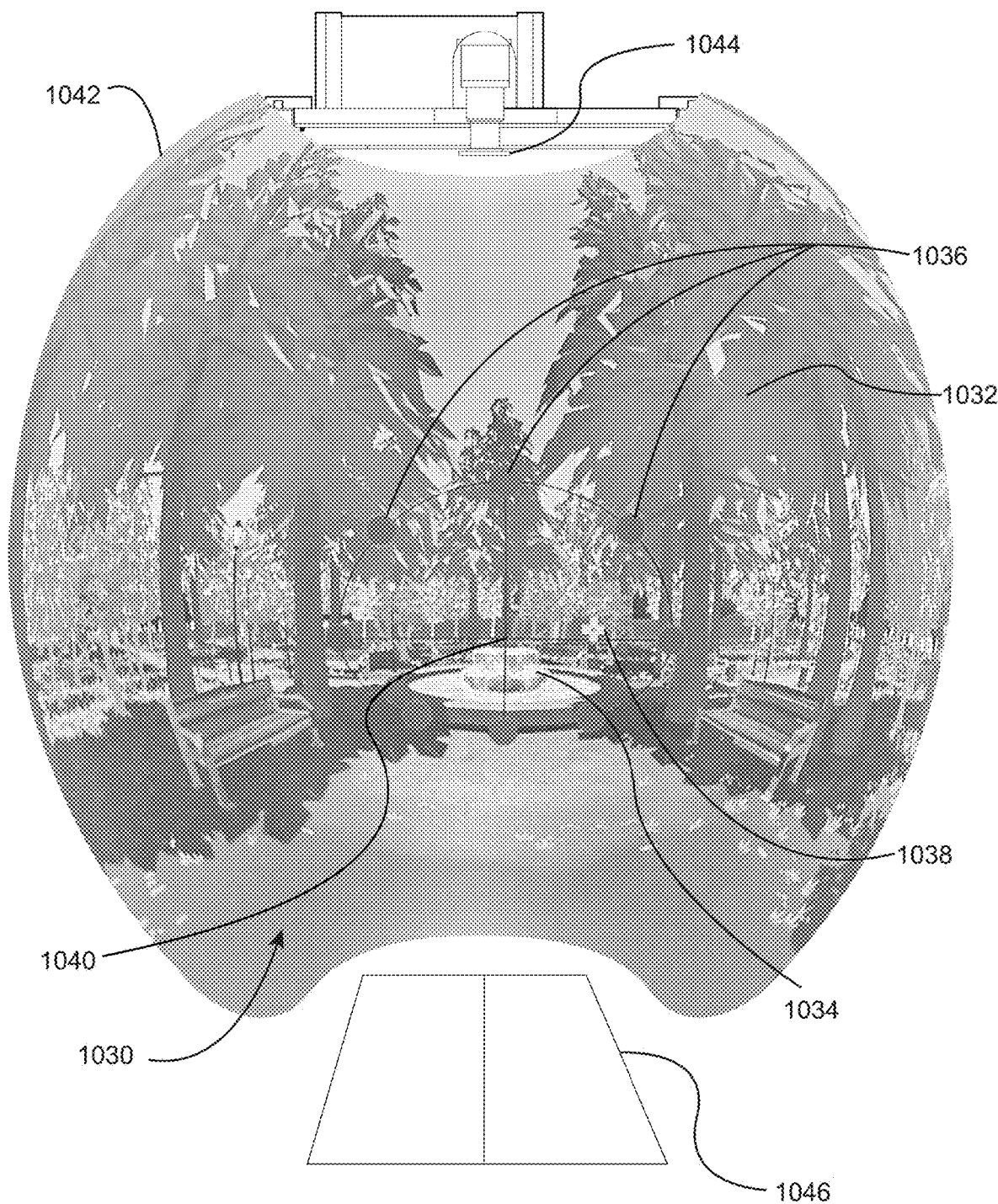
FIG. 71 is a first exemplary balance quick training scene displayed on the subject visual display device of the force measurement system, according to an embodiment of the invention.
Figure 72:
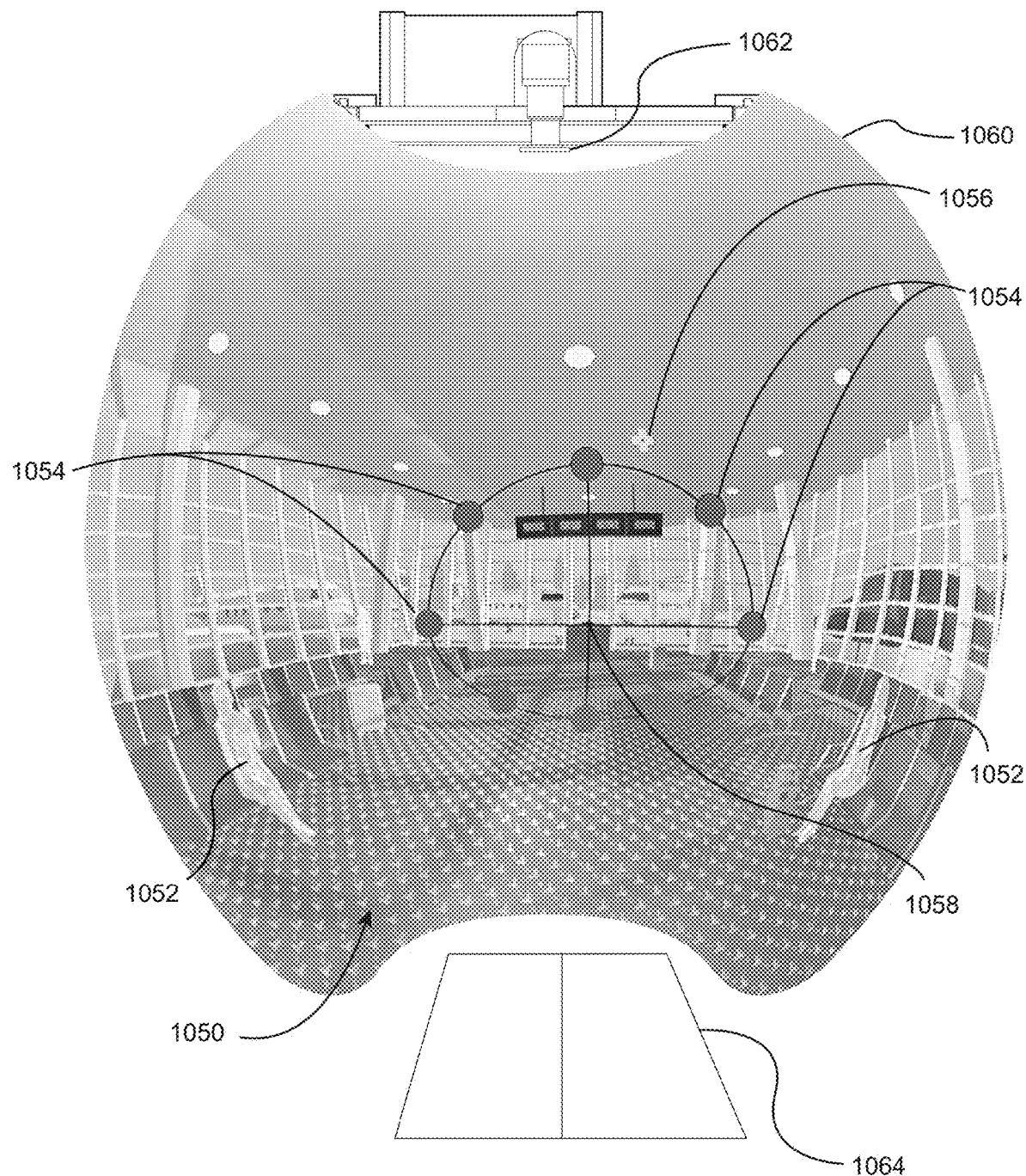
FIG. 72 is a second exemplary balance quick training scene displayed on the subject visual display device of the force measurement system, according to an embodiment of the invention.

Now, turning to FIGS. 71 and 72, in these one or more further embodiments, the data acquisition/data processing device 104 of the force measurement system 100 may be further programmed to generate and display at least one displaceable visual object 1038, 1056 and a plurality of visual targets 1036, 1054 on the output screen of the visual display device 1042, 1060, the plurality of visual targets 1036, 1054 being superimposed on the one or more scenes being displayed on the output screen; receive one or more additional input signals from the one or more user input devices 132, 134 based upon an input response by the user; and control the movement of the at least one displaceable visual object 1038, 1056 towards the plurality of visual targets 1036, 1054 based upon the one or more additional input signals received from the input device 132, 134. As described above, the fountain scene 1030 of FIG. 71 and the airport lounge scene 1050 of FIG. 72 may be used when performing Quick Training protocols. As shown in FIGS. 71 and 72, these scenes 1030, 1050 may be displayed with a Limits of Stability ("LOS") ellipse with visual targets 1036, 1054 layered on top of the scenes 1030, 1050. The visual targets 1036, 1054 on the ellipse change depending on the particular protocol that is chosen by a user.

As shown in FIG. 71, the fountain scene 1030, which is projected onto the dome-shaped output screen 1042 by the projector lens 1044, includes a forest background 1032, a fountain 1034 with squirting water in the foreground, a plurality of visual targets 1036 on an LOS ellipse and superimposed on the scene, a displaceable cursor 1038 representing the center-of-gravity of the user, and a center location 1040 for the cursor 1038. In the illustrative fountain scene 1030, the subject is instructed to displace the cursor 1038 from the center location 1040 to each of the visual targets 1036 in succession by shifting his or her center-of-pressure on the force plate 1046. In the training routine performed using the fountain scene 1030, the data acquisition/data processing device 104 is further programmed to determine how closely the subject is able to displace the displaceable cursor 1038 to each of the plurality of visual targets 1036 on the dome-shaped output screen 1042 in succession. The objective in this training routine is for the user to have easy access to basic training exercises that test balances under distracting stimuli. The training exercises are designed to meet the basic needs of training quickly and easily. In the illustrative embodiment, the user (e.g., operator/clinician) can choose another type of scene that will be used during the training, such as the airport lounge scene 1050 that will be described in further detail hereinafter.

Now, as shown in FIG. 72, the airport lounge scene 1050, which is projected onto the dome-shaped output screen 1060 by the projector lens 1062, includes an airport lounge area with people 1052 disposed on opposite sides thereof, a plurality of visual targets 1054 on an LOS ellipse and superimposed on the scene, a displaceable cursor 1056 representing the center-of-gravity of the user, and a center location 1058 for the cursor 1056. In the illustrative airport lounge scene 1050, the subject is instructed to displace the cursor 1056 from the center location 1058 to each of the visual targets 1054 in succession by shifting his or her center-of-pressure on the force plate 1064. In the training routine performed using the airport lounge scene 1050, the data acquisition/data processing device 104 is further programmed to determine how closely the subject is able to displace the displaceable cursor 1056 to each of the plurality of visual targets 1054 on the dome-shaped output screen 1060 in succession.

Figure 70:
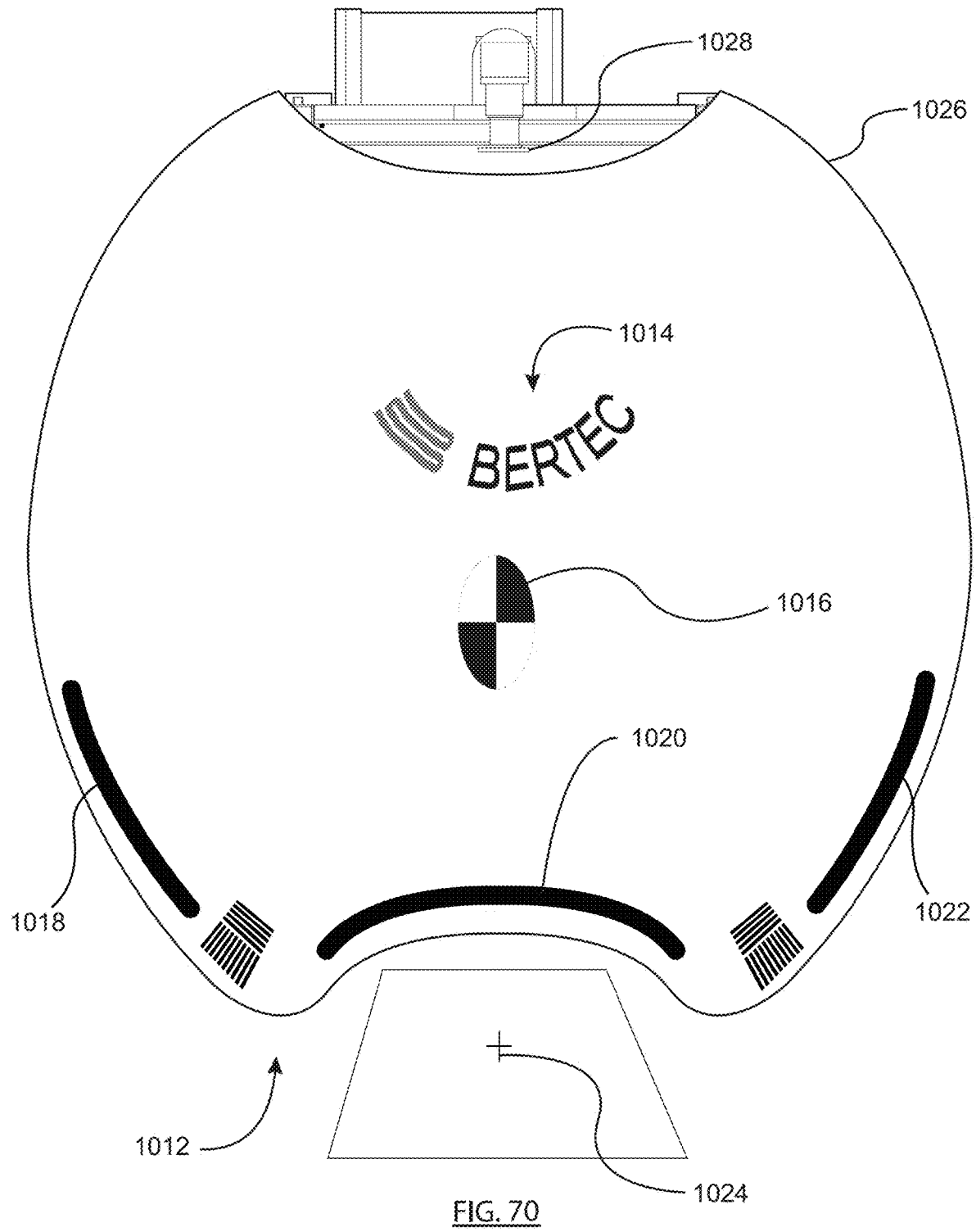
FIG. 70 is an exemplary projector calibration image displayed on the subject visual display device of the force measurement system, according to an embodiment of the invention.

Next, with reference to FIG. 70, in these one or more further embodiments, the data acquisition/data processing device 104 of the force measurement system 100 may be further programmed to generate and display a projector calibration image 1012 on the dome-shaped projection screen 1026 of the subject visual display device 107. As shown in FIG. 70, the projector calibration image 1012 comprises a plurality of curved alignment lines 1018, 1020, 1022 that correspond to one or more edges of the projection screen 1026. In these one or more further embodiments, the plurality of curved alignment lines 1018, 1020, 1022 are configured to be displaced towards the corresponding edges of the projection screen 1026 when the user adjusts one or more lens settings on the lens 1028 of the projector. As such, the projector calibration scene 1012 of FIG. 70 is used for aligning the projector lens 1028 of the projector to the dome-shaped screen 1026. The projector calibration image 1012 reflects an outline of the side and bottom edges of the dome-shaped screen 1026 (i.e., by means of curved alignment lines 1018, 1020, 1022 in FIG. 70). The "Bertec" text 1014 and black-and-white circle 1016 on the alignment image 1012 is used as a guide when setting the focus and zoom of the projector. In FIG. 70, the striated squares between the curved alignment lines 1018 and 1020, and between the curved alignment lines 1020 and 1022, are used as an image measurement tool (e.g., the squares should each measure approximately 5"×5" when the alignment image 1012 is projected onto the screen 1026). As shown in FIG. 70, the "+" symbol 1024 is configured to be projected onto the approximate center of the force measurement assembly. In the illustrative embodiment, the projector may include one or more lens adjustment knobs thereon for adjusting a positioning and/or focus of the projector lens 1028. As such, when the alignment image 1012 is projected onto the dome-shaped screen 1026, the user may use the one or more lens adjustment knobs on the projector to adjust the projector lens 1028 so that the curved alignment lines 1018, 1020, 1022 of the alignment image 1012 are properly positioned relative to the side and bottom edges of the dome-shaped screen 1026.

Figure 73:
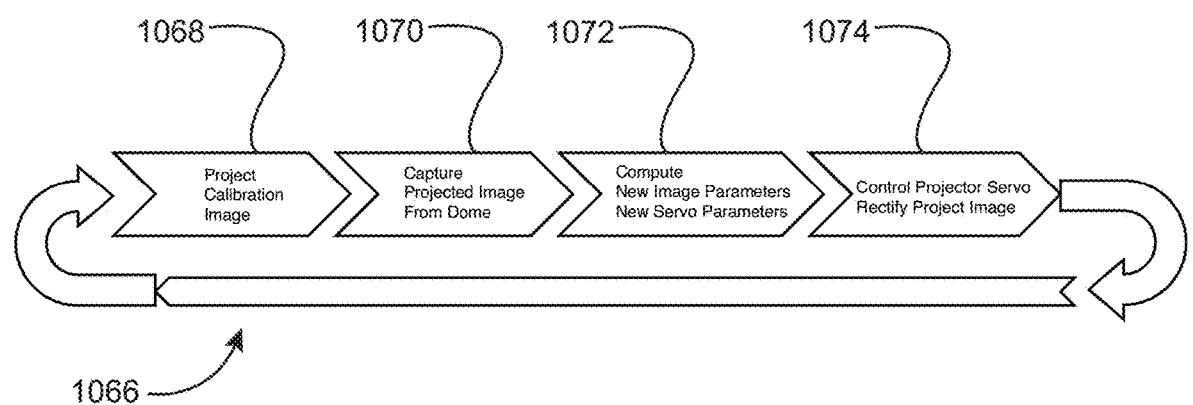
FIG. 73 is a process flow diagram for an automatic projector calibration subsystem of the force measurement system, according to an embodiment of the invention.
Figure 74:
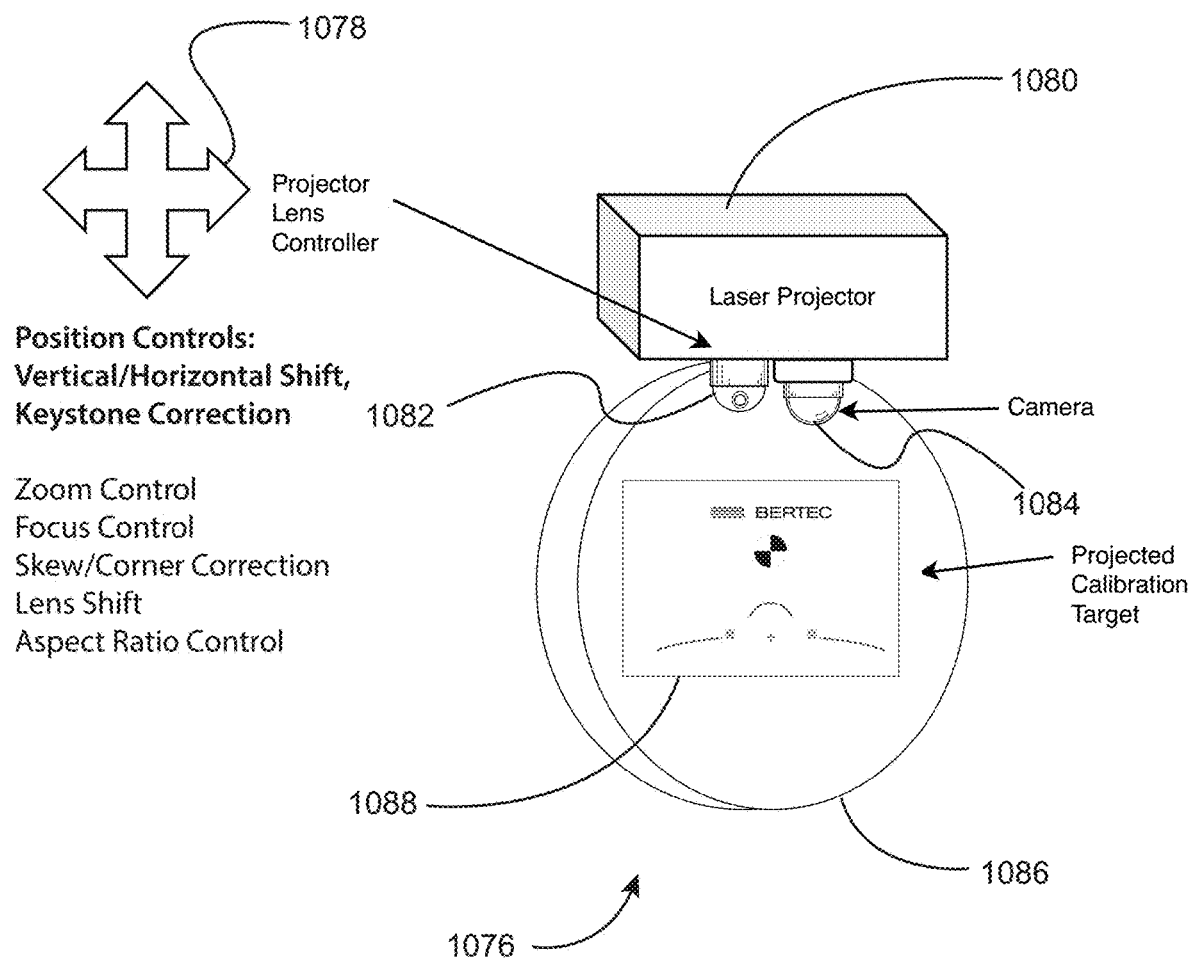
FIG. 74 is a diagram illustrating the components of the automatic projector calibration subsystem of the force measurement system, according to an embodiment of the invention.
Figure 75:
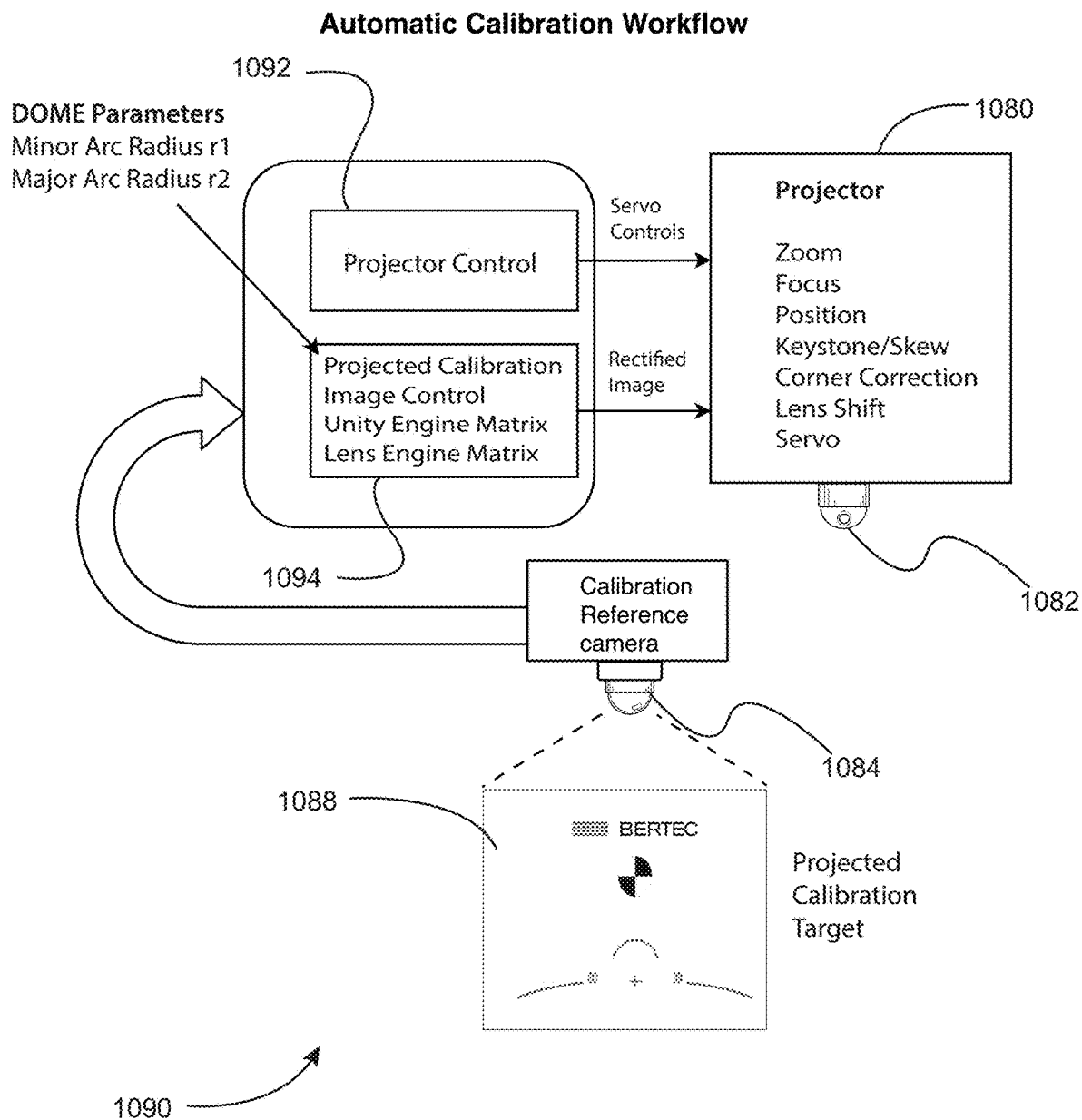
FIG. 75 is another diagram illustrating the components and process flow for the automatic projector calibration subsystem of the force measurement system, according to an embodiment of the invention.

Turning now to FIGS. 73-75, in these one or more further embodiments, the force measurement system 100 may further include at least one lens actuator (e.g., a servo motor for displacing lens 1082 in FIGS. 74 and 75) and at least one calibration reference camera 1084. The at least one lens actuator may be configured to adjust one or more lens settings on the lens 1082 of the projector. The at least one calibration reference camera 1084 may be configured to capture one or more images displayed on the projection screen 1086 (see FIG. 74). Also, in these one or more further embodiments, the data acquisition/data processing device 104 of the force measurement system 100 may be further programmed to: (i) generate and display a projector calibration image 1088 on the projection screen 1086 of the subject visual display device 107, the projector calibration image 1088 comprising a plurality of curved alignment lines (e.g., the alignment lines 1018, 1020, 1022 in FIG. 70) that correspond to edges of the projection screen 1086; (ii) capture the projector calibration image 1088 using the at least one calibration reference camera 1084; (iii) compute one or more image parameters based upon the projector calibration image 1088 captured by the at least one calibration reference camera 1084; and (iv) adjust, based upon the one or more computed image parameters, the one or more lens settings on the lens 1082 of the projector using the at least one lens actuator. In these one or more further embodiments, the one or more image parameters affect at least one of: (i) image position, (ii) image distortion, (iii) image focus, and (iv) image brightness.

With reference to FIGS. 73-75, the functionality of the illustrative automated calibration system for the projector of the dome-shaped screen will be further described. Initially, referring to the diagram 1090 in FIG. 75, the projector control 1092, the projected calibration image control 1094, the projector 1080 with lens 1082, and the calibration reference camera 1084 will be described. In the illustrative embodiment, the projector control 1092 is the central unit or software that controls all aspects of the projector's operation. The projected calibration image control 1094 is the functional module that handles the specific output of the calibration image. In the illustrative embodiment, the projected calibration image control 1094 includes a Unity Engine Matrix, which may be a Unity game engine for rendering the calibration image. This matrix can be used to adjust the image according to the projector's position and lens characteristics. The projected calibration image control 1094 further includes a Lens Engine Matrix for controlling the specific adjustments needed for the projector's lens system to ensure the image is correctly focused and aligned. In the illustrative embodiment, the projector 1080 itself has the following controls: (i) zoom/focus/position/Keystone controls, which adjust the size, sharpness, position, and shape of the projected image; (ii) skew/corner correction controls, which refine the alignment at the edges and corners of the image; (iii) lens shift controls, which adjust the lens to shift the image without moving the projector; (iv) servo controls, which make mechanical adjustments to the projector's components, which may include the lens and mirror systems for precise alignment. In the illustrative embodiment, the calibration reference camera 1084 is a camera that captures the projected image 1088 to compare it with the intended output. The feedback from this camera 1084 may be used to analyze the image 1088 and inform the adjustments made by the projector control system.

In the illustrative embodiment, because the automated calibration system for the projector is in the form of a closed-loop control system, the calibration process is dynamic and iterative. The projector 1080 outputs a calibration image 1088, which is then captured and analyzed by the reference camera 1084 (see FIG. 75). The projector control unit 1092 then processes this information and adjusts the projector's settings via the Unity Engine Matrix and Lens Engine Matrix 1094, as well as the physical servo mechanisms, to correct any distortion or misalignment. This process can be repeated until the image 1088 is calibrated to the desired specifications.

The diagram 1076 in FIG. 74 is similar in some respects to the diagram 1090 in FIG. 75 described above. Referring to FIG. 74, it can be seen that a projector 1080 with projector lens 1082 projects a calibration image 1088 onto a dome-shaped screen 1086, and then a camera 1084 captures the calibration image 1088. The projector control unit then processes this information captured by the camera 1084 and adjusts the projector's settings accordingly. The movement directions 1078 of the projector lens controller are diagrammatically represented in FIG. 74.

A flow diagram 1066 for an automatic projector calibration system is illustrated in FIG. 73. In the initial step 1068, the automated projector calibration system starts by projecting a calibration image onto the dome or screen. This image may have a pattern that can be easily analyzed for distortion. Next, in step 1070 of FIG. 73, once the calibration image is projected, the projected image is captured from the dome-shaped screen. This capturing of the image may be done with cameras or sensors placed in strategic locations to get an accurate representation of how the image looks when projected onto the curved surface. Then, in step 1072, after capturing the image, the system computes new image parameters and/or new servo parameters. These parameters may include adjustments for distortion, focus, brightness, or other factors that affect the quality of the projected image. The parameters also may include mechanical adjustment parameters, such as lens positioning. Finally, in step 1074 of FIG. 73, with the new parameters computed, the system then controls the projector's servo mechanisms to adjust the projection based on the computed parameters. This may involve physical adjustments to the projector's optics and/or digital adjustments to the image itself. The goal is to rectify or correct any distortion or misalignment in the projected image. This feedback loop may continue iteratively to fine-tune the image quality to ensure that the projected image is correctly aligned and undistorted, providing the best possible viewing experience. The aforedescribed projector calibration system also may be particularly useful in other applications, such as in planetariums, immersive environments, or other specialized projection setups where precise calibration is essential.

When using projectors, various types of distortions can affect the quality and alignment of the projected image. The first category of distortions includes those related to zoom, focus, position, and the Keystone effect. Zoom distortion occurs when the zoom level is not set correctly for the distance or screen size, the image can either be too small (minimized) or too large (maximized), leading to a loss of detail or part of the image being cut off. The zoom control adjusts the size of the image to fit the screen or viewing area properly. Focus distortion occurs when an improperly focused projector leads to a blurry image where details are not sharp. This can be due to the projector being too far or too close or simply not adjusted correctly. Focus control sharpens the image by adjusting the lens. Positional distortion occurs when the projector is not directly in front of the screen or at an optimal distance, the image can appear off-center or partially on an unintended surface. Position controls allow for the adjustment of the image's placement without physically moving the projector. Keystone distortion occurs when the projector is angled upwards or downwards relative to the screen, resulting in a trapezoidal image instead of a rectangular one. Keystone controls digitally manipulate the image to restore the proper rectangular shape.

The second category of distortions includes those related to skew and corner correction. Skew distortion occurs when the projector or screen is not perfectly aligned, causing the image to tilt to one side or appear as if it is leaning. Skew control allows for the adjustment of these angles to straighten the image. Sometimes, even when the center of the image is aligned, the corners can still be off due to the screen's angle or curvature. Corner correction tools allow for independent adjustment of each corner to ensure the entire image uniformly aligns with the screen edges.

The third category of distortions includes those related to lens shift distortions and mechanical distortions. If a projector needs to be placed off-center from the screen, it can lead to geometric distortions where the image is not evenly rectangular or has uneven focus across the surface (i.e., lens shift distortions). Lens shift mechanically moves the lens to adjust the image's position vertically or horizontally, correcting these distortions without moving the projector or compromising image quality. Over time or due to improper setup, mechanical components like lenses, mirrors, or internal projectors' structures can lead to mechanical-based image distortions. Servo mechanisms in higher-end projectors make precise adjustments to these components, ensuring the image remains well-aligned and focused. Each of these controls addresses specific types of distortions that can affect a projected image. By properly adjusting the projector controls, one can ensure that the image is clear, correctly aligned, and proportionally accurate, providing the best viewing experience for the user.

Although the invention has been shown and described with respect to a certain embodiment or embodiments, it is apparent that this invention can be embodied in many different forms and that many other modifications and variations are possible without departing from the spirit and scope of this invention. In particular, while an interactive airplane game is described in the embodiment described above, those of ordinary skill in the art will readily appreciate that the invention is not so limited. For example, as illustrated in the screen image 206 of FIG. 15, the immersive virtual reality environment 208 could alternatively comprise a scenario wherein the subject 204 is walking along a bridge 207. Also, the interactive game could involve navigating through a maze, walking down an endless grocery aisle, traversing an escalator, walking down a path in the woods, or driving around a course. For example, an exemplary interactive driving game may comprise various driving scenarios. In the beginning of the game, the scenario may comprise an open road on which the subject drives. Then, a subsequent driving scenario in the interactive driving game may comprise driving through a small, confined roadway tunnel. As such, the subject would encounter different conditions while engaging in the interactive driving game (e.g., a light-to-dark transition as a result of starting out on the open road and transitioning to the confines of the tunnel), and thus, the interactive game would advantageously challenge various senses of the subject. Of course, the interactive driving game could also be configured such that the subject first encounters the tunnel and then, subsequently encounters the open road (i.e., a dark-to-light transition). In addition, any other suitable game and/or protocol involving a virtual reality scenario can be used in conjunction with the aforedescribed force measurement system (e.g., any other interactive game that focuses on weight shifting by the subject and/or a virtual reality scenario that imitates depth in a 2-D painting). As such, the claimed invention may encompass any such suitable game and/or protocol.

Moreover, while reference is made throughout this disclosure to, for example, "one embodiment" or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Furthermore, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system, comprising:
   at least one user input device, the at least one user input device configured to output one or more input signals based upon one or more selections by a user performing a testing or training routine on a subject;
   a force measurement assembly configured to receive the subject, the force measurement assembly including:
      a top surface configured to receive at least one portion of a body of the subject; and
      at least one force transducer, the at least one force transducer configured to output one or more output signals that are representative of forces and/or moments being applied to the top surface of the force measurement assembly by the subject;
   at least one visual display device having an output screen, the at least one visual display device configured to display one or more scenes on the output screen so that the one or more scenes are visible to the subject; and one or more data processing devices operatively coupled to the at least one user input device, the force measurement assembly, and the at least one visual display device, the one or more data processing devices being programmed to:

receive the one or more input signals from the at least one user input device based upon the one or more selections by the user, the one or more selections by the user including a scene parameter for one or more scenes on the output screen of the at least one visual display device;

display the one or more scenes on the output screen of the at least one visual display device based upon the scene parameter selected by the user;

receive, from the at least one force transducer of the force measurement assembly, the one or more output signals that are representative of the forces and/or moments being applied to the top surface of the force measurement assembly by the subject; and convert the one or more output signals into output force and/or moment data.

2. The force measurement system according to claim 1, wherein the scene parameter selected by the user is selected from the group consisting of: (i) a direction of movement of one or more objects being displaced in the one or more scenes, (ii) a speed of movement of the one or more objects being displaced in the one or more scenes, and (iii) a density of the one or more objects being displaced in the one or more scenes.

3. The force measurement system according to claim 1, wherein the one or more scenes displayed on the output screen of the at least one visual display device comprise at least one of: (i) a starfield, (ii) a fountain, (iii) an airport, and (iv) a checkered room.

4. The force measurement system according to claim 3, wherein the one or more data processing devices are further programmed to:

generate and display a cognitive task on the output screen of the at least one visual display device with the one or more scenes; and determine whether the subject is able to correctly perform the cognitive task when the one or more scenes are being displayed on the output screen.

5. The force measurement system according to claim 3, wherein the one or more data processing devices are further programmed to:

generate and display at least one displaceable visual object and a plurality of visual targets on the output screen of the at least one visual display device, the plurality of visual targets being superimposed on the one or more scenes being displayed on the output screen;

receive one or more additional input signals from the at least one user input device based upon an input response by the user; and control movement of the at least one displaceable visual object towards the plurality of visual targets based upon the one or more additional input signals received from the input device.

6. The force measurement system according to claim 1, wherein the at least one visual display device further comprises a projector having a lens and a projection screen, the projector being configured to project an image through the lens, and onto the projection screen.

7. The force measurement system according to claim 6, wherein the one or more data processing devices are further programmed to:

generate and display a projector calibration image on the projection screen of the at least one visual display device, the projector calibration image comprising one or more alignment lines that correspond to one or more edges of the projection screen; and wherein the one or more alignment lines are configured to be displaced towards the one or more corresponding edges of the projection screen when the user adjusts one or more lens settings on the lens of the projector.

8. The force measurement system according to claim 6, further comprising:

at least one lens actuator, the at least one lens actuator configured to adjust one or more lens settings on the lens of the projector; and at least one calibration reference camera, the at least one calibration reference camera configured to capture one or more images displayed on the projection screen;

wherein the one or more data processing devices are further programmed to:

generate and display a projector calibration image on the projection screen of the at least one visual display device, the projector calibration image comprising one or more alignment lines that correspond to one or more edges of the projection screen;

capture the projector calibration image using the at least one calibration reference camera;

compute one or more image parameters based upon the projector calibration image captured by the at least one calibration reference camera; and adjust, based upon the one or more computed image parameters, the one or more lens settings on the lens of the projector using the at least one lens actuator.

9. The force measurement system according to claim 8, wherein the one or more computed image parameters affect at least one of: (i) image position, (ii) image distortion, (iii) image focus, and (iv) image brightness.

10. The force measurement system according to claim 1, wherein the force measurement assembly is in a form of a force plate or a balance plate.

11. The force measurement system according to claim 1, further comprising a base assembly having a stationary portion and a displaceable portion, the force measurement assembly forming a part of the displaceable portion of the base assembly, and the force measurement system additionally comprising at least one actuator operatively coupled to the one or more data processing devices, the at least one actuator configured to displace the force measurement assembly relative to the stationary portion of the base assembly.

12. The force measurement system according to claim 11, wherein the at least one actuator comprises a first actuator configured to rotate the force measurement assembly about a transverse rotational axis and a second actuator configured to translate the displaceable portion of the base assembly that includes the force measurement assembly.

13. The force measurement system according to claim 1, wherein the force measurement assembly is in a form of an instrumented treadmill.

14. The force measurement system according to claim 1, wherein the at least one user input device comprises at least one of: (i) a mouse, (ii) a keyboard, (iii) a touchscreen user interface, and (iv) a voice recognition device.

* * * * *